United States Patent
Bourke, Jr. et al.

(10) Patent No.: US 12,121,746 B2
(45) Date of Patent: *Oct. 22, 2024

(54) ENERGY AUGMENTATION STRUCTURES, ENERGY EMITTERS OR ENERGY COLLECTORS CONTAINING THE SAME, AND THEIR USE IN METHODS AND SYSTEMS FOR TREATING CELL PROLIFERATION DISORDERS

(71) Applicant: IMMUNOLIGHT, LLC, Detroit, MI (US)

(72) Inventors: Frederic A. Bourke, Jr., Detroit, MI (US); Harold Walder, Detroit, MI (US); Zakaryae Fathi, Detroit, MI (US); Wayne F. Beyer, Detroit, MI (US); Ronald A. Rudder, Detroit, MI (US); Joseph H. Simmons, Detroit, MI (US)

(73) Assignee: IMMUNOLIGHT, LLC, Detroit, MI (US)

( * ) Notice: Subject to any disclaimer, the term of this patent is extended or adjusted under 35 U.S.C. 154(b) by 401 days.

This patent is subject to a terminal disclaimer.

(21) Appl. No.: 17/433,890

(22) PCT Filed: Jan. 30, 2020

(86) PCT No.: PCT/US2020/015813
§ 371 (c)(1),
(2) Date: Aug. 25, 2021

(87) PCT Pub. No.: WO2020/180426
PCT Pub. Date: Sep. 10, 2020

(65) Prior Publication Data
US 2022/0184211 A1 Jun. 16, 2022

Related U.S. Application Data

(60) Provisional application No. 62/955,533, filed on Dec. 31, 2019, provisional application No. 62/946,648,
(Continued)

(51) Int. Cl.
| | |
|---|---|
| *A61N 5/06* | (2006.01) |
| *A61K 35/12* | (2015.01) |
| *A61K 41/00* | (2020.01) |
| *A61N 5/067* | (2006.01) |
| *C09J 133/08* | (2006.01) |
| *C09K 11/02* | (2006.01) |
| *C09K 11/59* | (2006.01) |
| *C09K 11/76* | (2006.01) |

(Continued)

(52) U.S. Cl.
CPC ............ *A61N 5/0625* (2013.01); *A61K 35/12* (2013.01); *A61K 41/00* (2013.01); *A61K 41/0057* (2013.01); *A61N 5/0601* (2013.01); *A61N 5/062* (2013.01); *A61N 5/067* (2021.08); *C09J 133/08* (2013.01); *C09K 11/025* (2013.01); *C09K 11/595* (2013.01); *C09K 11/76* (2013.01); *C09K 11/7701* (2013.01); *C09K 11/7792* (2013.01); *C12N 15/01* (2013.01); *F21K 2/00* (2013.01); *F21S 11/007* (2013.01); *F21V 9/40* (2018.02); *H01J 45/00* (2013.01); *H01L 24/29* (2013.01); *H01L 24/83* (2013.01); *H01L 31/035281* (2013.01); *H01L 31/054* (2014.12); *H01L 31/06* (2013.01); *A61N 2005/0661* (2013.01); *A61N 2005/0662* (2013.01); *A61N 2005/0663* (2013.01); *H01L 31/055* (2013.01); *H01L 2224/2919* (2013.01); *H01L 2224/29393* (2013.01); *H01L 2224/8322* (2013.01); *H01L 2224/83855* (2013.01)

(58) Field of Classification Search
None
See application file for complete search history.

(56) References Cited

U.S. PATENT DOCUMENTS

| 7,538,641 B2 | 5/2009 | Puente Baliarda et al. |
| 8,376,013 B2 | 2/2013 | Bourke |

(Continued)

FOREIGN PATENT DOCUMENTS

| EP | 1 917 556 B1 | 5/2008 |
| EP | 2 028 225 A1 | 2/2009 |

(Continued)

OTHER PUBLICATIONS

Supplementary European Search Report issued Mar. 27, 2023 in European Patent Application No. 20765910.3.

(Continued)

*Primary Examiner* — Sanza L. McClendon
(74) *Attorney, Agent, or Firm* — TUCKER ELLIS, L.L.P.; J. Derek Mason

(57) ABSTRACT

An emission enhancement structure having at least one energy augmentation structure; and an energy converter capable of receiving energy from an energy source, converting the energy and emitting therefrom a light of a different energy than the received energy. The energy converter is disposed in a vicinity of the at least one energy augmentation structure such that the emitted light is emitted with an intensity larger than if the converter were remote from the at least one energy augmentation structure. Also described are various uses for the energy emitters, energy augmentation structures and energy collectors in a wide array of fields, particularly medical uses for treatment of cell proliferation disorders.

166 Claims, 64 Drawing Sheets

Related U.S. Application Data filed on Dec. 11, 2019, provisional application No. 62/897,677, filed on Sep. 9, 2019, provisional application No. 62/855,508, filed on May 31, 2019, provisional application No. 62/813,390, filed on Mar. 4, 2019.

(51) Int. Cl.

| | | |
|---|---|---|
| C09K 11/77 | (2006.01) |
| C12N 15/01 | (2006.01) |
| F21K 2/00 | (2006.01) |
| F21S 11/00 | (2006.01) |
| F21V 9/40 | (2018.01) |
| H01J 45/00 | (2006.01) |
| H01L 23/00 | (2006.01) |
| H01L 31/0352 | (2006.01) |
| H01L 31/054 | (2014.01) |
| H01L 31/06 | (2012.01) |
| H01L 31/055 | (2014.01) |

(56) References Cited

U.S. PATENT DOCUMENTS

| | | |
|---|---|---|
| 8,383,836 B2 | 2/2013 | Toone |
| 8,389,958 B2 | 3/2013 | Vo-Dinh |
| 8,618,509 B2 | 12/2013 | Vo-Dinh |
| 8,658,086 B2 | 2/2014 | Bourke |
| 8,770,203 B2 | 7/2014 | Bourke |
| 8,791,275 B2 | 7/2014 | Toone |
| 8,907,109 B2 | 12/2014 | Toone |
| 8,951,561 B2 | 2/2015 | Vo-Dinh |
| 9,004,131 B2 | 4/2015 | Bourke |
| 9,005,406 B2 | 4/2015 | Bourke |
| 9,174,190 B2 | 11/2015 | Bourke |
| 9,232,618 B2 | 1/2016 | Bourke |
| 9,302,116 B2 | 4/2016 | Vo-Dinh |
| 9,352,040 B2 | 5/2016 | Bourke |
| 9,358,292 B2 | 6/2016 | Bourke |
| 9,439,897 B2 | 9/2016 | Xia |
| 9,488,916 B2 | 11/2016 | Bourke |
| 9,498,643 B2 | 11/2016 | Bourke |
| 9,526,913 B2 | 12/2016 | Vo-Dinh |
| 9,526,914 B2 | 12/2016 | Vo-Dinh |
| 9,630,022 B2 | 4/2017 | Bourke |
| 9,649,832 B2 | 5/2017 | Fathi |
| 9,662,388 B2 | 5/2017 | Vo-Dinh |
| 9,662,389 B2 | 5/2017 | Vo-Dinh |
| 9,682,146 B2 | 6/2017 | Bourke |
| 9,682,250 B2 | 6/2017 | Bourke |
| 9,715,159 B1 | 7/2017 | Akselrod et al. |
| 9,833,634 B2 | 12/2017 | Bourke |
| 9,907,976 B2 | 3/2018 | Bourke |
| 9,943,094 B2 | 4/2018 | Bourke |
| 9,993,661 B2 | 6/2018 | Bourke |
| 10,029,117 B2 | 7/2018 | Bourke |
| 10,080,275 B2 | 9/2018 | Bourke |
| 10,201,796 B2 | 2/2019 | Bourke |
| 10,213,763 B2 | 2/2019 | Bourke |
| 10,232,190 B2 | 3/2019 | Bourke |
| 10,272,262 B2 | 4/2019 | Bourke |
| 10,300,299 B2 | 5/2019 | Bourke |
| 10,384,071 B2 | 8/2019 | Vo-Dinh |
| 10,391,330 B2 | 8/2019 | Bourke |
| 10,398,777 B2 | 9/2019 | Bourke |
| 10,441,810 B2 | 10/2019 | Oldham |
| 10,493,296 B2 | 12/2019 | Vo-Dinh |
| 10,575,541 B2 | 3/2020 | Bourke |
| 10,596,387 B2 | 3/2020 | Walder |
| 10,709,900 B2 | 7/2020 | Bourke |
| 10,835,756 B2 | 11/2020 | Bourke |
| 10,940,329 B2 | 3/2021 | Walder |
| 11,077,316 B2 | 8/2021 | Bourke |
| 11,103,580 B2 | 8/2021 | Bourke |
| 11,135,294 B2 | 10/2021 | Oldham |
| 11,207,409 B2 | 12/2021 | Bourke |
| 11,260,129 B2 | 3/2022 | Walder |
| 11,278,042 B2 | 3/2022 | Bourke |
| 11,305,131 B2 | 4/2022 | Oldham |
| 11,324,965 B2 | 5/2022 | Vo-Dinh |
| 11,383,098 B2 | 7/2022 | Vo-Dinh |
| 11,452,884 B2 | 9/2022 | Toone |
| 11,534,622 B2 | 12/2022 | Bourke |
| 11,571,587 B2 | 2/2023 | Bourke |
| 11,577,092 B2 | 2/2023 | Walder |
| 11,589,432 B2 | 2/2023 | Bourke |
| 11,786,595 B2 | 10/2023 | Oldham |
| 2004/0233512 A1 | 11/2004 | Fujioka |
| 2008/0057000 A1 | 3/2008 | Loveridge |
| 2008/0248001 A1 | 10/2008 | Bourke |
| 2009/0159510 A1 | 6/2009 | Haushalter |
| 2009/0212696 A1 | 8/2009 | Terao |
| 2009/0314333 A1 | 12/2009 | Shepard |
| 2010/0016783 A1 | 1/2010 | Bourke, Jr. et al. |
| 2010/0188171 A1 | 7/2010 | Mohajer-Iravani et al. |
| 2010/0261263 A1 | 10/2010 | Vo-Dinh et al. |
| 2011/0126889 A1 | 6/2011 | Bourke, Jr. et al. |
| 2012/0064134 A1 | 3/2012 | Bourke, Jr. et al. |
| 2013/0171060 A1 | 7/2013 | Vo-Dinh |
| 2014/0269806 A1 | 9/2014 | Bora et al. |
| 2014/0323946 A1 | 10/2014 | Bourke, Jr. et al. |
| 2015/0014022 A1 | 1/2015 | Young |
| 2016/0027949 A1 | 1/2016 | Cooke |
| 2017/0154866 A1 | 6/2017 | Fathi et al. |
| 2017/0167977 A1 | 6/2017 | Rivera |
| 2017/0239489 A1 | 8/2017 | Bourke, Jr. et al. |
| 2018/0269174 A1 | 9/2018 | Fathi et al. |
| 2018/0271121 A1 | 9/2018 | Bourke, Jr. et al. |
| 2018/0271978 A1 | 9/2018 | Ngwa et al. |
| 2018/0311355 A1 | 11/2018 | Oldham et al. |
| 2018/0317307 A1 | 11/2018 | Bourke, Jr. et al. |
| 2018/0358327 A1 | 12/2018 | Fathi et al. |
| 2020/0114164 A1 | 4/2020 | Bourke |
| 2020/0222711 A1 | 7/2020 | Walder |
| 2020/0357943 A1 | 11/2020 | Rotschild |
| 2021/0353954 A1 | 11/2021 | Bourke |
| 2022/0080045 A1 | 3/2022 | Walder |
| 2022/0134131 A1 | 5/2022 | Bourke |
| 2022/0184211 A1 | 6/2022 | Bourke |
| 2022/0193441 A1* | 6/2022 | Bourke, Jr. ............... A23L 3/26 |
| 2022/0226666 A1 | 7/2022 | Oldham |
| 2023/0029054 A1 | 1/2023 | Bourke |
| 2023/0201624 A1 | 6/2023 | Vo-Dinh |
| 2023/0109074 A1 | 8/2023 | Bourke |
| 2023/0292413 A1 | 9/2023 | Bourke |
| 2023/0338539 A1 | 10/2023 | Bourke |

FOREIGN PATENT DOCUMENTS

| | | |
|---|---|---|
| EP | 3 273 278 A1 | 1/2018 |
| EP | 3 594 557 A1 | 1/2020 |
| JP | 2009-205928 | 9/2009 |
| JP | 2017-62902 | 3/2017 |
| JP | 2017-138558 | 8/2017 |
| JP | 2018-13688 | 1/2018 |
| JP | 2018-147725 | 9/2018 |
| KR | 10-1928757 | 1/2014 |
| WO | WO 99/11727 | 3/1999 |
| WO | WO 2010/107720 A2 | 9/2010 |
| WO | WO 2017/019520 A1 | 2/2017 |
| WO | WO 2019/014413 A1 | 1/2019 |

OTHER PUBLICATIONS

P. Jung, et al., "Progress in Superconducting Metamaterials", Superconductor Science and Technology, 27, 2014, 13pp.

P. Cai, et al., "Synthesis and Realization of Novel Ultra-Wideband Bandpass Filters Using $3/4$ Wavelength Parallel-Coupled Line Resonators", Proceedings of Asia-Pacific Microwave Conference, 2006, 4pp.

Search Report issued Mar. 14, 2023, in European Patent Application No. 20766537.3.

(56) References Cited

OTHER PUBLICATIONS

Search Report issued Mar. 24, 2023, in European Patent Application No. 20766868.2.
Search Report issued Feb. 17, 2023, in European Patent Application No. 20765906.1.
Search Report issued Feb. 21, 2023, in European Patent Application No. 20767183.5.
K. Watanabe, et al., "A Microstrip UWB Bandpass Filter Using a Stub-Loaded Dual-Mode Ring Resonator and a Step Impedance Two-Mode Resonator", Microwave Conference, 2008, 4pp. XP031636965.
L. Snehalatha, et al., "A Compact Half-Wave Folded Waveguide Resonator for Dual-Band Applications", National Conference on Recent Advances in Electronics & Computer Engineering, 2015, 4pp., XP032923138.
International Search Report and Written Opinion issued on Jun. 11, 2020 in PCT/US2020/015813 filed on Jan. 30, 2020.
Office Action issued Nov. 6, 2023, in Japanese Patent Application No. 2021-552649, filed Jan. 30, 2020 w/English translation.

\* cited by examiner

Fit: Annexin V (+) = A + B [Psoralen] + C [Phosphor] + D [Psoralen] [Phosphor]

| Equation Coefficients | Coefficient Estimate | P-value | | |
|---|---|---|---|---|
| A (intercept) | 3.7E-02 | 0.071 | | |
| B (8-MOP effects) | -1.2E-03 | 0.096 | | |
| C (phosphor effects) | -5.4E-04 | 0.050 | $R^2$ | 0.718 |
| D (interaction effects) | 5.8E-05 | <.0001 | | |

Figure 52A

ENERGY AUGMENTATION STRUCTURES, ENERGY EMITTERS OR ENERGY COLLECTORS CONTAINING THE SAME, AND THEIR USE IN METHODS AND SYSTEMS FOR TREATING CELL PROLIFERATION DISORDERS

CROSS REFERENCE TO RELATED APPLICATIONS

This application is a 371 of international PCT application PCT/US2020/015813, filed Jan. 30, 2020. This application is related to, and claims priority to, provisional application U.S. Ser. No. 62/955,533, filed Dec. 31, 2019, entitled ENERGY AUGMENTATION STRUCTURE; ENERGY COLLECTOR CONTAINING THE SAME; AND EMISSION ENHANCEMENTS UTILIZING AT LEAST ONE ENERGY AUGMENTATION STRUCTURE, the entire disclosure of which is incorporated herein by reference. This application is related to, and claims priority to, provisional application U.S. Ser. No. 62/946,648, filed Dec. 11, 2019, entitled ENERGY AUGMENTATION STRUCTURE; ENERGY COLLECTOR CONTAINING THE SAME; AND EMISSION ENHANCEMENTS UTILIZING AT LEAST ONE ENERGY AUGMENTATION STRUCTURE, the entire disclosure of which is incorporated herein by reference. This application is related to, and claims priority to, provisional application U.S. Ser. No. 62/897,677, filed Sep. 9, 2019, entitled ENERGY AUGMENTATION STRUCTURE; ENERGY COLLECTOR CONTAINING THE SAME; AND EMISSION ENHANCEMENTS UTILIZING AT LEAST ONE ENERGY AUGMENTATION STRUCTURE, the entire disclosure of which is incorporated herein by reference. This application is related to, and claims priority to, provisional application U.S. Ser. No. 62/855,508, filed May 31, 2019, entitled ENERGY AUGMENTATION STRUCTURE; ENERGY COLLECTOR CONTAINING THE SAME; AND COLOR ENHANCEMENT UTILIZING AT LEAST ONE ENERGY AUGMENTATION STRUCTURE, the entire disclosure of which is hereby incorporated by reference. This application is related to, and claims priority to, provisional application U.S. Ser. No. 62/813,390, filed Mar. 4, 2019, entitled COLOR ENHANCEMENT UTILIZING AT LEAST ONE ENERGY AUGMENTATION STRUCTURE, the entire disclosure of which is hereby incorporated by reference. This application is related to U.S. application Ser. No. 16/599,732, filed Oct. 11, 2019, pending, which claims priority to provisional application U.S. Ser. No. 62/745,057, filed Oct. 12, 2018, the entire contents of each of which are hereby incorporated by reference. This application is related to U.S. Ser. No. 13/204,355 filed Aug. 5, 2011, the entire disclosures of which are hereby incorporated by reference. This application is related to U.S. provisional patent application 61/371,549, filed Aug. 6, 2010. This application is related to U.S. provisional patent application 61/161,328, filed Mar. 18, 2009 and to U.S. provisional patent application 61/259,940, filed Nov. 10, 2009, the entire disclosures of which are hereby incorporated by reference. This application is related to U.S. Ser. No. 12/725,108, the entire disclosures of which are hereby incorporated by reference.

This application is related to Provisional Application Ser. No. 60/954,263, filed Aug. 6, 2007, and 61/030,437, filed Feb. 21, 2008, and U.S. application Ser. No. 12/059,484, filed Mar. 31, 2008, the contents of which are hereby incorporated herein by reference. This application is also related to U.S. application Ser. No. 11/935,655, filed Nov. 6, 2007; and Provisional Application Ser. No. 61/042,561, filed Apr. 4, 2008; 61/035,559, filed Mar. 11, 2008, and 61/080,140, filed Jul. 11, 2008, the entire contents of which are hereby incorporated herein by reference. This application is related to U.S. patent application Ser. No. 12/401,478 filed Mar. 10, 2009, the entire contents of which are hereby incorporated herein by reference. This application is related to U.S. patent application Ser. No. 11/935,655, filed Nov. 6, 2007, and Ser. No. 12/059,484, filed Mar. 31, 2008; U.S. patent application Ser. No. 12/389,946, filed Feb. 20, 2009; U.S. patent application Ser. No. 12/417,779, filed Apr. 3, 2009, the entire disclosures of which are hereby incorporated by reference.

BACKGROUND OF THE INVENTION

Field of the Invention

The invention relates to methods, systems, and devices for energy augmentation, with and without an energy modulation agent/energy conversion agent present, and uses particularly for generating or enhancing photon or electron emission and/or for enhancing light or photon collection, and particularly uses in treating cell proliferation disorders.

Discussion of the Background

Presently, light (i.e., electromagnetic radiation from the radio frequency through the visible to the X-ray wavelength range) is used in a number of industrial, communication, electronic, and pharmaceutical processes. Light in the infra-red and visible range is typically generated from an electrical energy source which for example either heats a material to extremely high temperatures where black body emission occurs (as in an incandescent lamp). Light in the visible and ultraviolet range is typically generated by heating a gas to an electrical discharge where transitions from one electronic state of the gas atom or molecule occur with the emission of light. There are also semiconductor based light sources (as in light emitting diodes and semiconducting lasers) where electrons/holes in a material recombine to produce light emission.

Visible light is defined as the electromagnetic radiation with wavelengths between 380 nm and 750 nm. In general, electromagnetic radiation including light is generated by the acceleration and deceleration or changes in movement (vibration) of electrically charged particles, such as parts of molecules (or adjacent atoms) with high thermal energy, or electrons in atoms (or molecules).

For reference purposes, infra-red (IR) radiation just beyond the red end of the visible region; and, ultra-violet (UV) radiation has a shorter wavelength than violet light. The UV portion of the spectrum is divided into three regions: UVA (315-400 nm), UVB (280-315 nm) and UVC (100-280 nm).

Industrial lamps used in lighting applications cover the visible range of wavelengths for proper white perception. Thermal sources like heated filaments can be made of different type conductors, including W-filaments, halogen-protected W-filaments, and electrically induced high temperature plasmas (arc lamps).

The power (energy emitted per second) of a radiant source is frequently expressed in watts (W), but light can also be expressed in lumens (lm) to account for the varying sensitivity of the eye to different wavelengths of light. The derived relevant units are the radiance (luminance) of a source in $W/m^2$ ($lm/m^2$) in a certain direction per steradian (unit of solid angle) and the irradiance (illuminance) of a surface in W/m² (lm/m² or lux).

With the development of ultraviolet sources, ultraviolet radiation is being increasingly utilized for industrial, chemical, and pharmaceutical purposes. For example, UV light is known to sterilize media and is known to drive a number of photo-activated chemical processes such as the cross-linking of polymers in adhesives or coatings. Typically, ultraviolet sources use gas discharge lamps to generate emitted light in the ultraviolet range. The emitted light is then optically filtered to remove many of not all of the non-ultraviolet frequencies. Ultraviolet light can also be produced in semiconductor phosphors from the excitation of these phosphors from high energy sources such as, for example, X-ray irradiation.

With the development of infrared radiation sources, infrared radiation is being increasingly utilized for communications and signaling purposes. Typically, infrared sources use broad spectrum light sources referred to as glowbars to generate a broad spectrum of light centered in the infrared range or use lasers to emit very specific infrared wavelengths. For the broad band sources, the emitted light is optically filtered to remove many, if not all, of the non-infrared frequencies.

It is generally desirable to have devices, materials, and capabilities to convert light from one frequency range to another. Down conversion has been one way to convert higher energy light to lower energy, as used in the phosphors noted above. Up conversion has also been shown where lower energy light is converted to higher energy light. Typically, this process is a multi-photon absorption process where two or more photons are used to promote an excited electronic state in a host medium which in turn radiates at a wavelength of light that has a higher energy than the energy of the incident light which promoted the multi-photon absorption process. Both down conversion and up conversion have been studied and documented in the past.

Indeed, workers have studied the phenomenon of photoluminescence and fluorescence, which is the ability of certain solids to emit light when driven or charged by an external energy source. Many well-known phosphors and fluorescors are triggered by high-energy electrons or photons and emit photons of lower energy. It has been recognized that certain infrared phosphors can convert infrared light to light in the visible range (violet through red).

The properties of light such as its radiance is particularly important in reading or display applications where the human eye has to perceive and discern temporary images or permanent images (as for example shown by road and highway signs) formed with visible light. Televisions, computer monitors, displays, and signs use a cathode ray technology (CRT) technology where high energy electrons impinge on phosphors that emit visible light. Televisions, computer monitors, displays, and signs more recently have used liquid crystal display or plasma display technology to generate visible images discernable to the human eye.

In these and other reading or display applications, attempts have been made to develop displays with relatively high contrast images while minimizing the amount of broadband light emitted or reflected from a display, which may detract from the contrast of the image displayed.

In general, the up conversion and the down conversion discussed above have been used in a number of fields to in effect convert an incident wavelength of light to a different wavelength. In one example, high energy photons such as X-rays are converted by absorption in phosphors of the x-ray energy, and luminescence from the phosphors in the ultraviolet, visible, and/or near infrared spectrum has been used for driving photoactive reactions. In other examples, infrared or near infrared light has been up converted by absorption in phosphors of the infrared or near infrared light, and luminescence from the phosphors in the visible and/or ultraviolet spectrum. In other examples, light within the visible region can be down converted or up converted (depending on the phosphors chosen) to a different band within the visible wavelengths. This shifting (energy conversion) can be for color enhancement and can be used in solar cells to convert one part of the solar spectrum to another part more favorable for a photovoltaic device to generate power.

In many of these prior applications, metallic structures have been placed on the phosphors or in a vicinity of the phosphors to generate a plasmonics effect which essentially is an amplification of the local field very nearby the outside of the metallic structures. Plasmonic effects can enhance coupling of incident light into the phosphors and/or enhance the reactivity of the converted light tons nearby receptor. While the plasmons in the metal can propagate along the metal, the plasmons decay evanescently in the z direction normal to the metal/dielectric interface with 1/e decay length of the order of half the wavelength (~200 nm for wavelengths in the visible range).

In some prior applications, photonic band gap structures have been used. In a photonics band gap structure, the materials thereof consist or photonic crystals (PhCs) are materials with a periodic dielectric profile, which can prevent light of certain frequencies or wavelengths from propagating in one, two or any number of directions within the materials.

In this way, light not suitable or detrimental to a process can be rejected while light more suitable for a process can be confined within the photonic band gap structure or better confined within the photovoltaic converter.

In the field of solar cells, the addition of plasmonics, photonics band gap, and up and down conversion is known in the literature. Additionally, antireflection coatings and concentrators are well known in the literature.

The problem with the plasmonics effect is that, as noted above, the plasmons and the electric field enhancement decays rapidly with distance away from the metal structure meaning that the effect is only useful for a small volume of interaction.

The problem with antireflection coatings is that, although sun light is not scattered away as much as if there were no coatings, the light transmitted is still predominantly that of wavelengths that are not optimum for power generation.

The problem with concentrators is that, besides concentrating light which can be converted to power, a concentrator also concentrates light which does not generate power, which in general makes for waste heat.

While photonic band gap structures can serve to reflect or confine light, they have no effective way to gain power from the discarded light.

Cell Proliferation Disorders

There are several types of cell proliferation disorders. Exemplary cell proliferation disorders may include, but are not limited to, cancer, bacterial infection, immune rejection response of organ transplant, solid tumors, viral infection, autoimmune disorders (such as arthritis, lupus, inflammatory bowel disease, Sjogrens syndrome, multiple sclerosis) or a combination thereof, as well as aplastic conditions wherein cell proliferation is low relative to healthy cells, such as aplastic anemia. Of these, cancer is perhaps the most well-known. The term "cancer" generally refers to a diverse class of diseases that are commonly characterized by an abnormal proliferation of the diseased cells. A unifying thread in all known types of cancer is the acquisition of abnormalities in the genetic material of the cancer cell and its progeny. Once a cell becomes cancerous, it will proliferate without respect to normal limits, invading and destroying adjacent tissues, and may even spread to distant anatomic sites through a process called metastasis. These life-threatening, malignant properties of cancers differentiate them from benign tumors, which are self-limited in their growth and do not invade or metastasize.

The impact of cancer on society cannot be overstated. The disease may affect people at all ages, with a risk factor that significantly increases with a person's age. It has been one of the principal causes of death in developed countries and, as our population continues to age, it is expected to be an even greater threat to our society and economy. Therefore, finding cures and effective treatments for cancer has been, and remains, a priority within the biomedical research community.

Treatment Methods

Existing treatments for cell proliferation disorders such as cancer include surgery, chemotherapy, radiation therapy, immunotherapy, monoclonal antibody therapy, and several other lesser known methods. The choice of therapy usually depends on the location and severity of the disorder, the stage of the disease, as well as the patient's response to the treatment.

While some treatments may only seek to manage and alleviate symptoms of the disorder, the ultimate goal of any effective therapy is the complete removal or cure of all disordered cells without damage to the rest of the body. With cancer, although surgery may sometimes accomplish this goal, the propensity of cancer cells to invade adjacent tissue or to spread to distant sites by microscopic metastasis often limits the effectiveness of this option. Similarly, the effectiveness of current chemotherapy is often limited by toxicity to other tissues in the body. Radiation therapy suffers from similar shortcomings as other aforementioned treatment methods. Most of these cancer treatment methods, including radiation therapy, are known to cause damage to DNA, which if not repaired during a critical stage in mitosis, the splitting of the cell during cell proliferation, leads to a programmed cell death, i.e. apoptosis. Further, radiation tends to damage healthy cells, as well as malignant tumor cells.

A number of patents describe ex vivo treatment of bodily fluids, for example blood. Blood is obtained from a patient, treated with a photosensitive agent, exposed to UV radiation, and reinjected to the patient (i.e. extracorporeal photopheresis). Alternatively, a patient can be treated in vivo with a photosensitive agent followed by the withdrawal of a sample from the patient, treatment with UV radiation in vitro (ex vivo), and reinjecting the patient with the treated sample. This method is known for producing an autovaccine. A method of treating a patient with a photosensitive agent, exposing the patient to an energy source and generating an autovaccine effect wherein all steps are conducted in vivo has not been described. See WO 03/049801, U.S. Pat. Nos. 6,569,467; 6,204,058; 5,980,954; 6,669,965; 4,838,852; 7,045,124, and 6,849,058. Moreover, the side effects of extracorporeal photopheresis are well known and include nausea, vomiting, cutaneous erythema, hypersensitivity to sunlight, and secondary hematologic malignancy. Researchers are attempting to use photopheresis in experimental treatments for patients with cardiac, pulmonary and renal allograft rejection; autoimmune diseases, and ulcerative colitis.

A survey of known treatment methods reveals that these methods tend to face a primary difficulty of differentiating between normal cells and target cells when delivering treatment, often due to the production of singlet oxygen which is known to be non-selective in its attack of cells, as well as the need to perform the processes ex vivo, or through highly invasive procedures, such as surgical procedures in order to reach tissues more than a few centimeters deep within the subject.

U.S. Pat. No. 5,829,448 describes simultaneous two photon excitation of photo-agents using irradiation with low energy photons such as infrared or near infrared light (NRI). A single photon and simultaneous two photon excitation is compared for psoralen derivatives, wherein cells are treated with the photo agent and are irradiated with NRI or UV radiation. The patent suggests that treating with a low energy irradiation is advantageous because it is absorbed and scattered to a lesser extent than UV radiation. However, the use of NRI or UV radiation is known to penetrate tissue to only a depth of a few centimeters. Thus any treatment deep within the subject would necessarily require the use of ex vivo methods or highly invasive techniques to allow the irradiation source to reach the tissue of interest.

Chen et al., J. Nanosci. and Nanotech., 6:1159-1166 (2006); Kim et al., JACS, 129:2669-2675 (2007); U.S. 2002/0127224; and U.S. Pat. No. 4,979,935 each describe methods for treatment using various types of energy activation of agents within a subject. However, each suffers from the drawback that the treatment is dependent on the production of singlet oxygen to produce the desired effect on the tissue being treated, and is thus largely indiscriminate in affecting both healthy cells and the diseased tissue desired to be treated.

U.S. Pat. No. 6,908,591 discloses methods for sterilizing tissue with irradiation to reduce the level of one or more active biological contaminants or pathogens, such as viruses, bacteria, yeasts, molds, fungi, spores, prions or similar agents responsible, alone or in combination, for transmissible spongiform encephalopathies and/or single or multi-cellular parasites, such that the tissue may subsequently be used in transplantation to replace diseased and/or otherwise defective tissue in an animal. The method may include the use of a sensitizer such as psoralen, a psoralen-derivative or other photosensitizer in order to improve the effectiveness of the irradiation or to reduce the exposure necessary to sterilize the tissue. However, the method is not suitable for treating a patient and does not teach any mechanisms for stimulating the photosensitizers, indirectly.

U.S. Pat. No. 6,235,508 discloses antiviral applications for psoralens and other photoactivatable molecules. It teaches a method for inactivating viral and bacterial contaminants from a biological solution. The method includes mixing blood with a photosensitizer and a blocking agent and irradiating the mixture to stimulate the photosensitizer, inactivating substantially all of the contaminants in the blood, without destroying the red blood cells. The blocking agent prevents or reduces deleterious side reactions of the photosensitizer, which would occur if not in the presence of the blocking agent. The mode of action of the blocking agent is not predominantly in the quenching of any reactive oxygen species, according to the reference.

Also, U.S. Pat. No. 6,235,508 suggests that halogenated photosensitizers and blocking agents might be suitable for replacing 8-methoxypsoralen (8-MOP) in photophoresis and in treatment of certain proliferative cancers, especially solid localized tumors accessible via a fiber optic light device or superficial skin cancers. However, the reference fails to address any specific molecules for use in treating lymphomas or any other cancer. Instead, the reference suggests a process of photophoresis for antiviral treatments of raw blood and plasma.

U.S. Pat. No. 6,235,508 teaches away from 8-MOP and 4'-aminomethyl-4,5',8-trimethylpsoralen (AMT) and many other photoactivatable molecules, which are taught to have certain disadvantages. Fluorescing photosensitizers are said to be preferred, but the reference does not teach how to select a system of fluorescent stimulation or photoactivation using fluorescent photosensitizers. Instead, the fluorescing photosensitizer is limited to the intercalator that is binding to the DNA. The reference suggests that fluorescence indicates that such an intercalator is less likely to stimulate oxygen radicals. Thus, the reference fails to disclose any mechanism of photoactivation of an intercalator other than by direct photoactivation by UV light, although use of a UV light probe or X-rays is suggested for penetrating deeper into tissues. No examples are provided for the use of a UV light probe or for use of X-rays. No example of any stimulation by X-ray radiation is taught.

Psoralens and Related Compounds

U.S. Pat. No. 6,235,508 further teaches that psoralens are naturally occurring compounds which have been used therapeutically for millennia in Asia and Africa. The action of psoralens and light has been used to treat vitiligo and psoriasis (PUVA therapy; Psoralen Ultra Violet A). Psoralen is capable of binding to nucleic acid double helices by intercalation between base pairs; adenine, guanine, cytosine and thymine (DNA) or uracil (RNA). Upon sequential absorption of two UV-A photons, psoralen in its excited state reacts with a thymine or uracil double bond and covalently attaches to both strands of a nucleic acid helix. The cross-linking reaction appears to be specific for a thymine (DNA) or a uracil (RNA) base. Binding proceeds only if psoralen is intercalated in a site containing thymine or uracil, but an initial photoadduct must absorb a second UVA photon to react with a second thymine or uracil on the opposing strand of the double helix in order to crosslink each of the two strands of the double helix, as shown below. This is a sequential absorption of two single photons as shown, as opposed to simultaneous absorption of two or more photons.

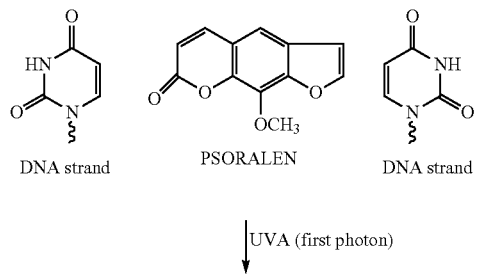

DNA strand  PSORALEN  DNA strand

UVA (first photon)

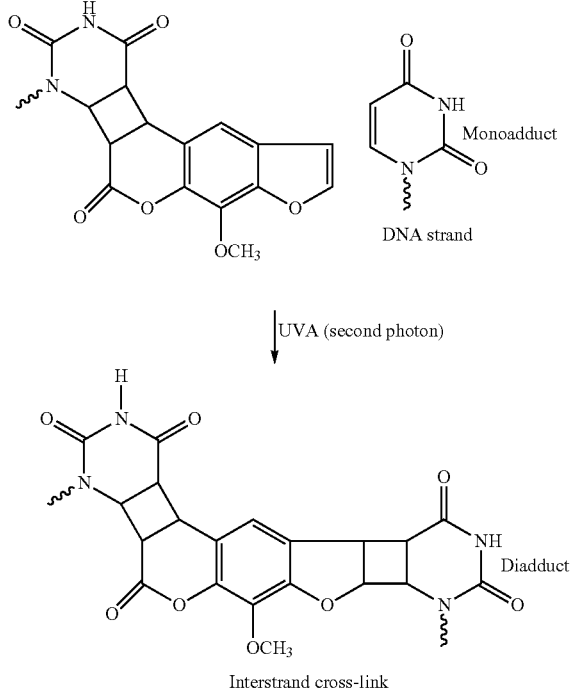

In addition, the reference teaches that 8-MOP is unsuitable for use as an antiviral, because it damages both cells and viruses. Lethal damage to a cell or virus occurs when the psoralen is intercalated into a nucleic acid duplex in sites containing two thymines (or uracils) on opposing strands but only when it sequentially absorbs 2 UVA photons and thymines (or uracils) are present. U.S. Pat. No. 4,748,120 of Wiesehan is an example of the use of certain substituted psoralens by a photochemical decontamination process for the treatment of blood or blood products.

Additives, such as antioxidants are sometimes used with psoralens, such as 8-MOP, AMT and I-IMT, to scavenge singlet oxygen and other highly reactive oxygen species formed during photoactivation of the psoralens. It is well known that UV activation creates such reactive oxygen species, which are capable of seriously damaging otherwise healthy cells. Much of the viral deactivation may be the result of these reactive oxygen species rather than any effect of photoactivation of psoralens. Regardless, it is believed that no auto vaccine effect has been observed.

The best known photoactivatable compounds are derivatives of psoralen or coumarin, which are nucleic acid intercalators. The use of psoralen and coumarin photosensitizers can give rise to alternative chemical pathways for dissipation of the excited state that are either not beneficial to the goal of viral inactivation, or that are actually detrimental to the process. For psoralens and coumarins, this chemical pathway is likely to lead to the formation of a variety of ring-opened species, such as shown below for coumarin:

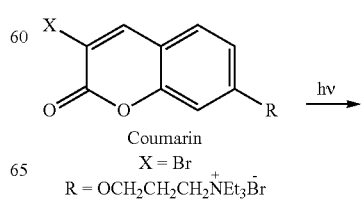

Coumarin
X = Br
R = OCH$_2$CH$_2$CH$_2$NEt$_3$Br

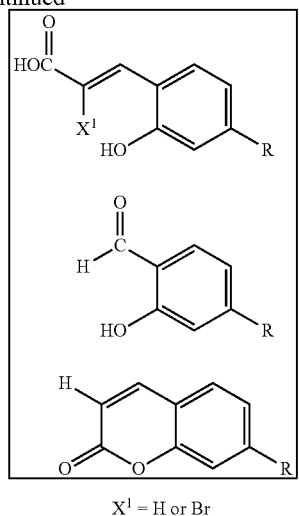

$X^1$ = H or Br

Research in this field over-simplifies mechanisms involved in the photoactivating mechanism and formation of highly reactive oxygen species, such as singlet oxygen. Both may lead to inactivating damage of tumor cells, viruses and healthy cells. However, neither, alone or combined, lead to an auto vaccine effect. This requires an activation of the body's own immune system to identify a malignant cell or virus as threat and to create an immune response capable of lasting cytotoxic effects directed to that threat. It is believed, without being limiting in any way, that photoactivation and the resulting apoptosis of malignant cells that occurs in extracorporeal photophoresis causes the activation of an immune response with cytotoxic effects on untreated malignant cells. While the complexity of the immune response and cytotoxic effects is fully appreciated by researchers, a therapy that harnesses the system to successfully stimulate an auto vaccine effect against a targeted, malignant cell has been elusive, except for extracorporeal photophoresis for treating lymphoma.

Midden (W. R. Midden, Psoralen DNA photobiology, Vol II (ed. F. P. Gaspalloco) CRC press, pp. 1. (1988) has presented evidence that psoralens photoreact with unsaturated lipids and photoreact with molecular oxygen to produce active oxygen species such as superoxide and singlet oxygen that cause lethal damage to membranes. U.S. Pat. No. 6,235,508 teaches that 8-MOP and AMT are unacceptable photosensitizers, because each indiscriminately damages both cells and viruses. Studies of the effects of cationic side chains on furocoumarins as photosensitizers are reviewed in Psoralen DNA Photobiology, Vol. I, ed. F. Gaspano, CRC Press, Inc., Boca Raton, Fla., Chapter 2. U.S. Pat. No. 6,235,508 gleans the following from this review: most of the amino compounds had a much lower ability to both bind and form crosslinks to DNA compared to 8-MOP, suggesting that the primary amino functionality is the preferred ionic species for both photobinding and crosslinking.

U.S. Pat. No. 5,216,176 of Heindel discloses a large number of psoralens and coumarins that have some effectiveness as photoactivated inhibitors of epidermal growth factor. Halogens and amines are included among the vast functionalities that could be included in the psoralen/coumarin backbone. This reference is incorporated herein by reference.

U.S. Pat. No. 5,984,887 discloses using extracorporeal photophoresis with 8-MOP to treat blood infected with CMV. The treated cells as well as killed and/or attenuated virus, peptides, native subunits of the virus itself (which are released upon cell break-up and/or shed into the blood) and/or pathogenic noninfectious viruses are then used to generate an immune response against the virus, which was not present prior to the treatment.

Photodynamic Therapy (PDT)

Photodynamic therapy (PDT) is a treatment modality that uses a photosensitizing agent and laser light to kill cells. PDT retains several photosensitizers in tumors for a longer time than in normal tissues, thus offering potential improvement in treatment selectivity. See Comer C., "Determination of [3H]- and [14C] hematoporphyrin derivative distribution in malignant and normal tissue," Cancer Res 1979, 3 9: 146-151; Young S W, et al., "Lutetium texaphyrin (PCI-0123) a near-infrared, water-soluble photosensitizer," Photochem Photobiol 1996, 63:892-897; and Berenbaum M C, et al., "Meso-Tetra(hydroxyphenyl)porphyrins, a new class of potent tumor photosensitizers with favorable selectivity," Br J Cancer 1986, 54:717-725. Photodynamic therapy uses light of a specific wavelength to activate the photosensitizing agent. Various light sources have been developed for PDT that include dye lasers and diode lasers. Light generated by lasers can be coupled to optical fibers that allow the light to be transmitted to the desired site. See Pass 1-11, "Photodynamic therapy in oncology: mechanisms and clinical use," J Natl Cancer Inst 1993, 85:443-456. According to researchers, the cytotoxic effect of PDT is the result of photooxidation reactions, as disclosed in Foote C S, "Mechanisms of photooxygenation," Proa Clin Biol Res 1984, 170:3-18. Light causes excitation of the photosensitizer, in the presence of oxygen, to produce various toxic species, such as singlet oxygen and hydroxyl radicals. It is not clear that direct damage to DNA is a major effect; therefore, this may indicate that photoactivation of DNA crosslinking is not stimulated efficiently.

Furthermore, when laser light is administered via external illumination of tissue surfaces, the treatment effect of PDT is confined to a few millimeters (i.e. superficial). The reason for this superficial limitation is mainly the limited penetration of the visible light used to activate the photosensitizer. Thus, PDT is used to treat the surfaces of critical organs, such as lungs or intra-abdominal organs, without damage to the underlying structures. However, even these treatments require significantly invasive techniques to treat the surface of the affected organs. Clinical situations use the procedure in conjunction with surgical debulking to destroy remnants of microscopic or minimal gross disease. It is possible that the laser light and small amount of remaining microscopic and minimal gross disease results in too little or highly damaged structures. Pre-clinical data show that some immune response is generated, but clinical trials have reported no auto vaccine effect similar to that produced by extracorporeal photophoresis in clinical conditions. Instead, immune response appears to be vigorous only under limited conditions and only for a limited duration.

Problems

It is well recognized that a major problem associated with the existing methods of diagnosis and treatment of cell proliferation disorders is in differentiation of normal cells from target cells. Such target specificity is difficult to achieve by way of surgery since the strategy there is simply to cut out a large enough portion of the affected area to include all diseased cells and hope that no diseased cells have spread to other distant locations.

With chemotherapy, while some degree of differentiation can be achieved, healthy cells are generally adversely affected by chemo-agents. As in surgery, the treatment strategy is also to kill off a large population of cells, with the understanding that there are far more normal cells than diseased cells so that the organism can recover from the chemical assault.

Radiation therapy works by irradiating cells with high levels of high energy radiation such as high energy photon, electron, or proton. These high energy beams ionize the atoms which make up a DNA chain, which in turn leads to cell death. Unlike surgery, radiation therapy does not require placing patients under anesthesia and has the ability to treat tumors deep inside the body with minimal invasion of the body. However, the high doses of radiation needed for such therapies damages healthy cells just as effectively as it does diseased cells. Thus, similar to surgery, differentiation between healthy and diseased cells in radiation therapy is only by way of location. There is no intrinsic means for a radiation beam to differentiate between a healthy cell and a diseased cell.

Other methods may be more refined. For example, one form of advanced treatment for lymphoma known as extracorporeal photopheresis involves drawing the patient's blood from his body into an instrument where the white cells (buffy coat) are separated from the plasma and the red blood cells. A small amount of the plasma separated in this process is then isolated and mixed with a photosensitizer (PS), a drug that can be activated by light. The buffy coat is then exposed to a light to activate the drug. The treated blood is then returned to the patient. In this example, one may think of the target-specificity problem as being solved by separating the blood from the rest of the body where the target components are easily exposed.

However, this procedure has its drawbacks; it requires drawing blood from the patient, thus requiring cumbersome machinery to perform and may require blood transfusion in order to maintain the volume of blood flow in the machine. Further, this also limits the size of the patient that can be treated, since the extracorporeal volume is great and too much withdrawal of blood increases the risk of hypovolemic shock. The method is also limited to treating blood-born cell proliferation related disorders such as lymphoma, and is not capable of treating solid tumors or other types of non-blood related cell proliferation disorders.

A problem encountered in PDT therapy is the inability to treat target areas that are more than a few centimeters beneath the surface of the skin without significant invasive techniques, and the fact that PDT typically operates by generation of sufficient quantities of singlet oxygen to cause cell lysis. However, singlet oxygen in sufficient concentration will lyse not only target cells, but also healthy cells rather indiscriminately.

Psoralens are naturally occurring compounds found in plants (furocoumarin family) with anti-cancer and immunogenic properties. Psoralens freely penetrate the phospholipid cellular bilayer membranes and intercalate into DNA between nucleic acid pyrimidines, where the psoralens are biologically inert (unless photo-activated) and ultimately excreted within 24 hours. However psoralens are photo-reactive, acquiring potent cytotoxicity after 'activation' by ultra-violet (UVA) light. When photo-activated, psoralens form mono-adducts and di-adducts with DNA leading to marked tumor cytotoxicity and apoptosis. Cell signaling events in response to DNA damage include up-regulation of $p21^{waf/Cip}$ and p53 activation, with mitochondrial induced cytochrome c release and consequent cell death. Photo-activated psoralen can also induce apoptosis by blocking oncogenic receptor tyrosine kinase signaling, and can affect immunogenicity and photochemical modification of a range of cellular proteins in treated cells.

Importantly, psoralen can promote a strong long-term clinical response, as observed in the treatment of cutaneous T Cell Lymphoma utilizing extracorporeal photopheresis (ECP). In ECP malignant CTCL cells (removed from a patient) are irradiated with ultraviolet A (UVA) light in the presence of psoralen, and then re-administered to the patient. Remarkably, complete long term responses over many decades have been observed in a subset of patients, even though only a small fraction of malignant cells were treated. In addition to ECP, psoralens have also found wide clinical application through PUVA treatment of proliferative skin disorders and cancer including psoriasis, vitiligo, mycosis fungoides, and melanoma. Together these results are consistent with an immunogenic role of psoralen in a number of cancers and proliferative disorders.

The cytotoxic and immunogenic effects of psoralen are often attributed to psoralen mediated photoadduct DNA damage. A principle mechanism underlying the long-term immunogenic clinical response likely derives from psoralen induced tumor cell cytotoxicity and uptake of the apoptotic cells by immature dendritic cells, in the presence of inflammatory cytokines. However, photochemical modification of proteins and other cellular components can also impact the antigenicity and potential immunogenicity of treated cells.

SUMMARY OF THE INVENTION

In one embodiment, there is provided an energy augmentation structure capable of capturing one or more wavelengths of electromagnetic energy, and augmenting the one or more wavelengths of electromagnetic energy in at least one property.

In one embodiment, the energy augmentation structure may be one or more of an electromagnetic resonator structure, a folded resonator structure, and a fractal structure having a region of an intensified electromagnetic field within the structure.

In a further embodiment, there is provided an energy collector comprising at least one energy augmentation structure; and at least one energy converter capable of receiving an applied electromagnetic energy, converting the applied electromagnetic energy and emitting therefrom an emitted electromagnetic energy shifted in wavelength or energy from the applied electromagnetic energy and the energy converter being disposed in a vicinity of the at least one energy augmentation structure such that the emitted electromagnetic energy is emitted with at least one augmented property compared to if the energy converter were remote from the at least one energy augmentation structure.

In one embodiment, the energy converter noted above is disposed with an energy augmentation structure comprising one or more of an electromagnetic resonator structure, a folded resonator structure, and a fractal structure, any of which having a region of an intensified electromagnetic field within the resonating structures.

In one embodiment, the energy converter noted above includes one or more luminescing materials. As described herein, there are uses of the energy augmentation structure and/or energy collector embodiments which enhance bioluminescence, chemo-luminescence, photoluminescence, fluorescence, and mechano-luminescence.

In one embodiment, the energy converter noted above includes for the one or more luminescent materials phosphorescent materials, fluorescent materials, electroluminescent materials, chemo-luminescent materials, bioluminescent materials, and mechano-luminescent materials used in conjunction with or not in conjunction with the energy augmentation structure noted above. When used in conjunction with the energy augmentation structure noted above, the emitted electromagnetic energy from the luminescent material is emitted with at least one augmented property compared to if the energy converter (e.g., the luminescent material) were remote from the at least one energy augmentation structure.

In one embodiment, the energy converter noted above includes for the one or more luminescing materials phosphorescent materials, fluorescent materials, electroluminescent materials, chemo-luminescent materials, bioluminescent materials, and mechano-luminescent materials used in conjunction with or not in conjunction with the energy augmentation structure noted above and which emit one of ultra-violet, visible, near infrared, and infrared light. In this embodiment, UV-emitting electroluminescent materials or mechano-luminescent devices and materials can be used. In this embodiment, UV-emitting bioluminescent materials can be used.

In additional embodiments, there are provided uses of the energy augmentation structure and energy collector embodiments in medical treatments, particularly of cell proliferation disorders, such as cancer, and other medically related end uses.

In another embodiment, the energy converter noted above is disposed with an energy augmentation structure such that x-ray induced photoluminescence or fluorescence is higher compared to if the energy converter (e.g., x-ray induced photoluminescence or fluorescence materials) were remote from the at least one energy augmentation structure.

In another embodiment, the above noted distributed energy collector can deliver light to different positions within a medium inside a patient.

In another embodiment, the above noted distributed energy collector can collect or deliver light from or to different positions within a patient, including for example collecting or delivering light to different positions within an organ.

In another embodiment, a UV-emitting luciferase may be used alone or in conjunction with the above-noted energy augmentation structures to generate light inside a patient.

In another embodiment, there are provided uses of the energy augmentation structure and/or energy converters inside plasma (light-emitting) capsules to promote generation and maintenance of plasma state ions which light.

In another embodiment, there are provided uses of the energy augmentation structure and/or energy converters to enhance electron emission from surfaces in a vicinity of the energy augmentation structure.

In one embodiment, the energy converter noted above includes one or more electron emitting materials. The electron emitting materials may be photon-induced materials which photo-eject an electron under exposure to UV light, The electron emitting materials may be thermally heated materials which emit electrons from heated surfaces of the emitting materials.

In one embodiment, the energy converter noted above includes for the one or more electron emitting materials nanoscale field emission tips. When used in conjunction with the energy augmentation structure noted above, the emitted electron flux from the electron emitting materials is higher compared to if the energy converter (e.g., the nanoscale field emission tips) were remote from the at least one energy augmentation structure.

It is to be understood that both the foregoing general description of the invention and the following detailed description are exemplary, but are not restrictive of the invention.

BRIEF DESCRIPTION OF THE FIGURES

A more complete appreciation of the invention and many of the attendant advantages thereof will be readily obtained as the same becomes better understood by reference to the following detailed description when considered in connection with the accompanying drawings, wherein:

FIG. 16 is a diagram showing a paired three-dimensional fractal structure with an intensified electric field in between;

FIG. 52A is a schematic depicting a multi-variable linear regression analysis of the resultant Annexin V (+) signal as a function of psoralen concentration and phosphor concentration;

DETAILED DESCRIPTION OF THE INVENTION

Figure 1:
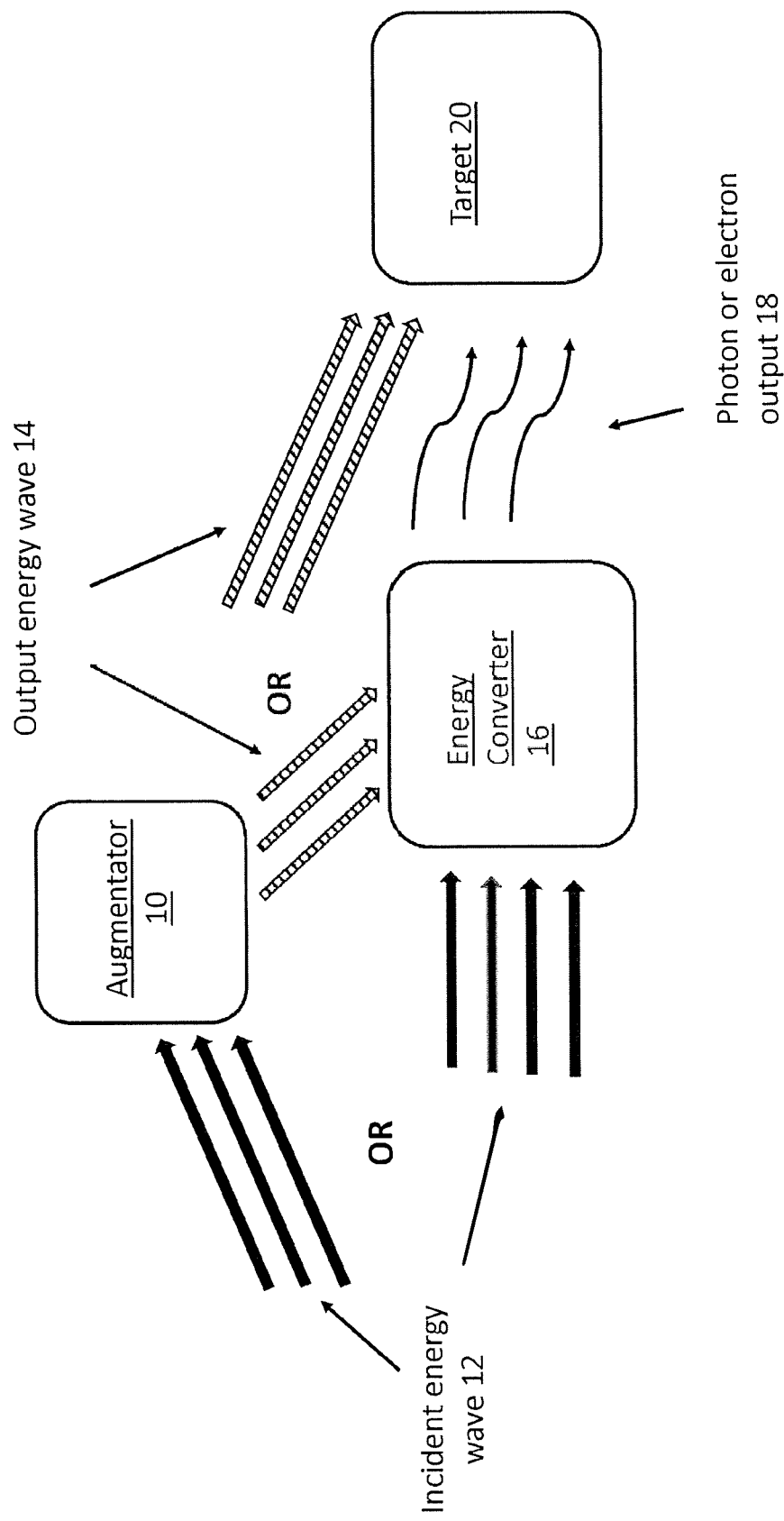
FIG. 1 is a schematic depicting an energy augmentator system of the invention with optional inclusion of an energy converter.

Reference will now be made in detail to a number of embodiments of the invention, examples of which are illustrated in the accompanying drawings, in which like reference characters refer to corresponding elements.

As noted above, energy converters such up conversion materials and down conversion materials have been used in a number of fields in effect to convert an incident wavelength of light to a different wavelength. Metallic structures have been placed on the phosphors or in a vicinity of the phosphors to generate a plasmonics effect which essentially is an amplification of the local field very nearby the outside of the metallic structures. In some applications, photonic band gap structures have been used in solar cell applications to prevent light of certain frequencies or wavelengths from propagating in one, two or any number of directions within the materials. Additionally, antireflection coatings and concentrators are well known in the literature.

The present inventors recognized that the shortcomings of these structures could be addressed by use of the energy augmentation structures described herein used separately or in conjunction with energy converters.

A. Energy Augmentation Structures

In the present invention, the term "energy augmentation" means effecting some change in one or more wavelengths of electromagnetic energy in at least one property, including, but not limited to, intensity, power, associated electrical field, associated magnetic field, wave amplitude, photonic flux, magnetic flux, phase, coherence, propagation direction, etc. The structure performing the energy augmentation can be termed an "energy augmentation structure" or an "energy augmentator". These terms are used interchangeably herein. Preferably the energy augmentation structure is a non-plasmonic structure (a structure that does not exhibit plasmonic properties).

The energy augmentator can take any desired form so long as it can perform the necessary function of augmenting the energy applied to it, causing a change in one or more wavelengths of electromagnetic energy in at least one property as noted above. Examples of such energy augmentators include, but are not limited to, at least one non-plasmonic member selected from the group consisting of resonators, fractal antennas, electrical grid patterns, antennas, cavities, etalons, nanoparticles, microparticles, nanostructures, and microstructures, just to name a few.

In one embodiment, as shown schematically in FIG. 1, an energy augmentator 10 is provided that is capable of receiving or capturing one or more wavelengths of electromagnetic energy representing an incident energy wave 12. Having received or captured the incident energy wave 12, the energy augmentator 10 is capable of augmenting the one or more wavelengths of received or captured energy wave flux 12 in at least one property. As shown in FIG. 1, in one embodiment, energy augmentator 10 then outputs an energy wave 14 with the at least one property augmented, with the augmented energy wave 14 incident on target 20. Details of the augmentation are described below.

In another embodiment, the output (augmented) energy wave 14 (i.e., one or more output wavelengths of electromagnetic energy) can be incident on an energy converter 16 (such as the up conversion materials and down conversion materials noted above). The energy converter 16 can output photons or electrons 18 which can be directed to target 20. In these embodiments, target 20 may receive the photons or electrons 18 or the output augmented energy wave 14 simultaneously or separately.

In one embodiment, the energy augmentator 10 may be one or more of an electromagnetic resonator structure, a folded resonator structure, and a fractal structure having a region of an intensified electromagnetic field within those structures.

Figure 2:
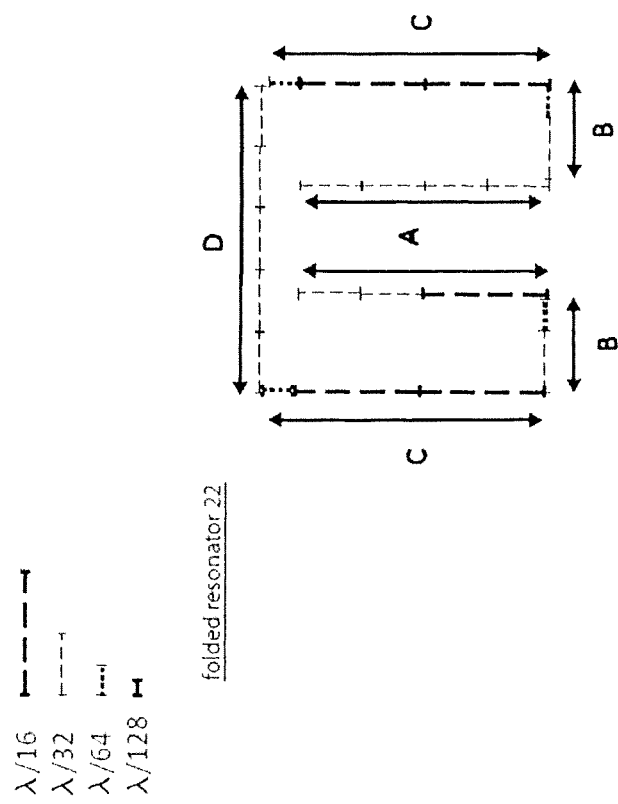
FIG. 2 is a schematic depicting a folded resonator as an illustrative energy augmentation structure of the invention.

FIG. 2 below is a diagram depicting a folded resonator structure 22 of this invention.

The resonator in one embodiment of the present invention is a ¾λ metal structure bent, as shown in FIG. 2 having a "folded" structure making for opposing electrodes between which an intense electric field is developed. Exemplary characteristics of the "folded structure" antenna are listed in the following table:

TABLE 1

| | Wavelength (nm) | | | | | | | | | | |
|---|---|---|---|---|---|---|---|---|---|---|---|
| Antenna Side | 1403 | 1330 | 1203 | 1100 | 1000 | 933 | 803 | 700 | 600 | 500 | 400 |
| A | 175.0 | 162.5 | 153.0 | 137.5 | 125.0 | 112.5 | 103.0 | 87.5 | 75.0 | 62.5 | 50.0 |
| B | 65.6 | 63.3 | 56.3 | 51.6 | 46.9 | 42.2 | 37.5 | 32.8 | 28.1 | 23.4 | 18.8 |
| C | 195.9 | 182.3 | 163.8 | 154.7 | 113.6 | 126.6 | 112.5 | 98.4 | 34.4 | 70.3 | 56.3 |
| D | 218.8 | 203.1 | 137.5 | 171.9 | 156.3 | 140.6 | 125.0 | 103.4 | 33.8 | 78.1 | 62.5 |
| Total | 1093.8 | 1015.6 | 937.5 | 859.4 | 781.3 | 703.1 | 625.3 | 546.3 | 468.8 | 330.6 | 312.5 |
| 3/4 lambda | 1050 | 975 | 900 | 825 | 753 | 575 | 603 | 525 | 453 | 375 | 303 |

The calculations of a theoretical ¾λ and the slightly oversized antenna to account for all the bending corners involved in making the antenna would result in this structure having a size between the theoretical 0.75*λ and the upper oversized limit 0.78*λ.

While the resonators shown in most of the drawings could be characterized as having a rectangular-shape loop connecting the opposing antenna sections or electrodes together, the invention is not so limited. Other "loop" shapes could be used, so long as the opposing electrodes are parallel and coplanar with one another, with the loop forming an electrical path having a length of ½λ, with the opposing electrodes having a length of ⅛λ each, thereby making the ¾λ resonator.

Figure 3:
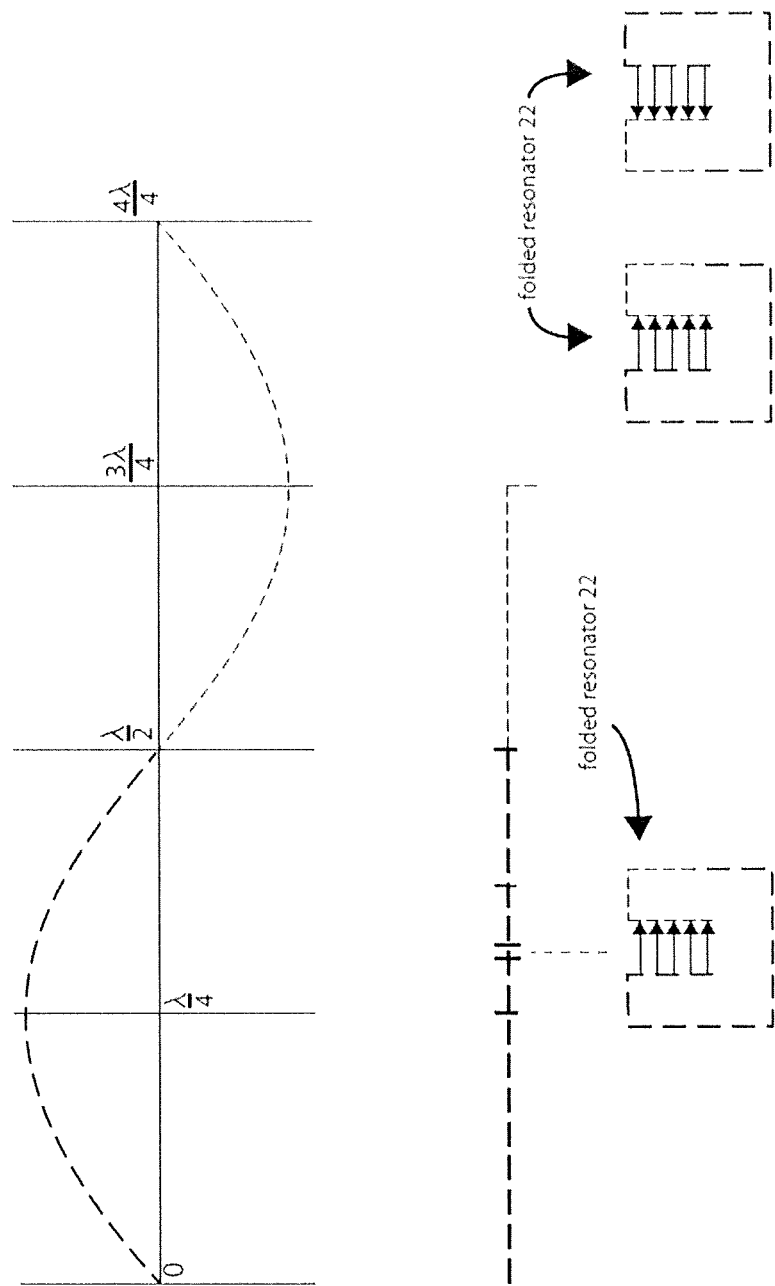
FIG. 3 is a diagram depicting the basic concepts underlying one of the energy augmentation structures of this invention.

FIG. 3 is a diagram depicting the basic concepts underlying one of the energy augmentation structures of this invention. In the depiction in FIG. 3 is a sinusoidal wave representing for example an instantaneous waveform of a light wave (an incident energy flux 12). The depiction shows the length of ¾ of the wavelength λ, and how in one embodiment a ¾λ resonator is constructed with the open ends of the resonator "folded" together to form in this embodiment a ¾λ folded resonator 22. As shown in FIG. 3, the folded ends form a region of an intensified, amplified electric field denoted by the horizontally directed arrows between the opposing open ends. When light nominally of a wavelength λ (or harmonics thereof 2λ, 3λ, 4λ, etc.) is incident on the folded antenna structure, a fraction-a of the light will be coupled into this structure establishing the amplified electric field. Since the light from sun comes continuously and at different rotational polarizations, subsequent light waves will continue to "pump" the electric fields in the resonant structure until some "loss" mechanism caps the strength of the electric fields. For resonators made of low loss materials, high Q-factors are obtained which, in this case, could mean that the electric field strength between the opposing electrodes may be for example 100 to 1000 times the peak amplitude of the electric field vector of the incident waveform.

Figure 4:
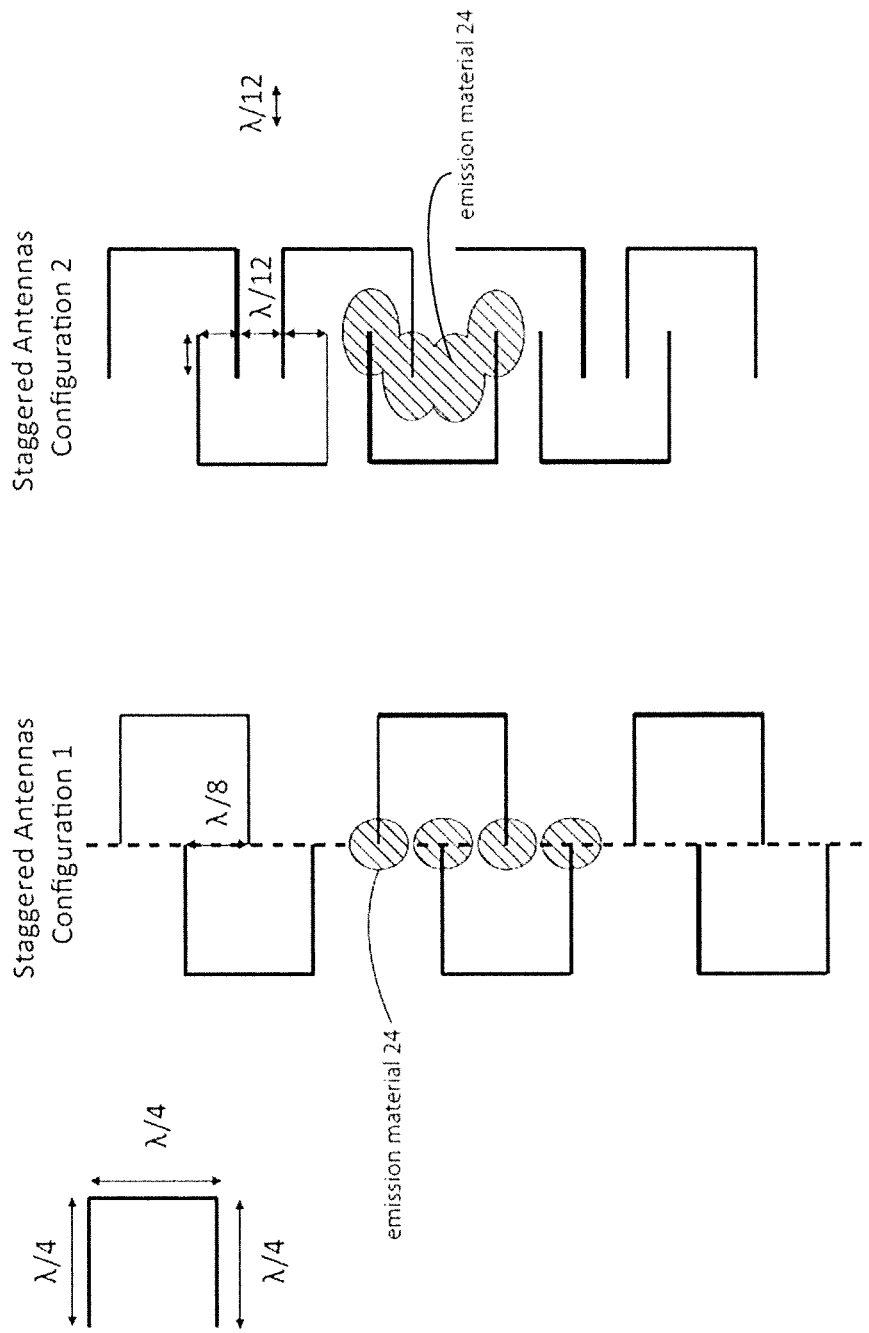
FIG. 4 is a schematic depicting a staggered antenna configuration as an illustrative energy augmentation structure of the invention.

In another embodiment, a resonating antenna could have the configuration below shown in FIG. 4. Here, the ¾λ structures oppose and are interdigitated together without a "folded" structure. In the depiction in FIG. 4, the horizontal stubs are ¼λ long, the vertical extending connectors are ¼ long, and the vertical spacing between the horizontal stubs and the extend of interdigitation varies as shown between configuration 1 and configuration 2. In one embodiment of the invention, an energy converter, a light or electron emitting material, or a color emitting or color converter material (i.e., emissive material 24) is placed inside or around the region of an intensified electric field, as shown in FIG. 4.

Figure 5:
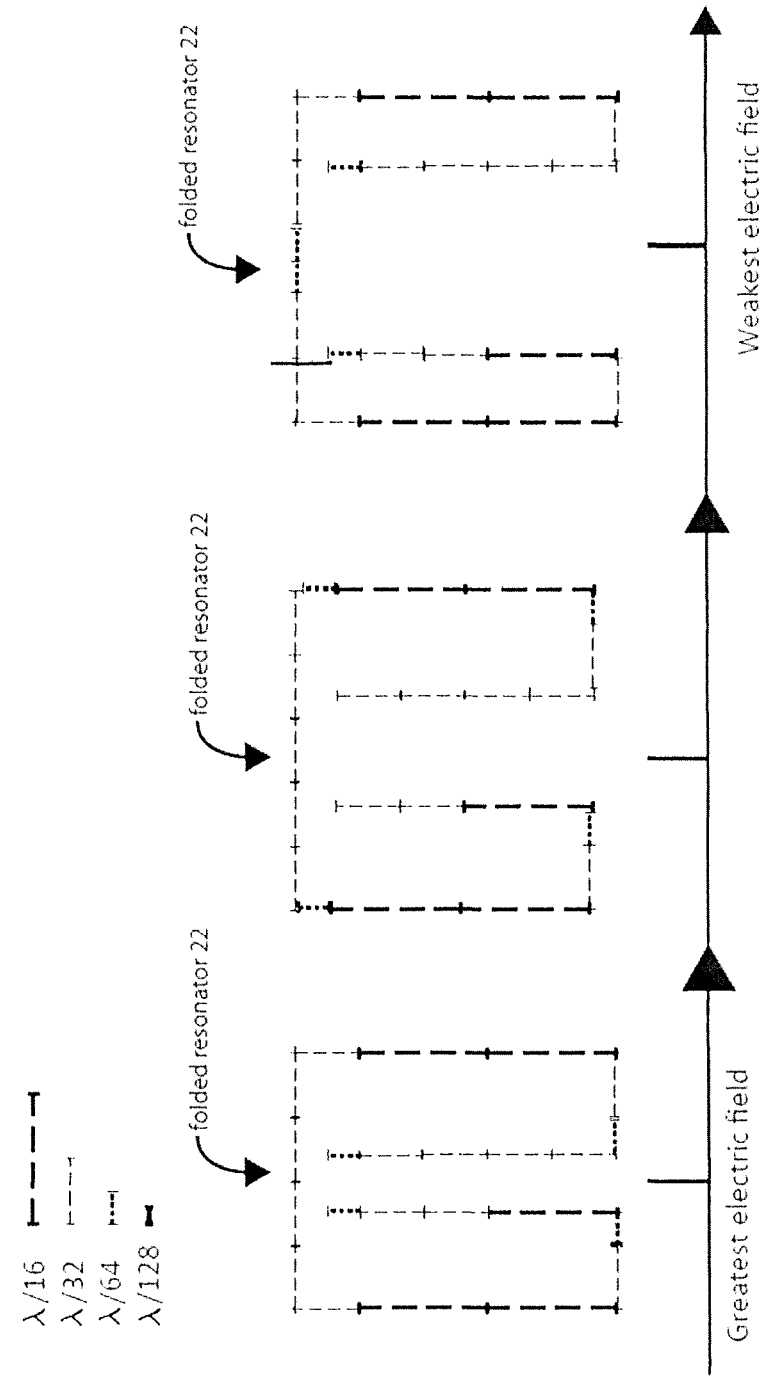
FIG. 5 is a schematic depicting the effect of electrode spacing in the folded resonator of the invention.

FIG. 5 shows that different ¾λ folded resonators can be made having different distances between the opposing electrodes and thus different electric field strengths. In this way, the folded resonators of the invention can be adjusted such that the strength of the electric field between the opposing electrodes does not exceed the dielectric strength of any material in between. Exceeding the dielectric strength of any material in between could result in destruction of that material as intense current (e.g., a micro-arc) would flow during any time that the dielectric strength was exceeded, thus breaking the material down. As shown, here the opposing sides need not have an exact length of ⅛λ.

In one embodiment of the invention, an energy converter, a light or electron emitting material, or a color emitting or color converter material (i.e., an emissive material) 24 is placed inside or around the regions of intensified electric field near/between the opposing electrodes. In one embodiment of the invention, the color emitting or color converter material may itself be absorbing a color light such as for example blue light and emitting lower energy, down-shifted red light. In this case, a red phosphor could be the color emitting or color converter material.

While the ¾λ folded resonator in one embodiment could be designed to resonate at blue light ($\lambda$=420 to 440 nm), the resonator is preferably designed to resonate from light at a different frequency than the blue light that is being absorbed by the red phosphor. In one embodiment, for color enhancement for objects under solar light, the ¾λ folded resonator could be designed to be driven by infrared light from the solar spectrum (e.g. $\lambda$=700 to 1000 nm) to generate the intensified electric field, and the red phosphor disposed in the region of intensified electric field would have a brighter red emission than if the intensified electric field were not present.

Figure 6:
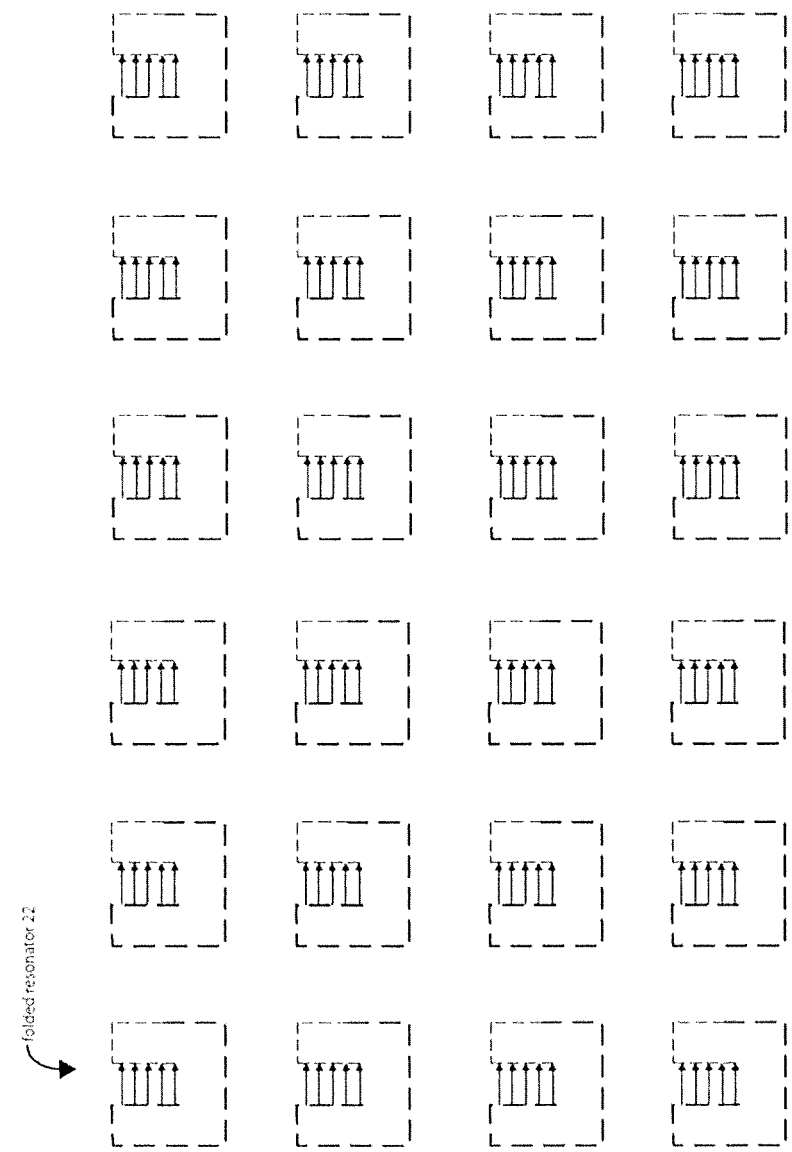
FIG. 6 is a diagram showing a pattern of ¾λ folded resonators distributed in space.

FIG. 6 is diagram showing a pattern of ¾λ folded resonators 22 distributed in space. As to be discussed in more detail later, there are numerous ways to distribute the ¾λ folded resonators. The present invention is not limited to the regular, uniformly spaced and sized resonators shown in FIG. 6. There is no requirement that the distribution be regular, uniformly spaced, uniformly sized, or uniformly oriented. Differently sized, spaced, and oriented resonators may provide better utilization of the full spectrum of the sun or any other light source incident on the object.

Figure 7A:
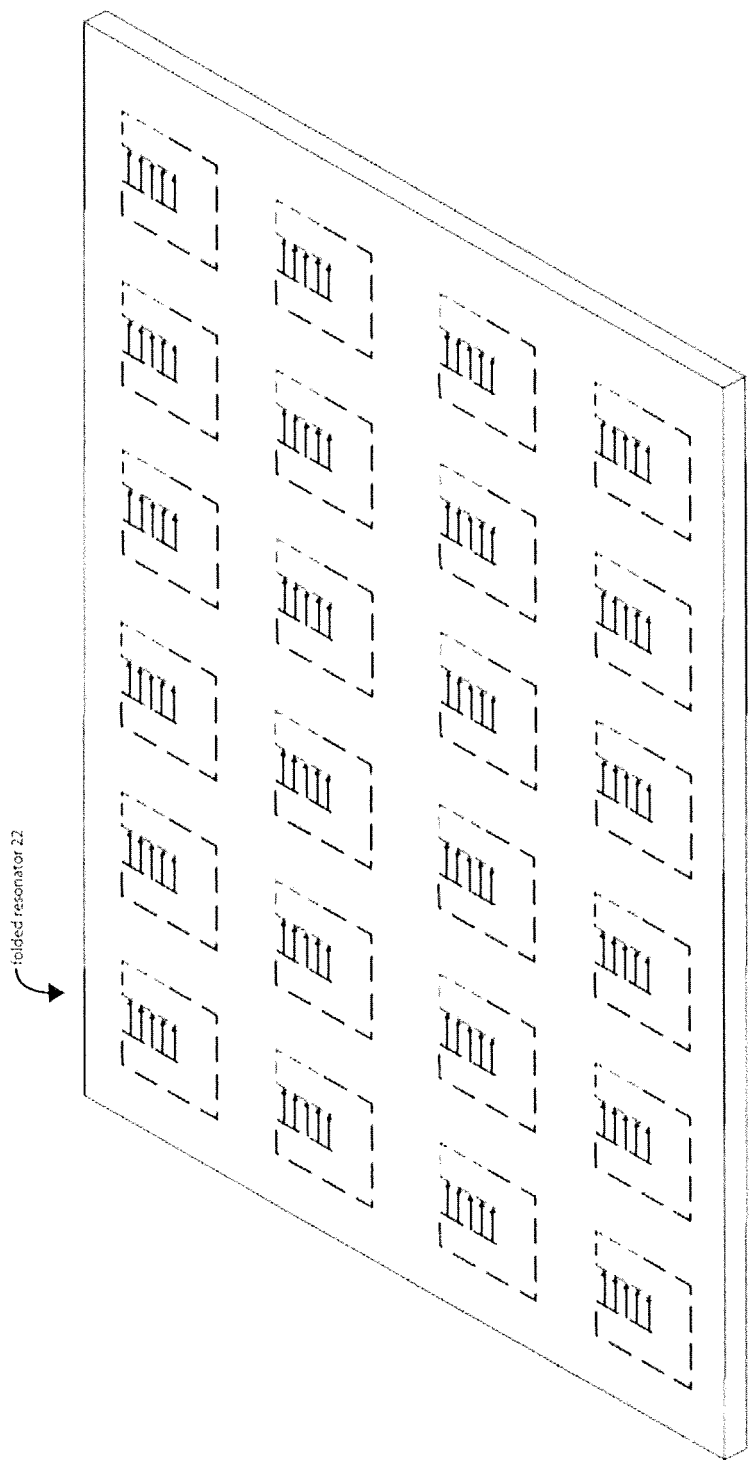
FIGS. 7A-7C are diagrams of several embodiments showing a pattern of ¾λ folded resonators distributed in a plane or otherwise along a surface of an object.

FIG. 7A is a diagram showing a pattern of ¾λ folded resonators 22 distributed in a plane or otherwise along a surface of an object. In one embodiment, this pattern could be formed by lithographic or stamping processes onto a planar surface such as a glass plate or onto a curved sheet type product. In one embodiment, the glass plate could itself be a phosphorescent plate or could have sections of different phosphorescent material deposited in a pattern that would align/match the respective positions of the opposing electrodes on each resonator. In one embodiment, the sheet product could be a laminate type of product applied to for example a nominally white object. Upon solar irradiation, the infrared part of the solar spectrum (normally only heating the surface) would generate the intensified electric field regions. In those regions, down converting phosphors converting deep blue and ultraviolet light to visible light would convert the deep blue and ultraviolet light of the solar spectrum to visible light, and the intensified electric field would enhance greater visible light emission.

Figure 7B:
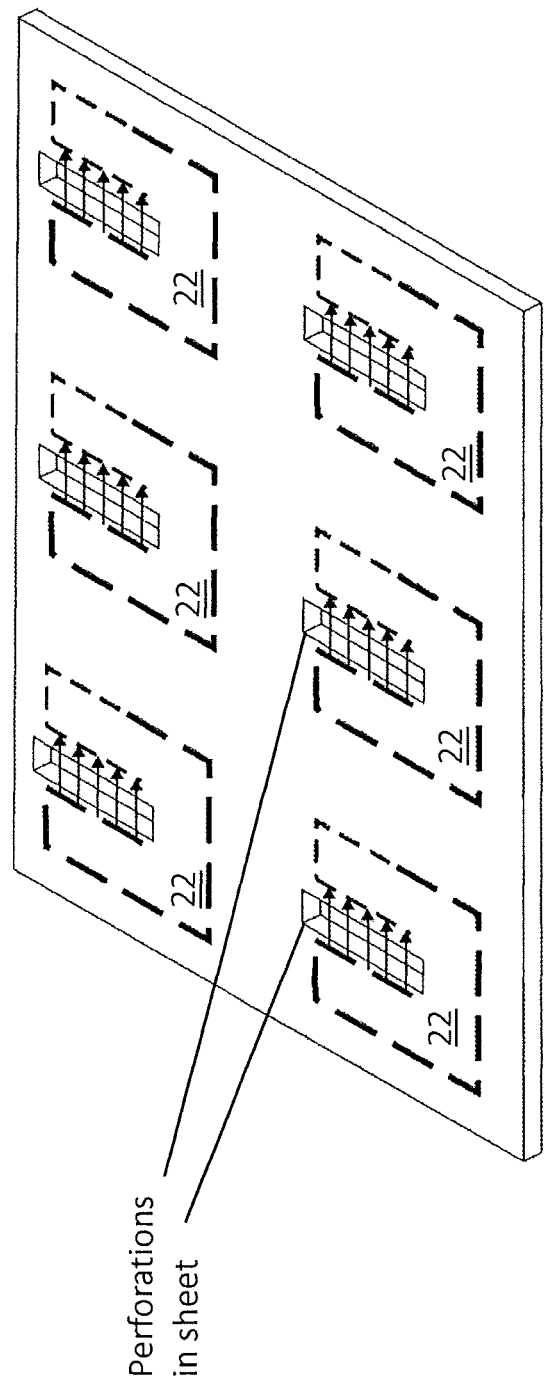

In one embodiment, the energy augmentators could be disposed on a perforated sheet, as shown in FIG. 7B. The perforations in one embodiment are in the regions of intensified electric field such that phosphors or other energy converting materials or devices could be disposed in the perforations.

In one embodiment (for color enhancement), the sheet product could be a laminate type of product applied to for example a nominally green object. Upon solar irradiation, the infrared part of the solar spectrum (normally only heating the surface) would generate the intensified electric field regions. In those regions, down converting phosphors converting blue, deep blue and ultraviolet light to green light would convert the blue, deep blue, and ultraviolet light of the solar spectrum to green light and the intensified electric field would enhance greater green light emission.

In one embodiment, the sheet product could be a laminate type of product applied to for example a nominally red object. Upon solar irradiation, the infrared part of the solar spectrum (normally only heating the surface) would generate the intensified electric field regions. In those regions, down converting phosphors converting green, blue, deep blue and ultraviolet light to red light would convert the green, blue, deep blue and ultraviolet light of the solar spectrum to red light and the intensified electric field would enhance greater red light emission.

Figure 7C:
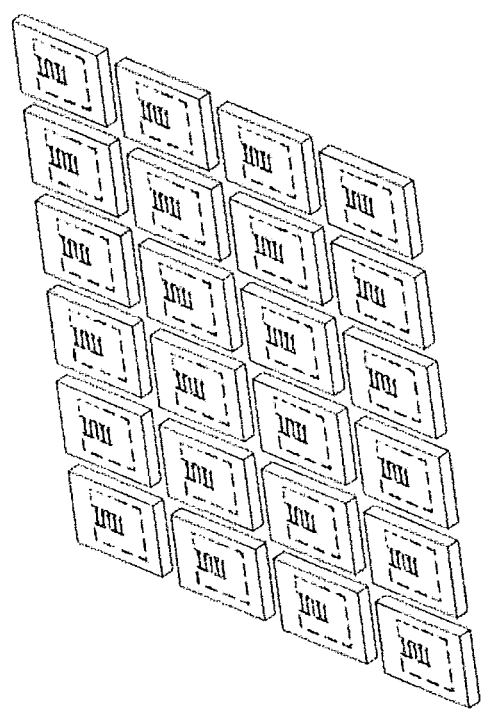

In one embodiment, the energy augmentators could be disposed on a sheet and then separated into distinct pieces, as shown in FIG. 7C, which could be readily added and mixed into a medium to be processed.

Figure 8:
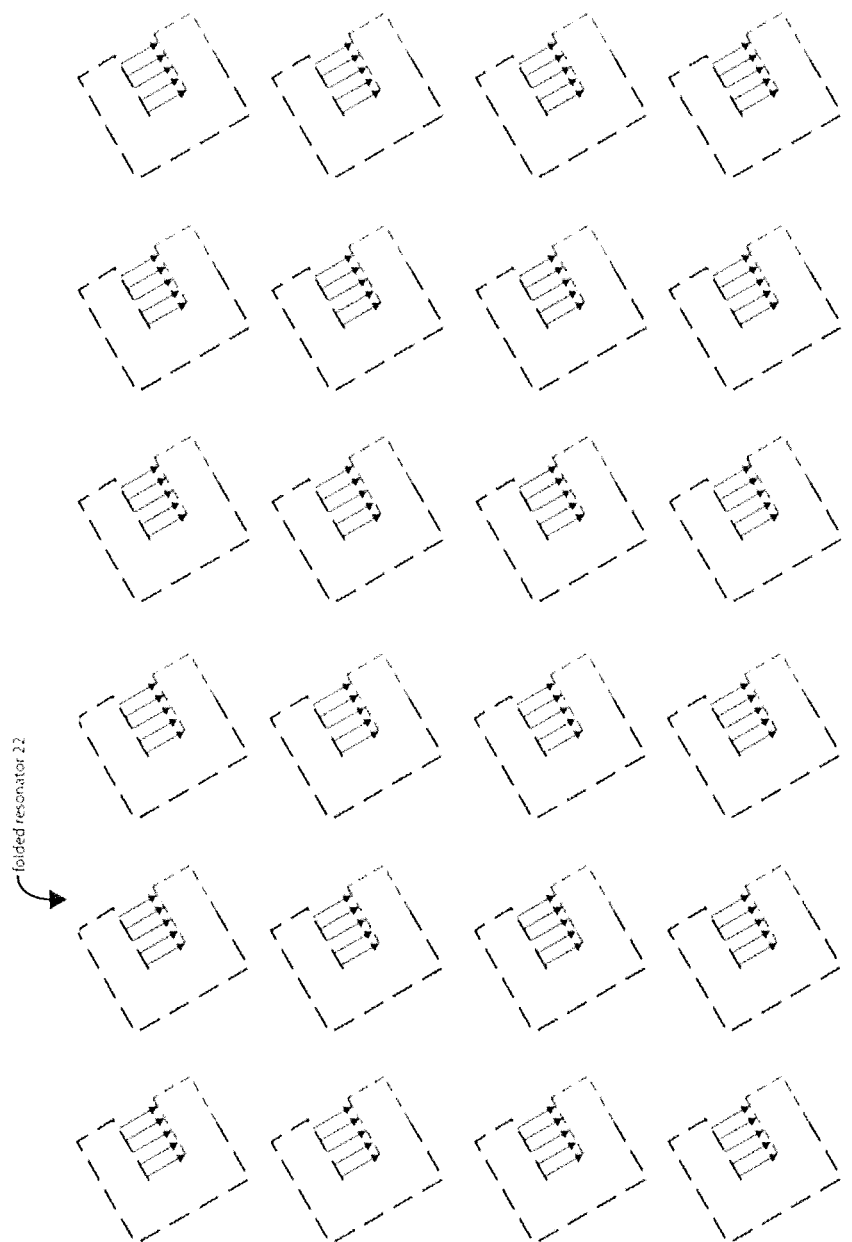
FIG. 8 is a diagram showing a pattern of ¾λ folded resonators distributed in a plane or otherwise along a surface of an object and having an angled orientation.

FIG. 8 is a diagram showing a pattern of ¾λ folded resonators 22 distributed in a plane or otherwise along a surface of an object and having a different orientation than in FIG. 7. By having different orientations, the rotating polarized sun light waves which may at one instance not have an electric field alignment conducive to driving the ¾λ folded resonators, would have their electric field alignment conducive to driving resonators of a different orientation and therefore better aligned. Accordingly, if the sheet type products were used, layers of differently oriented ¾λ folded resonators could be stacked together.

Figure 9:
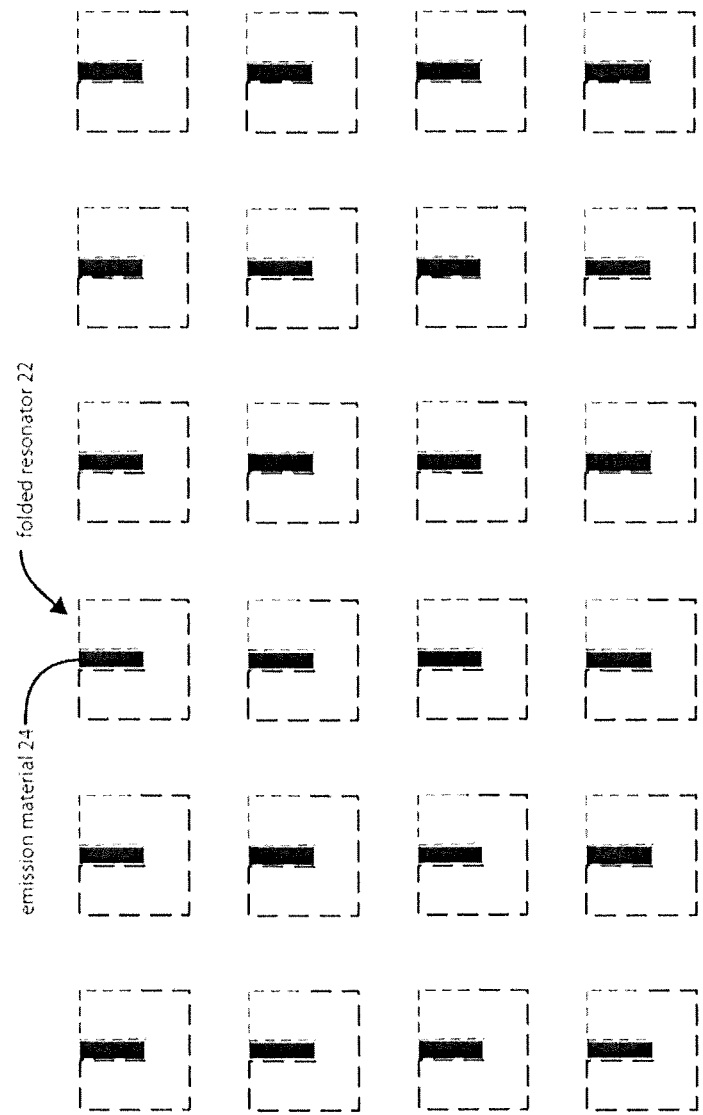
FIG. 9 is a diagram showing a pattern of ¾λ folded resonators having a light or photon or electron emitting material deposited in the region of between the opposing electrodes.

FIG. 9 is a diagram showing a pattern of ¾λ folded resonators 22 having an energy converter, a light or electron emitting material, or a color emitting or color converter material (i.e., emissive material 24) deposited in the region of between the opposing electrodes. Here, while shown in a plan view, the color converting or enhancing material deposited in the region of between the opposing electrodes may be deposited such that the color converting or enhancing material has an upper surface raised above the metal traces of the ¾λ folded resonators. In this embodiment, the raised sections would intercept fringing fields of the intensified electric field between the opposing electrodes.

Figure 10:
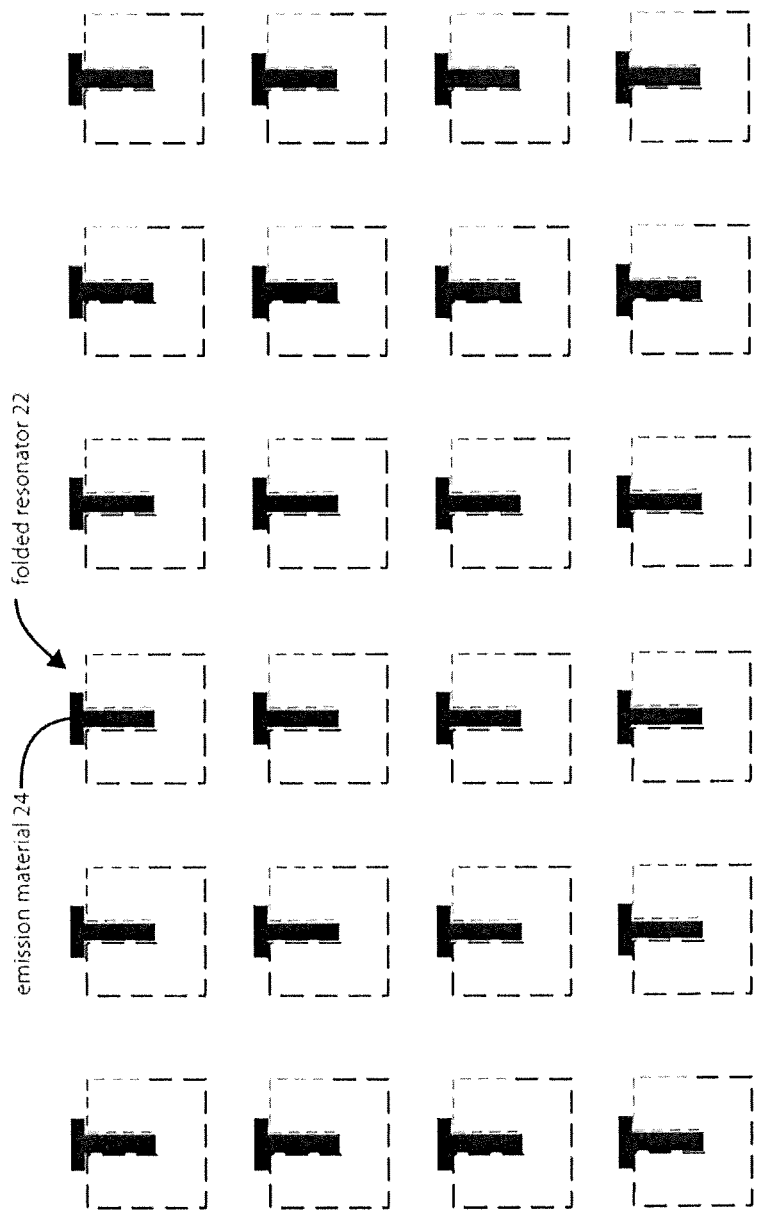
FIG. 10 is a diagram showing a pattern of ¾λ folded resonators having a patterned deposit of a light or photon or electron emitting material in the region of between the opposing electrodes.

FIG. 10 is a diagram showing a pattern of ¾λ folded resonators 22 having an energy converter, a light or electron emitting material, or a color emitting or color converter material (i.e., emissive material 24) deposited in the region of between the opposing electrodes. Here, as before, the color converting or enhancing material deposited in the region of between the opposing electrodes may be deposited such that the color converting or enhancing material has an upper surface raised above the metal traces of the ¾λ folded resonators. In this embodiment, the raised sections would intercept fringing fields of the intensified electric field between the opposing electrodes. In this embodiment, the raised sections would extend around the corners where geometrically the corners would further intensify the electric field.

Figure 11:
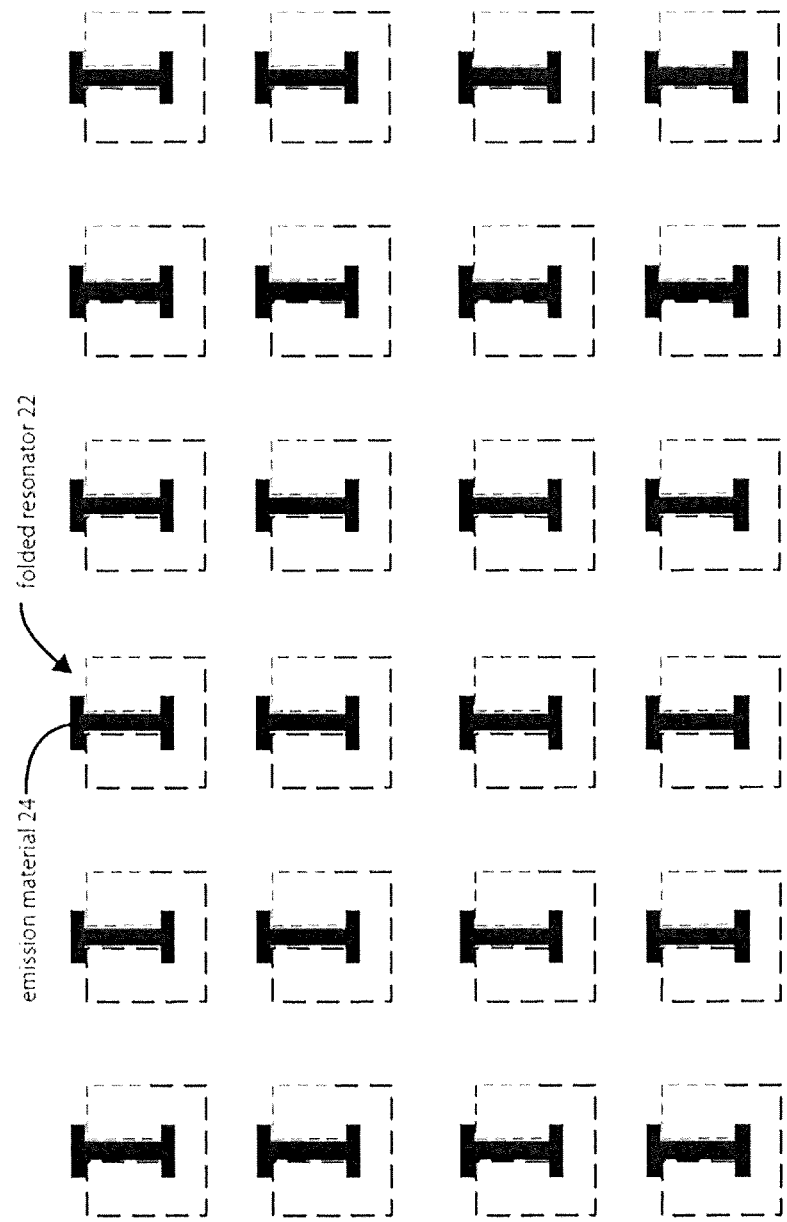
FIG. 11 is a diagram showing a pattern of ¾λ folded resonators having a patterned deposit of a light or photon or electron emitting material in the region of between the opposing electrodes.

FIG. 11 is a diagram showing a pattern of ¾λ folded resonators 22 having an energy converter, a light or electron emitting material, or a color emitting or color converter material (i.e., emissive material 24) deposited in the region of between the opposing electrodes. Here, as before, the color converting or enhancing material deposited in the region of between the opposing electrodes may be deposited such that the color converting or enhancing material has an upper surface raised above the metal traces of the ¾λ folded resonators. In this embodiment, the raised sections would intercept fringing fields of the intensified electric field between the opposing electrodes. In this embodiment, the raised sections would extend around the corners where geometrically the corners would further intensify the electric field and would extend around the ends of the opposing electrodes.

In these embodiments shown in FIGS. 9, 10, and 11, the energy converters, or light or electron emitting materials, or color emitting or color converter materials (i.e., emissive materials 24) are disposed in a vicinity of one or more energy augmentation structures (i.e., the ¾λ folded resonators). As such, the energy augmentation structures preferably are in a region of intensified electric field. The intensified electric field may represent a region of intensified energy especially if there is electrical current flow conductively coupling the energy converter to the one energy augmentation structures. In later embodiments, conductively coupling the energy converter to the one energy augmentation structures has advantages. Accordingly, the energy converters or color converting or enhancing materials disposed in a vicinity of one or more energy augmentation structures may have a physical conductive connection between the energy converter and the at least one energy augmentation structure. Alternatively, the coupling may be more that of radiatively or capacitively coupling the electric fields from the resonant structure into energy converters or color converting or enhancing materials disposed inside the energy augmentation structure, outside the energy augmentation structure, in a layer with the energy augmentation structure, or in a layer above or below the energy augmentation structure.

As used herein, in a vicinity of refers to the disposition of one thing inside the structure of another thing, outside and nearby or adjacent the structure of the other thing, and can include the disposition of one thing above or below the other thing in any three dimensional direction. Accordingly, in one embodiment of the present invention, the color converting or enhancing materials are disposed in a vicinity of the energy augmentation structures.

Figure 12:
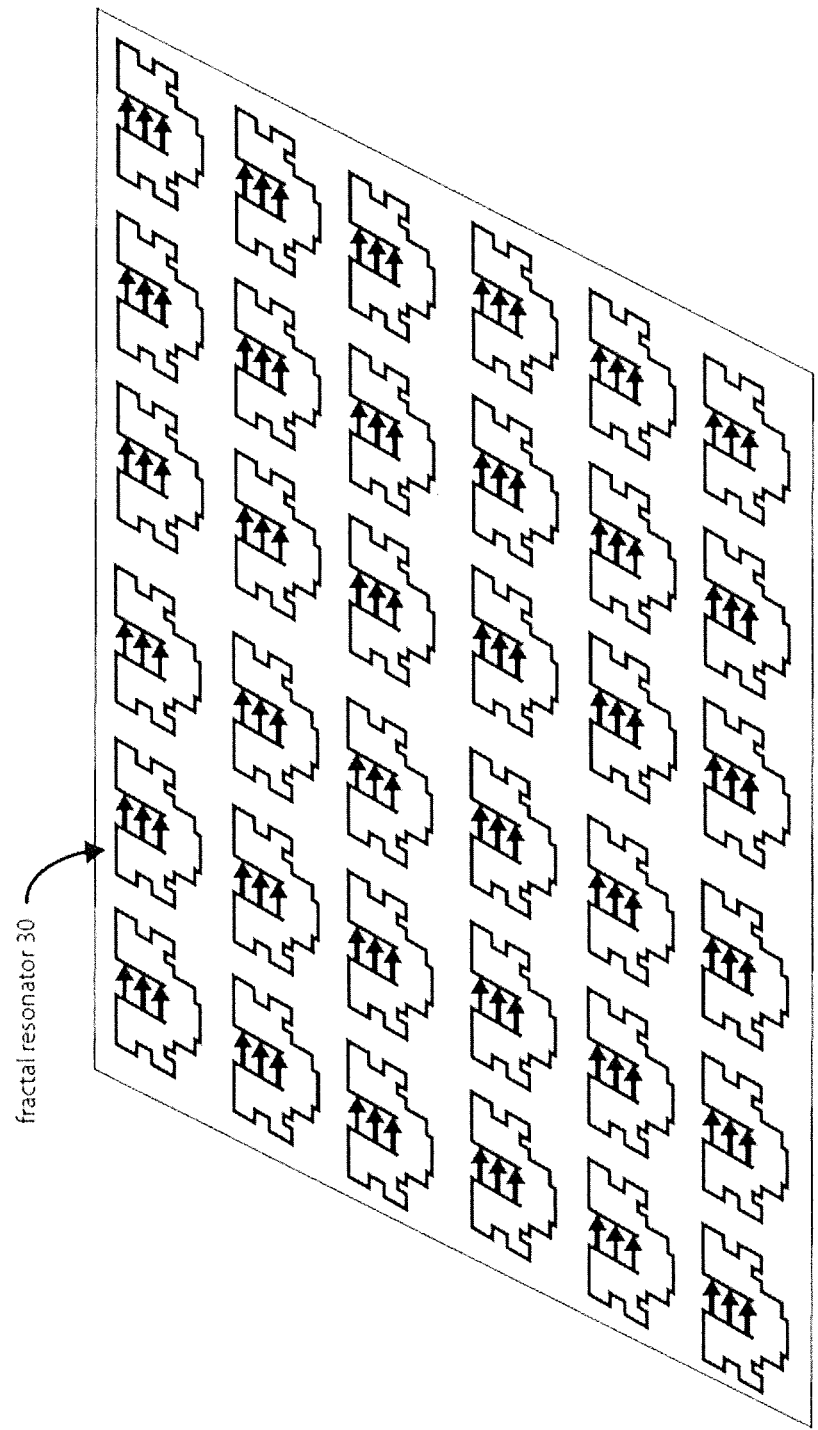
FIG. 12 is a diagram showing a pattern of ¾λ folded resonators having for the metal traces a fractal pattern for the electrical path that loops around to connect the opposing electrodes.

FIG. 12 is a diagram showing a pattern of ¾λ folded resonators 30 having for its metal traces a fractal pattern for the electrical path that loops around to connect the opposing electrodes. A fractal pattern for the electrical path with this pattern means that the metal trace can support various wavelengths resonating with the ¾λ characteristics because of the multiplicity of possible loop paths available because the widths of each segment of the conductive path vary in width permitting electrical paths of different physical lengths to exist around the loop.

Figure 13:
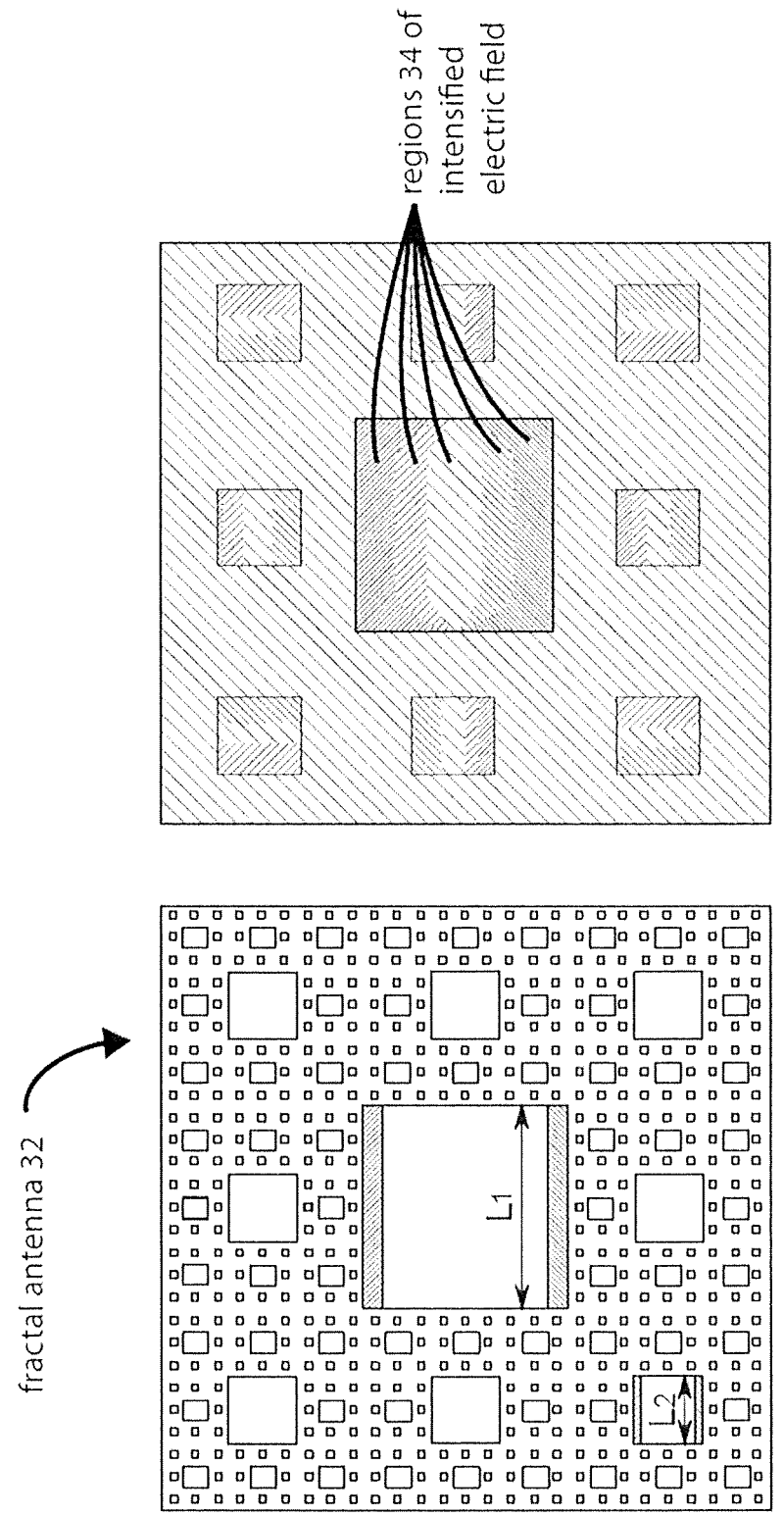
FIG. 13 is a diagram showing a fractal antenna segment where the straight-line sides of the metal pads have locally intensified electric field.

FIG. 13 is a diagram showing another fractal antenna segment 32 where the straight-line sides of the metal pads have regions 24 of locally intensified electric field. Here, in one embodiment, the fractal antenna segment is designed for resonance in the infrared range, with the intensifies electric field regions 34 (for example as shown toward the straight-line sides of the metal pads being the place where blue phosphors and red phosphors (or other emissive materials 24) would be deposited such that their emission, would be enhanced the intensified electric fields in those regions 34.

Figure 14:
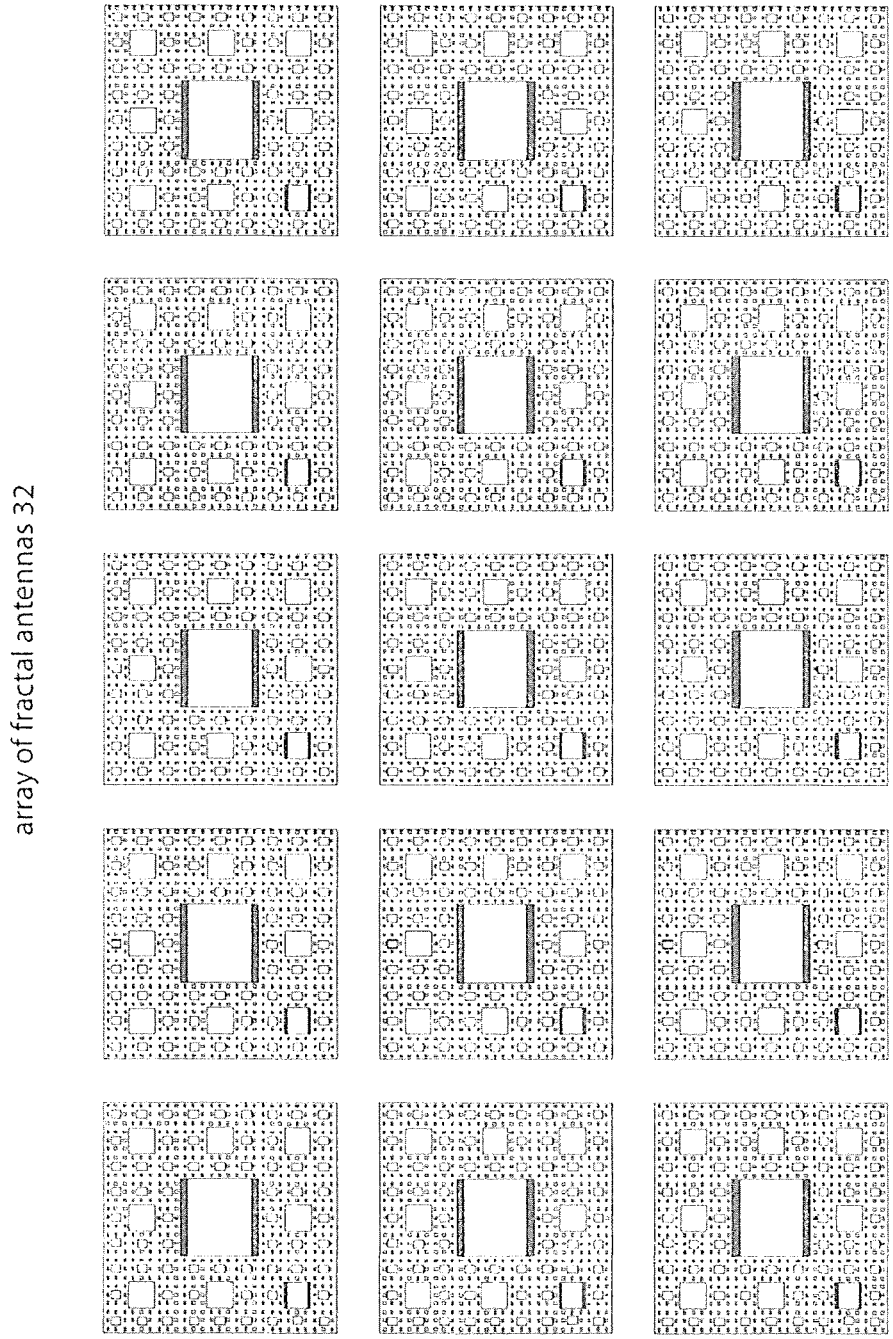
FIG. 14 is a diagram showing a repeated pattern of the fractal antenna segment of FIG. 13

FIG. 14 is a diagram showing a repeated pattern (array) of the fractal antenna segments 32 of FIG. 13.

Figure 15:
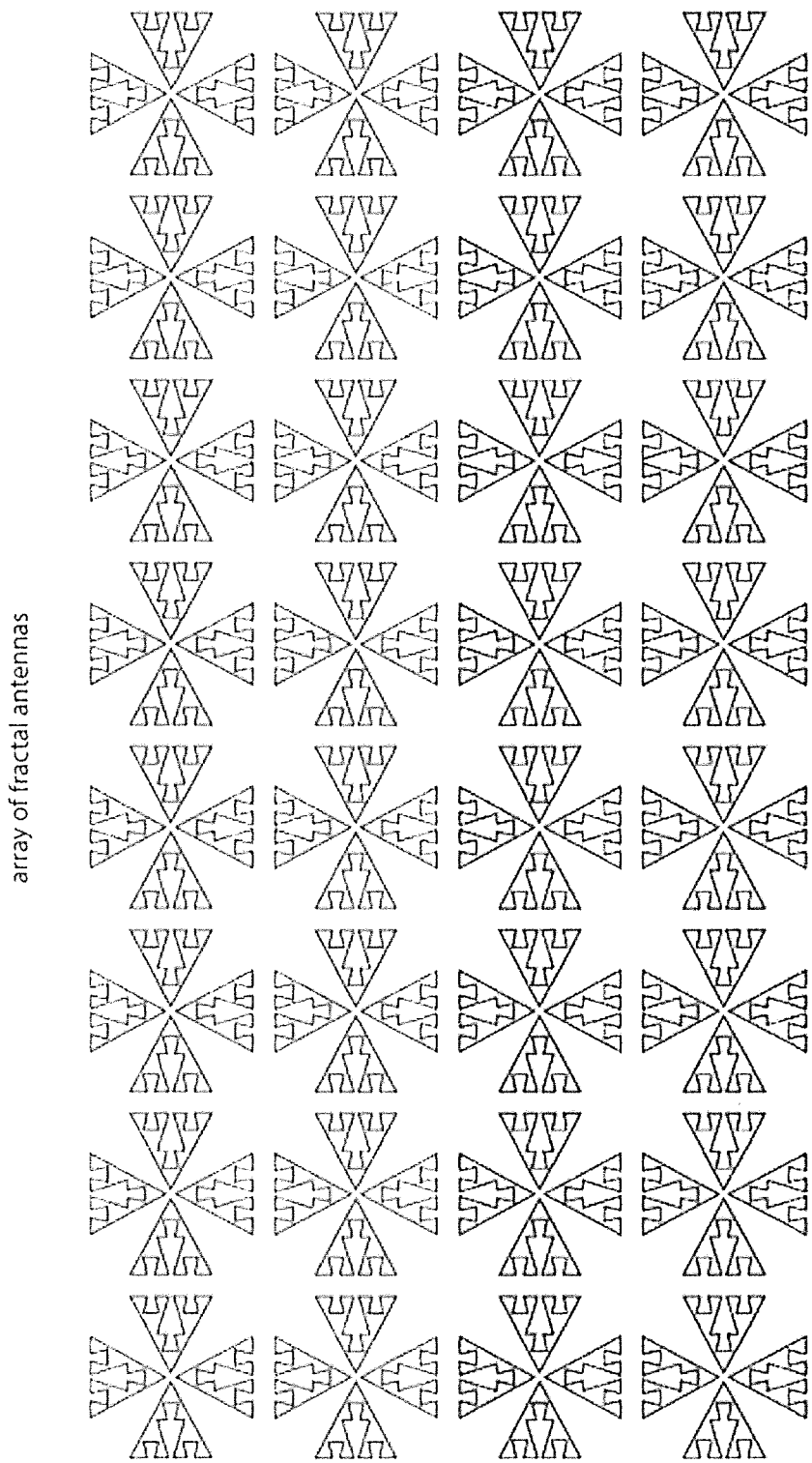
FIG. 15 is a diagram showing a pattern of bowtie fractal antenna segments.

FIG. 15 is a diagram showing a pattern (array) of bowtie fractal antenna segments, providing an alternative embodiment to the fractal antenna segments of FIG. 14.

In one embodiment of the invention, the resonant structures can comprise three-dimensional fractal patterns. Known in the art is the fabrication of three-dimensional fractal structures by nanoscale anisotropic etching of silicon such as described in Nanoscale etching of 3d fractal structures with many applications including 3d fractal antennas and structures for filters, by Brian Wang, Jun. 22, 2013, in the Journal of Micromechanics and Microengineering, (available at www.nextbigfuture.com/2013/06/nanoscale-etching-of-3d-fractal.html) the entire contents of which are incorporated herein by reference. In one embodiment of the invention, metal is deposited over a silicon three-dimensional fractal structure to form a multi-dimensional light collector.

Figure 16:
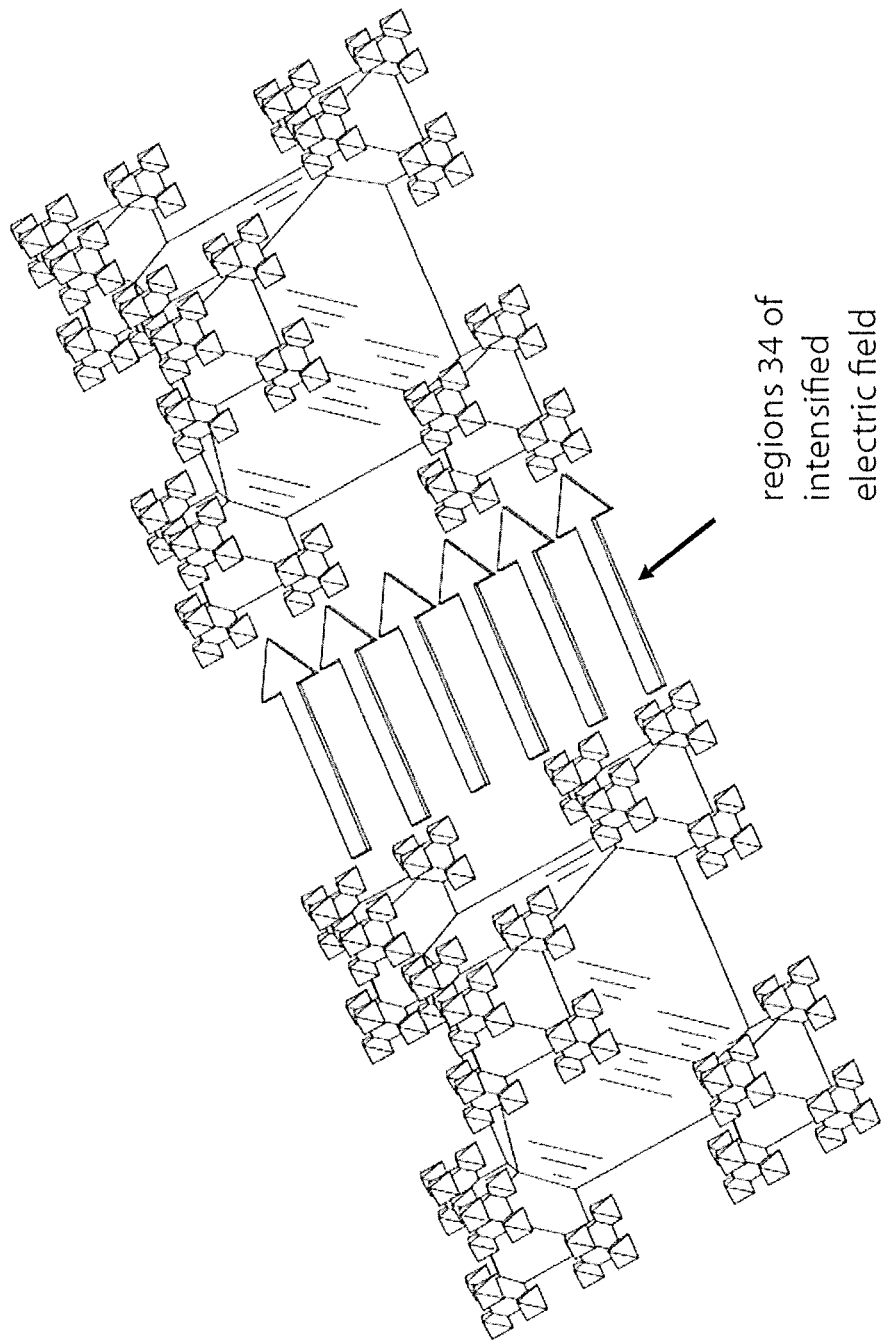

FIG. 16 is a diagram showing a paired three-dimensional fractal structure with regions 34 of an intensified electric field in between the pairs. The paired three-dimensional fractal structure is a color enhancement structure according to one embodiment of the invention. In one embodiment of the invention, these pyramidal type structures would be metallized with opposing faces metalized, a first loop conductor formed around the other sides of the first pyramid, then connecting across a region between the pair, and then a second loop formed around the sides of the second pyramid to the metallized opposing face of the second pyramid, to mimic (as seem from above) the ¾λ folded resonators shown in FIG. 3.

In one embodiment, converter (emissive) materials 24 would be disposed nearby different sections of the pyramidal type structures and preferably between the opposing faces of the pair where the intensified electric field (depicted by the arrows) exists. With the three-dimensional aspect of this invention, red, yellow, green, and blue converters (or other designated emitters) could be disposed at different levels within this region of intensified electric field.

Figure 17:
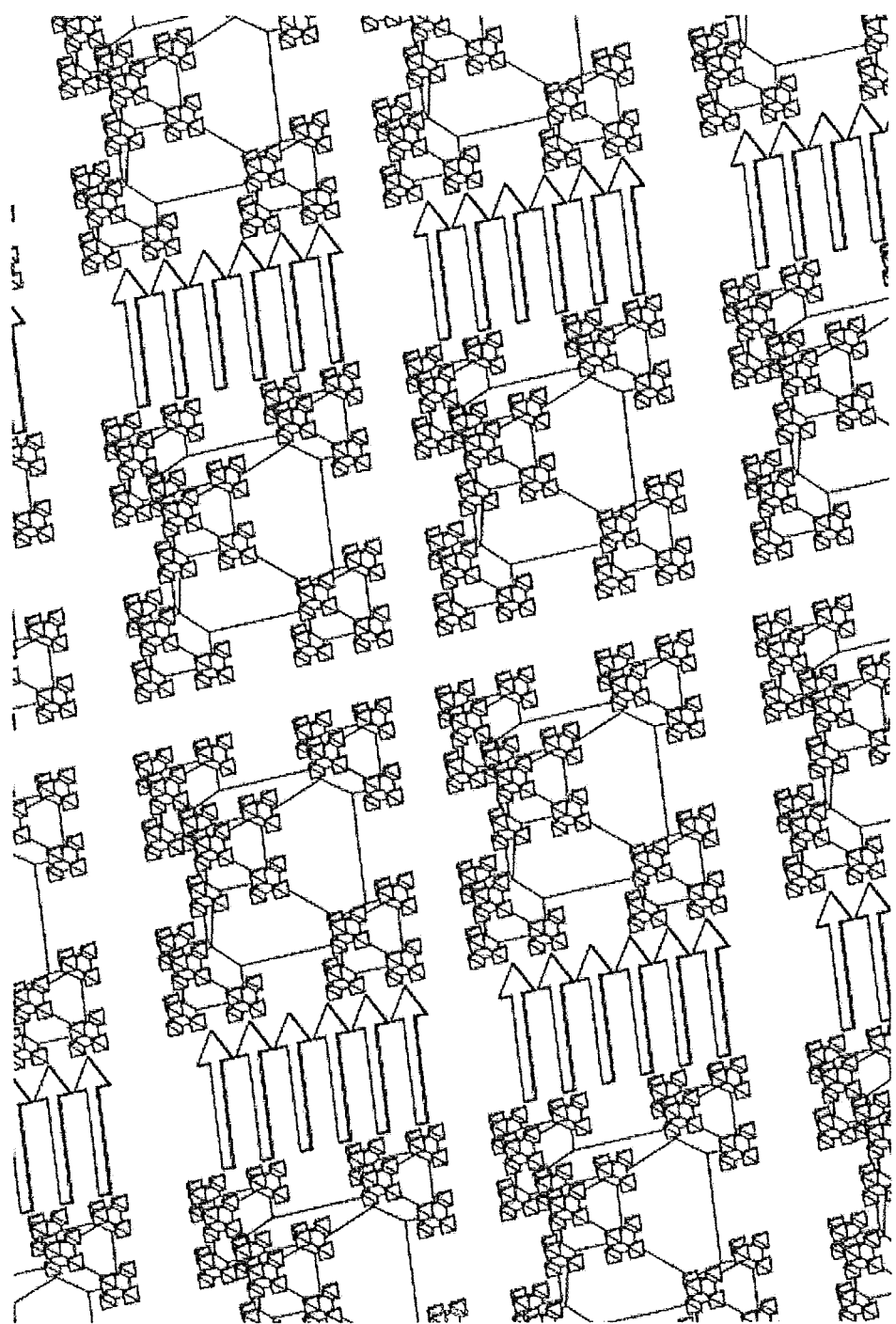
FIG. 17 is a diagram showing a pattern of the paired three-dimensional fractal structures.

FIG. 17 is a diagram showing a pattern (array) of the paired three-dimensional fractal structures of FIG. 16.

In these embodiments shown in FIGS. 12 to 17, the energy converters, or light or electron emitting materials, or color emitting or color converter materials (i.e., emissive materials 24) are disposed in a vicinity of one or more energy augmentation structures (i.e., the ¾λ folded resonators). As such, the energy augmentation structures preferably are in a region of intensified electric field. The intensified electric field may represent a region of intensified energy especially if there is electrical current flow conductively coupling the energy converter to the one energy augmentation structures. In later embodiments, conductively coupling the energy converter to the one energy augmentation structures has advantages. Accordingly, the energy converters, or light or electron emitting materials, or color emitting or color converter materials disposed in a vicinity of one or more energy augmentation structures may have a physical conductive connection between the energy converter and the at least one energy augmentation structure. Alternatively, the coupling may be more that of radiatively coupling the electric fields from the resonant structure into energy converters or color converting or enhancing materials disposed inside the energy augmentation structure, outside the energy augmentation structure, in a layer with the energy augmentation structure, or in a layer above or below the energy augmentation structure.

Figure 18:
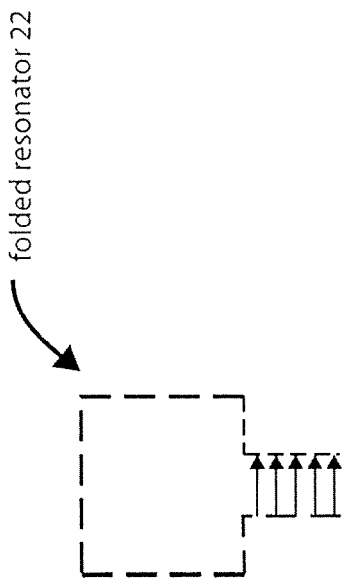
FIG. 18 is a diagram showing a ¾ wavelength resonator with the distal ends of the resonator antenna protruding outwardly while maintaining parallelism.

The energy augmentation structures are not limited to those shown above. Other variants are possible. Moreover, in one embodiment of the invention, the ¾λ folded resonators need not to have the "folded sections" which fold inwards as shown in FIG. 3. Instead, as shown in FIG. 18, the ¾λ resonators of the invention can have folded sections which fold outward with the regions of intensified electric field being outside of the "loop" of the resonator. The distal ends of the antenna protrude outwardly while maintaining parallelism. Specifically, FIG. 8 is a schematic of a ¾λ external-electrode folded resonator 22. This external, opposed electrode pair design follows the general apportioning, scaling aspects, converter material placement, etc., shown in FIGS. 5 through 11 but with the internal folded sections being replaced by the external-electrode pair.

Figure 19:
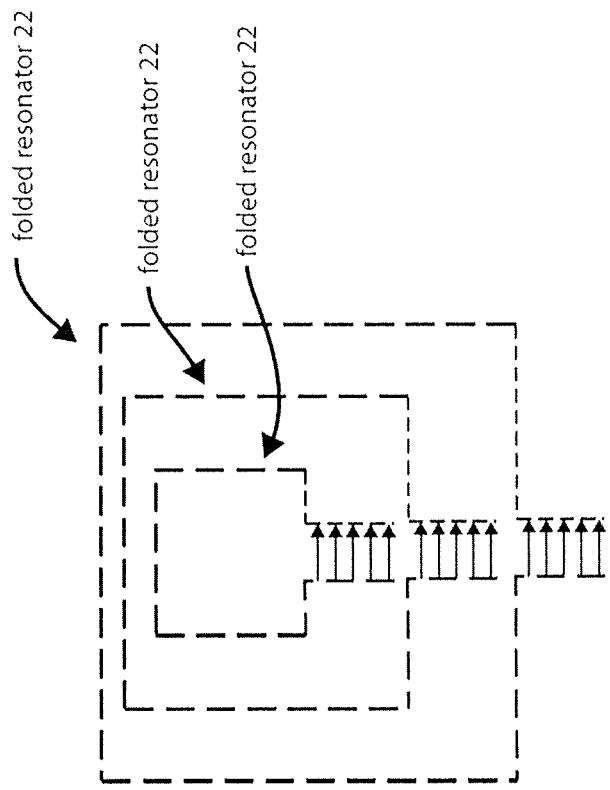
FIG. 19 is a diagram showing a packing configuration for three different ¾ wavelength resonators, that are maintained in plane with no overlapping distal ends.

In one embodiment of the invention, the ¾λ external-electrode folded resonator 22 provides the capability to be packed in a concentric-type arrangement with progressively increasing or decreasing size resonators. These resonators are maintained in plane with no overlapping distal ends. FIG. 19 is a schematic of a plurality of concentric-type ¾λ external-electrode folded resonators 22. Since each of the ¾λ external-electrode folded resonators 22 has a different electrical length, the plurality of concentric-type ¾λ external-electrode resonators will be "tuned" to the different wavelengths associated with the respective electrical lengths. Three different frequencies are therefore focused between the distal ends of the antennas.

Figure 20:
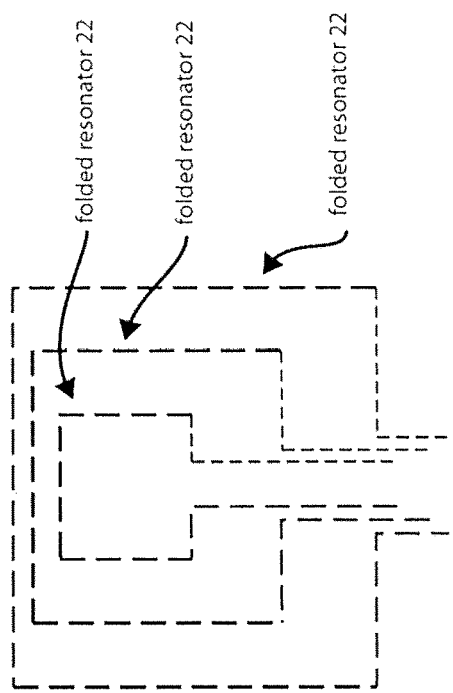
FIG. 20 is a diagram showing another packing configuration for three different ¾ wavelength resonators, that are maintained in plane with overlapping distal ends.

In another embodiment, FIG. 20 is a schematic of a plurality of concentric-type ¾λ external-electrode folded resonators 22 with overlapping electrodes. In one embodiment, the overlapping provides a more concentrated/enhanced field region than in the non-overlapping arrangement of FIG. 19.

Figure 21:
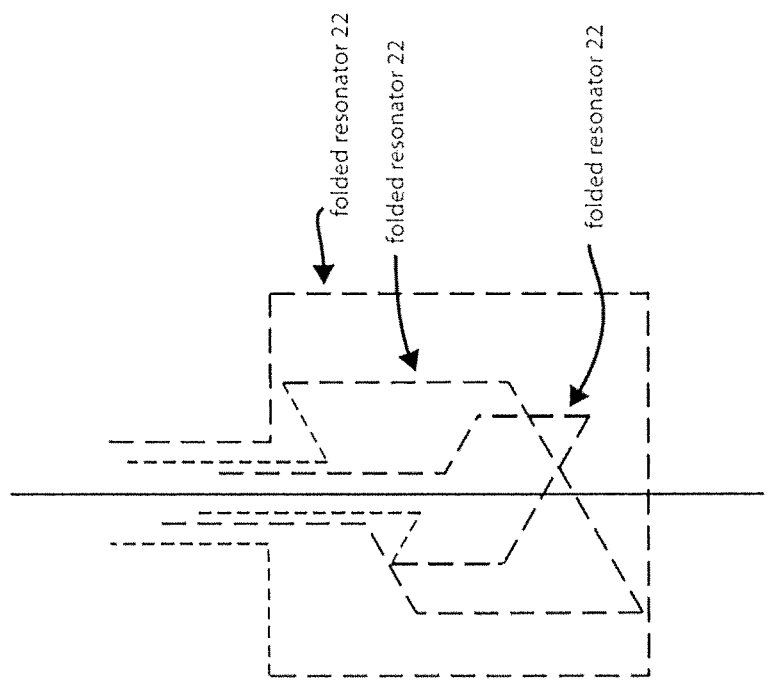
FIG. 21 is a diagram showing yet another packing configuration for the ¾ wavelength resonators, with an off (or out of) plane axial symmetry.

The present invention is not limited to planar concentric type packing arrangements as shown in FIG. 19 or 20. The three different ¾ wavelength resonators in FIG. 20 are maintained in plane with overlapping distal ends. These antennas are inductively coupled. In one embodiment, the present invention utilizes an off plane configuration with axial symmetry where the antennas are in an axially rotated, multiple frequency, interleaved ¾ wave resonator structure. FIG. 21 is a schematic of an axially rotated, multiple frequency, interleaved ¾ wave resonators 22 showing (in this example) three differently sized resonators for multiple frequency resonance disposed about/along a common axis but axially rotated. In one embodiment, in this configuration, the resultant electric field is concentrated without one electrode section perturbing the electric fields from another.

In a further embodiment, there is provided an energy collector comprising at least one energy augmentation structure; and at least one energy converter capable of receiving an applied electromagnetic energy, converting the applied electromagnetic energy and emitting therefrom an emitted electromagnetic energy shifted in wavelength or energy from the applied electromagnetic energy and the energy converter being disposed in a vicinity of the at least one energy augmentation structure such that the emitted electromagnetic energy is emitted with at least one augmented property compared to if the energy converter were remote from the at least one energy augmentation structure.

Figure 22:
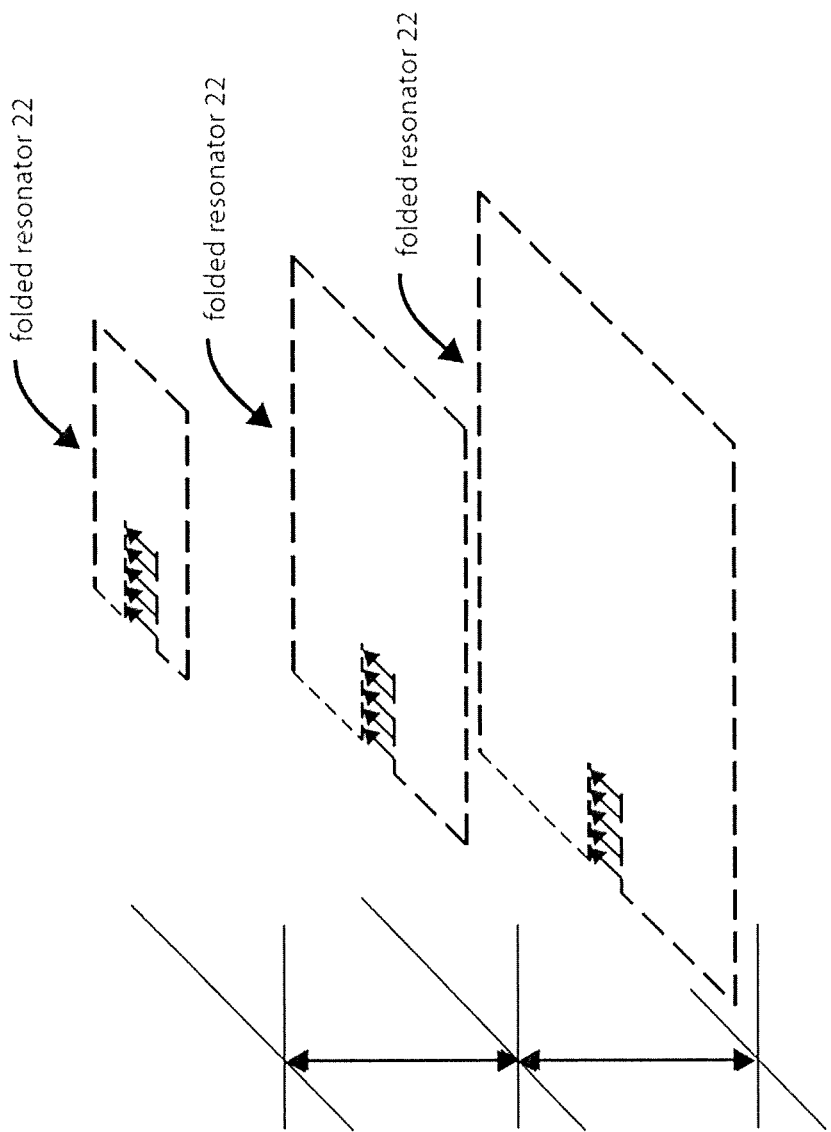
FIG. 22 is a diagram showing a multi-level packing configuration in parallel planes for the folded % wavelength resonator shown.
Figure 23:
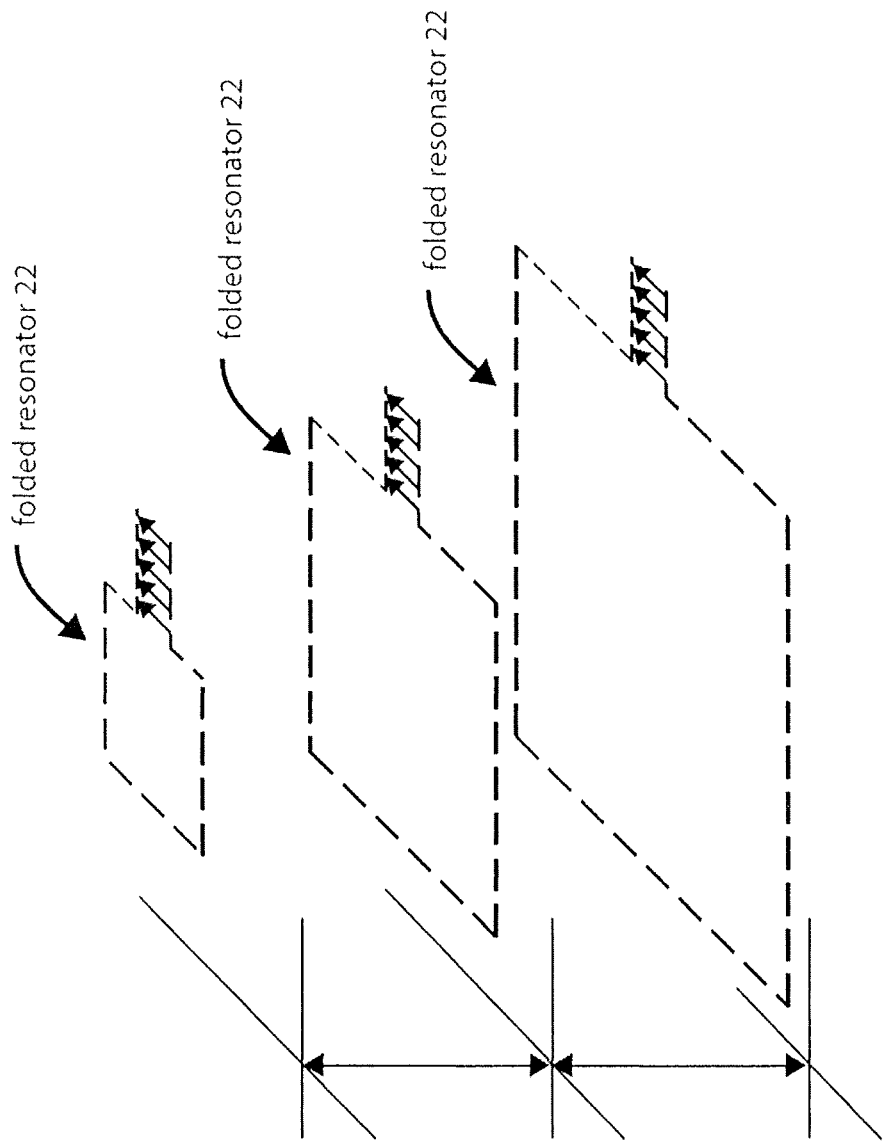
FIG. 23 is a diagram showing a multi-level packing configuration in parallel planes with distal ends protruding out for the % wavelength resonator in FIG. 22.

In one embodiment, the present invention can use different levels for disposing ¾λ resonators thereon regardless of the resonators being ¾λ internally-folded resonators or ¾λ external-electrode resonators. This packing is shown in FIGS. 22 and 23 for configuration in parallel planes with distal ends folded in or protruding out respectively.

Figure 24A:
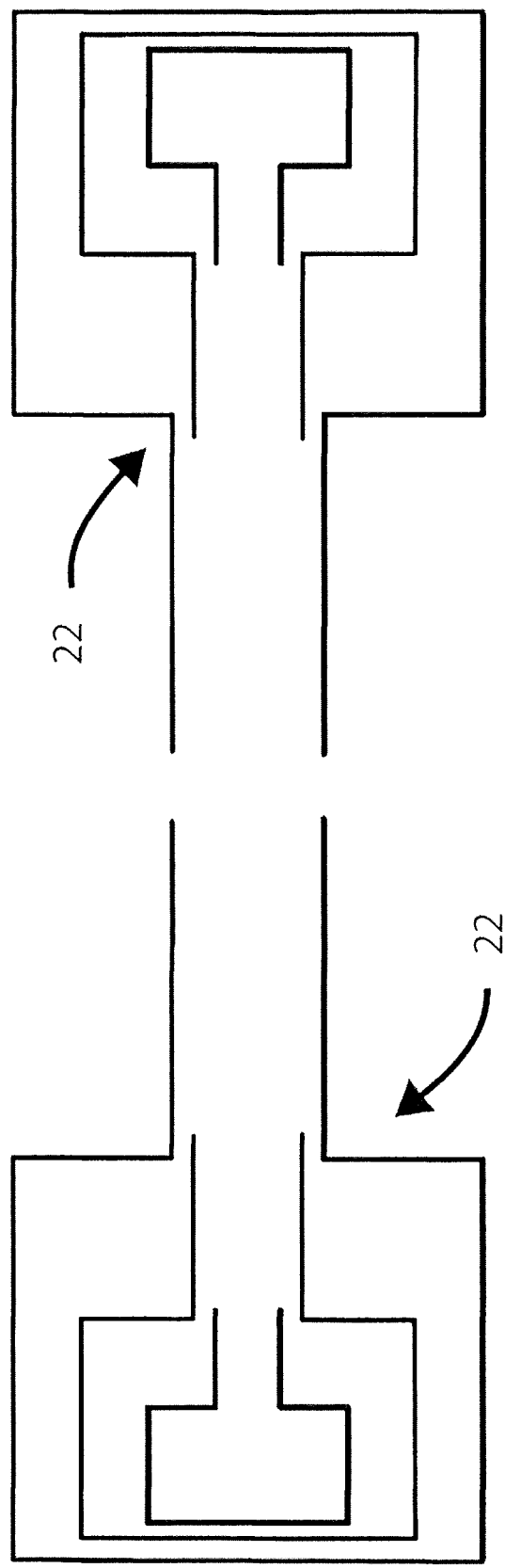
FIG. 24A is a diagram showing a different in-plane packing configuration.

In the embodiment of the invention depicted in FIG. 20 having a plurality of concentric-type ¾λ external-electrode resonators 22, the antennas are inductively decoupled. This configuration allows the electric field to be focused from three different frequencies in a longer path. This configuration can be used to create a mirror image configuration to extend the length of focused electric field as is illustrated in FIG. 24A.

Figure 24B:
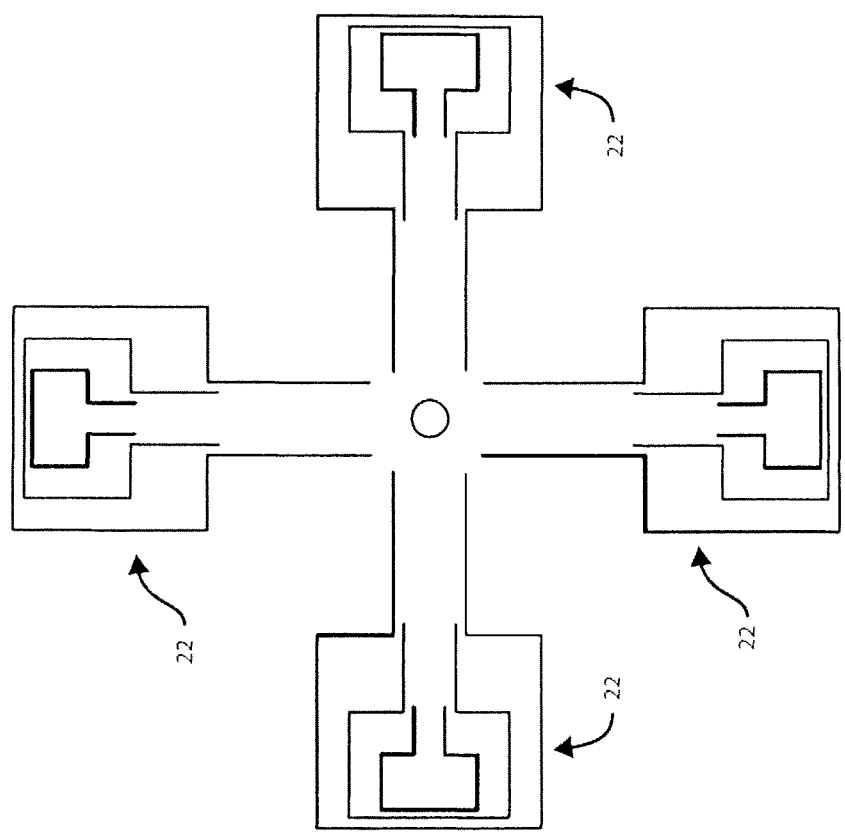
FIG. 24B is a diagram showing another different in-plane packing configuration.

The resonator configuration in this case is mirror imaged with another set of antennas (folded resonators 22) to create a longer path (doubled) of focused electric field. Furthermore, the resonator antenna configuration can be placed in more creative ways to enhance the electric field focusing around a target as is illustrated in the FIG. 24B.

The configuration in FIG. 25 allows the surrounding of a target within the plane of the resonator structure/antenna for the purpose of heating and focusing energy around the target. This prevents heat dissipation in silicon where the thermal conductivity is high. The silicon substrate in such an instance can be single crystalline, polycrystalline or amorphous.

In one embodiment of the present invention, an "energy augmentation structure" represents a structure whereby a spatial region of the energy collector contains a converter material (or other light or electron emitting material) exposed to energy which stimulates emission of light at a different energy (wavelength) from that to which it is exposed while being in a spatial area/volume (e.g., between or around or in a vicinity of the folded structures or the external-electrode pairs) where there is an artificially induced higher electrical field and/or a higher energy density. These artificial regions can be produced for example by use of structures including, but not limited to, multiple level collection optics, resonators, fractal antennas, and electrical grid (or electrode) patterns.

By having the light or electron emitting materials disposed in a vicinity of the energy augmentation structures of this invention, regardless of the whether the energy augmentation structure is in a region of intensified electric field or otherwise outside the region of intensified electric field, the energy augmentation structures of the invention are able to produce light which can be used for a variety of applications, in particular for photo-stimulation of biological, chemical, and physical reactions such as for example photoactivation of photoreactive drugs, photoactivation of photosensitive materials such as adhesives or lithographic photoresists, or for direct interaction with biological and chemical agents in the environment of the augmentation structures, as in sterilization.

In one embodiment, the light or electron emitting materials noted above are disposed with an energy augmentation structure comprising one or more of an electromagnetic resonator structure, a folded resonator structure, and a fractal resonating structure, any of which having a region of an intensified electromagnetic field within the resonating structures.

In one embodiment, the energy converter or light or electron emitting materials noted above includes one or more luminescing materials. As described herein, there are uses of the energy augmentation structure and/or energy collector embodiments which enhance bioluminescence, chemo-luminescence, photoluminescence, fluorescence, mechano-luminescence, and/or electron emission.

In one embodiment, the energy converter or light emitting materials noted above includes for the one or more luminescent materials phosphorescent materials, fluorescent materials, electroluminescent materials, chemo-luminescent materials, bioluminescent materials, and mechano-luminescent materials used in conjunction with or not in conjunction with the energy augmentation structure noted above. When used in conjunction with the energy augmentation structure noted above, the emitted electromagnetic energy from the luminescent material is emitted with at least one augmented property compared to if the energy converter (e.g., the luminescent material) were remote from the at least one energy augmentation structure.

In one embodiment, the bioluminescent materials are UV-emitting bioluminescent materials such as catalyzed luciferase and luminescent proteins.

In one embodiment, the energy converter or light emitting materials noted above includes for the one or more luminescing materials phosphorescent materials, fluorescent materials, electroluminescent materials, chemo-luminescent materials, bioluminescent materials, and mechano-luminescent materials used in conjunction with or not in conjunction with the energy augmentation structure noted above and which emit one of ultra-violet, visible, near infrared, and infrared light. In this embodiment, UV-emitting electroluminescent materials or mechano-luminescent devices and materials can be used. In this embodiment, UV-emitting bioluminescent materials can be used.

In some embodiments, metallic patterns form a folded resonator having opposing electrodes with electric fields directed in between, and a converter is positioned between the opposing electrodes or within fringing electric field of the opposing electrodes or otherwise in a vicinity of the opposing electrodes. In one example, the folded resonator is a ¾λ folded resonator. In one example, metallic patterns comprise at least one of Au, Ag, Cu, Al, or transparent metal oxides. In another example, the metallic patterns can be formed with refractory metals such for example Ti, W, and Mo.

In some embodiments, the metallic patterns referenced above comprise an external external-electrode pair structure having opposing electrodes with electric fields directed in between, and a converter is positioned between the opposing electrodes or within fringing electric field of the opposing electrodes or otherwise in a vicinity of the opposing electrodes.

In one example, the resonator is a ⅝ external-electrode pair resonator. In one example, metallic patterns comprise at least one of Au, Ag, Cu, Al, or transparent metal oxides. In another example, the metallic patterns can be formed with refractory metals such for example Ti, W, and Mo.

In some embodiments, plural resonators and plural converters are disposed at multiple positions throughout a light collector. In one example, the plural converters are positioned to convert light being internally scattered within the light collector.

In some embodiments of the energy augmentation structures, a first level of metallic patterns (or a second level of metallic patterns) comprises a metal core cladded with a high-K dielectric and a subsequent cladding of a low-K dielectric. In some embodiments of the energy augmentation structures, the first level of metallic patterns noted above (or the second level of metallic patterns) comprises a radial pattern of conductors. In some embodiments of the energy augmentation structures, the first level of metallic patterns noted above (or the second level of metallic patterns) comprises a fractal pattern. In one example, the fractal pattern is embedded within a dielectric material.

In some embodiments of the energy augmentation structures, the first level of metallic patterns noted above (or the second level of metallic patterns) comprises a three-dimensional fractal structure.

In some embodiments of the energy augmentation structures, there is provided a panel with the first level of metallic patterns and the second level of metallic patterns and optionally multiple converters formed therein or thereon. In some embodiments of the augmentation structures, there is provided a sheet with the first level of metallic patterns and the second level of metallic patterns and optionally multiple converters formed therein or thereon.

In some embodiments of the energy augmentation structures, the first level of metallic patterns noted above (or the second level of metallic patterns) is of different sizes and/or orientations to each other of the first level of metallic patterns or with respect to the second level of metallic patterns.

In another embodiment, the energy augmentator can collect or distribute light.

Figure 25A:
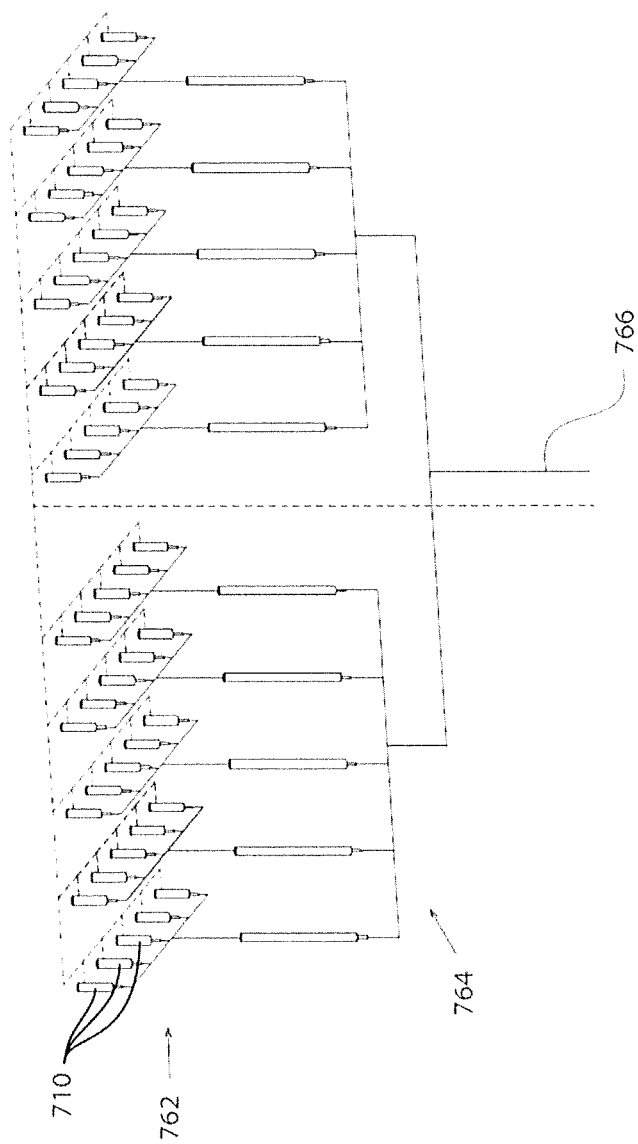
FIG. 25A is a schematic illustrating a distributed point light collector/transmitter of the invention.
Figure 25B:
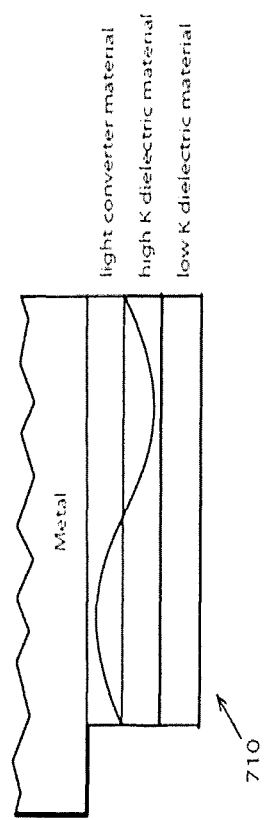
FIG. 25B is a schematic of a cross section of the collector/transmitter of FIG. 25A.

FIG. 25A is a schematic illustrating a distributed point light collector/transmitter of the invention showing a distribution of branches that can either collect light from distributed points 710 or conversely can distribute light from a central source 766 to the distributed points 710. The section of the collector/transmitter is shown in FIG. 25B showing a core metal, an optional light converter material, a high K dielectric, and a low K dielectric. In this arrangement, as shown, light is confined and not loss to scatter out of the collector/transmitter, except at the ends.

B. Energy Converters

In various embodiments of the invention, energy converters can be used with or without the energy augmentators described above. In some embodiments, the converters are for up conversion of light e.g., from the IR regime into visible electromagnetic radiation and for down conversion of light e.g., from the UV range into visible electromagnetic radiation. The invention in various embodiments up converts energy, preferably light in the visible spectrum. The invention encompasses a variety of applications where the up and down conversion materials with or without the energy augmentators are included to enhance electromagnetic energy emission, preferably light or photon emission. When an energy augmentator is present, it may be separate from or connected to the energy converter. In certain embodiments, the energy converter can have the energy augmentator formed on its surface through chemical vapor deposition ("CVD") or physical vapor deposition ("PVD") processes or other nanoscale "printing" methods. Such embodiments may be particularly useful in methods for treating human or animal patients, in which having such energy augmentators "imprinted" on a surface of the energy converter can guarantee proximity between the energy augmentator and the energy converter to maximize the interaction with the energy being applied. Alternatively, the energy augmentator can be formed on a surface of an inert non-energy converting particle, formed, for example, from silica or formed from a non-energy converting particle coated with an biologically and/or chemically inert coating (such as, for example, diamond, diamond-like carbon, or similar inert materials). Such an energy augmentator can then be co-administered with the energy converter to the human or animal patient.

Suitable energy modulation agents or energy converters (the two terms are used interchangeably herein) of the invention include, but are not limited to, a biocompatible fluorescing metal nanoparticle, fluorescing dye molecule, gold nanoparticle, a water soluble quantum dot encapsulated by polyamidoamine dendrimers, a luciferase (bioluminescence), a biocompatible phosphorescent molecule, a combined electromagnetic energy harvester molecule, and a lanthanide chelate capable of intense luminescence.

Alternatively, the energy modulation agent or energy converter can emit energy in a form suitable for absorption at a target site or receptor. For example, the initiation energy source may be acoustic energy and one energy converter may be capable of receiving acoustic energy and emitting photonic energy (e.g. sonoluminescent molecules) to be received by another energy converter that is capable of receiving photonic energy. Other examples include energy converters that receive energy at x-ray wavelength and emit energy at UV wavelength, preferably at UV-A wavelength. A plurality of such energy converters may be used to form a cascade to transfer energy from initiation energy source via a series of energy converters.

Resonance Energy Transfer (RET) is an energy transfer mechanism between two molecules having overlapping emission and absorption bands. Electromagnetic emitters are capable of converting an arriving wavelength to a longer wavelength. For example, UV-B energy absorbed by a first molecule may be transferred by a dipole-dipole interaction to a UV-A-emitting molecule in close proximity to the UV-B-absorbing molecule. Alternatively, a material absorbing a shorter wavelength may be chosen to provide RET to a non-emitting molecule that has an overlapping absorption band with the transferring molecule's emission band. Alternatively, phosphorescence, chemiluminescence, or bioluminescence may be used to transfer energy to a target site or a receptor such as a photoactivatable agent.

In a further embodiment, a biocompatible emitting source, such as a fluorescing metal nanoparticle or fluorescing dye molecule, is selected as an energy converter that emits in the UV-A band. In another embodiment, an energy converter comprising a UV-A emitting source can be a gold nanoparticle comprising for example a cluster of 5 gold atoms.

In another embodiment, an energy converter comprising a UV- or light-emitting luciferase is selected as the emitting source. A luciferase may be combined with ATP or another molecule, which may then be oxygenated with additional molecules to stimulate light emission at a desired wavelength. Alternatively, a phosphorescent emitting source may be used as the energy converter. One advantage of a phosphorescent emitting source is that the phosphorescent emitting molecules or other source may be electroactivated or photoactivated prior to insertion into the tumor either by systemic administration or direct insertion into the region of the tumor. Phosphorescent materials may have longer relaxation times than fluorescent materials, because relaxation of a triplet state is subject to forbidden energy state transitions, storing the energy in the excited triplet state with only a limited number of quantum mechanical energy transfer processes available for returning to the lower energy state. Energy emission is delayed or prolonged from a fraction of a second to several hours. Otherwise, the energy emitted during phosphorescent relaxation is not otherwise different than fluorescence, and the range of wavelengths may be selected by choosing a particular phosphor.

In one embodiment, the energy converters of the invention can include persistent after-glow phosphor materials emitting light in the visible to near ultraviolet and ultraviolet range. In one embodiment, Eu-doped strontium aluminate is used as an energy converter in which deep UV light or x-ray or electron beans "charge" the photoluminescence such that these phosphors can be charged outside for example a patient and then injected into target or diseased site where UV photons would be emitted. In another embodiment, gadolinium strontium magnesium aluminate is used as an energy converter in which deep UV light or x-ray or electron beans "charge" the photoluminescence such that these phosphors can be charged outside for example a patient and then injected into target or diseased site where UV photons would be emitted. U.S. Pat. Appl. Publ. No. 20070221883 (the entire contents of which are incorporated herein by reference) describes specifically gadolinium-activated strontium magnesium aluminate having an excitation maximum at about 172 nm, and which emits in a narrow-band UV emission at about 310 nm. The '883 publication also describes other useful energy converters for this invention, making note of emission spectra between 300 nm and 320 nm for a $Sr(Al,Mg)_{12}O_{19}$:Gd phosphor and two 312 nm line emitting phosphors, $YMgB_5O_{10}$:Gd, Ce and $YMgB_5O_{10}$: Gd, Ce, Pr. WO2016200349 (the entire contents of which are incorporated herein by reference) describes long lasting yellowish-green emitting phosphorescent pigments in the strontium aluminate (SrAl2O4) system, which could serve as energy converters in the present invention. WO 2016200348 (the entire contents of which are incorporated herein by reference) describes long lasting bluish-green emitting phosphorescent pigments in the strontium aluminate (Sr4Al14O25) system, which could serve as energy converters in the present invention. Xiong et al in "Recent advances in ultraviolet persistent phosphors," Optical Materials X 2 (2019) (the entire contents of which are incorporated herein by reference) describes a number of ultraviolet persistent phosphors that could as energy converters in the present invention. The table below provides a listing of such persistent phosphors:

| | | |
|---|---|---|
| $SrO:Pb^{2+}$ | 390 | >1 h |
| $CaAl_2O_4:Ce^{3+}\ Tb^{3+}$ | 400 | >10 h |
| $CaAl_2O_4:Ce^{3+}\ Tb^{3+}$ | 413 | >10 h |
| $Sr_2Al_2SiO_7:Ce^{3+}$ | 400 | several minutes |
| $SrZrO_3$ | 395 | <1000 s |
| $BaZrO_3:Mg^{2+}$ | 400 | >2400 s |
| $SrZrO_3:Pr^{3+}$ | 356 | |
| $CdSiO_3:Bi^{3+}$ | 360 | |
| $CdSiO_3:Bi^{3+}\ Dy^{3+}$ | 360 | |
| $CdSiO_3:Bi^{3+}\ Gd^{3+}$ | 344 | >6 h |
| $Sr_2MgGe_2O_7:Pb^{2+}$ | 370 | >12 h |
| $NaLuGeO_4:Bi^{3+}\ Eu^{3+}$ | 400 | >63 h |
| $CaZnGe_2O_6:Bi^{3+}$ | 300-700 | >12 h |
| $Cs_2NaYF_6:Pr^{3+}$ | 250 | >2 h |

In one embodiment, the phosphor described by Xiong et al as $CaAl_2O_4:Ce^{3+}$ having an emission peak of 400 nm and a persistent time of more than 10 h could be used, where it would be charged by x-ray irradiation outside a patient and then injected at a diseased site to provide internally generated UV light.

In one embodiment, the persistent phosphors noted could be activated ex vivo and introduced along with psoralen (or other photoactivatable drug) into the patient by exchange of a bodily fluid or for example by supplying the persistent phosphors and the photoactivatable drug into a patient's blood stream.

In one embodiment, the persistent phosphors noted could be activated in vivo by injection of the phosphors into a diseased site and then exposure to x-rays.

In another embodiment, a combined electromagnetic energy harvester molecule is designed, such as the combined light harvester disclosed in J. Am. Chem. Soc. 2005, 127, 9760-9768, the entire contents of which are hereby incorporated by reference. By combining a group of fluorescent molecules in a molecular structure, a resonance energy transfer cascade may be used to harvest a wide band of electromagnetic radiation resulting in emission of a narrow band of fluorescent energy. In another embodiment, a Stokes shift of an emitting source or a series of emitting sources arranged in a cascade is selected to convert a shorter wavelength energy, such as X-rays, to a longer wavelength fluorescence emission such an optical or UV-A.

In one embodiment, a lanthanide chelate capable of intense luminescence is used as an energy converter. In another embodiment, a biocompatible, endogenous fluorophore emitter is selected as an energy converter.

In one embodiment, the energy converters of the invention can include visible and UV-light emitting bioluminescent materials. In one embodiment, bioluminescent materials such as coelenterate-type luciferin analogues could be used including amide monoanion known to emit at 480 nm and oxyluciferin known to emit at 395 nm.

Among various materials, luminescent nanoparticles have attracted increasing technological and industrial interest. In the context of the invention, nanoparticle refers to a particle having a size less than one micron. While the description of the invention describes specific examples using nanoparticles, the invention in many embodiments is not limited to particles having a size less than one micron. However, in many of the embodiments, the size range of less than one micron, and especially less than 100 nm produces properties of special interest such as for example emission lifetime luminescence quenching, luminescent quantum efficiency, and concentration quenching and such as for example diffusion, penetration, and dispersion into mediums where larger size particles would not migrate.

This invention in various embodiments can use a wide variety of down conversion materials (or mixtures of down conversion materials) with or without the energy augmentators to enhance light or photon emission. These down conversion materials can include quantum dots, semiconductor materials, alloys of semiconductor materials, scintillation and phosphor materials, materials that exhibit X-ray excited luminescence (XEOL), organic solids, metal complexes, inorganic solids, crystals, rare earth materials (lanthanides), polymers, scintillators, phosphor materials, etc., and materials that exhibit excitonic properties. Accordingly, the down conversion materials to enhance light or photon emission can convert energy from one of ultraviolet light, x-rays, and high energy particles to visible light. The down conversion materials to enhance light or photon emission can convert energy from higher energy visible light to lower energy visible light.

In one embodiment of the invention, a quantum dot mixture with or without the energy augmentators can be used for the multiple nanoparticles. Quantum dots are in general nanometer size particles whose energy states in the material of the quantum dot are dependent on the size of the quantum dot. For example, quantum dots are known to be semiconductors whose conducting characteristics are closely related to the size and shape of the individual crystal. Generally, the smaller the size of the crystal, the larger the band gap, the greater the difference in energy between the highest valence band and the lowest conduction band becomes. Therefore, more energy is needed to excite the dot, and concurrently, more energy is released when the crystal returns to its resting state. In fluorescent dye applications, this equates to higher frequencies of light emitted after excitation of the dot as the crystal size grows smaller, resulting in a color shift from red to blue in the light emitted. Quantum dots represent one way to down convert ultraviolet light of the spectrum to a targeted wavelength or energy emission. Quantum dots represent one way to down convert blue light of the spectrum to a targeted wavelength or energy emission.

As described in U.S. Pat. No. 6,744,960 (the entire contents of which are incorporated by reference), different size quantum dots produce different color emissions. In that work and applicable to this invention, quantum dots can comprise various materials including semiconductors such as zinc selenide (ZnSe), cadmium selenide (CdSe), cadmium sulfide (CdS), indium arsenide (InAs), and indium phosphide (InP). Another material that may suitably be employed is titanium dioxide ($TiO_2$). The size of the particle, i.e., the quantum dot 18, may range from about 2 to 10 nm. Since the size of these particles is so small, quantum physics governs many of the electrical and optical properties of the quantum dot. One such result of the application of quantum mechanics to the quantum dot 18 is that quantum dots absorb a broad spectrum of optical wavelengths and re-emit radiation having a wavelength that is longer than the wavelength of the absorbed light. The wavelength of the emitted light is governed by the size of the quantum dot. For example, CdSe quantum dots 5.0 nm in diameter emit radiation having a narrow spectral distribution centered about 625 nm while quantum dots 18 including CdSe 2.2 nm in size emit light having a center wavelength of about 500 nm. Semiconductor quantum dots comprising CdSe, InP, and InAs, can emit radiation having center wavelengths in the range between 400 nm to about 1.5 m. Titanium dioxide $TiO_2$ also emits in this range. The linewidth of the emission, i.e., full-width half-maximum (FWHM), for these semiconductor materials may range from about 20 to 30 nm. To produce this narrowband emission, quantum dots simply need to absorb light having wavelengths shorter than the wavelength of the light emitted by the dots. For example, for 5.0 nm diameter CdSe quantum dots light having wavelengths shorter than about 625 nm is absorbed to produce emission at about 625 nm while for 2.2 nm quantum dots comprising CdSe light having wavelengths smaller than about 500 nm is absorbed and re-emitted at about 500 nm. In practice, however, the excitation or pump radiation is at least about 50 nanometers shorter than the emitted radiation.

Specifically, in one embodiment of the invention, a quantum dot mixture (QDM) coating can be deposited using CVD and or sol-gel techniques using standard precipitation techniques. The QDM coating can be made of a silicate structure that does not diminish UV output. Within the silicate family, silica ($SiO_2$) is suitable since it maximizes UV transmission through the coating. The coating can further include a second layer of a biocompatible glass. Such bio-compatible glass and glass ceramic compositions can contain calcium, a lanthanide or yttrium, silicon, phosphorus and oxygen. Other biocompatible materials and techniques are described in the following patents which are incorporated herein in their entirety: U.S. Pat. Nos. 5,034,353; 4,786,617; 3,981,736; 3,922,155; 4,120,730; and U.S. Pat. Appl. Nos. 2008/0057096; 2006/0275368; and 2010/0023101.

Further, the down conversion materials for the invention described here can be coated with insulator materials such as for example silica which will reduce the likelihood of any chemical interaction between the luminescent particles and the medium the particles are included therein. These and the other conversion materials described here can be used with or without energy augmentators. For biocompatible applications of inorganic nanoparticles, one of the major limiting factors is their toxicity. Generally speaking, all semiconductor nanoparticles are more or less toxic. For biocompatible applications, nanoparticles with toxicity as low as possible are desirable or else the nanoparticles have to remain separated from the medium. Pure $TiO_2$, ZnO, and $Fe_2O_3$ are biocompatible. CdTe and CdSe are toxic, while ZnS, CaS, BaS, SrS and $Y_2O_3$ are less toxic. In addition, the toxicity of nanoparticles can result from their inorganic stabilizers, such as TGA, or from dopants such as $Eu^{2+}$, $Cr^{3+}$ or $Nd^{3+}$. Other suitable down conversion materials which would seem the most biocompatible are zinc sulfide, $ZnS:Mn^{2+}$, ferric oxide, titanium oxide, zinc oxide, zinc oxide containing small amounts of $Al_2O_3$, and AgI nanoclusters encapsulated in zeolite. For non-medical applications, where toxicity may not be as critical a concern, the following materials (as well as those listed elsewhere) are considered suitable: lanthanum and gadolinium oxyhalides activated with thulium; $Er^{3+}$ doped $BaTiO_3$ nanoparticles, $Yb^{3+}$ doped $CsMnCl_3$ and $RbMnCl_3$, $BaFBr:Eu^{2+}$ nanoparticles, Cesium Iodine, Bismuth Germanate, Cadmium Tungstate, and CsBr doped with divalent Eu.

In various embodiments of the invention, the following luminescent polymers with or without energy augmentators are also suitable as conversion materials: poly(phenylene ethynylene), poly(phenylene vinylene), poly(p-phenylene), poly(thiophene), poly(pyridyl vinylene), poly(pyrrole), poly(acetylene), poly(vinyl carbazole), poly(fluorenes), and the like, as well as copolymers and/or derivatives thereof.

In various embodiments of the invention, the following materials with or without energy augmentators can be used similar to that detailed in U.S. Pat. No. 7,090,355, the entire contents of which are incorporated herein by reference. For down-conversion, the following materials can be used. Inorganic or ceramic phosphors or nano-particles, including but not limited to metal oxides, metal halides, metal chalcogenides (e.g. metal sulfides), or their hybrids, such as metal oxo-halides, metal oxo-chalcogenides. Laser dyes and small organic molecules, and fluorescent organic polymers. Semiconductor nano-particles, such as II-VI or III-V compound semiconductors, e.g. fluorescent quantum dots. Organometallic molecules including at least a metal center such as rare earth elements (e.g. Eu, Tb, Ce, Er, Tm, Pr, Ho) and transitional metal elements such as Cr, Mn, Zn, Ir, Ru, V, and main group elements such as B, Al, Ga, etc. The metal elements are chemically bonded to organic groups to prevent the quenching of the fluorescence from the hosts or solvents. Phosphors can be used including the Garnet series of phosphors: $(Y_mA_{1-m})_3(Al_nB_{1-n})_5O_{12}$, doped with Ce; where 0≤m, n≤1, where A includes other rare earth elements, B includes B, Ga. In addition, phosphors containing metal silicates, metal borates, metal phosphates, and metal aluminates hosts can be used. In addition, nano-particulates phosphors containing common rare earth elements (e.g. Eu, Tb, Ce, Dy, Er, Pr, and Tm) and transitional or main group elements (e.g. Mn, Cr, Ti, Ag, Cu, Zn, Bi, Pb, Sn, and Tl) as the fluorescent activators, can be used. Materials such as Ca, Zn, Cd in tungstates, metal vanadates, ZnO, etc. can be used.

The commercial laser dye materials obtained from several laser dye vendors, including Lambda Physik, and Exciton, etc. can also be used with or without energy augmentators. A partial list of the preferred laser dye classes includes: Pyrromethene, Coumarin, Rhodamine, Fluorescein, other aromatic hydrocarbons and their derivatives, etc. In addition, there are many polymers containing unsaturated carbon-carbon bonds, which also serve as fluorescent materials and find many optical and fluorescent applications. For example, MEH-PPV, PPV, etc. have been used in optoelectronic devices, such as polymer light emitting diodes (PLED). Such fluorescent polymers can be used directly as the fluorescent layer of the transparent 2-D display screen with and without energy augmentators.

As noted above, semiconductor nanoparticles (e.g., quantum dots) can be used with or without energy augmentators. The terms "semiconductor nanoparticles," in the art refers to an inorganic crystallite between 1 nm and 1000 nm in diameter, preferably between 2 nm to 50 nm. A semiconductor nano-particle is capable of emitting electromagnetic radiation upon excitation (i.e., the semiconductor nanoparticle is luminescent). The nanoparticle can be either a homogeneous nano-crystal, or comprises of multiple shells. For example, the nanoparticle can include a "core" of one or more first semiconductor materials, and may be surrounded by a "shell" of a second semiconductor material. The core and/or the shell can be a semiconductor material including, but not limited to, those of the group II-VI (ZnS, ZnSe, ZnTe, CdS, CdSe, CdTe, HgS, HgSe, HgTe, MgS, MgSe, MgTe, CaS, CaSe, CaTe, SrS, SrSe, SrTe, BaS, BaSe, BaTe, and the like) and III-V (GaN, GaP, GaAs, GaSb, InN, InP, InAs, InSb, and the like) and IV (Ge, Si, and the like) materials, and an alloy or a mixture thereof.

Fluorescent organometallic molecules containing rare earth or transitional element cations can be used for down conversion materials with or without energy augmentators. Such molecules include a metal center of rare earth elements including Eu, Tb, Er, Tm, Ce protected with organic chelating groups. The metal center may also include transitional elements such as Zn, Mn, Cr, Ir, etc. and main group elements such as B, Al, Ga. Such organometallic molecules can readily dissolve in liquid or transparent solid host media. Some examples of such fluorescent organometallic molecules include: 1. Tris(dibenzoylmethane)mono(phenanthroline)europium(III); 2. Tris(8-hydroxyquinoline) erbium; 3. Tris(1-phenyl-3-methyl-4-(2,2-dimethylpropan-1-oyl)pyrazolin-5-one)terbium(III); 4. Bis(2-methyl-8-hydroxyquinolato)zinc; 5. Diphenylborane-8-hydroxyquinolate.

Specific examples of down-conversion materials for red emission include those discussed above and europium complexes such as those described in JP Laid-open Patent Publication (Kokai) No. 2003-26969, constructed such that β-diketone ligand is coordinated to europium forming an europium complex capable of emitting red fluorescence. Other specific examples of the rare earth element complexes include complexes include lanthanum (Ln), europium (Eu), terbium (Tb), and gadolinium (Gd) and combinations thereof. An europium (Eu) complex is capable of emitting red fluorescence when irradiated with ultraviolet rays having a wavelength ranging from 365 nm to 410 nm. Terbium (Tb) is capable of emitting green fluorescence when irradiated with ultraviolet rays having a wavelength of 365 nm.

In other down-conversion embodiments, the down conversion materials which emit red light may include europium, light emitting particles which emit green light may include Terbium, and light emitting particles which emit blue or yellow light may include cerium (and/or thulium). In up-conversion embodiments, up conversion materials which emit red light may include praseodymium, light emitting particles which emit green light may include erbium, and light emitting particles which emit blue light may include thulium. In embodiments, the conversion materials can be light emitting particles made of fluorescent molecules that emit different colors (e.g. red, green, and blue), or different wavelengths or energies of light. In embodiments, the conversion materials can be light emitting particles made of pure organic or organo-metallic dyes with or without energy augmentators.

In addition to the combinations of rare earth complexes, such as a combination of a europium complex and a terbium complex, it is also possible employ a combination of a europium complex and a green-emitting fluorescent substance which is not a complex, or a combination of a terbium complex and a red-emitting fluorescent substance which is not a complex.

Other down converter materials (which can be used with or without energy augmentators) include for example ZnS, PbS, SbS$_3$, MoS$_2$, PbTe, PbSe, BeO, MgO. Li$_2$CO$_3$, Ca(OH)$_2$, MoO$_3$, SiO$_2$, Al$_2$O$_3$, TeO$_2$, SnO$_2$, KBr, KCl, and NaCl. These materials can include dopants to tailor the emission properties, as noted above. Examples of doped (or alloyed) glass systems suitable for the include Y$_2$O$_3$:Gd, Y$_2$O$_3$:Dy, Y$_2$O$_3$:Tb, Y$_2$O$_3$:Ho, Y$_2$O$_3$:Er, Y$_2$O$_3$:Tm, Gd$_2$O$_3$:Eu, Y$_2$O$_2$S:Pr, Y$_2$O$_2$S:Sm, Y$_2$O$_2$S:Eu, Y$_2$O$_2$S:Tb, Y$_2$O$_2$S:Ho, Y$_2$O$_2$S:Er, Y$_2$O$_2$S:Dy, Y$_2$O$_2$S:Tm, ZnS:Ag:Cl (blue), ZnS:Cu:Al (green), Y$_2$O$_2$S:Eu (red), Y$_2$O$_3$:Eu (red), YVO$_4$:Eu (red), and Zn$_2$SiO$_4$:Mn (green).

With regard more specifically to down converter materials suitable for the invention, U.S. Pat. No. 4,705,952 (the contents of which are hereby incorporated herein by reference) describes an infrared-triggered phosphor that stores energy in the form of visible light of a first wavelength and released energy in the form of visible light of a second wavelength when triggered by infrared light. The phosphors in U.S. Pat. No. 4,705,952 were compositions of alkaline earth metal sulfides, rare earth dopants, and fusible salts. The phosphors in U.S. Pat. No. 4,705,952 were more specifically phosphors made from strontium sulfide, barium sulfide and mixtures thereof; including a dopant from the rare earth series and europium oxide, and mixtures thereof; and including a fusible salt of fluorides, chlorides, bromides, and iodides of lithium, sodium, potassium, cesium, magnesium, calcium, strontium, and barium, and mixtures thereof. The materials described in U.S. Pat. No. 4,705,952 are useful in various embodiments of the invention with or without energy augmentators. In one example, the infrared-triggered phosphors would be used in conjunction with the folded resonators, and the receipt of a microwave or IR signal would locally heat and trigger emission. (This application would be particularly well suited for color enhancement and/or security applications.)

In other embodiments of the invention, the down converter materials (or mixtures of down converters materials (which can be used with or without energy augmentators) can include Y$_2$O$_3$: Li. Sun et al "Luminescent properties of Li+ doped nanosized Y$_2$O$_3$:Eu," Solid State Comm. 119 (2001) 393-396 (the entire contents of which are incorporated herein by reference) describe such materials. Hou et al "Luminescent properties nano-sized Y$_2$O$_3$:Eu fabricated by co-precipitation method," Journal of Alloys and Compounds, vol. 494, issue 1-2, 2 Apr. 2010, pages 382-385 (the entire contents of which are incorporated herein by reference) describe that nano-sized yttria (Y$_2$O$_3$) powders have been successfully synthesized by a co-precipitation method. The powders were well crystallized, and the grains were almost spherical with good dispersibility. The quenching concentration of Eu$^{3+}$ ions is 9 mol % which is much higher than micro-scaled powders. The incorporation of Li+ ions greatly improved the luminescence intensity. The highest emission intensity was observed with 4 mol % Li+ doped Y$_2$O$_3$:Eu powder ((Y$_{0.87}$Eu$_{0.09}$Li$_{0.04}$)$_2$O$_3$) and the fluorescence intensity was increased by as much as 79%. Yi et al "Improved cathodoluminescent characteristics of Y$_2$O$_3$:Eu$^{3+}$ thin films by Li-doping," Appl. Phys. A 87, 667-671 (2007) (the entire contents of which are incorporated herein by reference) describe cathodoluminescent spectra for both Y$_2$O$_3$:Eu$^{3+}$ and Li-doped Y$_2$O$_3$:Eu$^{3+}$ films and methods for making these materials.

Specific downconverting materials may also include at least one or more of Y$_2$O$_3$, Y$_2$O$_3$:Gd, Y$_2$O$_2$S, NaYF$_4$, NaYbF$_4$, YAG, YAP, Nd$_2$O$_3$, LaF$_3$, LaCl$_3$, La$_2$O$_3$, TiO$_2$, LuPO$_4$, YVO$_4$, YbF$_3$, YF$_3$, Na-doped YbF$_3$, ZnS, ZnSe, MgS, CaS, Zn$_2$SiO$_4$:Mn, LaOBr:Tm and alkali lead silicate including compositions of SiO$_2$, B$_2$O$_3$, Na$_2$O, K$_2$O, PbO, MgO, or Ag, and combinations or alloys or layers thereof. Furthermore, the down-converting materials can be sulfur containing phosphors, which can help for example in the rubber vulcanization or other photoactivated processes. An example of such a sulfur containing phosphor is: (Sr,Ca)Ga$_2$S$_4$. Other examples wherein said phosphor particles comprise a thiogallate host material selected from the group consisting of SrGa$_2$S$_4$, CaGa$_2$S$_4$ BaGa$_2$S$_4$, MgGa$_2$S$_4$ and solid solutions thereof. The particle size of such phosphor can be controlled from 25 nm to 300 microns in size as described in U.S. Pat. No. 6,153,123A. The downconverting materials can include a dopant including at least one of Er, Eu, Yb, Tm, Nd, Mn, Sb, Tb, Ce, Y, U, Pr, La, Gd and other rare-earth species or a combination thereof. The dopant can be included at a concentration of 0.01%-50% by mol concentration. At times it is preferable to have a combination of dopants rather than one dopant such is the case for a Mn and Sb in silicate matrices.

The invention in other embodiments can use a wide variety of up conversion materials (or mixtures of up converters) with or without the energy augmentators to enhance a particular wavelength or energy of light emitted from a material or surface. These up conversion materials can include similar materials as discussed above with regard to down conversion but typically included doped or impurity states in a host crystal that provide a mechanism for up conversion pumping. Accordingly, the up conversion materials to enhance wavelength or energy emission can convert energy from one of near infrared, infrared, and microwave irradiation. The upconversion materials to enhance color emission can convert energy from lower energy visible light to higher energy visible light.

In one example, a nanoparticle of a lanthanide doped oxide can be excited with near infrared light such as laser light at 980 nm and 808 nm to produce visible light in different parts of the red, green, blue spectrum (different wavelengths or energies) depending on the dopant trivalent rare earth ion(s) chosen, their concentration, and the host lattice.

The lanthanide doped oxides suitable for this invention differ from more traditional multi-photon up conversion processes where the absorption of, for example, two photons is needed in a simultaneous event to promote an electron from a valence state directly into an upper level conduction band state where relaxation across the band gap of the material produces fluorescence. Here, the co-doping produces states in the band gap of the NaYF$_4$ such that the Yb$^{3+}$ ion has an energy state at $^2F_{5/2}$ pumpable by a single photon event and from which other single photon absorption events can populate even higher states. Once in this exited state, transitions to higher energy radiative states are possible, from which light emission will be at a higher energy than that of the incident light pumping the $^2F_{5/2}$ energy state. In other words, the energy state at $^2F_{5/2}$ of the $Yb^{3+}$ ion is the state that absorbs 980 nm light permitting a population build up serving as the basis for the transitions to the higher energy states such as the $^4F_{7/2}$ energy state. Here, transitions from the $^4F_{7/2}$ energy state produce visible emissions.

U.S. Pat. No. 7,008,559 (the entire contents of which are incorporated herein by reference) describes the upconversion performance of ZnS where excitation at 767 nm produces emission in the visible range. The materials described in U.S. Pat. No. 7,008,559 (including the ZnS as well as $Er^{3+}$ doped $BaTiO_3$ nanoparticles and $Yb^{3+}$ doped $CsMnCl_3$) are suitable in various embodiments of the invention with or without the energy augmentators.

Further, materials specified for up conversion materials in the invention (with or without energy augmentation) include CdTe, CdSe, ZnO, CdS, $Y_2O_3$, MgS, CaS, SrS and BaS. Such up conversion materials may be any semiconductor and more specifically, but not by way of limitation, sulfide, telluride, selenide, and oxide semiconductors and their nanoparticles, such as $Zn_{1-x}Mn_xS_y$, $Zn_{1-x}Mn_xSe_y$, $Zn_{1-x}Mn_xTe_y$, $Cd_{1-x}MnS_y$, $Cd_{1-x}Mn_xSe_y$, $Cd_{1-x}Mn_xTe_y$, $Pb_{1-x}Mn_xS_y$, $Pb_{1-x}Mn_xSe_y$, $Pb_{1-x}Mn_xTe_y$, $Mg_{1-x}MnS_y$, $Ca_{1-x}Mn_xS_y$, $Ba_{1-x}Mn_xS_y$, and $Sr_{1-x}$, etc. (wherein, $0<x\le1$, and $0<y\le1$). Complex compounds of the above-described semiconductors are also contemplated for use in the invention—e.g. $(M_{1-z}N_z)_{1-x}Mn_xA_{1-y}B_y$ (M=Zn, Cd, Pb, Ca, Ba, Sr, Mg; N=Zn, Cd, Pb, Ca, Ba, Sr, Mg; A=S, Se, Te, O; B=S, Se, Te, O; $0<x\le1$, $0<y\le1$, $0<z\le1$). Two examples of such complex compounds are $Zn_{0.4}Cd_{0.4}Mn_{0.2}S$ and $Zn_{0.9}Mn_{0.1}S_{0.8}Se_{0.2}$. Additional conversion materials include insulating and non-conducting materials such as $BaF_2$, BaFBr, and $BaTiO_3$, to name but a few exemplary compounds. Transition and rare earth ion co-doped semiconductors suitable for the invention include sulfide, telluride, selenide and oxide semiconductors and their nanoparticles, such as ZnS; Mn; Er; ZnSe; Mn, Er; MgS; Mn, Er; CaS; Mn, Er; ZnS; Mn, Yb; ZnSe; Mn,Yb; MgS; Mn, Yb; CaS; Mn,Yb etc., and their complex compounds: $(M_{1-z}N_z)_{1-x}(Mn_qR_{1-q})_xA_{1-y}B_y$ (M=Zn, Cd, Pb, Ca, Ba, Sr, Mg; N=Zn, Cd, Pb, Ca, Ba, Sr, Mg; A=S, Se, Te, O; B=S, ... $0<z\le1$, $o<q\le1$).

Some nanoparticles such as $ZnS:Tb^{3+}$, $Er^{3+}$; $ZnS:Tb^{3+}$; $Y_2O_3:Tb^{3+}$; $Y_2O_3:Tb^{3+}$, Er3+; $ZnS:Mn^{2+}$; $ZnS:Mn,Er^{3+}$ are known in the art to function for both down-conversion luminescence and upconversion luminescence and would be suitable for the invention with or without energy augmentators. In up-conversion embodiments, light emitting particles which emit red light may include praseodymium, light emitting particles which emit green light may include erbium, and light emitting particles which emit blue light may include thulium.

In general, the upconversion process generally requires one of more rare-earth dopants, such as Er, Eu, Yb, Tm, Nd, Tb, Ce, Y, U, Pr, La, Gd and other rare-earth species or a combination thereof, doped into a dielectric crystal (of any size>0.1 nm), including at least one of $Y_2O_3$, $Y_2O_2S$, $NaYF_4$, $NaYbF_4$, YAG, YAP, $Nd_2O_3$, $LaF_3$, $LaCl_3$, $La_2O_3$, $TiO_2$, $LuPO_4$, $YVO_4$, $YbF_3$, $YF_3$, Na-doped $YbF_3$, or $SiO_2$, where incident radiation is at longer wavelength than emissive radiation from the crystal. The wavelength emitted in based entirely on the dopant ion(s) chosen and their associated and relative concentration in the host crystal. For the example of upconversion in a $Y_2O_3$ host crystal, to achieve a blue emission (~450-480 nm) one could synthesize [$Y_2O_3$; Yb (3%), Tm (0.2%)], where the Yb and Tm are the percentages doped in the crystal relative to the Y atoms being 100%. Likewise, typical green upconversion materials are [$Y_2O_3$; Yb (5%), Ho (1%)] and [$Y_2O_3$; Yb (2%), Er (1%)], and typical red upconversion materials are [$Y_2O_3$; Yb (10%), Er (1%)] and [$Y_2O_3$; Yb (5%), Eu (1%)]. The concentrations of dopants relative to each other and the crystal matrix must be tuned for every combination, and there are multiple ways to achieve multiple wavelength or energy emissions from even the same dopants.

Up-conversion of red light with a wavelength of about 650 nm in $Tm^{3+}$ doped flourozirconate glasses can be used in the invention to produce blue light. In this system, the blue light consists of two emission bands; one at 450 nm which is ascribed to the 1D2→3H4 transition, the others at 475 nm is ascribed to the 1G4→3H6 transition. The emission intensities of both bands have been observed by others to vary quadratically with the excitation power. For glasses with a $Tm^{3+}$ concentration of 0.2 mol % and greater, cross-relaxation processes occur which decrease the up-conversion efficiency.

The emission of visible light upon excitation in the near-infrared (NIR) has been observed in optically clear colloidal solutions of $LuPO_4:Yb^{3+}$, $Tm^{3+}$, and $YbPO_4:Er^{3+}$ nanocrystals in chloroform. Excitation at 975 nm has been shown by others to produce visible emission in the blue, green, or red spectral regions.

Tellurium and germanium oxides (tellurites and germanates) are also suitable upconverters. These glasses can be doped with Tm, Yb, Ho, Er, Pr, for example.

$Yb^{3+}$ doped $BaZrO_3$ is also suitable for upconversion. $Er^{3+}$ and/or $Tm^{3+}$ doping are also suitable for tailoring the emission wavelengths.

In another embodiment, $Nd^{3+}:Cs_2NaGdCl_6$ and $Nd^{3+}$, $Yb^{3+}:Cs_2NaGdCl_6$ polycrystalline powder samples prepared by Morss method have been reported to be up converters and are suitable for the present invention. These materials, under 785 nm irradiation, have shown upconversion emissions near 538 nm (Green), 603 nm (Orange), and 675 nm (Red) were observed and assigned to 4G7/2→4I9/2, (4G7/2→4I11/2; 4G5/2→4I9/2), and (4G7/2→4I13/2; 4G5/2→4I11/2), respectively.

In another embodiment, $Nd^{3+}$ and $Ho^{3+}$ co-doped-based $ZrF_4$ fluoride glasses under 800 nm excitation have been reported to be up converters and are suitable for the present invention. Among the up-conversion luminescences for the $ZrF_4$ fluoride glasses, the green emission was seen to be extremely strong and the blue and red emission intensities were very weak.

In another embodiment, $Tm^{3+}/Yb^{3+}$-codoped $TeO_2$—$Ga_2O_3$—$R_2O$ (R=Li, Na, K) glasses have been reported to be up converters and are suitable for the present invention. These materials, under excitation at 977 nm, showed intense blue upconversion emission centered at 476 nm along with a weak red emission at 650 nm.

In another embodiment, metal-to-ligand charge transfer (MLCT) transition in $[Ru(dmb)_3]^{2+}$ (dmb=4,4'-dimethyl-2,2'-bipyridine) in the presence of anthracene or 9,10-diphenylanthracene have been reported to be up converters and are suitable for the present invention. Upconverted singlet fluorescence resulting from triplet-triplet annihilation at low excitation power has been reported. In particular 9,10-diphenylanthracene (DPA) (substituted for anthracene) showed higher efficiencies for upconversion. In these experiments, workers with this material system assumed that DPA's increased singlet fluorescence quantum yield (=0.95)

relative to anthracene (=0.27)7. This work lead to an approximate 24.4±6.1 enhancement of green-to-blue light upconversion permitting direct visualization of the process at low excitation power, for example by a commercial green laser pointer ($\lambda_{ex}$=532 nm, <5 mW peak power).

In certain embodiments, further energy converters include, but are not limited to, (not ranked by order of preference or utility):

$CaF_2$, $ZnF_2$, $KMgF_3$, $ZnGa_2O_4$, $ZnAl_2O_4$, $Zn_2SiO_4$, $Zn_2GeO_4$, $Ca_5(PO_4)_3F$, $Sr_5(PO_4)_3F$, $CaSiO_3$, $MgSiO_3$, ZnS, $MgGa_2O_4$, $LaAl_{11}O_{18}$, $Zn_2SiO_4$, $Ca_5(PO_4)_3F$, $Mg_4Ta_2O_9$, $CaF_2$, $LiAl_5O_8$, $LiAlO_2$, $CaPO_3$, $AlF_3$, and $LuPO_4:Pr^{3+}$. Examples further include the alkali earth chalcogenide phosphors which are in turn exemplified by the following non-inclusive list: $MgS:Eu^{3+}$, $CaS:Mn^{2+}$, CaS:Cu, CaS:Sb, $CaS:Ce^{3+}$, $CaS:Eu^{2+}$, $CaS:Eu^{2+}Ce^{3+}$, $CaS:Sm^{3+}$, $CaS:Pb^{2+}$, $CaO:Mn^{2+}$, $CaO:Pb^{2+}$.

Further examples include the ZnS type phosphors that encompass various derivatives: ZnS:Cu,Al(Cl), ZnS:Cl(Al), ZnS:Cu,I(Cl), ZnS:Cu, ZnS:Cu,In.

Also included are the compound IIIb-Vb phosphors which include the group IIIb and Vb elements of the periodic table. These semiconductors include BN, BP, BSb, AlN, AlP, AlAs, AlSb, GaN, GaP, GaAs, GaSb, InN, InP, InAs, InSb and these materials may include donors and acceptors that work together to induce light emission diodes. These donors include, but are not limited to, Li, Sn, Si, Li, Te, Se, S, O and acceptors include, but are not limited to, C, Be, Mg, Zn, Cd, Si, Ge. Further included are the major GaP light emitting diodes which include, but are not limited to, GaP:Zn,O, GaP:NN, Gap:N and GaP, which emit colors Red, Yellow, Green and Pure Green respectively.

The materials can further include such materials as GaAs with compositional variation of the following sort: $In_{1-y}(Ga_{1-x}Al_x)_yP$.

Also included is silicon carbide SiC, which has commercial relevancy as a luminescent platform in blue light emitting diodes. These include the polytypes 3C—SiC, 6H—SiC, 4H—SiC with donors such as N and Al and acceptors such as Ga and B.

Further examples include multiband luminescent materials include, but not limited to, the following compositions $(Sr, Ca, Ba)_5(PO_4)_3Cl:Eu^{2+}$, $BaMg_2Al_{16}O_{27}:Eu^{2+}$, $CeMgAl_{11}O_{19}:Ce^{3+}:Tb^{3+}$, $LaPO_4:Ce^{3+}:Tb^{3+}$, $GdMgB_5O_{10}:Ce_3:Tb^{3+}$, $Y_2O_3:Eu^{3+}$, $(Ba,Ca,Mg)_5(PO_4)_3Cl:Eu^{2+}$, $2SrO_{0.84}P2O50.16B2O3:Eu^{2+}$, $Sr_4Al_{14}O_{25}:Eu^{2+}$.

Materials typically used for fluorescent high pressure mercury discharge lamps are also included. These can be excited with X-Ray and are exemplified by way of family designation as follows: Phosphates $(Sr, M)(PO_4)_2:Sn^{2+}$, Mg or Zn activator, Germanate $4MgO \cdot GeO_2:Mn^{4+}$, $4(MgO, MgF_2)GeO_2:Mn^{4+}$, Yttrate $Y_2O_3:Eu^{3+}$, Vanadate $YVO_4:Eu^{3+}$, $Y(P,V)O_4:Eu^{3+}$, $Y(P,V)O_4:In^+$, Halo-Silicate $Sr_2Si_3O_{82}SrCl_2:Eu^{2+}$, Aluminate $(Ba,Mg)_2Al_{16}O_{24}:Eu^{2+}$, $(Ba, Mg)_2Al_{16}O_{24}:Eu^{2+},Mn^{2+}$, $Y_2O_3Al_2O_3:Tb^{3+}$.

Another grouping by host compound includes chemical compositions in the halophosphates phosphors, phosphate phosphors, silicate phosphors, aluminate phosphors, borate phosphors, tungstate phosphors, and other phosphors. The halophosphates include, but are not limited to: $3Ca_3(PO_4)_2 \cdot Ca(F,Cl)_2:Sb^{3+}$, $3Ca_3(PO_4)_2 \cdot Ca(F,Cl)_2:Sb^{3+}/Mn^{2+}$, $Sr_{10}(PO_4)_6Cl_2:Eu^{2+}$, $(Sr,Ca)_{10}(PO_4)_6Cl_2:Eu^{2+}$, $(Sr,Ca)_{10}(PO_4)_6 \cdot nB_2O_3:Eu^{3+}$, $(Sr, Ca,Mg)_{10}(PO_4)_6Cl_2:Eu^{2+}$. The phosphate phosphors include, but are not limited to: $Sr_2P_2O_7:Sn^{2+}$, $(Sr,Mg)_3(PO_4)_2:Sn^{2+}$, $Ca_3(PO_4)_2:Sn^{2+}$, $Ca_3(PO_4)_2:Tl^+$, $(Ca,Zn)_3(PO_4)_2:Tl^+$, $Sr_2P_2O_7:Eu^{2+}$, $SrMgP_2O_7:Eu^{2+}$, $Sr_3(PO_4)_2:Eu^{2+}$, $LaPO_4:Ce^{3+}$, $Tb^{3+}$, $La_2O_3 \cdot 0.2SiO_2 \cdot 0.9P_2O_5:Ce^{3+} \cdot Tb^{3+}$, $BaO \cdot TiO_2 \cdot P_2O_5$. The silicate phosphors $Zn_2SiO_4:Mn^{2+}$, $CaSiO_3:Pb^{2+}/Mn^{2+}$, $(Ba, Sr, Mg) \cdot 3Si_2O_7:Pb^{2+}$, $BaSi_2O_5:Pb^{2+}$, $Sr_2Si_3O_8 \cdot 2SrCl_2:Eu^{2+}$, $Ba_3MgSi_2O_8:Eu^{2+}$, $(Sr,Ba)Al_2Si_2O_8:Eu^{2+}$.

The aluminate phosphors include, but are not limited to: $LiAlO_2:Fe^{3+}$, $BaAl_8O_{13}:Eu^{2+}$, $BaMg_2Al_{16}O_{27}:Eu^{2+}$, $BaMg_2Al_{16}O_{27}:Eu^{2+}/Mn^{2+}$, $Sr_4Al_{14}O_{25}:Eu^{2+}$, $CeMgAl_{11}O_{19}:Ce^{3+}/Tb^{3+}$.

The borate phosphors include: $Cd_2B_2O_5:Mn^{2+}$, $SrB_4O_7F:Eu^{2+}$, $GdMgB_5O_{10}:Ce^{3+}/Tb^{3+}$, $GdMgB_5O_{10}:Ce^{3+}/Mn^{3+}$, $GdMgB_5O_{10}:Ce^{3+}/Tb^{3+}/Mn^{2+}$.

The tungstate phosphors include, but are not limited to: $CaWO_4$, $(Ca,Pb)WO_4$, $MgWO_4$. Other phosphors $Y_2O_3:Eu^{3+}$, $Y(V,P)O_4:Eu^{2+}$, $YVO_4:Dy^{3+}$, $MgGa_2O_4:Mn^{2+}$, $6MgO \cdot As_2O_5:Mn^{2+}$, $3.5MgO \cdot 0.5MgF_2 \cdot GeO_2:Mn^{4+}$.

The activators to the various doped phosphors include, but are not limited to: $Tl^+$, $Pb^{2+}$, $Ce^{3+}$, $Eu^{2+}$, $WO_4^{2-}$, $Sn^{2+}$, $Sb^{3+}$, $Mn^{2+}$, $Tb^{3+}$, $Eu^{3+}$, $Mn^{4+}$, $Fe^{3+}$. The luminescence center $Tl^+$ is used with a chemical composition such as: $(Ca,Zn)_3(PO_4)_2:Tl^+$, $Ca_3(PO_4)_2:Tl^+$. The luminescence center $Mn^{2+}$ is used with chemical compositions such as $MgGa_2O_4:Mn^{2+}$, $BaMg_2Al_{16}O_{27}:Eu^{2+}/Mn^{2+}$, $Zn_2SiO_4:Mn^{2+}$, $3Ca_3(PO_4)_2 \cdot Ca(F,Cl)_2:Sb^{2+}/Mn^{2+}$, $CaSiO_3:Pb^{2+}/Mn^{2+}$, $Cd_2B_2O_5:Mn^{2+}$, $CdB_2O_5:Mn^{2+}$, $GdMgB_5O_{10}:Ce^{3+}/Mn^{2+}$, $GdMgB_5O_{10}:Ce^{3+}/Tb^{3+}/Mn^{2+}$. The luminescence center Sn2+ is used with chemical compositions such as: $Sr_2P_2O_7:Sn^{2+}$, $(Sr,Mg)_3(PO_4)_2:Sn^{2+}$. The luminescence center $Eu^{2+}$ is used with chemical compositions such as: $SrB_4O_7F:Eu^{2+}$, $(Sr,Ba)Al_2Si_2O_8:Eu^{2+}$, $Sr_3(PO_4)_2:Eu^{2+}$, $Sr_2P_2O_7:Eu^{2+}$, $Ba_3MgSi_2O_8:Eu^{2+}$, $Sr_{10}(PO_4)_6Cl_2:Eu^{2+}$, $BaMg_2Al_{16}O_{27}:Eu^{2+}/Mn^{2+}$, $(Sr,Ca)_{10}(PO_4)_6Cl_2:Eu^{2+}$. The luminescence center $Pb^{2+}$ is used with chemical compositions such as: $(Ba,Mg,Zn)_3Si_2O_7:Pb^{2+}$, $BaSi_2O_5:Pb^{2+}$, $(Ba,Sr)_3Si_2O_7:Pb^{2+}$.

The luminescence center $Sb^{2+}$ is used with chemical compositions such as: $3Ca_3(PO_4)_2 \cdot Ca(F,Cl)_2:Sb^{3+}$, $3Ca_3(PO_4)_2 \cdot Ca(F,Cl)_2:Sb^{3+}/Mn^{2+}$.

The luminescence center $Tb^{3+}$ is used with chemical compositions such as: $CeMgAl_{11}O_{19}:Ce^{3+}/Tb^{3+}$, $LaPO_4:Ce^{3+}/Tb^{3+}$, $Y_2SiO_5:Ce^{3+}/Tb^{3+}$, $GdMgB_5O_{10}:Ce^{3+}/Tb^{3+}$. The luminescence center $Eu^{3+}$ is used with chemical compositions such as: $Y_2O_3:Eu^{3+}$, $Y(V,P)O_4:Eu^{3+}$. The luminescence center $Dy^{3+}$ is used with chemical compositions such as: $YVO_4:Dy^{3+}$. The luminescence center $Fe^{3+}$ is used with chemical compositions such as: $LiAlO_2:Fe^{3+}$. The luminescence center $Mn^{4+}$ is used with chemical compositions such as: $6MgO \cdot As_2O_5:Mn^{4+}$, $3.5MgO0.5MgF_2 \cdot GeO_2:Mn^{4+}$. The luminescence center $Ce^{3+}$ is used with chemical compositions such as: $Ca_2MgSi_2O_7:Ce^{3+}$ and $Y_2SiO_5:Ce^{3+}$. The luminescence center $WO_4^{2-}$ is used with chemical compositions such as: $CaWO_4$, $(Ca,Pb)WO_4$, $MgWO_4$. The luminescence center $TiO_4^{4-}$ is used with chemical compositions such as: $BaO \cdot TiO_2 \cdot P_2O_5$.

Additional phosphor chemistries of interest using X-Ray excitations include, but are not limited to, the k-edge of these phosphors. Low energy excitation can lead to intense luminescence in materials with low k-edge. Some of these chemistries and the corresponding k-edge are listed below:

| | |
|---|---|
| $BaFCl:Eu^{2+}$ | 37.38 keV |
| $BaSO_4:Eu^{2+}$ | 37.38 keV |
| $CaWO_4$ | 69.48 keV |
| $Gd_2O_2S:Tb^{3+}$ | 50.22 keV |
| $LaOBr:Tb^{3+}$ | 38.92 keV |
| $LaOBr:Tm^{3+}$ | 38.92 keV |
| $La_2O_2S:Tb^{3+}$ | 38.92 keV |

-continued

| | |
|---|---|
| $Y_2O_2S:Tb^{3+}$ | 17.04 keV |
| $YTaO_4$ | 67.42 keV |
| $YTaO_4:Nb$ | 67.42 keV |
| ZnS:Ag | 9.66 keV |
| (Zn, Cd)S:Ag | 9.66/26.7 keV |

These materials can be used alone or in combinations of two or more. A variety of compositions can be prepared to obtain the desired output wavelength or spectrum of wavelengths.

In the present invention, the phosphor selection could be chosen such that under x-ray or other high energy source irradiation, the light emitted from the phosphors could, for example, have exemplary characteristics including:

Emissions in 190-250 nm wavelength range;
Emissions in the 330-340 nm wavelength range.

Mechanoluminescent Materials (Organic and Inorganic):

In another embodiment of the invention, mechano-luminescent materials can be used as energy converters and optionally can be used with the energy augmentation structures described above.

Mechano-luminescent materials convert ultrasonic or mechanical energy (such as vibrations naturally existing on an article such as motor or vibrations from driven by transducers) into visible light. Here, for example, the mechano-luminescent materials would be placed in a vicinity (e.g., between or around or inside) the folded structures or the external-electrode pairs.

In one embodiment, an electromagnetic wave energy augmentator captures one or more wavelengths of electromagnetic energy, and augments the one or more wavelengths of electromagnetic energy in at least one property (such as electric field intensity in a vicinity of the mechano-luminescent materials), while at the same time the mechano-luminescent materials can be considered an energy converter converting the ultrasonic or mechanical energy into electromagnetic radiation (i.e., emitted light).

In one embodiment of the invention, the increased electric field in the folded structure or the external electrode pair increases the luminescence of the mechano-luminescent materials. The energy used to build the electric field in the folded structure or the external electrode pair being provided separately from the mechanical energy driving the mechano-luminescence.

Various mechano-luminescent materials suitable for the present invention with or without energy augmentators include $ZnS:Mn^{2+}$, $SrAl_2O_4:Eu^{2+}$, ZnS:Cu, $SrAMgSi_2O_7$: $Eu^{2+}$ (A=Ca, Sr, Ba), KCl, KI, KBr, NaF, NaCl, LiF, RbCl, RbBr, RbI, MgO, $SrAl_2O_4$, $CaAl_2O_4$, $Sr_{1-x}Ba_xAl_2O_4$ (x=0, 0.1, 0.2, 0.4), $Sr_{0.9}Ca_{0.1}Al_2O_4$, $Zn_2Ge_{0.9}Si_{0.1}O_4$, $MgGa_2O_4$, $ZnGa_2O_4$, $ZnAl_2O_4$, ZnS, ZnTe, $(ZnS)_{1-x}(MnTe)_x$ (x<¼), CaZnOS, BaZnOS, $Ca_2MgSi_2O_7$, $Sr_2MgSi_2O_7$, $Ba_2MgSi_2O_7$, $SrCaMgSi_2O_7$, $SrBaMgSi_2O_7$, $Sr_nMgSi_2O_{5+n}$ (1≤n≤2), $Ca_2Al_2SiO_7$, $Sr_2Al_2SiO_7$, $CaYAl_3O_7$, $CaAl_2Si_2O$, $Ca_{1-x}Sr_xAl_2Si_2O_8$(x<0.8), $SrMg_2(PO_4)_2$, $Ba_{1-x}Ca_xTiO_3$ (0.25<x<0.8), $Ba_{1-x}Ca_xTiO_3$, $LiNbO_3$, $Sr_2SnO_4$, (Ca, Sr, Ba)$_2SnO_4$, $Sr_3Sn_2O_7$, $Sr_3(Sn, Si)_2O_7$, $Sr_3(Sn, Ge)_2O_7$, $Ca_3Ti_2O_7$, $CaNb_2O_6$, $Ca_2Nb_2O_7$, $Ca_3Nb_2O$, $BaSi_2O_2N_2$, $SrSi_2O_2N_2$, $CaZr(PO_4)_2$, $ZrO_2$.

In one embodiment, a europium-holmium co-doped strontium aluminate can be used as a mechano-luminescent material (i.e., an energy converter) alone or in conjunction with the energy augmentators. The europium-holmium co-doped strontium aluminate and the other mechano-luminescent materials convert sonic or acoustic energy into photon emissions which may or may not be placed in a vicinity of the energy augmentators.

Yanim Jia, in "Novel Mechano-Luminescent Sensors Based on Piezoelectric/Electroluminescent Composites," Sensors (Basel). 2011; 11(4): 3962-396, the entire contents of which are incorporated by reference, describes a mechanoluminescent composite made of a piezoelectric material and an electroluminescent material. In this composite device, when a stress is applied to the piezoelectric layer, electrical charges will be induced at both the top and bottom faces of piezoelectric layer due to the piezoelectric effect. These induced electrical charges will result in a light output from the electroluminescent layer due to the electroluminescent effect.

Here, in one embodiment of the present invention with or without energy augmentators, such composites made of a piezoelectric material and an electroluminescent material, hereinafter "composite mechano-luminescent emitters," provides a structure that, upon stimulation with mechanical or vibrational energy such as from an acoustic or ultrasonic transducer, emit light.

Electroluminescent and phosphorescent materials (organic and inorganic): The present invention in various embodiments can utilize organic fluorescent molecules or inorganic particles capable or fluorescence and phosphorescence having crystalline, polycrystalline or amorphous micro-structures for the converters (optionally including the energy augmentation structures described above).

The list of inorganic molecules that can be used with or without energy augmentators for the electroluminescence and phosphorescent materials described below include but is not limited to the following inorganic electroluminescent phosphor materials:

$SrS:Ce^{3+}$
$CaGa_2S_4:Ce^{3+}$
$SrS:Cu^+$
$CaS:Pb^{2+}$
$BaAl_2S_4:Eu^{2+}$
$ZnS:Tb^{3+}$
$ZnMgS:Mn^{2+}$
$SrGa_2S_4:Eu^{2+}$
$CaAl_2S_4:Eu^{2+}$
$BaAl_2S_4:Eu^{2+}$
$ZnS:Mn^{2+}$
$MgGa_2O_4:Eu^{3+}$
(Ca, Sr)$Y_2S_4:Eu^{2+}$
$BaAl_2S_4:Eu^{2+}$

Organic molecules that can phosphoresce under the influence of an electric field are also of interest in the present application. The organic fluorescent compounds with high quantum yield include by way of illustration:

Naphthalene,
Pyrene,
Perylene,
Anthracene,
Phenanthrene,
p-Terphenyl,
p-Quartphenyl,
Trans-stilbene,
Tetraphenylbutadiene,
Distyrylbenzene,
2,5-Diphenyloxazole,
4-Methyl-7-diethylaminocoumarin,
2-Phenyl-5-(4-biphenyl)-1,3,4-oxadiazole, 3-Phenylcarbostyryl,
1,3,5-Triphenyl-2-pyrazoline,
1,8-Naphthoylene-1',2'-bezimidazole,
4-Amino-N-phenyl-naphthalimide.

The inorganic fluorescent and phosphorescent materials detailed here are numerous, and various examples are given by way of illustration rather than limitation and can be used with or without energy augmentators. Furthermore, these materials can be doped with specific ions (activators or a combination of activators) that occupy a site in the lattice structure in the case of crystalline or polycrystalline materials and could occupy a network forming site or a bridging and/or non-bridging site in amorphous materials. These compounds could include (not ranked by order of preference or utility) the following material examples:

$CaF_2$, $ZnF_2$, $KMgF_3$, $ZnGa_2O_4$, $ZnAl_2O_4$, $Zn_2SiO_4$, $Zn_2GeO_4$, $Ca_5(PO_4)_3F$, $Sr_5(PO_4)_3F$, $CaSiO_3$, $MgSiO_3$, ZnS, $MgGa_2O_4$, $LaAl_{11}O_{18}$, $Zn_2SiO_4$, $Ca_5(PO_4)_3F$, $Mg_4Ta_2O_9$, $CaF_2$, $LiAl_5O_8$, $LiAlO_2$, $CaPO_3$, $AlF_3$.

Further included are alkali earth chalcogenide phosphors which are in turn exemplified by the following non-inclusive list:

MgS:$Eu^{3+}$, CaS:$Mn^{2+}$, CaS:Cu, CaS:Sb, CaS:$Ce^{3+}$, CaS: $Eu^{2+}$, CaS: $Eu^{2+}Ce^{3+}$, CaS: $Sm^{3+}$, CaS:$Pb^{2+}$, CaO: $Mn^{2+}$, CaO:$Pb^{2+}$.

The examples include the ZnS type phosphors that encompass various derivatives:

ZnS:Cu,Al(Cl), ZnS:Cl(Al), ZnS:Cu,I(Cl), ZnS:Cu, ZnS:Cu,In.

Compound IIIb-Vb phosphors which include the group IIIb and Vb elements of the periodic table are suitable for converter materials. These semiconductors include BN, BP, BSb, AlN, AlP, AlAs, AlSb, GaN, GaP, GaAs, GaSb, InN, InP, InAs, InSb and these materials have donors and acceptors that work in together to induce light emission diodes. The donors include Li, Sn, Si, Li, Te, Se, S, O, and acceptors include C, Be, Mg, Zn, Cd, Si, Ge. As an example, GaP light emitting diodes include GaP:Zn, O, GaP:NN, Gap:N and GaP which emit colors Red, Yellow, Green and Pure Green respectively.

The compounded materials further include such materials as GaAs with compositional variation of the following sort: In1−y(Ga1−xAlx)yP (provides a simple example). Silicon Carbide SiC as a luminescent platform has commercial relevancy if the blue light emitting diodes. These include the polytypes 3C—SiC, 6H—SiC, 4H—SiC with donors such as N and Al and acceptors such as Ga and B.

Multiband luminescent materials suitable for converter materials include for example the following compositions:

(Sr, Ca, Ba)$_5$(PO$_4$)$_3$Cl:$Eu^{2+}$, $BaMg_2Al_{16}O_{27}$:$Eu^{2+}$, $CeMgAl_{11}O_{19}$:$Ce^{3+}$:$Tb^{3+}$, $LaPO_4$:$Ce^{3+}$:$Tb^{3+}$, $GdMgB_5O_{10}$:$Ce^{3+}$:$Tb^{3+}$, $Y_2O_3$:$Eu^{3+}$, (Ba,Ca,Mg)$_5$(PO$_4$)$_3$Cl:$Eu^{2+}$, $2SrO_{0.84}P_2O_5 \cdot 0.16B_2O_3$:$Eu^{2+}$, $Sr_4Al_{14}O_{25}$:$Eu^{2+}$.

Other materials suitable for converter materials include those materials used for fluorescent high pressure mercury discharge lamps can be excited with X-Ray and are exemplified by way of family designation as follows:

Phosphates (Sr, M)(PO$_4$)$_2$:$Sn^{2+}$, Mg or Zn activator, Germanate $4MgO \cdot GeO_2$:$Mn^{4+}$, $4(MgO, MgF_2)GeO_2$:$Mn^{4+}$, Yttrate $Y_2O_3$:$Eu^{3+}$, Vanadate $YVO_4$:$Eu^{3+}$, Y(P,V)O$_4$:$Eu^{3+}$, Y(P,V)O$_4$:$In^+$, Halo-Silicate $Sr_2Si_3O_8 \cdot 2SrCl_2$:$Eu^{2+}$, Aluminate (Ba,Mg)$_2$Al$_{16}$O$_{24}$:$Eu^{2+}$, (Ba, Mg)$_2$Al$_{16}$O$_{24}$:$Eu^{2+}$,$Mn^{2+}$, $Y_2O_3Al_2O_3$:$Tb^{3+}$.

Another grouping of materials suitable for converter materials by host compound include chemical compositions in the Halophosphates phosphors, Phosphate phosphors, Silicate phosphors, Aluminate phosphors, Borate phosphors, Tungstate phosphors, and other phosphors.

The halophosphates include by way of illustration:

$3Ca_3(PO_4)_2 \cdot Ca(F,Cl)_2$:$Sb^{3+}$, $3Ca_3(PO_4)_2 \cdot Ca(F,Cl)_2$:$Sb^{3+}$/$Mn^{2+}$, $Sr_{10}(PO_4)_6Cl_2$:$Eu^{2+}$, (Sr,Ca)$_{10}$(PO$_4$)$_6$Cl$_2$:$Eu^{2+}$, (Sr,Ca)$_{10}$(PO$_4$)$_6 \cdot nB_2O_3$:$Eu^{3+}$, (Sr, Ca,Mg)$_{10}$(PO$_4$)$_6$Cl$_2$:$Eu^{2+}$. The phosphate phosphors include by way of illustration $Sr_2P_2O_7$:$Sn^{2+}$, $(Sr,Mg)_3(PO_4)_2$:$Sn^{2+}$, $Ca_3(PO_4)_2$:$Sn^{2+}$, $Ca_3(PO_4)_2$:$Tl^+$, $(Ca,Zn)_3(PO_4)_2$:$Tl^+$, $Sr_2P_2O_7$:$Eu^{2+}$, $SrMgP_2O_7$:$Eu^{2+}$, $Sr_3(PO_4)_2$:$Eu^{2+}$, $LaPO_4$:$Ce^{3+}$, $Tb^{3+}$, $La_2O_3 \cdot 0.2SiO_2 \cdot 0.9P_2O_5$:$Ce^{3+} \cdot Tb^{3+}$, $BaO \cdot TiO_2$—$P_2O_5$. The silicate phosphors $Zn_2SiO_4$:$Mn^{2+}$, $CaSiO_3$:$Pb^{2+}$/$Mn^{2+}$, (Ba, Sr, Mg)$\cdot 3Si_2O_7$:$Pb^{2+}$, $BaSi_2O_5$:$Pb^{2+}$, $Sr_2Si_3O_8 \cdot 2SrCl_2$:$Eu^{2+}$, $Ba_3MgSi_2O_8$:$Eu^{2+}$, (Sr,Ba)Al$_2$Si$_2$O$_8$:$Eu^{2+}$.

The aluminate phosphors include:

$LiAlO_2$:$Fe^{3+}$, $BaAl_8O_{13}$:$Eu^{2+}$, $BaMg_2Al_{16}O_{27}$:$Eu^{2+}$, $BaMg_2Al_{16}O_{27}$:$Eu^{2+}$/$Mn^{2+}$, $Sr_4Al_{14}O_{25}$:$Eu^{2+}$, $CeMgAl_{11}O_{19}$:$Ce^{3+}$/$Tb^{3+}$.

The borate phosphors include:

$Cd_2B_2O_5$:$Mn^{2+}$, $SrB_4O_7F$:$Eu^{2+}$, $GdMgB_5O_{10}$:$Ce^{3+}$/$Tb^{3+}$, $GdMgB_5O_{10}$:$Ce^{3+}$/$Mn^{3+}$, $GdMgB_5O_{10}$:$Ce^{3+}$/$Tb^{3+}$/$Mn^{2+}$.

The tungstate phosphors include:

$CaWO_4$, (Ca,Pb)WO$_4$, $MgWO_4$. Other phosphors $Y_2O_3$:$Eu^{3+}$, $Y(V,P)O_4$:$Eu^{2+}$, $YVO_4$:$Dy^{3+}$, $MgGa_2O_4$:$Mn^{2+}$, $6MgO \cdot As_2O_5$:$Mn^{2+}$, $3.5MgO \cdot 0.5MgF_2 \cdot GeO_2$:$Mn^{4+}$.

Activators of relevance to the various doped phosphors include the following list:

$Tl^+$, $Pb^{2+}$, $Ce^{3+}$, $Eu^{2+}$, $WO_4^{2-}$, $Sn^{2+}$, $Sb^{3+}$, $Mn^{2+}$, $Tb^{3+}$, $Eu^{3+}$, $Mn^{4+}$, $Fe^{3+}$.

In various embodiments, the luminescence center $Tl^+$ can be used with a chemical composition such as:

$(Ca,Zn)_3(PO_4)_2$:$Tl^+$, $Ca_3(PO_4)_2$:$Tl^+$.

Similarly, the luminescence center Mn2+ can be used with chemical compositions such as $MgGa_2O_4$:$Mn^{2+}$, $BaMg_2Al_{16}O_{27}$:$Eu^{2+}$/$Mn^{2+}$, $Zn_2SiO_4$:$Mn^{2+}$, $3Ca_3(PO_4)_2 \cdot Ca(F,Cl)_2$:$Sb^{2+}$/$Mn^{2+}$, $CaSiO_3$:$Pb^{2+}$/$Mn^{2+}$, $Cd_2B_2O_5$:$Mn^{2+}$, $CdB_2O_5$:$Mn^{2+}$, $GdMgB_5O_{10}$:$Ce^{3+}$/$Mn^{2+}$, $GdMgB_5O_{10}$:$Ce^{3+}$/$Tb^{3+}$/$Mn^{2+}$.

Further, the luminescence center $Sn^{2+}$ can be used with chemical compositions such as:

$Sr_2P_2O_7$:$Sn^{2+}$, $(Sr,Mg)_3(PO_4)_2$:$Sn^{2+}$.

The luminescence center $Eu^{2+}$ can also be used with chemical compositions such as:

$SrB_4O_7F$:$Eu^{2+}$, (Sr,Ba)Al$_2$Si$_2$O$_8$:$Eu^{2+}$, $Sr_3(PO_4)_2$:$Eu^{2+}$, $Sr_2P_2O_7$:$Eu^{2+}$, $Ba_3MgSi_2O_8$:$Eu^{2+}$, $Sr_{10}(PO_4)_6Cl_2$:$Eu^{2+}$, $BaMg_2Al_{16}O_{27}$:$Eu^{2+}$/$Mn^{2+}$, (Sr,Ca)$_{10}$(PO$_4$)$_6$Cl$_2$:$Eu^{2+}$.

The luminescence center $Pb^{2+}$ can be used with chemical compositions such as:

(Ba,Mg,Zn)$_3$Si$_2$O$_7$:$Pb^{2+}$, $BaSi_2O_5$:$Pb^{2+}$, (Ba,Sr)$_3$Si$_2$O$_7$:$Pb^{2+}$.

The luminescence center $Sb^{2+}$ can be used with chemical compositions such as:

$3Ca_3(PO_4)_2 \cdot Ca(F,Cl)_2$:$Sb^{3+}$, $3Ca_3(PO_4)_2 \cdot Ca(F,Cl)_2$:$Sb^{3+}$/$Mn^{2+}$.

The luminescence center Tb3+ can be used with chemical compositions such as:

$CeMgAl_{11}O_{19}$:$Ce^{3+}$/$Tb^{3+}$, $LaPO_4$:$Ce^{3+}$/$Tb^{3+}$, $Y_2SiO_5$:$Ce^{3+}$/$Tb^{3+}$, $GdMgB_5O_{10}$:$Ce^{3+}$/$Tb^{3+}$.

The luminescence center $Eu^{3+}$ can be used with chemical compositions such as:

$Y_2O_3$:$Eu^{3+}$, $Y(V,P)O_4$:$Eu^{3+}$.

The luminescence center $Dy^{3+}$ can be used with chemical compositions such as:

$YVO_4:Dy^{3+}$.

The luminescence center $Fe^{3+}$ can be used with chemical compositions such as:

$LiAlO_2:Fe^{3+}$.

The luminescence center $Mn^{4+}$ can be used with chemical compositions such as:

$6MgO \cdot As_2O_5:Mn^{4+}$, $3.5MgO \cdot 0.5MgF_2$—$GeO_2:Mn^{4+}$.

The luminescence center $Ce^{3+}$ can be used with chemical compositions such as:

$Ca_2MgSi_2O_7:Ce^{3+}$ and $Y_2SiO_5:Ce^{3+}$.

The luminescence center $WO_4^{2-}$ can be used with chemical compositions such as:

$CaWO_4$, $(Ca,Pb)WO_4$, $MgWO_4$.

The luminescence center $TiO_4^{4-}$ can be used with chemical compositions such as:

$BaO \cdot TiO_2 \cdot P_2O_5$.

In various embodiments of this invention, the phosphor chemistry utilized in x-ray excitations can be used with or without energy augmentators. Of particular interest is the k-edge of these phosphors. Low energy excitation can lead to intense luminescence in materials with low k-edge. Some of these chemistries and the corresponding k-edge are included as follows:

| | |
|---|---|
| $BaFCl:Eu^{2+}$ | 37.38 keV |
| $BaSO_4:Eu^{2+}$ | 37.38 keV |
| $CaWO_4$ | 69.48 keV |
| $Gd_2O_2S:Tb^{3+}$ | 50.22 keV |
| $LaOBr:Tb^{3+}$ | 38.92 keV |
| $LaOBr:Tm^{3+}$ | 38.92 keV |
| $La_2O_2S:Tb^{3+}$ | 38.92 keV |
| $Y_2O_2S:Tb^{3+}$ | 17.04 keV |
| $YTaO_4$ | 67.42 keV |
| $YTaO_4:Nb$ | 67.42 keV |
| ZnS:Ag | 9.66 keV |
| (Zn, Cd)S:Ag | 9.66/26.7 keV |

In one embodiment of this invention, light from these materials (excited for example by high energy particles including x-rays, gamma rays, protons, and electrons) can have their emissions modulated by having those materials included in a vicinity of (including inside) the color enhancing structures described herein. For example, in medical treatments where x-ray excites phosphorescence to photostimulate reactions in a patient, simultaneous with irradiation by the high energy particles, there could be applied infrared irradiation to drive resonance in the energy augmentation structures described herein, where the x-ray phosphors would have enhanced light emissions when in the presence of the intensified electric fields. In another example, in medical or scientific instruments, for simultaneous with irradiation by the high energy particles, there could be applied electric fields to enhance emissions from these x-ray phosphors.

Electro Luminescent Materials: Various materials used for the electroluminescence in the present invention with or without energy augmentators can include but are not limited to:

4,4',4"-Tris[phenyl(m-tolyl)amino]triphenylamine (m-MTDATA)

N,N'-Bis(3-methylphenyl)-N,N'-diphenylbenzidine (TPD)

4,4',4"-Tris[phenyl(m-tolyl)amino]triphenylamine (m-MTDATA)

N,N'-Bis(3-methylphenyl)-N,N'-diphenylbenzidine (TPD)

Tris-(8-hydroxyquinoline)aluminum 2,4,6-Tris(2-pyridyl)-s-triazine (TPT)

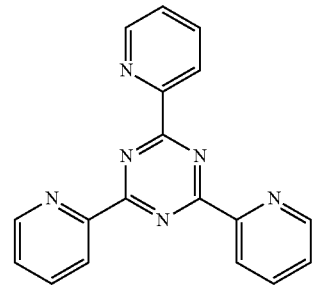 [SMILES: c1ccc(-c2nc(-c3ccccn3)nc(-c3ccccn3)n2)nc1]

2,2',2"-(1,3,5-Benzinetriyl)-tris(1-phenyl-1-H-benzimidazole) Alq

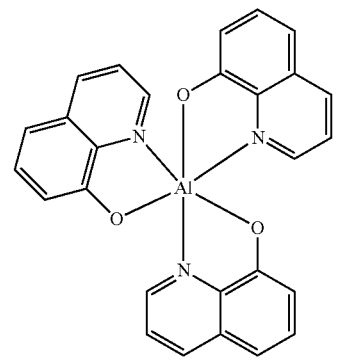

2,2',2"-(1,3,5-Benzinetriyl)-tris(1-phenyl-1-H-benzimidazole) TPBI

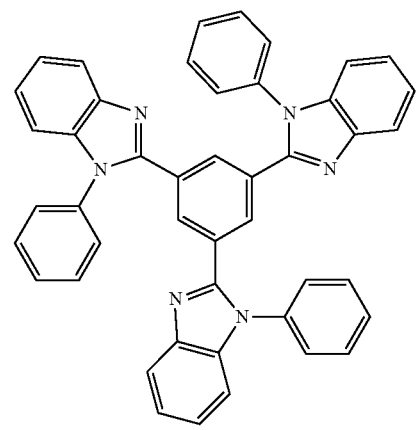 [SMILES: c1ccc(-n2c(-c3cc(-c4nc5ccccc5n4-c4ccccc4)cc(-c4nc5ccccc5n4-c4ccccc4)c3)nc3ccccc32)cc1]

2,9-Dimethyl-4,7-diphenyl-1,10-phenanthroline, BCP2,9-Dimethyl-4,7-diphenyl-1,10-phenanthroline, BCP

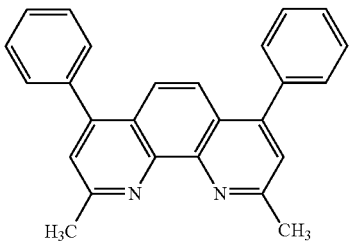 [SMILES: Cc1cc(-c2ccccc2)c2ccc3c(-c4ccccc4)cc(C)nc3c2n1]

Figure 26:
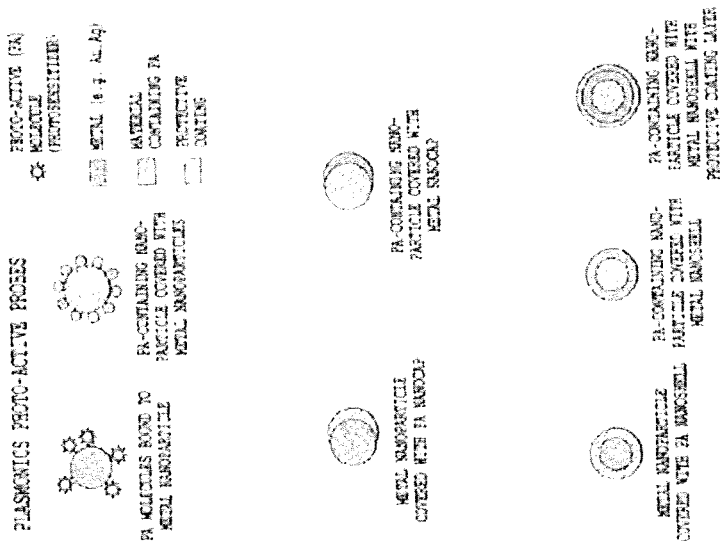
FIG. 26 is a schematic illustrating various converter structures of the invention.

Plasmonic enhancement structures: FIG. 26 is a schematic of a depiction of an upconverter or a down converter material (i.e., a photoactive material) according to one embodiment of the invention to be utilized in the color enhancement/augmentation structures noted herein with or without energy augmentators. FIG. 26 shows a number of structural configurations for placement of a dielectric core upconverter or a down converter material (which is of a nanometer sized scale) in proximity to a metal shell. Incident light at a wavelength $\lambda_1$ interacts with the upconverting dielectric core. The interaction of light $\lambda_1$ with the dielectric core produces a secondary emission at a frequency $\lambda_2$ which has a shorter wavelength than $\lambda_1$ and accordingly has a higher energy than $\lambda_1$. While the exact physical mechanisms for the upconversion may depend on the particular upconversion material and process being used in a particular application, for the purposes for discussion and illustration, the following explanation is offered.

In the context of FIG. 26, when a wavelength $\lambda_1$ interacts with a dielectric material core, three separate processes are well understood for the upconversion process involving trivalent rare earth ions. These three processes are:
1) excited state absorption whereby two photons are absorbed sequentially by the same ion to excite and populate one or more states;
2) energy transfer upconversion which is a transfer of excitation from one ion to another already in an excited state; and
3) a cooperative process of multiphotons where two nearby ions in excited states are emitting collectively from a virtual state.

Regardless of which one of these processes is occurring between the chosen ion(s) and the host lattice, the end result is a photon of energy greater than the excitation energy being emitted from the host lattice for the upconversion or down conversion process.

Therefore, the particular ion being activated (whether it be a dopant ion or a host ion of a lattice such as in the neodymium oxide) will be chosen based on the host material being processed, in order that the dopant ion or the host ion in the dielectric core provide ion states which are pumpable by a NIR source to generate the resultant emission $\lambda_2$.

Hence, the invention in one embodiment provides an upconversion or a down conversion material configured, upon exposure to a first wavelength $\lambda_1$ of radiation, to generate a second wavelength $\lambda_2$ of radiation having an energy higher or lower than the first wavelength $\lambda_1$. The system can include a metallic structure disposed in relation to the nanoparticle (e.g. a metallic shell covering a fraction of the nanoparticle). The system may include a receptor disposed in the medium in proximity to the nanoparticle. The receptor upon activation by the second wavelength $\lambda_2$ may itself fluoresce producing visible light. In one embodiment of the invention, a physical characteristic of metallic structure (such as those described above and below in the drawings) is set to a value where a surface plasmon resonance in the metallic structure resonates at a frequency which provides spectral overlap with either the first wavelength $\lambda_1$ or the second wavelength $\lambda_2$. This system with a metallic structure disposed in relation to an up-conversion or a down-conversion nanoparticle becomes the converter utilized in the color enhancement/augmentation structures noted herein.

Within the context of the invention, the term "physical characteristic" of the metallic shell or core can relate to any characteristic of the metal itself or the shell or core dimensions or shape which affects the surface plasmon resonance frequency. Such physical characteristics can include, but are not limited to, a conductivity, a radial dimension, a chemical composition or a crystalline state of the metal shell or core.

In various embodiments, the metallic structures can be a metallic shell encapsulating at least a fraction of the nanoparticle in the metallic shell wherein a conductivity, a radial dimension, or a crystalline state of the metallic shell sets the surface plasmon resonance in the metallic structure to resonate at a frequency which provides spectral overlap with either the first wavelength $\lambda_1$ or the second wavelength $\lambda_2$. In various embodiments, the metallic structures can be a multi-layer metallic shell encapsulating at least a fraction of the nanoparticle in the metallic shell wherein a conductivity, a radial dimension, or a crystalline state of the metallic shell sets the surface plasmon resonance in the metallic structure to resonate at the first wavelength k, and the second wavelength $\lambda_2$. This capability permits radiation at $\lambda_1$ and $\lambda_2$ to be amplified.

In various embodiments, the metallic structures can be a metallic particle existing in one or more multiple structures. These multiple structures can have a variety of shapes including for example sphere, spheroid, rod, cube, triangle, pyramid, pillar, crescent, tetrahedral shape, star or combination thereof disposed adjacent the nanoparticle wherein a conductivity, a dimension (e.g. a lateral dimension or a thickness), or a crystalline state of the metallic structure sets the surface plasmon resonance in the metallic particle or rod to resonate at a frequency which provides spectral overlap with either the first wavelength $\lambda_1$ or the second wavelength $\lambda_2$. Such shapes are described in the present figures and in the figures in U.S. Ser. No. 12/401,478 which is incorporated by reference in its entirety. The shape choice can affect the frequency of the surface plasmon resonance. It is known that the plasmon band is changed by the shape of nanoparticles (e.g., prolate and obloid spheroids). The paper "Spectral bounds on plasmon resonances for Ag and Au prolate and oblate nanospheroids," in the Journal of Nanophotonics, Vol. 2, 029501 (26 Sep. 2008), the entire contents of which are incorporated by reference, shows plasmon resonance shifts for shaping of Ag and plasmon resonance shifts for shaping of Au of prolate and obloid spheroids. In one embodiment of the invention, with an increasing aspect ratio for a metallic structure of the invention, the prolate spheroid resonance is red shifted relative to a sphere with no lower limit (under the assumptions of a Drude dispersion model). On the other hand, the oblate resonances are "blue shifted" as the spheroid becomes increasingly flat, but up to a limit.

In various embodiments, the metallic structures disposed in relation to an up-conversion or a down-conversion nanoparticle can be a metallic structure disposed interior to the nanoparticle wherein a conductivity or a dimension (e.g. a lateral dimension or a thickness) of the metallic structure sets the surface plasmon resonance in the metallic structure to resonate at a frequency which provides spectral overlap with either the first wavelength $\lambda_1$ or the second wavelength $\lambda_2$. In various embodiments, the metallic structures can be a metallic multi-layer structure disposed interior to the nanoparticle wherein a conductivity or a dimension (e.g. a lateral dimension or a thickness) of the metallic structure sets the surface plasmon resonance in the metallic structure to resonate at the first wavelength $\lambda_1$ and the second wavelength $\lambda_2$. This capability once again permits radiation at $\lambda_1$ and $\lambda_2$ to be amplified.

In another embodiment, the invention provides a nanoparticle structure including a sub 1000 nm dielectric core and a metallic structure disposed in relation to the nanoparticle. The dielectric core includes at least one of $Y_2O_3$, $Y_2O_2S$, $NaYF_4$, $NaYbF_4$, YAG, YAP, $Nd_2O_3$, $LaF_3$, $LaCl_3$, $La_2O_3$, $TiO_2$, $LuPO_4$, $YVO_4$, $YbF_3$, $YF_3$, Na-doped $YbF_3$, or $SiO_2$. Such nanoparticle structures can exhibit in certain embodiments surface plasmon resonance in the metallic structures to enhance upconversion of light from a first wavelength $\lambda_1$ to a second wavelength $\lambda_2$.

As described above, a shell (or other structure) is in particular designed with a layer thickness (or for example a lateral dimension) to enhance the photon upconversion process through plasmonic enhancement. The thickness of the shell (or other physical characteristic) is "tuned" in its thickness to the absorption process by having a dimension in which plasmons (i.e., electrons oscillations) in shell have a resonance in frequency which provides spectral overlap with the absorption band targeted. Thus, if the upconversion is to be stimulated by 980 nm NIR light, then the thickness of the shell is "tuned" in a thickness to where a plasmon resonance resonates at a frequency also of 980 nm (or in the neighborhood thereof as plasmon resonances are typically broad at these wavelengths).

Figure 27:
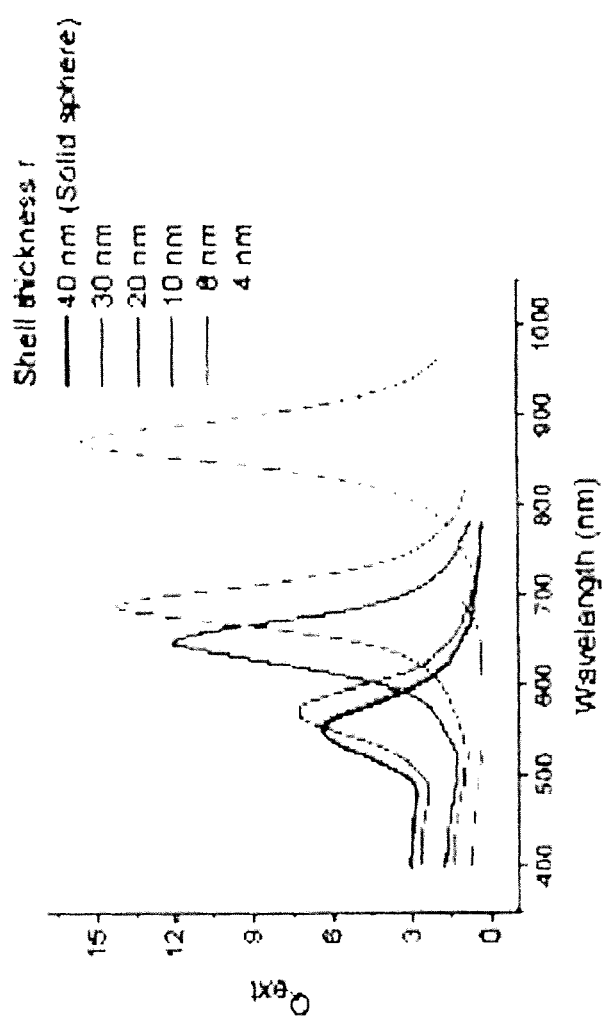
FIG. 27 is a schematic illustration of plasmon resonance as a function of shell thickness.

A plasmon resonating shell can be made of numerous transition metals, including though not limited to gold, silver, platinum, palladium, nickel, ruthenium, rhenium, copper, and cobalt or a combination or alloys or layers thereof. Such a plasmon resonating shell can be also made of a combination of metals and non-metals. When formed of a gold nanoshell, the recommended thickness to resonate with 980 nm light is approximately 3.5 nm surrounding an 80 nm upconverting core, as projected by extended Mie theory calculations. (See Jain et al., *Nanolett.* 2007, 7(9), 2854 the entire contents of which are incorporated herein by reference.) FIG. 27 is reproduced from Jain et al and illustrates the capability in the invention to "tune" the metal shell to have a spectral overlap with the excitation and/or emission radiation wavelengths.

In one embodiment of the invention, the metallic structures disposed in relation to an up-conversion or a down-conversion nanoparticle can be an alloy such as for example a Au:Ag alloy. The alloy content can be set to adjust the frequency of the surface plasmon resonance. In one embodiment of the invention, the metallic structures can be an alloy such as for example a Pt:Ag alloy. The alloy content can be set to adjust the frequency of the surface plasmon resonance. In one embodiment of the invention, the metallic structures can be an alloy such as for example a Pt:Au alloy. The alloy content can be set to adjust the frequency of the surface plasmon resonance.

In one embodiment of the invention, the converter nanoparticle can be an alloy of two or more materials. In this embodiment, the alloy can have a composition between the two or more materials which is set to a compositional value where excitation of the alloy at first wavelength $\lambda_1$ produces emission at the second wavelength $\lambda_2$. In one embodiment of the invention, the nanoparticle can be a zinc sulfide and zinc selenide alloy. In one embodiment of the invention, the nanoparticle can be a zinc sulfide and cadmium sulfide alloy.

In one embodiment of the invention, the zinc sulfide and zinc selenide nanoparticle alloy can have an alloy content set to provide a predetermined surface plasmon resonance. In one embodiment of the invention, the zinc sulfide and cadmium sulfide nanoparticle alloy can have an alloy content is set to provide a predetermined surface plasmon resonance.

Some techniques for producing nanoparticles and nanoparticle alloys which are suitable for the invention are described in the following documents, all of which are incorporated herein in their entirety: U.S. Pat. Nos. 7,645,318; 7,615,169; 7,468,146; 7,501,092; U.S. Pat. Appl. Publ. No. 2009/0315446; 2008/0277270; 2008/0277267; 2008/0277268; and WO 2009/133138.

In one embodiment of the invention, the thickness of the metal shell disposed in relation to an up-conversion or a down-conversion nanoparticle is set depending on the absorption frequency (or in some cases the emission frequency) of the particular dopant ions in the dielectric core to enhance the total efficiency of the emission process of the upconverted light. Accordingly, the thickness of the shell can be considered as a tool that in one instance enhances the absorption of $\lambda_1$, and in another instance can be considered as a tool that enhances the emission of $\lambda_2$, or in other situations can be considered an enhancement feature that in combination enhances the overall net process.

Additionally, plasmon-phonon coupling may be used to reduce a resonance frequency through the tuning of the bands to a degree off resonance. This may be useful in optimizing resonance energy transfer processes for the purpose of shifting the outputted color to a color desirable for a painted, colored, or displayed surface. In one example, FIG. 27 shows an example of the plasmon resonance shift as a function of shell thickness.

Here, in one embodiment of the invention, the capability to produce stimulated emission at a targeted wavelength or color or energy is complemented by the ability to design nanoparticles that have designed absorption bands. Such absorption materials could for example further serve to improve the monochromaticity of light observed from a paint, ink, dye, or otherwise reflecting surface treated with the color enhancing compositions of the invention.

Details of the preparation of this nanoparticle system are included in U.S. Ser. No. 12/725,108, the entire contents of which are incorporated herein by reference. The absorption spectrum of $Y_2O_3$ alone (lower trace) is fairly featureless, showing absorption due to the tri-arginine near 200 nm and a gentle slope associated with scattering and absorption by the $Y_2O_3$ nanoparticles extending into the visible portion of the spectrum. The gold-coated $Y_2O_3$ (upper trace), on the other hand, exhibit a strong absorption band at 546 nm, which is characteristic of the plasmonics resonance band due to the gold shell around the $Y_2O_3$ cores. The red-shifting of the plasmon absorption to 546 nm is consistent with the presence of a gold shell around a dielectric core.

In one embodiment of the invention, the converter materials for the upconverter dielectric core can include a wide variety of dielectric materials, as described above. In various embodiments of the invention, the upconverter dielectric core includes more specifically lanthanide doped oxide materials. Lanthanides include lanthanum (La), cerium (Ce), praseodymium (Pr), neodymium (Nd), promethium (Pm), samarium (Sm), europium (Eu), gadolinium (Gd), terbium (Tb), dysprosium (Dy), holmium (Ho), erbium (Er), thulium (Tm), ytterbium (Yb), and lutetium (Lu). Other suitable dielectric core materials include non-lanthanide elements such as yttrium (Y) and scandium (Sc). Hence, suitable dielectric core materials include $Y_2O_3$, $Y_2O_2S$, $NaYF_4$, $NaYbF_4$, Na-doped $YbF_3$, YAG, YAP, $Nd_2O_3$, $LaF_3$, $LaCl_3$, $La_2O_3$, $TiO_2$, $LuPO_4$, $YVO_4$, $YbF_3$, $YF_3$, or $SiO_2$. These dielectric cores can be doped with Er, Eu, Yb, Tm, Nd, Tb, Ce, Y, U, Pr, La, Gd and other rare-earth species or a combination thereof.

Lanthanides usually exist as trivalent cations, in which case their electronic configuration is (Xe) $4f^n$, with n varying from 1 ($Ce^{3+}$) to 14 ($Lu^{3+}$). The transitions within the f-manifold are responsible for many of the photo-physical properties of the lanthanide ions, such as long-lived luminescence and sharp absorption and emission lines. The f-electrons are shielded from external perturbations by filled 5s and 5p orbitals, thus giving rise to line-like spectra. The f-f electronic transitions are LaPorte forbidden, leading to long excited state lifetimes, in the micro- to millisecond range.

Accordingly, examples of doped materials in the invention include oxides such as yttrium oxide and neodymium oxide and aluminum oxide as well as sodium yttrium fluoride and nanocrystalline perovskites and garnets such as yttrium aluminum garnet (YAG) and yttrium aluminum perovskite (YAP). Of these materials, doping is required for some, but not all of these materials, for promoting upconversion efficiencies. In various embodiments of the invention, the host nanocrystals are doped with trivalent rare earth lanthanide ions from those lanthanide series elements given above.

More specifically, in various embodiments of the invention, pairs of these dopants are introduced in order to make accessible more energy states in the host crystal. The activation and pumping of these energy states follows closely the principles discussed above. Doping concentrations in the invention can range from 0.2% to 20% roughly per ion into the host lattice or in a weight or mol % variation. The efficiency of the upconversion processes of specific bands in these materials can be modulated by the percentages doped to induce and enhance targeted emissions. Lanthanide doped upconverters while not limited to, can use the following mol percent dopant compositions: 5% Er, 10% Yb, 0.2% Tm+3% Yb, and 1% Er+10% Yb.

The size of the nanocrystal will also have an effect on the efficiency of the upconversion process, as a larger nanocrystal will have more sites for dopant ions to be accommodated into the host lattice, therefore enabling more emissions from the same doped host than if the nanocrystal were smaller. While the dopant percentages listed above are not rigidly fixed, these numbers provide a rudimentary teaching of the typical percentages one would use in obtaining a particular dielectric core material of the invention.

Moreover, some of these host crystals (e.g., neodymium oxide) in one embodiment of the invention may require no specific doping to facilitate upconversion, which has been seen in one instance in $Nd_2O_3$ with an excitation wavelength of 587 nm producing emissions at 372 nm, 402 nm, and 468 nm. See Que, W et al. Journal of Applied Physics 2001, vol 90, pg. 4865, the entire contents of which are incorporated herein by reference. Doping neodymium oxide with $Yb^{3+}$, in one embodiment of the invention, would enhance upconversion through sensitizing the $Nd^{3+}$ ions with a lower energy $Yb^{3+}$ activator.

In one embodiment of the invention, the dielectric core is coated, such as for example with a metallic shell, to enhance electron-phonon coupling and thereby increase up conversion or down conversion efficiency, as discussed above. In another embodiment of the invention, the shell can include a $SiO_2$- and/or $TiO_2$-coating, and this coating is in one embodiment coated on doped $Y_2O_3$ upconverting nanoparticles to thereby, in some instances, increase the upconversion efficiency relative to an uncoated nanocrystal. In another embodiment of the invention, the shell can include a $SiO_2$- and/or $TiO_2$-coating, and this coating is in one embodiment coated on doped $Y_2O_3$ down converting nanoparticles to thereby, in some instances, increase the down conversion efficiency relative to an uncoated nanocrystal. Further, in one embodiment of the invention, the coating can be a polymer. In one embodiment, this coating is provided on $NaYF_4$:Ln/$NaYF_4$ dielectric core. Such coatings can increase the upconversion efficiency relative to an uncoated upconverter.

In another embodiment of the invention, phonon modes of undoped host-lattice (e.g., $Y_2O_3$) nanocrystals are modulated, for example, by Au, Ag, Pt, and Pd shells of varying thicknesses. In various embodiments of the invention, the upconverter dielectric core and the shell system includes as upconverting nanocrystals $Y_2O_3$:Ln with $NaYF_4$ shells, $Y_2O_3$:Ln with Au(Ag,Pt) shells, $NaYF_4$:Ln with $Y_2O_3$ shells, $NaYF_4$:Ln with Au(Ag,Pt) shells. In this system, the core diameter and shell outer/inner diameter of the metallic coatings can be set to dimensions that are expected to be tunable to a plasmon mode overlap.

In other embodiments as discussed below, the metal coating or the metallic structure disposed in relation to an up-conversion or a down-conversion nanoparticle can exist inside the dielectric and the relative position of the metal structure to the dielectric structure can enhance plasmon resonance. These structures with the metallic structure inside can be referred to as a metallic core up converter or a metallic core down converter. The metallic core technique for energy conversion is useful since it takes advantage of metal nano-particles that have improved surface morphology compared to shell coatings on core dielectrics. The metal or metallic alloy in the inner core metallic energy converter can be selected to tune its plasmonic activity. These structures with the metallic structure outside can be referred to as a core up converter or a core down converter.

In various embodiments of the invention, the upconverter or down converter dielectric core can be coated with thiol-terminated silanes to provide a coating of $SiO_2$ about the core of similar reactivity to $Y_2O_3$. In one embodiment of the invention, the above-described methodology is used to synthesize core-shell nanoparticles of $Y_2O_3$:Ln with $NaYF_4$ shells, $Y_2O_3$:Ln with Au(Ag,Pt) shells, $NaYF_4$:Ln with $Y_2O_3$ shells, $NaYF_4$:Ln with Au(Ag,Pt) shells where core and shell diameters varying from 2 to 20 nm. In these material systems, the tuned ratio of core-to-shell diameter may permit a plasmon-phonon resonance which should amplify absorption of NIR light and/or upconverted emission. In these material systems, control of the core and shell diameters is one factor determining the size dependent effect and subsequent tuning of plasmon-phonon resonance.

In one embodiment of the invention, the upconverter dielectric core can be mixed core-shell materials including for example semiconducting $Y_2O_3$ and $NaYF_4$ cores doped with various Ln series metals, which have been shown to possess large upconverting efficiencies. These doped $Y_2O_3$ and $NaYF_4$ cores will have shells of Au(Ag,Pt, Pd) or undoped $Y_2O_3$ and $NaYF_4$ matrices which have the potential to enhance or tune the phonon modes needed for energy transfer in the upconversion process. Solubility can be enhanced, for example, by addition of thiolated organics (Au shell), organic chain triethanolsilane ($Y_2O_3$ shell), and trioctylphosphine-oleic amine ($NaYF_4$ shell). All core-shell nanoparticles may further be solubilized into a colloidal suspension with the addition of triarginine peptide, polyethylene glycol, and polyethyleneimine surfactants.

Figure 28A:
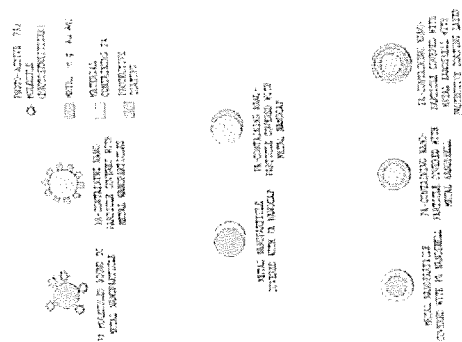
FIG. 28A is a schematic illustrating other various converter structures of the invention.

FIG. 28A shows some of the various embodiments of the converter structures of the invention that can be designed: (a) a structure including upconverter (UC) molecules bound to a metal (gold) nanoparticle; (b) a structure including an UC-containing nanoparticle covered with metal nanoparticles, (c) a metal nanoparticle covered with an UC-containing nanocap; (d) an UC-containing nanoparticle covered with metal nanocap, (e) a metal nanoparticle covered with UC nanoshell, (f) an UC-containing nanoparticle covered with metal nanoshell, (g) an UC-containing nanoparticle covered with metal nanoshell with protective coating layer.

Figure 28B:
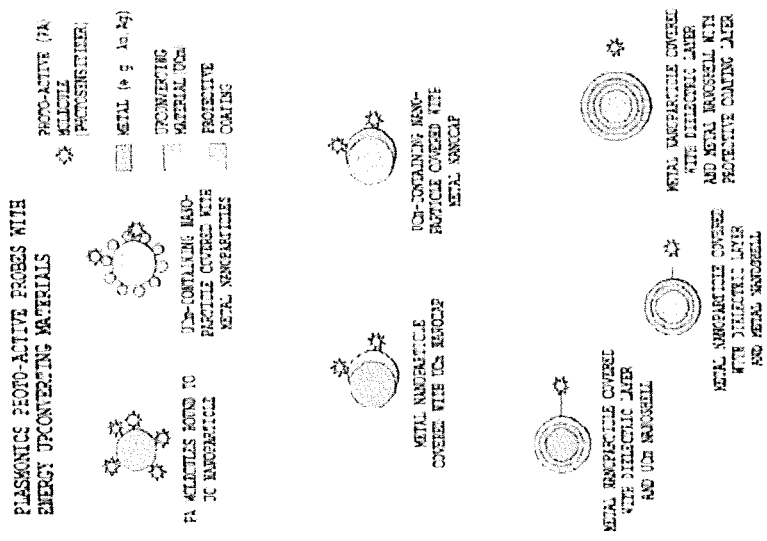
FIG. 28B is a further schematic illustrating other various converter structures of the invention.

The configurations (while shown in the FIG. 28A with UC-containing materials) would be applicable for enhancement for down converting materials such as the quantum dots or phosphors described herein. Moreover, in one embodiment of the invention, dielectric spacers (for examples silicates as discussed below) can be used with the structure of FIG. 6A-b to space apart the particle type metallic structures. In another embodiment of the invention, dielectric spacers can be used with the structure of FIG. 28A to space apart the metal layers, whether or not these layers are partial metal layers or continuous metal layers. See the schematics in FIG. 28B In various embodiments of the invention, multi-layer metallic nanoshells discussed in this application have the potential capability to enhance electromagnetically two spectral regions. Accordingly, the metallic structures of the invention can be used in the upconverting mode to enhance both the excitation at wavelength $\lambda_1$ and the emission at wavelength $\lambda_2$. This feature also can be used in the down converting to enhance primarily the emission at wavelength $\lambda_2$ and potentially the excitation at wavelength $\lambda_1$.

Such metallic structures in various embodiments of the invention include conducting materials made for example of metals, or doped glasses or doped semiconductors. These conducting materials can be in the form of pure or nearly pure elemental metals, alloys of such elemental metals, or layers of the conducting materials regardless of the constituency. The conducting materials can (as noted above) include non-metallic materials as minor components which do not at the levels of incorporation make the composite material insulating.

Similarly, in various embodiments of the invention, the up or down converting materials can include at least one of a dielectric, a glass, or a semiconductor. The up or down converting materials can include an alloy of two or more dielectric materials, an alloy of two or more glasses, or an alloy of two or more semiconductors.

Accordingly, FIG. 28A represents embodiments of the invention where the dielectric core is supplemented with a shell. The shell can include a metal layer of a prescribed thickness. The metal layer can include materials such as nickel, gold, iron, silver, palladium, platinum and copper and combinations thereof. The metal layer can be also made of a combination of metals and non-metals. The shell functions as a plasmonic shell where surface plasmons can form in the metal between the dielectric core and the outer environment acting as an exterior dielectric. The shell (as shown) may not be a complete shell. Partial metallic shells or metallic shells of varying thicknesses are also acceptable in the invention.

As discussed below, the metallic shells in another embodiment of the invention serve as scattering centers for UV light where UV light which, even if absorbed in a paint or coating layer contributes at a minimum to localized heating of the paint or coating layer material, will be scattered from the paint or coated layer.

Figure 28C:
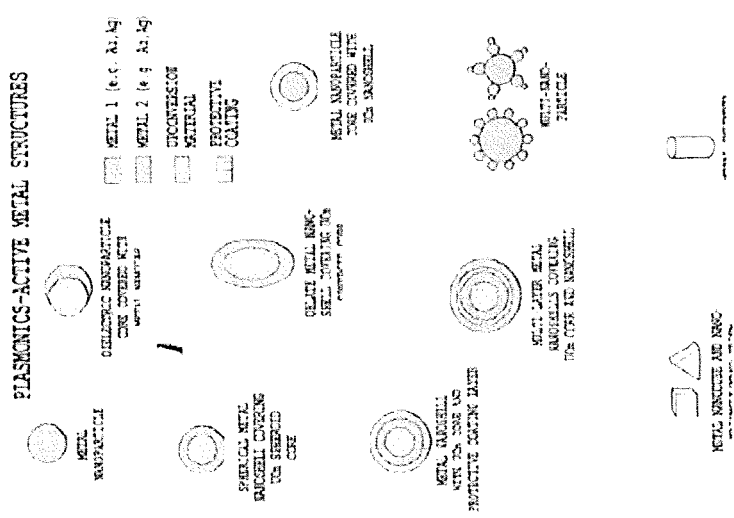
FIG. 28C is a schematic illustrating various plasmonics-active converter structures of the invention.

FIG. 28C shows still further embodiments of plasmonics-active nanostructures having upconverting (UC) materials that can be designed: (a) a metal nanoparticle, (b) an UC nanoparticle core covered with metal nanocap, (c) a spherical metal nanoshell covering an UC spheroid core, (d) an oblate metal nanoshell covering UC spheroid core, (e) a metal nanoparticle core covered with UC nanoshell, (f) a metal nanoshell with protective coating layer, (g) multi-layer metal nanoshells covering an UC spheroid core, (h) multi-nanoparticle structures, (i) a metal nanocube and nanotriangle/nanoprism, and (j) a metal cylinder.

Figure 28D:
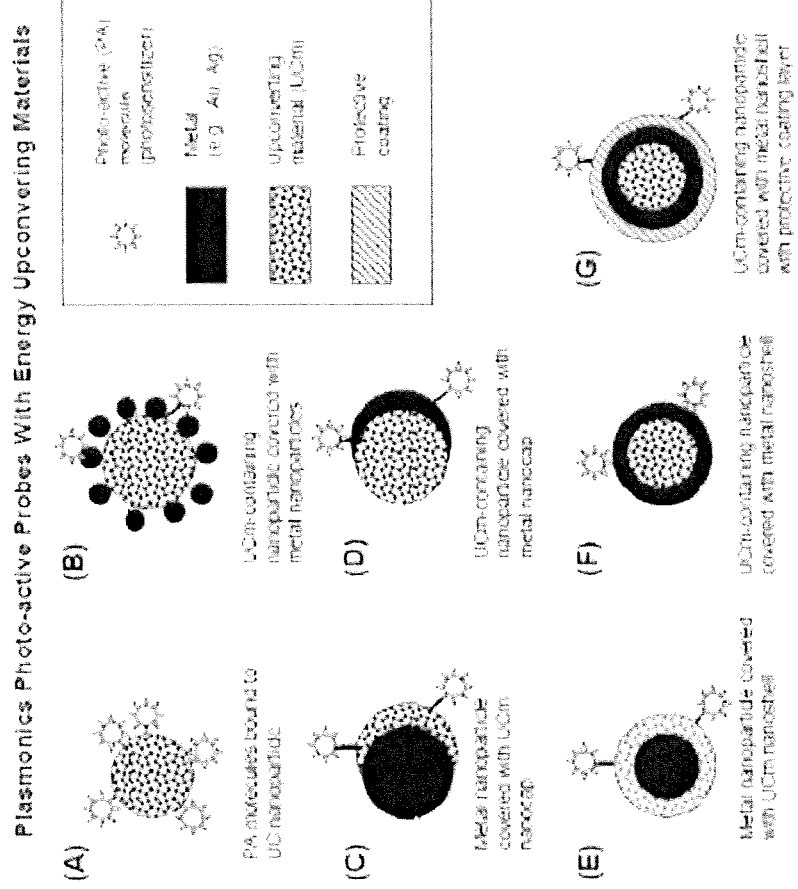
FIG. 28D is a schematic illustration of photo-active molecules linked to plasmonics-active upconverter structures of the invention.

FIG. 28D shows yet other embodiments of plasmonics-active nanostructures having upconverting materials with linked photo-active (PA) molecules that can be designed. For example, for the case of psoralen (as the PA molecule), the length of the linker between the PA molecule and the UC material or the metal surface is tailored such that it is sufficiently long to allow the PA molecules to be active (attach to DNA) and short enough to allow efficient excitation of light from the UC to efficiently excite the PA molecules. FIG. 28D shows (a) PA molecules bound to an UC nanoparticle, (b) an UC material-containing a nanoparticle covered with metal nanoparticles, (c) a metal nanoparticle covered with UC material nanocap, (D) an UC material-containing nanoparticle covered with metal nanocap, (e) a metal nanoparticle covered with an UC material nanoshell, (f) an UC material-containing nanoparticle covered with metal nanoshell, (g) an UC material-containing nanoparticle covered with metal nanoshell with protective coating layer.

With the upconverter and down converter structures of the invention, a plasmonics effect is advantageous. A plasmonics effect can increase the local intensity of the received light or the local intensity of the emitted light from the up and/or down converter structures of the invention. A plasmonics effect can occur throughout the electromagnetic region provided the suitable nanostructures, nanoscale dimensions, metal types are used. Plasmonic effects are possible over a wide range of the electromagnetic spectrum, ranging from gamma rays and X rays throughout ultraviolet, visible, infrared, microwave and radio frequency energy. However, for practical reasons, visible and NIR light are used for metal structures such as for example silver and gold nanoparticles, since the plasmon resonances for silver and gold occur in the visible and NIR region, respectively.

In various embodiments, nanoparticles of neodymium and ytterbium doped yttrium oxide, europium and ytterbium doped yttrium oxide, and any combination of rare earth trivalent ions doped into a neodymium oxide nanocrystal can be used. The dual doped yttrium oxide of composition neodymium and ytterbium and also the dual doped europium and ytterbium are new for the yttrium oxide host lattice, although such dual doped systems have been shown to work in other host lattices such as YAG.

These dual doped lanthanide glasses have been shown to upconvert efficiently on bulk materials, and thereby can provide new upconverter structures at the nano-scale. There are advantages offered by these yttrium oxide nanostructures of the invention. The small scale synthetic methodology for creating nanoscale yttrium oxide is easier to control and produce in yttrium oxide than in YAG. The host structure of yttrium oxide scintillates by down conversion. These combinations of dopants in yttrium oxide for example can provide predetermined emission colors for the yttrium oxide nanocrystal for the color shifting of the invention.

In one embodiment of the invention, a dual dopant permits excitation of either ion in the host glass. For instance, excitation by 980 nm light excites an ytterbium ion, where through transfer of energy from one excited state of the ytterbium ion to another dopant provides a mechanism for upconversion emission of light in the visible and NIR spectral regions.

Up-conversion phosphors similar in chemical compositions to the down-conversion fluorescent materials discussed above can be used. The up-conversion phosphors can include laser dyes, e.g., the organic small molecules that can be excited by the absorption of at least two infrared photons with emission of visible light. The up-conversion phosphors can include fluorescent polymers, e.g., the class of polymers that can be excited by the absorption of at least two infrared photons with emission of visible light. The up-conversion phosphors can include inorganic or ceramic particles or nano-particles, including the conventional up-conversion phosphors (e.g. metal fluorides, metal oxides) that can be excited by the absorption of at least two infrared photons with emission of visible light. The up-conversion phosphors can include semiconductor particles, including nano-particles such as II-VI or III-V compound semiconductors, e.g. quantum dots, described in details in the "down-conversion" semiconductors above.

Fluorescent up-conversion inorganic phosphors can include but are not limited to metal oxides, metal halides, metal chalcogenides (e.g. sulfides), or their hybrids, such as metal oxo-halides, metal oxo-chalcogenides. Fluorescent up-conversion inorganic phosphors are usually doped with rare earth elements (e.g. $Yb^{3+}$, $Er^{3+}$, $Tm^{3+}$). Some host examples include, but are not limited to: $NaYF_4$, $YF_3$, $BaYF_5$, $LaF_3$, $La_2MoO_8$, $LaNbO_4$, $LnO_2S$; where Ln is the rare earth elements, such as Y, La, Gd).

These converters (and the other energy converters described herein which receive energy and generate light or electron emission) can optionally include any of the energy augmentation structures described above.

In various embodiments of the invention, energy converters can be used with the energy augmentators described above for color enhancement. In some embodiments, the converters are up conversion of light e.g., from the IR regime into visible electromagnetic radiation and for down conversion of light e.g., from the UV range into visible electromagnetic radiation. The invention in various embodiments up converts energy, preferably light in the visible spectrum. The invention encompasses a variety of applications where the up and down conversion materials with or without energy augmentators are included to enhance the color of the object being displayed. These application areas can include paints on signs, walls, cars, buildings, boats, airplanes. These application areas can include display monitors, computer monitors, telephone displays, watch dials, instrument dials to name but a few.

Among various materials, luminescent nanoparticles have attracted increasing technological and industrial interest. In the context of the invention, nanoparticle refers to a particle having a size less than one micron. While the description of the invention describes specific examples using nanoparticles, the invention in many embodiments is not limited to particles having a size less than one micron. However, in many of the embodiments, the size range of less than one micron, and especially less than 100 nm produces properties of special interest such as for example emission lifetime luminescence quenching, luminescent quantum efficiency, and concentration quenching and such as for example diffusion, penetration, and dispersion into mediums where larger size particles would not migrate.

This invention in various embodiments can use a wide variety of down conversion materials (or mixtures of down conversion materials) with or without the energy augmentators to enhance a particular color of light observable to an observer. These down conversion materials can include quantum dots, semiconductor materials, alloys of semiconductor materials, scintillation and phosphor materials, materials that exhibit X-ray excited luminescence (XEOL), organic solids, metal complexes, inorganic solids, crystals, rare earth materials (lanthanides), polymers, scintillators, phosphor materials, etc., and materials that exhibit excitonic properties. Accordingly, the down conversion materials to enhance color emission can convert energy from one of ultraviolet light, x-rays, and high energy particles to visible light. The down conversion materials to enhance color emission can convert energy from higher energy visible light to lower energy visible light with or without the energy augmentators.

In one embodiment of the invention, a quantum dot mixture with or without the energy augmentators can be used for color enhancement. Quantum dots are in general nanometer size particles whose energy states in the material of the quantum dot are dependent on the size of the quantum dot. For example, quantum dots are known to be semiconductors whose conducting characteristics are closely related to the size and shape of the individual crystal. Generally, the smaller the size of the crystal, the larger the band gap, the greater the difference in energy between the highest valence band and the lowest conduction band becomes. Therefore, more energy is needed to excite the dot, and concurrently, more energy is released when the crystal returns to its resting state. In fluorescent dye applications, this equates to higher frequencies of light emitted after excitation of the dot as the crystal size grows smaller, resulting in a color shift from red to blue in the light emitted. Quantum dots represent one way to down convert ultraviolet light of the spectrum to a targeted color emission, such as for example a green light emission. Quantum dots represent one way to down convert blue light of the spectrum to a targeted color emission, such as for example a green light emission.

As described in U.S. Pat. No. 6,744,960 (the entire contents of which are incorporated by reference), different size quantum dots produce different color emissions. In that work and applicable to this invention, quantum dots can comprise various materials including semiconductors such as zinc selenide (ZnSe), cadmium selenide (CdSe), cadmium sulfide (CdS), indium arsenide (InAs), and indium phosphide (InP). Another material that may suitably be employed is titanium dioxide ($TiO_2$). The size of the particle, i.e., the quantum dot 18, may range from about 2 to 10 nm. Since the size of these particles is so small, quantum physics governs many of the electrical and optical properties of the quantum dot. One such result of the application of quantum mechanics to the quantum dot 18 is that quantum dots absorb a broad spectrum of optical wavelengths and re-emit radiation having a wavelength that is longer than the wavelength of the absorbed light. The wavelength of the emitted light is governed by the size of the quantum dot. For example, CdSe quantum dots 5.0 nm in diameter emit radiation having a narrow spectral distribution centered about 625 nm while quantum dots 18 including CdSe 2.2 nm in size emit light having a center wavelength of about 500 nm. Semiconductor quantum dots comprising CdSe, InP, and InAs, can emit radiation having center wavelengths in the range between 400 nm to about 1.5 m. Titanium dioxide $TiO_2$ also emits in this range. The linewidth of the emission, i.e., full-width half-maximum (FWHM), for these semiconductor materials may range from about 20 to 30 nm. To produce this narrowband emission, quantum dots simply need to absorb light having wavelengths shorter than the wavelength of the light emitted by the dots. For example, for 5.0 nm diameter CdSe quantum dots light having wavelengths shorter than about 625 nm is absorbed to produce emission at about 625 nm while for 2.2 nm quantum dots comprising CdSe light having wavelengths smaller than about 500 nm is absorbed and re-emitted at about 500 nm. In practice, however, the excitation or pump radiation is at least about 50 nanometers shorter than the emitted radiation.

Specifically, in one embodiment of the invention, a quantum dot mixture (QDM) coating can be deposited using CVD and or sol-gel techniques using standard precipitation techniques to be used with or without the energy augmentators. The QDM coating can be made of a silicate structure that does not diminish UV output. Within the silicate family, silica ($SiO_2$) is suitable since it maximizes UV transmission through the coating. The coating can further include a second layer of a biocompatible glass. Such bio-compatible glass and glass ceramic compositions can contain calcium, a lanthanide or yttrium, silicon, phosphorus and oxygen. Other biocompatible materials and techniques are described in the following patents which are incorporated herein in their entirety: U.S. Pat. Nos. 5,034,353; 4,786,617; 3,981,736; 3,922,155; 4,120,730; and U.S. Pat. Appl. Nos. 2008/0057096; 2006/0275368; and 2010/0023101.

Further, the down conversion materials for the invention described here can be coated with insulator materials such as for example silica which will reduce the likelihood of any chemical interaction between the luminescent particles and the medium the particles are included therein. These and the other conversion materials here can be used with or without the energy augmentators. For biocompatible applications of inorganic nanoparticles, one of the major limiting factors is their toxicity. Generally speaking, all semiconductor nanoparticles are more or less toxic. For biocompatible applications, nanoparticles with toxicity as low as possible are desirable or else the nanoparticles have to remain separated from the medium. Pure $TiO_2$, ZnO, and $Fe_2O_3$ are biocompatible. CdTe and CdSe are toxic, while ZnS, CaS, BaS, SrS and $Y_2O_3$ are less toxic. In addition, the toxicity of nanoparticles can result from their inorganic stabilizers, such as TGA, or from dopants such as $Eu^{2+}$, Cr 3+ or $Nd^{3+}$. Other suitable down conversion materials which would seem the most biocompatible are zinc sulfide, $ZnS:Mn^{2+}$, ferric oxide, titanium oxide, zinc oxide, zinc oxide containing small amounts of $Al_2O_3$, and AgI nanoclusters encapsulated in zeolite. For non-medical applications, where toxicity may not be as critical a concern, the following materials (as well as those listed elsewhere) are considered suitable: lanthanum and gadolinium oxyhalides activated with thulium; $Er^{3+}$ doped $BaTiO_3$ nanoparticles, $Yb^{3+}$ doped $CsMnCl_3$ and $RbMnCl_3$, $BaFBr:Eu^{2+}$ nanoparticles, Cesium Iodine, Bismuth Germanate, Cadmium Tungstate, and CsBr doped with divalent Eu.

In various embodiments of the invention, the following luminescent polymers are also suitable as conversion materials with or without the energy augmentators: poly(phenylene ethynylene), poly(phenylene vinylene), poly(p-phenylene), poly(thiophene), poly(pyridyl vinylene), poly (pyrrole), poly(acetylene), poly(vinyl carbazole), poly (fluorenes), and the like, as well as copolymers and/or derivatives thereof.

In various embodiments of the invention, the following materials can be used similar to that detailed in U.S. Pat. No. 7,090,355, the entire contents of which are incorporated herein by reference. For down-conversion, the following materials can be used with or without the energy augmentators. Inorganic or ceramic phosphors or nano-particles, including but not limited to metal oxides, metal halides, metal chalcogenides (e.g. metal sulfides), or their hybrids, such as metal oxo-halides, metal oxo-chalcogenides. Laser dyes and small organic molecules, and fluorescent organic polymers. Semiconductor nano-particles, such as II-VI or III-V compound semiconductors, e.g. fluorescent quantum dots. Organometallic molecules including at least a metal center such as rare earth elements (e.g. Eu, Tb, Ce, Er, Tm, Pr, Ho) and transitional metal elements such as Cr, Mn, Zn, Ir, Ru, V, and main group elements such as B, Al, Ga, etc. The metal elements are chemically bonded to organic groups to prevent the quenching of the fluorescence from the hosts or solvents. Phosphors can be used including the Garnet series of phosphors: $(Y_mA_{1-m})_3(Al_nB_{1-n})_5O_{12}$, doped with Ce; where 0≤m, n≤1, where A includes other rare earth elements, B includes B, Ga. In addition, phosphors containing metal silicates, metal borates, metal phosphates, and metal aluminates hosts can be used. In addition, nano-particulates phosphors containing common rare earth elements (e.g. Eu, Tb, Ce, Dy, Er, Pr, Tm) and transitional or main group elements (e.g. Mn, Cr, Ti, Ag, Cu, Zn, Bi, Pb, Sn, Tl) as the fluorescent activators, can be used. Materials such as Ca, Zn, Cd in tungstates, metal vanadates, ZnO, etc. can be used with or without the energy augmentators.

The commercial laser dye materials obtained from several laser dye vendors, including Lambda Physik, and Exciton, etc. can also be used with or without the energy augmentators. A partial list of the preferred laser dye classes includes: Pyrromethene, Coumarin, Rhodamine, Fluorescein, other aromatic hydrocarbons and their derivatives, etc. In addition, there are many polymers containing unsaturated carbon-carbon bonds, which also serve as fluorescent materials and find many optical and fluorescent applications. For example, MEH-PPV, PPV, etc. have been used in optoelectronic devices, such as polymer light emitting diodes (PLED). Such fluorescent polymers can be used directly as the fluorescent layer of the transparent 2-D display screen.

As noted above, semiconductor nanoparticles (e.g., quantum dots) can be used with or without the energy augmentators. The terms "semiconductor nanoparticles," in the art refers to an inorganic crystallite between 1 nm and 1000 nm in diameter, preferably between 2 nm to 50 nm. A semiconductor nano-particle is capable of emitting electromagnetic radiation upon excitation (i.e., the semiconductor nano-particle is luminescent). The nanoparticle can be either a homogeneous nano-crystal, or comprises of multiple shells. For example, the nanoparticle can include a "core" of one or more first semiconductor materials, and may be surrounded by a "shell" of a second semiconductor material. The core and/or the shell can be a semiconductor material including, but not limited to, those of the group II-VI (ZnS, ZnSe, ZnTe, CdS, CdSe, CdTe, HgS, HgSe, HgTe, MgS, MgSe, MgTe, CaS, CaSe, CaTe, SrS, SrSe, SrTe, BaS, BaSe, BaTe, and the like) and III-V (GaN, GaP, GaAs, GaSb, InN, InP, InAs, InSb, and the like) and IV (Ge, Si, and the like) materials, and an alloy or a mixture thereof.

Fluorescent organometallic molecules containing rare earth or transitional element cations can be used for down conversion materials with or without the energy augmentators. Such molecules include a metal center of rare earth elements including Eu, Tb, Er, Tm, Ce protected with organic chelating groups. The metal center may also include transitional elements such as Zn, Mn, Cr, Ir, etc. and main group elements such as B, Al, Ga. Such organometallic molecules can readily dissolve in liquid or transparent solid host media. Some examples of such fluorescent organometallic molecules include: 1. Tris(dibenzoylmethane)mono(phenanthroline)europium(III); 2. Tris(8-hydroxyquinoline) erbium; 3. Tris(I-phenyl-3-methyl-4-(2,2-dimethylpropan-1-oyl)pyrazolin-5-one)terbium(III); 4. Bis(2-methyl-8-hydroxyquinolato)zinc; 5. Diphenylborane-8-hydroxyquinolate.

Specific examples of down-conversion materials for red emission include those discussed above and europium complexes such as those described in JP Laid-open Patent Publication (Kokai) No. 2003-26969, constructed such that β-diketone ligand is coordinated to europium forming an europium complex capable of emitting red fluorescence. Other specific examples of the rare earth element complexes include complexes include lanthanum (Ln), europium (Eu), terbium (Tb), and gadolinium (Gd) and combinations thereof. A europium (Eu) complex is capable of emitting red fluorescence when irradiated with ultraviolet rays having a wavelength ranging from 365 nm to 410 nm. Terbium (Tb) is capable of emitting green fluorescence when irradiated with ultraviolet rays having a wavelength of 365 nm.

In other down-conversion embodiments with or without the energy augmentators, the down conversion materials which emit red light may include europium, light emitting particles which emit green light may include Terbium, and light emitting particles which emit blue or yellow light may include cerium (and/or thulium). In up-conversion embodiments, up conversion materials which emit red light may include praseodymium, light emitting particles which emit green light may include erbium, and light emitting particles which emit blue light may include thulium. In embodiments, the conversion materials can be light emitting particles made of fluorescent molecules that emit different colors (e.g. red, green, and blue). In embodiments, the conversion materials can be light emitting particles made of pure organic or organo-metallic dyes with or without the energy augmentators.

In addition to the combinations of rare earth complexes, such as a combination of a europium complex and a terbium complex, it is also possible employ a combination of a europium complex and a green-emitting fluorescent substance which is not a complex, or a combination of a terbium complex and a red-emitting fluorescent substance which is not a complex.

Other down converter materials with or without the energy augmentators include for example ZnS, PbS, SbS$_3$, MoS$_2$, PbTe, PbSe, BeO, MgO. Li$_2$CO$_3$, Ca(OH)$_2$, MoO$_3$, SiO$_2$, Al$_2$O$_3$, TeO$_2$, SnO$_2$, KBr, KCL, and NaCl. These materials can include dopants to tailor the emission properties, as noted above. Examples of doped (or alloyed) glass systems suitable for the include Y$_2$O$_3$:Gd, Y$_2$O$_3$:Dy, Y$_2$O$_3$:Tb, Y$_2$O$_3$:Ho, Y$_2$O$_3$:Er, Y$_2$O$_3$:Tm, Gd$_2$O$_3$:Eu, Y$_2$O$_2$S:Pr, Y$_2$O$_2$S:Sm, Y$_2$O$_2$S:Eu, Y$_2$O$_2$S:Tb, Y$_2$O$_2$S:Ho, Y$_2$O$_2$S:Er, Y$_2$O$_2$S:Dy, Y$_2$O$_2$S:Tm, ZnS:Ag:Cl (blue), ZnS:Cu:Al (green), Y$_2$O$_2$S:Eu (red), Y$_2$O$_3$:Eu (red), YVO$_4$:Eu (red), and Zn$_2$SiO$_4$:Mn (green).

With regard more specifically to down converter materials suitable for the invention with or without the energy augmentators, U.S. Pat. No. 4,705,952 (the contents of which are hereby incorporated herein by reference) describes an infrared-triggered phosphor that stores energy in the form of visible light of a first wavelength and released energy in the form of visible light of a second wavelength when triggered by infrared light. The phosphors in U.S. Pat. No. 4,705,952 were compositions of alkaline earth metal sulfides, rare earth dopants, and fusible salts. The phosphors in U.S. Pat. No. 4,705,952 were more specifically phosphors made from strontium sulfide, barium sulfide and mixtures thereof; including a dopant from the rare earth series and europium oxide, and mixtures thereof; and including a fusible salt of fluorides, chlorides, bromides, and iodides of lithium, sodium, potassium, cesium, magnesium, calcium, strontium, and barium, and mixtures thereof. The materials described in U.S. Pat. No. 4,705,952 are useful in various embodiments of the invention with or without the energy augmentators.

In other embodiments of the invention, the down converter materials (or mixtures of down converters materials can include Y$_2$O$_3$: Li. Sun et al "Luminescent properties of Li+ doped nanosized Y$_2$O$_3$:Eu," Solid State Comm. 119 (2001) 393-396 (the entire contents of which are incorporated herein by reference) describe such materials. Hou et al "Luminescent properties nano-sized Y$_2$O$_3$:Eu fabricated by co-precipitation method," Journal of Alloys and Compounds, vol. 494, issue 1-2, 2 Apr. 2010, pages 382-385 (the entire contents of which are incorporated herein by reference) describe that nano-sized yttria (Y$_2$O$_3$) powders have been successfully synthesized by a co-precipitation method. The powders were well crystallized, and the grains were almost spherical with good dispersibility. The quenching concentration of Eu$^{3+}$ ions is 9 mol % which is much higher than micro-scaled powders. The incorporation of Li+ ions greatly improved the luminescence intensity. The highest emission intensity was observed with 4 mol % Li+ doped Y$_2$O$_3$:Eu powder (($Y_{0.87}Eu_{0.09}Li_{0.04})_2O_3$) and the fluorescence intensity was increased by as much as 79%. Yi et al "Improved cathodoluminescent characteristics of Y$_2$O$_3$:Eu$^{3+}$ thin films by Li-doping," Appl. Phys. A 87, 667-671 (2007) (the entire contents of which are incorporated herein by reference) describe cathodoluminescent spectra for both Y$_2$O$_3$:Eu$^{3+}$ and Li-doped Y$_2$O$_3$:Eu$^{3+}$ films and methods for making these materials.

The invention in other embodiments can use a wide variety of up conversion materials (or mixtures of up converters) with or without the energy augmentators to enhance a particular color of light observable from reflective material or surface. These up conversion materials can include similar materials as discussed above with regard to down conversion but typically included doped or impurity states in a host crystal that provide a mechanism for up conversion pumping. Accordingly, the up conversion materials to enhance color emission can convert energy from one of near infrared, infrared, and microwave irradiation. The upconversion materials to enhance color emission can convert energy from lower energy visible light to higher energy visible light.

Upconversion materials with or without the energy augmentators can be used in various ways to enhance visible light emission by way of conversion of infrared light from a solar spectrum (as in daylight exposure) or a black body spectrum (as in an incandescent lamp). In one example, a nanoparticle of a lanthanide doped oxide can be excited with near infrared light such as laser light at 980 nm and 808 nm to produce visible light in different parts of the red, green, blue spectrum depending on the dopant trivalent rare earth ion(s) chosen, their concentration, and the host lattice.

The lanthanide doped oxides suitable for this invention differ from more traditional multi-photon up conversion processes where the absorption of, for example, two photons is needed in a simultaneous event to promote an electron from a valence state directly into an upper level conduction band state where relaxation across the band gap of the material produces fluorescence. Here, the co-doping produces states in the band gap of the NaYF$_4$ such that the Yb$^{3+}$ ion has an energy state at $^2F_{5/2}$ pumpable by a single photon event and from which other single photon absorption events can populate even higher states. Once in this exited state, transitions to higher energy radiative states are possible, from which light emission will be at a higher energy than that of the incident light pumping the $^2F_{5/2}$ energy state. In other words, the energy state at $^2F_{5/2}$ of the Yb$^{3+}$ ion is the state that absorbs 980 nm light permitting a population build up serving as the basis for the transitions to the higher energy states such as the $^4F_{7/2}$ energy state. Here, transitions from the $^4F_{7/2}$ energy state produce visible emissions.

U.S. Pat. No. 7,008,559 (the entire contents of which are incorporated herein by reference) describes the upconversion performance of ZnS where excitation at 767 nm produces emission in the visible range. The materials described in U.S. Pat. No. 7,008,559 (including the ZnS as well as Er$^{3+}$ doped BaTiO$_3$ nanoparticles and Yb$^{3+}$ doped CsMnCl$_3$) are suitable in various embodiments of the invention with or without the energy augmentators.

Further, materials specified for up conversion materials in the invention with or without the energy augmentators include CdTe, CdSe, ZnO, CdS, Y$_2$O$_3$, MgS, CaS, SrS and BaS. Such up conversion materials may be any semiconductor and more specifically, but not by way of limitation, sulfide, telluride, selenide, and oxide semiconductors and their nanoparticles, such as $Zn_{1-x}Mn_xS_y$, $Zn_{1-x}Mn_xSe_y$, $Zn_{1-x}Mn_xTe_y$, $Cd_{1-x}Mn_xS_y$, $Cd_{1-x}Mn_xSe_y$, $Cd_{1-x}Mn_xTe_y$, $Pb_{1-x}Mn_xS_y$, $Pb_{1-x}Mn_xSe_y$, $Pb_{1-x}Mn_xTe_y$, $Mg_{1-x}Mn_xS_y$, $Ca_{1-x}Mn_xS_y$, $Ba_{1-x}Mn_xS_y$ and $Sr_{1-x}$, etc. (wherein, $0<x\le1$, and $0<y\le1$). Complex compounds of the above-described semiconductors are also contemplated for use in the invention—e.g. $(M_{1-z}N_z)_{1-x}Mn_xA_{1-y}B_y$ (M=Zn, Cd, Pb, Ca, Ba, Sr, Mg; N=Zn, Cd, Pb, Ca, Ba, Sr, Mg; A=S, Se, Te, O; B=S, Se, Te, O; $0<x\le1$, $0<y\le1$, $0<z\le1$). Two examples of such complex compounds are $Zn_{0.4}Cd_{0.4}Mn_{0.2}S$ and $Zn_{0.9}Mn_{0.1}S_{0.8}Se_{0.2}$. Additional conversion materials include insulating and nonconducting materials such as BaF$_2$, BaFBr, and BaTiO$_3$, to name but a few exemplary compounds. Transition and rare earth ion co-doped semiconductors suitable for the invention include sulfide, telluride, selenide and oxide semiconductors and their nanoparticles, such as ZnS; Mn; Er; ZnSe; Mn, Er; MgS; Mn, Er; CaS; Mn, Er; ZnS; Mn, Yb; ZnSe; Mn,Yb; MgS; Mn, Yb; CaS; Mn,Yb etc., and their complex compounds: $(M_{1-z}N_z)_{1-x}(Mn_qR_{1-q})_xA_{1-y}B_y$ (M=Zn, Cd, Pb, Ca, Ba, Sr, Mg; N=Zn, Cd, Pb, Ca, Ba, Sr, Mg; A=S, Se, Te, O; B=S, . . . $0<z\le1$, $o<q\le1$).

Some nanoparticles such as ZnS:Tb$^{3+}$, Er$^{3+}$; ZnS:Tb$^{3+}$; Y$_2$O$_3$:Tb$^{3+}$; Y$_2$O$_3$:Tb$^{3+}$, Er3+; ZnS:Mn$^{2+}$; ZnS:Mn,Er$^{3+}$ are known in the art to function for both down-conversion luminescence and upconversion luminescence and would be suitable for the invention with or without the energy augmentators. In up-conversion embodiments, light emitting particles which emit red light may include praseodymium, light emitting particles which emit green light may include erbium, and light emitting particles which emit blue light may include thulium.

In general, the upconversion process generally requires one of more rare-earth dopants, such as Er, Eu, Yb, Tm, Nd, Tb, Ce, Y, U, Pr, La, Gd and other rare-earth species or a combination thereof, doped into a dielectric crystal (of any size>0.1 nm), including at least one of Y$_2$O$_3$, Y$_2$O$_2$S, NaYF$_4$, NaYbF$_4$, YAG, YAP, Nd$_2$O$_3$, LaF$_3$, LaCl$_3$, La$_2$O$_3$, TiO$_2$, LuPO$_4$, YVO$_4$, YbF$_3$, YF$_3$, Na-doped YbF$_3$, or SiO$_2$, where incident radiation is at longer wavelength than emissive radiation from the crystal. The wavelength emitted is based entirely on the dopant ion(s) chosen and their associated and relative concentration in the host crystal. For the example of upconversion in a Y$_2$O$_3$ host crystal, to achieve a blue emission (~450-480 nm) one could synthesize [Y$_2$O$_3$; Yb (3%), Tm (0.2%)], where the Yb and Tm are the percentages doped in the crystal relative to the Y atoms being 100%. Likewise, typical green upconversion materials are [Y$_2$O$_3$; Yb (5%), Ho (1%)] and [Y$_2$O$_3$; Yb (2%), Er (1%)], and typical red upconversion materials are [Y$_2$O$_3$; Yb (10%), Er (1%)] and [Y$_2$O$_3$; Yb (5%), Eu (1%)]. The concentrations of dopants relative to each other and the crystal matrix must be tuned for every combination, and there are multiple ways to achieve multiple colors from even the same dopants with or without the energy augmentators.

Up-conversion of red light with a wavelength of about 650 nm in Tm$^{3+}$ doped flourozirconate glasses can be used in the invention to produce blue light. In this system, the blue light consists of two emission bands; one at 450 nm which is ascribed to the 1D2→3H4 transition, the others at 475 nm is ascribed to the 1G4→3H6 transition. The emission intensities of both bands have been observed by others to vary quadratically with the excitation power. For glasses with a Tm$^{3+}$ concentration of 0.2 mol % and greater, cross-relaxation processes occur which decrease the up-conversion efficiency.

The emission of visible light upon excitation in the near-infrared (NIR) has been observed in optically clear colloidal solutions of LuPO$_4$:Yb$^{3+}$, Tm$^{3+}$, and YbPO$_4$:Er$^{3+}$ nanocrystals in chloroform. Excitation at 975 nm has been shown by others to produce visible luminescence in the blue, green, or red spectral regions.

Tellurium and germanium oxides (tellurites and germinates) are also suitable upconverters. These glasses can be doped with Tm, Yb, Ho, Er, Pr, for example.

Yb$^{3+}$ doped BaZrO$_3$ is also suitable for upconversion. Er$^{3+}$ and/or Tm$^{3+}$ doping are also suitable for tailoring the emission wavelengths.

In another embodiment, Nd$^{3+}$:Cs$_2$NaGdCl$_6$ and Nd$^{3+}$, Yb$^{3+}$:Cs$_2$NaGdCl$_6$ polycrystalline powder samples prepared by Morss method have been reported to be up converters and are suitable for the present invention. These materials, under 785 nm irradiation, have shown upconversion emissions near 538 nm (Green), 603 nm (Orange), and 675 nm (Red) were observed and assigned to 4G7/2→4I9/2, (4G7/2→4I11/2; 4G5/2→4I9/2), and (4G7/2→4I13/2; 4G5/2→4I11/2), respectively.

In another embodiment, Nd$^{3+}$ and Ho$^{3+}$ co-doped-based ZrF$_4$ fluoride glasses under 800 nm excitation have been reported to be up converters and are suitable for the present invention. Among the up-conversion luminescences for the ZrF$_4$ fluoride glasses, the green emission was seen to be extremely strong and the blue and red emission intensities were very weak.

In another embodiment, Tm$^{3+}$/Yb$^{3+}$-codoped TeO$_2$—Ga$_2$O$_3$—R$_2$O (R=Li, Na, K) glasses have been reported to be up converters and are suitable for the present invention. These materials, under excitation at 977 nm, showed intense blue upconversion emission centered at 476 nm along with a weak red emission at 650 nm.

In another embodiment, metal-to-ligand charge transfer (MLCT) transition in [Ru(dmb)$_3$]$^{2+}$ (dmb=4,4'-dimethyl-2, 2'-bipyridine) in the presence of anthracene or 9,10-diphenylanthracene have been reported converters and are suitable for the present invention. Upconverted to up converters and are suitable for the present invention. Upconverted singlet fluorescence resulting from triplet-triplet annihilation at low excitation power has been reported. In particular 9,10-diphenylanthracene (DPA) (substituted for anthracene) showed higher efficiencies for upconversion. In these experiments, workers with this material system assumed that DPA's increased singlet fluorescence quantum yield (=0.95) relative to anthracene (=0.27)7. This work lead to an approximate 24.4±6.1 enhancement of green-to-blue light upconversion permitting direct visualization of the process at low excitation power, for example by a commercial green laser pointer ($\lambda_{ex}$=532 nm, <5 mW peak power).

The structures described herein for color enhancement with the energy augmentation structures are denoted as color enhancing/energy augmentation structures or as energy enhancing/augmentation structures.

By having the energy converters or color converting or enhancing materials disposed in a vicinity of the energy augmentation structures of this invention, regardless of the whether the energy augmentation structure is in a region of intensified electric field or otherwise outside the region of intensified electric field, the color enhancing/energy augmentation structures or the energy enhancing/augmentation structures of the invention are able to produce light which can be used for a variety of applications, in particular for photo-stimulation of biological, chemical, and physical reactions such as for example photoactivation of photoreactive drugs, photoactivation of photosensitive materials such as adhesives or lithographic photoresists, or for direct interaction with biological and chemical agents in the environment of the augmentation structures, as in sterilization.

Accordingly, in one embodiment of the invention, the color enhancement structures described herein can receive polychromatic light from a variety of sources such as sunlight, incandescent bulbs, fluorescent tube, and LED light sources with each having different wavelengths or wavelength bands. For these wavelength different bands, the resonators are "matched" or "tuned" to those wavelengths such that an intense electric field is established especially between the external-electrode pairs, or the folded resonator electrode pairs if used. In those regions of intense electric field can be disposed color converters (up and/or down phosphors) which can take light from one of the different wavelengths or wavelength bands, and have light of another wavelength or of different wavelength bands be emitted therefrom. In one embodiment, the intense electric field increases the intensity of the emitted light from the phosphors. Moreover, unlike the above-noted plasmonics where the electric field enhancement is restricted to regions within 100 to 200 nm of the metal, the resonators establish an increased electric field within the volume of the external-electrode pair, or the folded resonator electrode pairs if used, such that the phosphor material in a vicinity and within the external-electrode pair (or the folded resonator electrode pairs) exhibits an intensity larger than if the converter were remote from the resonator.

In view of the above, this invention is directed in general to methods and systems for color enhancement utilizing a color enhancement structure having a) an energy collector comprising at least one energy augmentation structure, and b) an energy converter capable of converting a second wavelength/quantum of electromagnetic energy into and emitting therefrom a third wavelength of light shifted in wavelength/energy from the second wavelength/quantum of electromagnetic energy. In one embodiment, the energy converter is disposed in a vicinity of the at least one energy augmentation structure such that the light shifted in wavelength is emitted with an intensity larger than if the converter were remote from the at least one energy augmentation structure. For ease of understanding, the term "wavelength" will be used to describe the electromagnetic energy entering into the energy converter, even though that electromagnetic energy may be better described in certain embodiments based upon its energy level or strength.

By having the energy converters or color converting or enhancing materials disposed in a vicinity of the energy augmentation structures of this invention, regardless of the whether the energy augmentation structure is in a region of intensified electric field or otherwise outside the region of intensified electric field, the color enhancing/augmentation structures or the energy enhancing/augmentation structures of the invention are able to enhance the conversion of one form of energy to another, as a conversion from one or more wavelengths of light to other wavelengths of light, or as a conversion from the one or more wavelengths of light to electrical energy, or as a conversion from the one or more wavelengths of light to heat.

Conversion from the one or more wavelengths of light to other wavelengths of light is useful for color shifting and color enhancement applications. Conversion from the one or more wavelengths of light to electrical energy is useful for harvesting solar energy using for example photovoltaic cells. Conversion from the one or more wavelengths of light to heat is useful also for harvesting solar energy using for example thermoelectric cells or other heat-to-electrical energy devices such as thermoelectric generators.

In some embodiments of the color enhancing/energy augmentation structures, the color enhancing structure includes a multi-dimensional light collector comprising a first level of metallic patterns and a second level of metallic patterns offset in at least one of a lateral or axial direction from the first level of metallic patterns. At least one of the metallic patterns optionally comprises a first resonator dimensioned to be resonant with a first wavelength of light. The first resonator can be one of a folded structure or an external-electrode pair structure as noted above. The color enhancement structure has a converter capable of converting a second wavelength of light into and emitting therefrom a third wavelength of light shifted in wavelength from the second wavelength of light. The converter is disposed with the first resonator such that the light shifted in wavelength is emitted with an intensity larger than if the converter were remote from the first resonator.

In some embodiments, the energy converter being disposed in a vicinity of the at least one energy augmentation structure is conductively coupled the energy converter to the at least one energy augmentation structure.

For example, in some embodiments, the energy converter being disposed in a vicinity of the at least one energy augmentation structure comprises a physical conductive connection between the energy converter and the at least one energy augmentation structure.

In some embodiments of the color enhancing/energy augmentation structures, the color enhancing structure, the energy converter comprises a down converter converting ultraviolet or blue light into red, yellow, or green light. In some embodiments of the color enhancing/augmentation structures, the energy converter comprises an up converter converting infrared or red light into yellow, green light, or blue light.

In some embodiments of the color enhancing/energy augmentation structures, the metallic patterns referenced above comprises a folded resonator having opposing electrodes with electric fields directed in between, and the converter is positioned between the opposing electrodes or within fringing electric field of the opposing electrodes or otherwise in a vicinity of the opposing electrodes. In one example, the folded resonator is a ¾ λ folded resonator. In one example, metallic patterns comprise at least one of Au, Ag, Cu, Al, or transparent metal oxides. In another example, the metallic patterns can be formed with refractory metals such for example Ti, W, and Mo.

In some embodiments of the color enhancing/energy augmentation structures, the metallic patterns referenced above comprises an external external-electrode pair structure having opposing electrodes with electric fields directed in between, and the converter is positioned between the opposing electrodes or within fringing electric field of the opposing electrodes or otherwise in a vicinity of the opposing electrodes. In one example, the resonator is a ¾λ external-electrode pair resonator. In one example, metallic patterns comprise at least one of Au, Ag, Cu, Al, or transparent metal oxides. In another example, the metallic patterns can be formed with refractory metals such for example Ti, W, and Mo.

In some embodiments of the color enhancing/energy augmentation structures, the color enhancing structure, there is an antireflection film disposed on at least one of the metallic patterns or on the converter.

In some embodiments of the color enhancing/energy augmentation structures, the color enhancing structure, the first resonator noted above comprises plural resonators, the converter noted above comprises plural converters, and the plural converters are disposed at multiple positions throughout the light collector. In one example, the plural converters are positioned to convert light being internally scattered within the light collector.

In some embodiments of the color enhancing/energy augmentation structures, the first level of metallic patterns noted above (or the second level of metallic patterns) comprises a metal core cladded with a high-K dielectric and a subsequent cladding of a low-K dielectric. In some embodiments of the color enhancing/energy augmentation structures, the first level of metallic patterns noted above (or the second level of metallic patterns) comprises a radial pattern of conductors. In some embodiments of the color enhancing/energy augmentation structures, the first level of metallic patterns noted above (or the second level of metallic patterns) comprises a fractal pattern. In one example, the fractal pattern is embedded within a dielectric material.

In some embodiments of the color enhancing/energy augmentation structures, the first level of metallic patterns noted above (or the second level of metallic patterns) comprises a three-dimensional fractal structure.

In some embodiments of the color enhancing/energy augmentation structures, the light collector comprises a transparent panel with the first level of metallic patterns and the second level of metallic patterns and optionally multiple converters formed therein. In some embodiments of the color enhancing/augmentation structures, the light collector comprises a transparent sheet with the first level of metallic patterns and the second level of metallic patterns and optionally multiple converters formed therein.

In some embodiments of the color enhancing/energy augmentation structures, the first level of metallic patterns noted above (or the second level of metallic patterns) are of different sizes and/or orientations to each other of the first level of metallic patterns or with respect to the second level of metallic patterns.

Figure 29:
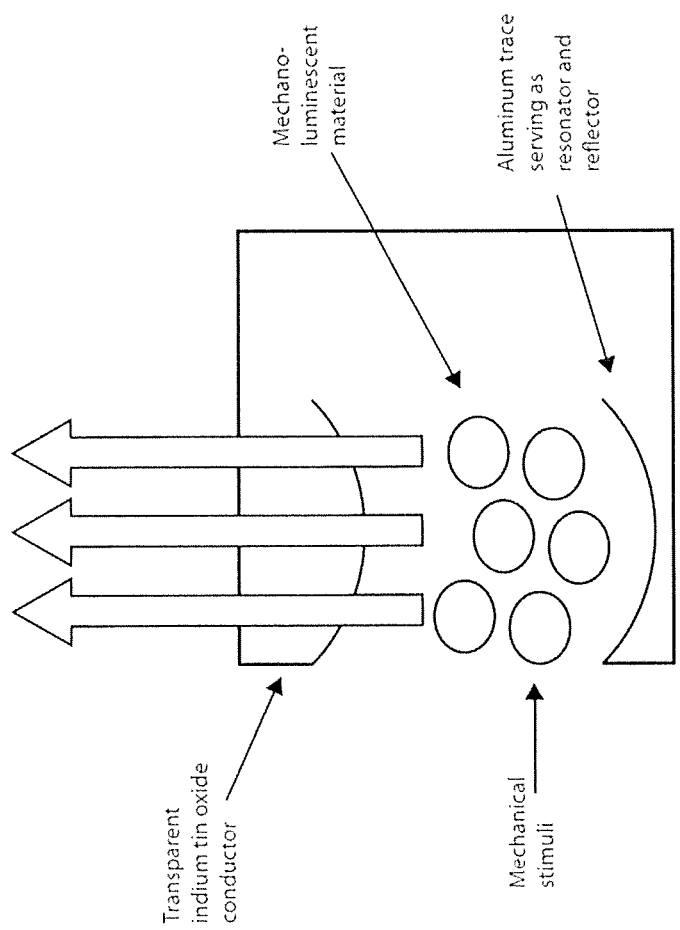
FIG. 29 is a diagram showing a mechanoluminescent emitter of the present invention.

Indeed, FIG. 29 is a schematic of a reflective resonator of this invention including mechano-luminescent materials, in this example the mechano-luminescent materials being placed between a folded resonator structure, although mechano-luminescent materials could be placed between an external electrode pair resonator structure. Thus, in one embodiment, an electromagnetic wave energy augmentator captures one or more wavelengths of electromagnetic energy, and augments the one or more wavelengths of electromagnetic energy in at least one property (such as electric field intensity in a vicinity of the mechano-luminescent materials), while at the same time the mechano-luminescent materials can be considered an energy converter converting the ultrasonic or mechanical energy into electromagnetic radiation (i.e., emitted light).

In one embodiment of the invention, the increased electric field in the folded structure or the external electrode pair increases the luminescence of the mechano-luminescent materials. The energy used to build the electric field in the folded structure or the external electrode pair being provided separately from the mechanical energy driving the mechano-luminescence.

For example, the reflective resonator of FIG. 29 could be placed adjacent an exhaust stack of an engine or other waste heat dissipating machine. In one embodiment, the reflective resonator of FIG. 29 would be mounted on a stainless steel arm connected to the heat stack. The stainless steel would couple mechanical vibrations to the reflective resonator while thermally isolating the reflective resonator from the exhaust stack, thereby permitting even inorganic mechano-luminescent materials to be used.

When the engine began to show higher levels of vibration or vibrations at different frequencies, the intensity of the light emitted would change providing a visible light signal that the engine or machine was under stress from power loads or wear or mechanical failure.

In one embodiment of the invention, the reflective structure shown in FIG. 29 need not include the resonator and its resonating elements. In one embodiment of the invention, the reflective structure shown in FIG. 29 could be placed directly on a machine operating at a relatively cold temperature around 100° C. In this embodiment, the reflective structure need not include the resonator and its resonating elements. However, if the resonator and its resonating elements were present, a laser such as 656 nm laser could "probe" the resonator and intensify "on demand" the mechano-luminescence. In this way, early detection of developing mechanical problems could be detected.

Various mechano-luminescent materials suitable for the present invention include $ZnS:Mn^{2+}$, $SrAl_2O_4:Eu^{2+}$, $ZnS:Cu$, $SrAMgSi_2O_7:Eu^{2+}$ (A=Ca, Sr, Ba), KCl, KI, KBr, NaF, NaCl, LiF, RbCl, RbBr, RbI, MgO, $SrAl_2O_4$, $CaAl_2O_4$, $Sr_{1-x}Ba\ Al_2O_4$ (x=0, 0.1, 0.2, 0.4), $Sr_{0.9}Ca_{0.1}Al_2O_4$, $Zn_2Ge_{0.9}Si_{0.1}O_4$, $MgGa_2O_4$, $ZnGa_2O_4$, $ZnAl_2O_4$, $ZnS$, $ZnTe$, $(ZnS)_{1-x}(MnTe)_x$ (x<¼), $CaZnOS$, $BaZnOS$, $Ca_2MgSi_2O_7$, $Sr_2MgSi_2O_7$, $Ba_2MgSi_2O_7$, $SrCaMgSi_2O_7$, $SrBaMgSi_2O_7$, $Sr_nMgSi_2O_{5+n}$ (1≤n≤2), $Ca_2Al_2SiO_7$, $Sr_2Al_2SiO_7$, $CaYAl_3O_7$, $CaAl_2Si_2O_8$, $Ca_{1-x}Sr_xAl_2Si_2O_8$ (x<0.8), $SrMg_2(PO_4)_2$, $Ba_{1-x}Ca_xTiO_3$ (0.25<x<0.8), $Ba_{1-x}Ca_xTiO_3$, $LiNbO_3$, $Sr_2SnO_4$, $(Ca, Sr, Ba)_2SnO_4$, $Sr_3Sn_2O_7$, $Sr_3(Sn, Si)_2O_7$, $Sr_3(Sn, Ge)_2O_7$, $Ca_3Ti_2O_7$, $CaNb_2O_6$, $Ca_2Nb_2O_7$, $Ca_3Nb_2O_8$, $BaSi_2O_2N_2$, $SrSi_2O_2N_2$, $CaZr(PO_4)_2$, $ZrO_2$.

Yanim Jia, in "Novel Mechano-Luminescent Sensors Based on Piezoelectric/Electroluminescent Composites," Sensors (Basel). 2011; 11(4): 3962-396, the entire contents of which are incorporated by reference, describes a mechanoluminescent composite made of a piezoelectric material and an electroluminescent material. In this composite device, when a stress is applied to the piezoelectric layer, electrical charges will be induced at both the top and bottom faces of piezoelectric layer due to the piezoelectric effect. These induced electrical charges will result in a light output from the electroluminescent layer due to the electroluminescent effect.

Here, in one embodiment of the present invention, such composites made of a piezoelectric material and an electroluminescent material, hereinafter "composite mechano-luminescent emitters," provides a structure that, upon stimulation with mechanical or vibrational energy such as from an acoustic or ultrasonic transducer, emit light. Details of various electroluminescent materials that can be used for the composite mechano-luminescent emitters are provided in the next section where electroluminescent materials alone are placed in vicinity of the opposing resonator electrodes.

Figure 30:
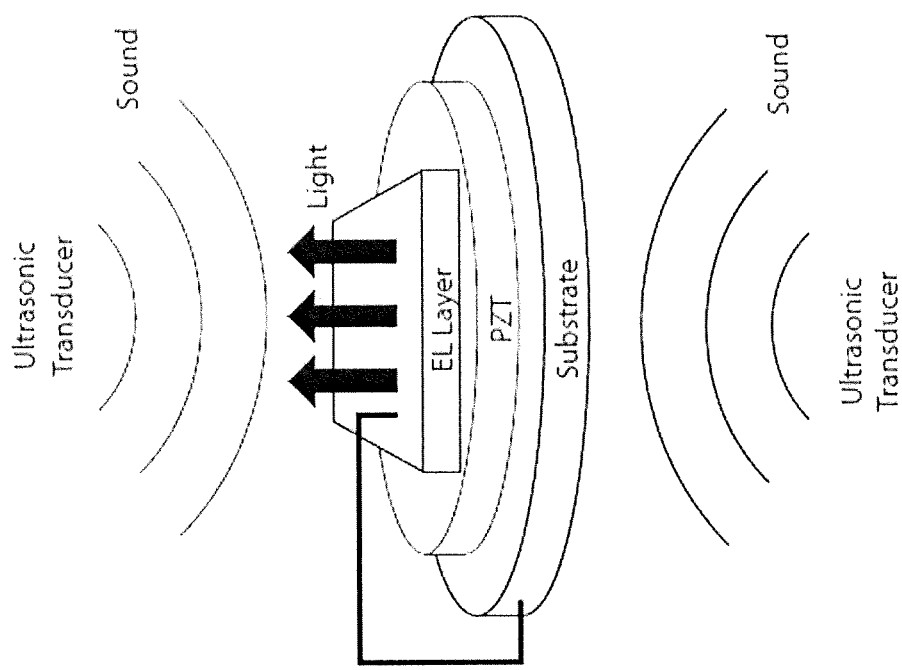
FIG. 30 is a diagram showing a composite piezoelectric/electroluminescent emitter of the present invention.

FIG. 30 is a schematic of composite mechano-luminescent emitter composed of a piezoelectric material and an electroluminescent material which, in one embodiment, could be mechano-luminescent light emitters in FIG. 29.

Figure 31:
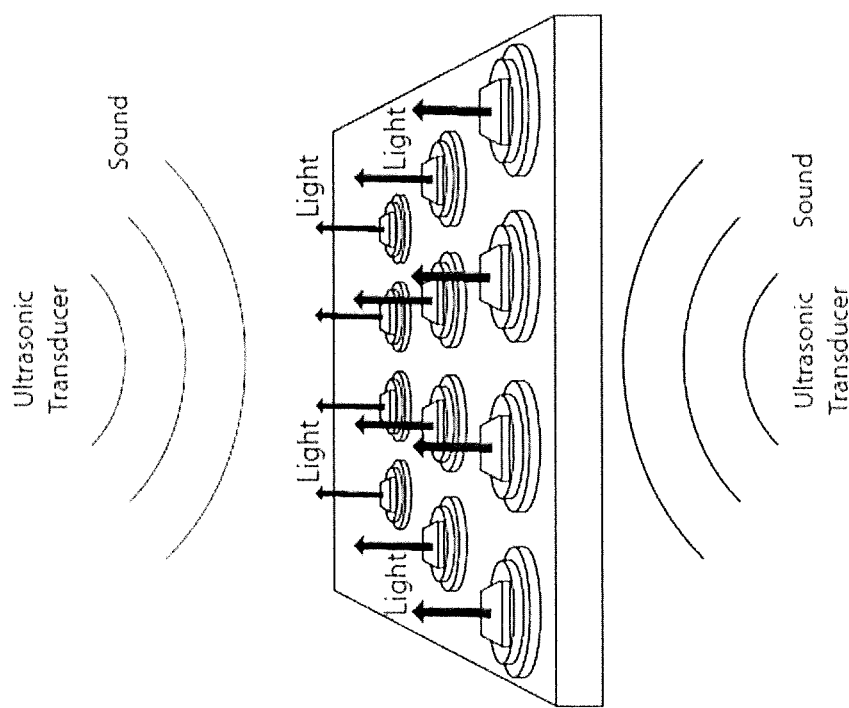
FIG. 31 is a diagram showing a distribution of the composite emitters of FIG. 30 across a surface for light emission.

In another embodiment, the composite mechano-luminescent emitters could be used without need for any resonator structure. FIG. 31 is schematic showing the composite mechano-luminescent emitters distributed across a sector of interest for generation of light therefrom. FIG. 31 shows that an ultrasonic transducer can be used for stimulation/activation of these composite mechano-luminescent emitters.

In color enhancement applications, application of ultrasonic energy could change the color emission from a surface. Such applications could be for security systems where an item would contain a pattern of the composite mechano-luminescent emitters. The pattern would not be apparent until it was activated with ultrasonic or acoustic energy upon which time light of a predetermined wavelength would be emitted. The light emitted might be visible or infrared light depending on the type of detector used to detect the emitted light.

Figure 32:
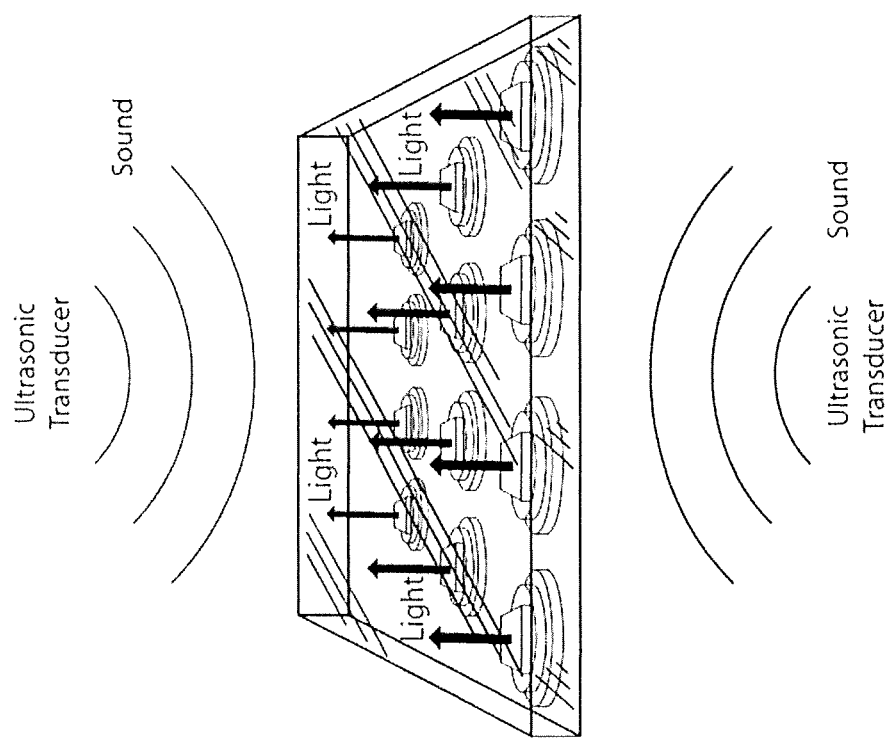
FIG. 32 is a diagram showing a distribution of the composite emitters of FIG. 30 within a target region for light emission.

In a related application of these composite mechano-luminescent emitters, FIG. 32 is schematic showing the composite mechano-luminescent emitters distributed inside a medium of interest for generation of light therein or therefrom. With the present invention, light can be turned on and off with the on/off status of an ultrasonic transducer and the intensity of the light can be varied. There are no power leads to run into the medium of interest. There is no space taken up by batteries or control elements to turn power on and off. The composite mechano-luminescent emitters can be miniaturized. The composite mechano-luminescent emitters could be agglomerated in a container. In some embodiments, the container would not be completely packed permitting the tilting of the container to relocate the composite mechano-luminescent emitters within the container.

Electroluminescent and phosphorescent materials (organic and inorganic): The present invention in various embodiments with or without energy augmentors can utilize in organic fluorescent molecules or inorganic particles capable or fluorescence and phosphorescence having crystalline, polycrystalline or amorphous micro-structures for the converters (optionally including the energy augmentation structures described above).

The list of inorganic molecules that can be used in the resonating structures to enhance the color emission include but is not limited to the following inorganic electroluminescent phosphor materials:
  $SrS:Ce^{3+}$
  $CaGa_2S_4:Ce^{3+}$
  $SrS:Cu^+$
  $CaS:Pb^{2+}$
  $BaAl_2S_4:Eu^{2+}$
  $ZnS:Tb^{3+}$
  $ZnMgS:Mn^{2+}$
  $SrGa_2S_4:Eu^{2+}$
  $CaAl_2S_4:Eu^{2+}$
  $BaAl_2S_4:Eu^{2+}$
  $ZnS:Mn^{2+}$
  $MgGa_2O_4:Eu^{3+}$
  $(Ca, Sr)Y_2S_4:Eu^{2+}$
  $BaAl_2S_4:Eu^{2+}$ The organic molecules that can phosphoresce under the influence of an electric field are also of interest in the present application. The organic fluorescent compounds with high quantum yield include by way of illustration:
  Naphthalene,
  Pyrene,
  Perylene,
  Anthracene,
  Phenanthrene,
  p-Terphenyl,
  p-Quartphenyl,
  Trans-stilbene,
  Tetraphenylbutadiene,
  Distyrylbenzene,
  2,5-Diphenyloxazole,
  4-Methyl-7-diethylaminocoumarin,
  2-Phenyl-5-(4-biphenyl)-1,3,4-oxadiazole,
  3-Phenylcarbostyryl,
  1,3,5-Triphenyl-2-pyrazoline,
  1,8-Naphthoylene-1',2'-bezimidazole,
  4-Amino-N-phenyl-naphthalimide.

The inorganic fluorescent and phosphorescent materials detailed here are numerous, and various examples are given by way of illustration rather than limitation. Furthermore, these materials can be doped with specific ions (activators or a combination of activators) that occupy a site in the lattice structure in the case of crystalline or polycrystalline materials and could occupy a network forming site or a bridging and/or non-bridging site in amorphous materials. These compounds could include (not ranked by order of preference or utility) the following material examples:
  $CaF_2$, $ZnF_2$, $KMgF_3$, $ZnGa_2O_4$, $ZnAl_2O_4$, $Zn_2SiO_4$, $Zn_2GeO_4$, $Ca_5(PO_4)_3F$, $Sr_5(PO_4)_3F$, $CaSiO_3$, $MgSiO_3$, ZnS, $MgGa_2O_4$, $LaAl_{11}O_{18}$, $Zn_2SiO_4$, $Ca_5(PO_4)_3F$, $Mg_4Ta_2O_9$, $CaF_2$, $LiAl_5O_8$, $LiAlO_2$, $CaPO_3$, $AlF_3$.

Further included are alkali earth chalcogenide phosphors which are in turn exemplified by the following non-inclusive list:
  $MgS:Eu^{3+}$, $CaS:Mn^{2+}$, CaS:Cu, CaS:Sb, $CaS:Ce^{3+}$, $CaS: Eu^{2+}$, $CaS: Eu^{2+}Ce^{3+}$, $CaS: Sm^{3+}$, $CaS:Pb^{2+}$, $CaO: Mn^{2+}$, $CaO:Pb^{2+}$.

The examples include the ZnS type phosphors that encompass various derivatives:
  ZnS:Cu,Al(Cl), ZnS:Cl(Al), ZnS:Cu,I(Cl), ZnS:Cu, ZnS: Cu,In.

Compound IIIb-Vb phosphors which include the group IIIb and Vb elements of the periodic table are suitable for converter materials. These semiconductors include BN, BP, BSb, AlN, AlP, AlAs, AlSb, GaN, GaP, GaAs, GaSb, InN, InP, InAs, InSb and these materials have donors and acceptors that work in together to induce light emission diodes. The donors include Li, Sn, Si, Li, Te, Se, S, O, and acceptors include C, Be, Mg, Zn, Cd, Si, Ge. As an example, GaP light emitting diodes include GaP:Zn, O, GaP:NN, Gap:N and GaP which emit colors Red, Yellow, Green and Pure Green respectively.

The compounded materials further include such materials as GaAs with compositional variation of the following sort: In1−y(Ga1−xAlx)yP (provides a simple example). Silicon Carbide SiC as a luminescent platform has commercial relevancy if the blue light emitting diodes. These include the polytypes 3C—SiC, 6H—SiC, 4H—SiC with donors such as N and Al and acceptors such as Ga and B.

Multiband luminescent materials suitable for converter materials include for example the following compositions:
(Sr, Ca, Ba)$_5$(PO$_4$)$_3$Cl:Eu$^{2+}$, BaMg$_2$Al$_{16}$O$_{27}$:Eu$^{2+}$, CeMgAl$_{11}$O$_{19}$:Ce$^{3+}$:Tb$^{3+}$, LaPO$_4$:Ce$^{3+}$:Tb$^{3+}$, GdMgB$_5$O$_{10}$:Ce$^{3+}$:Tb$^{3+}$, Y$_2$O$_3$:Eu$^{3+}$, (Ba,Ca,Mg)$_5$(PO$_4$)$_3$Cl:Eu$^{2+}$, 2SrO$_{0.84}$P$_2$O$_5$·0.16B$_2$O$_3$:Eu$^{2+}$, Sr$_4$Al$_{14}$O$_{25}$:Eu$^{2+}$.

Other materials suitable for converter materials include those materials used for fluorescent high pressure mercury discharge lamps can be excited with X-Ray and are exemplified by way of family designation as follows:

Phosphates (Sr, M)(PO$_4$)$_2$:Sn$^{2+}$, Mg or Zn activator, Germanate 4MgO·GeO$_2$:Mn$^{4+}$, 4(MgO, MgF$_2$)GeO$_2$:Mn$^{4+}$, Yttrate Y$_2$O$_3$:Eu$^{3+}$, Vanadate YVO$_4$:Eu$^{3+}$, Y(P,V)O$_4$:Eu$^{3+}$, Y(P,V)O$_4$:In$^+$, Halo-Silicate Sr2Si3O$_8$·2SrCl$_2$:Eu$^{2+}$, Aluminate (Ba,Mg)$_2$Al$_{16}$O$_{24}$:Eu$^{2+}$, (Ba, Mg)$_2$Al$_{16}$O$_{24}$:Eu$^{2+}$,Mn$^{2+}$, Y$_2$O$_3$Al$_2$O$_3$:Tb$^{3+}$.

Another grouping of materials suitable for converter materials by host compound include chemical compositions in the Halophosphates phosphors, Phosphate phosphors, Silicate phosphors, Aluminate phosphors, Borate phosphors, Tungstate phosphors, and other phosphors.

The halophosphates include by way of illustration:
3Ca$_3$(PO$_4$)$_2$·Ca(F,C)$_2$:Sb$^{3+}$, 3Ca$_3$(PO$_4$)$_2$·Ca(F,Cl)$_2$:Sb$^{3+}$/Mn$^{2+}$, Sr$_{10}$(PO$_4$)$_6$Cl$_2$:Eu$^{2+}$, (Sr,Ca)$_{10}$(PO$_4$)$_6$Cl$_2$:Eu$^{2+}$, (Sr,Ca)$_{10}$(PO$_4$)$_6$·nB$_2$O$_3$:Eu$^{3+}$, (Sr, Ca,Mg)$_{10}$(PO$_4$)$_6$Cl$_2$:Eu$^{2+}$. The phosphate phosphors include by way of illustration Sr$_2$P$_2$O$_7$:Sn$^{2+}$, (Sr,Mg)$_3$(PO$_4$)$_2$:Sn$^{2+}$, Ca$_3$(PO$_4$)$_2$·Sn$^{2+}$, Ca$_3$(PO$_4$)$_2$:Tl$^+$, (Ca,Zn)$_3$(PO$_4$)$_2$:Tl$^+$, Sr$_2$P$_2$O$_7$:Eu$^{2+}$, SrMgP$_2$O$_7$:Eu$^{2+}$, Sr$_3$(PO$_4$)$_2$:Eu$^{2+}$, LaPO$_4$:Ce$^{3+}$, Tb$^{3+}$, La$_2$O$_3$·0.2SiO$_2$·0.9P$_2$O$_5$:Ce$^{3+}$·Tb$^{3+}$, BaO·TiO$_2$·P$_2$O$_5$. The silicate phosphors Zn$_2$SiO$_4$:Mn$^{2+}$, CaSiO$_3$:Pb$^{2+}$/Mn$^{2+}$, (Ba, Sr, Mg)·3Si$_2$O$_7$:Pb$^{2+}$, BaSi$_2$O$_5$:Pb$^{2+}$, Sr$_2$Si$_3$O$_8$·2SrCl$_2$:Eu$^{2+}$, Ba$_3$MgSi$_2$O$_8$:Eu$^{2+}$, (Sr,Ba)Al$_2$Si$_2$O$_8$:Eu$^{2+}$.

The aluminate phosphors include:
LiAlO$_2$:Fe$^{3+}$, BaAl$_8$O$_{13}$:Eu$^{2+}$, BaMg$_2$Al$_{16}$O$_{27}$:Eu$^{2+}$, BaMg$_2$Al$_{16}$O$_{27}$:Eu$^{2+}$/Mn$^{2+}$, Sr$_4$Al$_{14}$O$_{25}$:Eu$^{2+}$, CeMgAl$_{11}$O$_{19}$:Ce$^{3+}$/Tb$^{3+}$.

The borate phosphors include:
Cd$_2$B$_2$O$_5$:Mn$^{2+}$, SrB$_4$O$_7$F:Eu$^{2+}$, GdMgB$_5$O$_{10}$:Ce$^{3+}$/Tb$^{3+}$, GdMgB$_5$O$_{10}$:Ce$^{3+}$/Mn$^{3+}$, GdMgB$_5$O$_{10}$:Ce$^{3+}$/Tb$^{3+}$/Mn$^{2+}$.

The tungstate phosphors include:
CaWO$_4$, (Ca,Pb)WO$_4$, MgWO$_4$. Other phosphors Y$_2$O$_3$:Eu$^{3+}$, Y(V,P)O$_4$:Eu$^{2+}$, YVO$_4$:Dy$^{3+}$, MgGa$_2$O$_4$:Mn$^{2+}$, 6MgO·As$_2$O$_5$:Mn$^{4+}$, 3.5MgO·0.5MgF$_2$·GeO$_2$:Mn$^{4+}$.

Activators of relevance to the various doped phosphors include the following list:
Tl$^+$, Pb$^{2+}$, Ce$^{3+}$, Eu$^{2+}$, WO$_4^{2-}$, Sn$^{2+}$, Sb$^{3+}$, Mn$^{2+}$, Tb$^{3+}$, Eu$^{3+}$, Mn$^{4+}$, Fe$^{3+}$.

In various embodiments, the luminescence center Tl+ can be used with a chemical composition such as:
(Ca,Zn)$_3$(PO$_4$)$_2$:Tl$^+$, Ca$_3$(PO$_4$)$_2$:Tl$^+$.

Similarly, the luminescence center Mn2+ can be used with chemical compositions such as
MgGa$_2$O$_4$:Mn$^{2+}$, BaMg$_2$Al$_{16}$O$_{27}$:Eu$^{2+}$/Mn$^{2+}$, Zn$_2$SiO$_4$:Mn$^{2+}$, 3Ca$_3$(PO$_4$)$_2$·Ca(F,Cl)$_2$:Sb$^{2+}$/Mn$^{2+}$, CaSiO$_3$:Pb$^{2+}$/Mn$^{2+}$, Cd$_2$B$_2$O$_5$:Mn$^{2+}$, CdB$_2$O$_5$:Mn$^{2+}$, GdMgB$_5$O$_{10}$:Ce$^{3+}$/Mn$^{2+}$, GdMgB$_5$O$_{10}$:Ce$^{3+}$/Tb$^{3+}$/Mn$^{2+}$.

Further, the luminescence center Sn$^{2+}$ can be used with chemical compositions such as:
Sr$_2$P$_2$O$_7$:Sn$^{2+}$, (Sr,Mg)$_3$(PO$_4$)$_2$:Sn$^{2+}$.

The luminescence center Eu$^{2+}$ can also be used with chemical compositions such as:
SrB$_4$O$_7$F:Eu$^{2+}$, (Sr,Ba)Al$_2$Si$_2$O$_8$:Eu$^{2+}$, Sr$_3$(PO$_4$)$_2$:Eu$^{2+}$, Sr$_2$P$_2$O$_7$:Eu$^{2+}$, Ba$_3$MgSi$_2$O$_8$:Eu$^{2+}$, Sr$_{10}$(PO$_4$)$_6$Cl$_2$:Eu$^{2+}$, BaMg$_2$Al$_{16}$O$_{27}$:Eu$^{2+}$/Mn$^{2+}$, (Sr,Ca)$_{10}$(PO$_4$)$_6$Cl$_2$:Eu$^{2+}$.

The luminescence center Pb$^{2+}$ can be used with chemical compositions such as:
(Ba,Mg,Zn)$_3$Si$_2$O$_7$:Pb$^{2+}$, BaSi$_2$O$_5$:Pb$^{2+}$, (Ba,Sr)$_3$Si$_2$O$_7$:Pb$^{2+}$.

The luminescence center Sb$^{2+}$ can be used with chemical compositions such as:
3Ca$_3$(PO$_4$)$_2$·Ca(F,Cl)$_2$:Sb$^{3+}$, 3Ca$_3$(PO$_4$)$_2$·Ca(F,CL)$_2$:Sb$^{3+}$/Mn$^{2+}$.

The luminescence center Tb3+ can be used with chemical compositions such as:
CeMgAl$_{11}$O$_{19}$:Ce$^{3+}$/Tb$^{3+}$, LaPO$_4$:Ce$^{3+}$/Tb$^{3+}$, Y$_2$SiO$_5$:Ce$^{3+}$/Tb$^{3+}$, GdMgB$_5$O$_{10}$:Ce$^{3+}$/Tb$^{3+}$.

The luminescence center Eu$^{3+}$ can be used with chemical compositions such as:
Y$_2$O$_3$:Eu$^{3+}$, Y(V,P)O$_4$:Eu$^{3+}$.

The luminescence center Dy$^{3+}$ can be used with chemical compositions such as:
YVO$_4$:Dy$^{3+}$.

The luminescence center Fe$^{3+}$ can be used with chemical compositions such as:
LiAlO$_2$:Fe$^{3+}$.

The luminescence center Mn$^{4+}$ can be used with chemical compositions such as:
6MgO·As$_2$O$_5$:Mn$^{4+}$, 3.5MgO·0.5MgF$_2$—GeO$_2$:Mn$^{4+}$.

The luminescence center Ce$^{3+}$ can be used with chemical compositions such as:
Ca$_2$MgSi$_2$O$_7$:Ce$^{3+}$ and Y$_2$SiO$_5$:Ce$^{3+}$.

The luminescence center WO$_4^{2-}$ can be used with chemical compositions such as:
CaWO$_4$, (Ca,Pb)WO$_4$, MgWO$_4$.

The luminescence center TiO$_{44}$ can be used with chemical compositions such as:
BaO·TiO$_2$·P$_2$O$_5$.

In various embodiments of this invention, the phosphor chemistry utilized in X-Ray excitations can be used. Of particular interest is the k-edge of these phosphors. Low energy excitation can lead to intense luminescence in materials with low k-edge. Some of these chemistries and the corresponding k-edge are included as follows:

| | |
|---|---|
| BaFCl:Eu$^{2+}$ | 37.38 keV |
| BaSO$_4$:Eu$^{2+}$ | 37.38 keV |

| | |
|---|---|
| CaWO$_4$ | 69.48 keV |
| Gd$_2$O$_2$S:Tb$^{3+}$ | 50.22 keV |
| LaOBr:Tb$^{3+}$ | 38.92 keV |
| LaOBr:Tm$^{3+}$ | 38.92 keV |
| La$_2$O$_2$S:Tb$^{3+}$ | 38.92 keV |
| Y$_2$O$_2$S:Tb$^{3+}$ | 17.04 keV |
| YTaO$_4$ | 67.42 keV |
| YTaO$_4$:Nb | 67.42 keV |
| ZnS:Ag | 9.66 keV |
| (Zn, Cd)S:Ag | 9.66/26.7 keV |

In one embodiment of this invention, light from these materials (excited for example by high energy particles including x-rays, gamma rays, protons, and electrons) can have their emissions modulated by having those materials included in a vicinity of (including inside) the color enhancing structures described herein. For example, in medical treatments where x-ray excites phosphorescence to photostimulate reactions in a patient, simultaneous with irradiation by the high energy particles there could be applied infrared irradiation to drive resonance in the color enhancing structures/energy augmentation structures described herein, where the x-ray phosphors would have enhanced emissions when in the presence of the intensified electric fields. In another example, in medical or scientific instruments, simultaneous with irradiation by the high energy particles there could be applied electric fields to enhance emissions from these x-ray phosphors.

Medical

In one embodiment of the present invention, there are provided methods and systems for treating cell proliferation disorders with or without energy augmentators and with the specialized energy converters of the present invention. With the energy augmentators present, this invention can generate local regions of intense electric fields to enhance light or photon or electron emission from materials in proximity to those local regions.

In-Situ Photoactivated Treatment (with and without Energy Augmentators)

The present invention sets forth a novel method of treating cell proliferation disorders that is effective, specific, and has few side-effects to those described above. The present invention advances the cell proliferation treatments described in U.S. Pat. No. 9,352,004 to Bourke, the entire contents of which are incorporated herein by reference. Cells suffering from a cell proliferation disorder are referred to herein as the target cells. A treatment for cell proliferation disorders, including solid tumors, is capable of chemically binding cellular nucleic acids, including but not limited to, the DNA or mitochondrial DNA or RNA of the target cells. For example, a photoactivatable agent, such as a psoralen or a psoralen derivative, is exposed in situ to an energy source capable of activating the photoactivatable agent or agents selected with the exposure occurring with or without the energy augmentators noted above. In another example, the photoactivatable agent is a photosensitizer. The photoactivatable agent may be a metal nanocluster or a molecule. With the energy augmentators present, this invention can generate local regions of intense electric fields to enhance light or photon or electron emission from materials in proximity to those local regions.

The present invention can thus treat cell proliferation disorders using the energy converters described above with or without the energy augmentators noted above. Exemplary cell proliferation disorders may include, but are not limited to, cancer, as well as bacterial and viral infections where the invading bacteria grows at a much more rapid rate than cells of the infected host. In addition, treatment for certain developmental stage diseases related to cell proliferation, such as syndactyly, is also contemplated.

Accordingly, in one embodiment, the present invention provides method in accordance with the present invention which utilizes the principle of energy transfer to and among molecular agents to control delivery and activation of pharmaceutically active agents such that delivery of the desired pharmacological effect is more focused, precise, and effective than prior techniques. Generally, the present invention provides methods for the treatment of cell proliferation disorders, in which an initiation energy source provides an initiation energy that with or without energy augmentators activates an activatable pharmaceutical agent to treat target cells within the subject. In one preferred embodiment, the initiation energy source is applied indirectly to the activatable pharmaceutical agent, preferably in proximity to the target cells. Within the context of the present invention, the phrase "applied indirectly" (or variants of this phrase, such as "applying indirectly", "indirectly applies", "indirectly applied", "indirectly applying", etc.), when referring to the application of the initiation energy, means the penetration by the initiation energy into the subject beneath the surface of the subject and to the activatable pharmaceutical agent within a subject. In one embodiment, the initiation energy interacts with a previously administered energy converter which then activates the activatable pharmaceutical agent. In another embodiment, the initiation energy itself activates the activatable pharmaceutical agent. In either embodiment, the initiation energy source cannot be within line-of-sight of the activatable pharmaceutical agent. By "cannot be within line-of-sight" is meant that if a hypothetical observer were located at the location of the activatable pharmaceutical agent, that observer would be unable to see the source of the initiation energy. With the energy augmentators present, this invention can generate local regions of intense electric fields to enhance light or photon or electron emission from materials in proximity to those local regions, and thereby assist in the treatment of cell proliferation.

Although not intending to be bound by any particular theory or be otherwise limited in any way, the following theoretical discussion of scientific principles and definitions are provided to help the reader gain an understanding and appreciation of the present invention.

As used herein, the term "subject" is not intended to be limited to humans, but may also include animals, plants, or any suitable biological organism.

As used herein, the phrase "cell proliferation disorder" refers to any condition where the growth rate of a population of cells is less than or greater than a desired rate under a given physiological state and conditions. Although, preferably, the proliferation rate that would be of interest for treatment purposes is faster than a desired rate, slower than desired rate conditions may also be treated by methods of the present invention. Exemplary cell proliferation disorders may include, but are not limited to, cancer, bacterial infection, immune rejection response of organ transplant, solid tumors, viral infection, autoimmune disorders (such as arthritis, lupus, inflammatory bowel disease, Sjogrens syndrome, multiple sclerosis) or a combination thereof, as well as aplastic conditions wherein cell proliferation is low relative to healthy cells, such as aplastic anemia. Particularly preferred cell proliferation disorders for treatment using the present methods are cancer, *Staphylococcus aureus* (particularly antibiotic resistant strains such as methicillin resistant *Staphylococcus aureus* or MRSA), and autoimmune disorders.

As used herein, an "activatable pharmaceutical agent" is an agent that normally exists in an inactive state in the absence of an activation signal. When the agent is activated by a matching activation signal under activating conditions, it is capable of effecting the desired pharmacological effect on a target cell (i.e. preferably a predetermined cellular change). Signals that may be used to activate a corresponding agent may include, but are not limited to, photons of specific wavelengths (e.g. x-rays, or visible light), electromagnetic energy (e.g. radio or microwave), thermal energy, acoustic energy, or any combination thereof. Activation of the agent may be as simple as delivering the signal to the agent or may further premise on a set of activation conditions. For example, in the former case, an activatable pharmaceutical agent, such as a photosensitizer, may be activated by UV-A radiation. Once activated, the agent in its active-state may then directly proceed to effect a cellular change. Where activation may further premise upon other conditions, mere delivery of the activation signal may not be sufficient to bring about the desired cellular change. For example, a photoactive compound that achieves its pharmaceutical effect by binding to certain cellular structure in its active state may require physical proximity to the target cellular structure when the activation signal is delivered. For such activatable agents, delivery of the activation signal under non-activating conditions will not result in the desired pharmacologic effect. Some examples of activating conditions may include, but are not limited to, temperature, pH, location, state of the cell, presence or absence of co-factors.

Selection of an activatable pharmaceutical agent greatly depends on a number of factors such as the desired cellular change, the desired form of activation, as well as the physical and biochemical constraints that may apply. Exemplary activatable pharmaceutical agents may include, but are not limited to, agents that may be activated by photonic energy, electromagnetic energy, acoustic energy, chemical or enzymatic reactions, thermal energy, or any other suitable activation mechanisms.

When activated, the activatable pharmaceutical agent may effect cellular changes that include, but are not limited to, apoptosis, redirection of metabolic pathways, up-regulation of certain genes, down-regulation of certain genes, secretion of cytokines, alteration of cytokine receptor responses, or combinations thereof.

The mechanisms by which an activatable pharmaceutical agent may achieve its desired effect are not particularly limited. Such mechanisms may include direct action on a predetermined target as well as indirect actions via alterations to the biochemical pathways. A preferred direct action mechanism is by binding the agent to a critical cellular structure such as nuclear DNA, mRNA, rRNA, ribosome, mitochondrial DNA, or any other functionally important structures. Indirect mechanisms may include releasing metabolites upon activation to interfere with normal metabolic pathways, releasing chemical signals (e.g. agonists or antagonists) upon activation to alter the targeted cellular response, and other suitable biochemical or metabolic alterations.

In one preferred embodiment, the activatable pharmaceutical agent is capable of chemically binding to the DNA or mitochondria at a therapeutically effective amount. In this embodiment, the activatable pharmaceutical agent, preferably a photoactivatable agent, is exposed in situ to an activating energy emitted from an energy converter, which, in turn receives energy from an initiation energy source.

Suitable activatable agents include, but are not limited to, photoactive agents, sono-active agents, thermo-active agents, and radio/microwave-active agents. An activatable agent may be a small molecule; a biological molecule such as a protein, a nucleic acid or lipid; a supramolecular assembly; a nanoparticle; or any other molecular entity having a pharmaceutical activity once activated.

The activatable agent may be derived from a natural or synthetic origin. Any such molecular entity that may be activated by a suitable activation signal source to effect a predetermined cellular change may be advantageously employed in the present invention.

Suitable photoactive agents include, but are not limited to: psoralens and psoralen derivatives, pyrene cholesteryloleate, acridine, porphyrin, fluorescein, rhodamine, 16-diazorcortisone, ethidium, transition metal complexes of bleomycin, transition metal complexes of deglycobleomycin, organoplatinum complexes, alloxazines such as 7,8-dimethyl-10-ribityl isoalloxazine (riboflavin), 7,8,10-trimethylisoalloxazine (lumiflavin), 7,8-dimethylalloxazine (lumichrome), isoalloxazine-adenine dinucleotide (flavine adenine dinucleotide [FAD]), alloxazine mononucleotide (also known as flavine mononucleotide [FMN] and riboflavine-5-phosphate), vitamin Ks, vitamin L, their metabolites and precursors, and napththoquinones, naphthalenes, naphthols and their derivatives having planar molecular conformations, porphyrins, dyes such as neutral red, methylene blue, acridine, toluidines, flavine (acriflavine hydrochloride) and phenothiazine derivatives, coumarins, quinolones, quinones, and anthroquinones, aluminum (111) phthalocyanine tetrasulfonate, hematoporphyrin, and phthalocyanine, and compounds which preferentially adsorb to nucleic acids with little or no effect on proteins. The term "alloxazine" includes isoalloxazines.

Endogenously-based derivatives include synthetically derived analogs and homologs of endogenous photoactivated molecules, which may have or lack lower (1 to 5 carbons) alkyl or halogen substituents of the photosensitizers from which they are derived, and which preserve the function and substantial non-toxicity. Endogenous molecules are inherently non-toxic and may not yield toxic photoproducts after photoradiation.

Table 1 lists some photoactivatable molecules capable of being photoactivated to induce an auto vaccine effect.

| | | | | SSET and TTET rate constants for bichromophoric peptides | | | | | | |
|---|---|---|---|---|---|---|---|---|---|---|
| Compound | $\lambda_{ex}$ (nm) | $E_{SSET}$ | $k_s$ of donor (s$^{-1}$) | $k_{SSET}$(s$^{-1}$) | $k_{SSET}$(s$^{-1}$) (Average) | $R_0$(Å) | R(Å) | $R_{model}$(Å) (Average) | $E_{TTET}$ | $k_{TTET}$(s$^{-1}$) |
| 1/B | 224 | 96.3 | $9.5 \times 10^5$ | $2.44 \times 10^8$ | $1.87 \times 10^3$ | 14.7 | 9 | 9.5 | | |
| | 266 | 95 | | $1.8 \times 10^8$ | | | | | 2.5 | $5 \times 10^2$ |
| | 280 | 94 | | $1.36 \times 10^8$ | | | | | | |

-continued
| | | | | | | | | | | |
|---|---|---|---|---|---|---|---|---|---|---|
| Compound | $\lambda_{ex}$ (nm) | $E_{SSET}$ | $k_s$ of donor (s$^{-1}$) | $k_{SSET}$(s$^{-1}$) | $k_{SSET}$(s$^{-1}$) (Average) | $R_0$(Å) | $R$(Å) | $R_{model}$(Å) (Average) | $E_{TTET}$ | $k_{TTET}$(s$^{-1}$) |
| 1A | 224 | 80 | $9.5 \times 10^6$ | $3.8 \times 10^7$ | $3.67 \times 10^7$ | 14.7 | 11.8 | 14.1 | | |
| | 266 | 79 | | $3.6 \times 10^7$ | | | | | 2 | $3.6 \times 10^2$ |
| | 280 | 79 | | $3.6 \times 10^7$ | | | | | | |
| 2B | 224 | 77 | $9.5 \times 10^5$ | $3.1 \times 10^7$ | $3.9 \times 10^7$ | 14.7 | 11.9 | 6.5 | | |
| | 266 | 81 | | $3.9 \times 10^7$ | | | | | 32 | $9.4 \times 10^3$ |
| | 280 | 83 | | $4.7 \times 10^7$ | | | | | | |
| 2A | 224 | 69 | $9.5 \times 10^5$ | $2.1 \times 10^7$ | $3 \times 10^7$ | 14.7 | 12.2 | 8.1 | | |
| | 266 | 80 | | $3.7 \times 10^7$ | | | | | 74.3 | $5.7 \times 10^4$ |
| | 280 | 77 | | $3.1 \times 10^7$ | | | | | | |
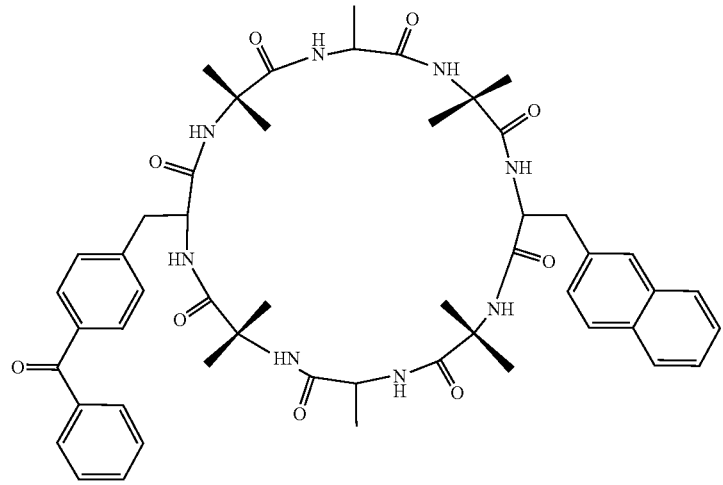
1A
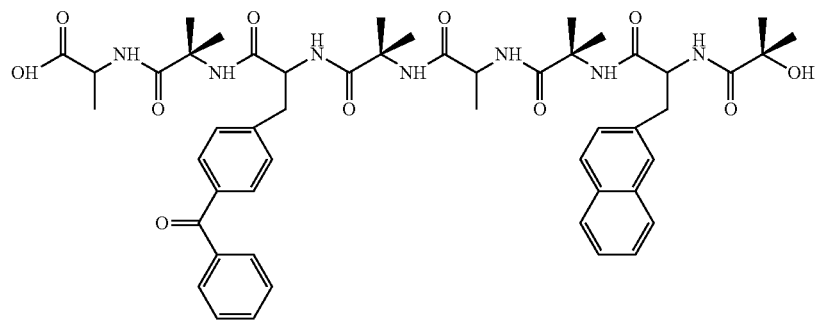
1B TABLE-continued SSET and TTET rate constants for bichromophoric peptides

| Compound | $\lambda_{ex}$ (nm) | $E_{SSET}$ | $k_s$ of donor (s⁻¹) | $k_{SSET}$(s⁻¹) | $k_{SSET}^{(s-1)}$ (Average) | $R_0$(Å) | $R$(Å) | $R_{model}$(Å) (Average) | $E_{TTET}$ | $k_{TTET}$(s⁻¹) |
|---|---|---|---|---|---|---|---|---|---|---|

2A

2B

Table 2 lists some additional endogenous photoactivatable molecules.

TABLE 2

Biocompatible, endogenous fluorophore emitters.

| Endogenous Fluorophores | Excitation Max. (nm) | Emission Max. (nm) |
|---|---|---|
| Amino acids: | | |
| Tryptophan | 280 | 350 |
| Tyrosine | 275 | 300 |
| Phenylalanine | 260 | 280 |
| Structural Proteins: | | |
| Collagen | 325, 360 | 400, 405 |
| Elastin | 290, 325 | 340, 400 |
| Enzymes and Coenzymes: | | |
| flavin adenine dinucleotide | 450 | 535 |
| reduced nicotinamide dinucelotide | 290, 351 | 440, 460 |
| reduced nicotinamide dinucelotide phosphate | 336 | 464 |
| Vitamins: | | |
| Vitamins A | 327 | 510 |
| Vitamins K | 335 | 480 |
| Vitamins D | 390 | 480 |
| Vitamins $B_6$ compounds: | | |
| Pyridoxine | 332, 340 | 400 |
| Pyridoxamine | 335 | 400 |
| Pyridoxal | 330 | 385 |
| Pyridoxic acid | 315 | 425 |
| Pyridoxal phosphate | 5'-330 | 400 |
| Vitamin $B_{12}$ | 275 | 305 |
| Lipids: | | |
| Phospholipids | 436 | 540, 560 |
| Lipofuscin | 340-395 | 540, 430-460 |
| Ceroid | 340-395 | 430-460, 540 |
| Porphyrins | 400-450 | 630, 690 |

Figure 33:
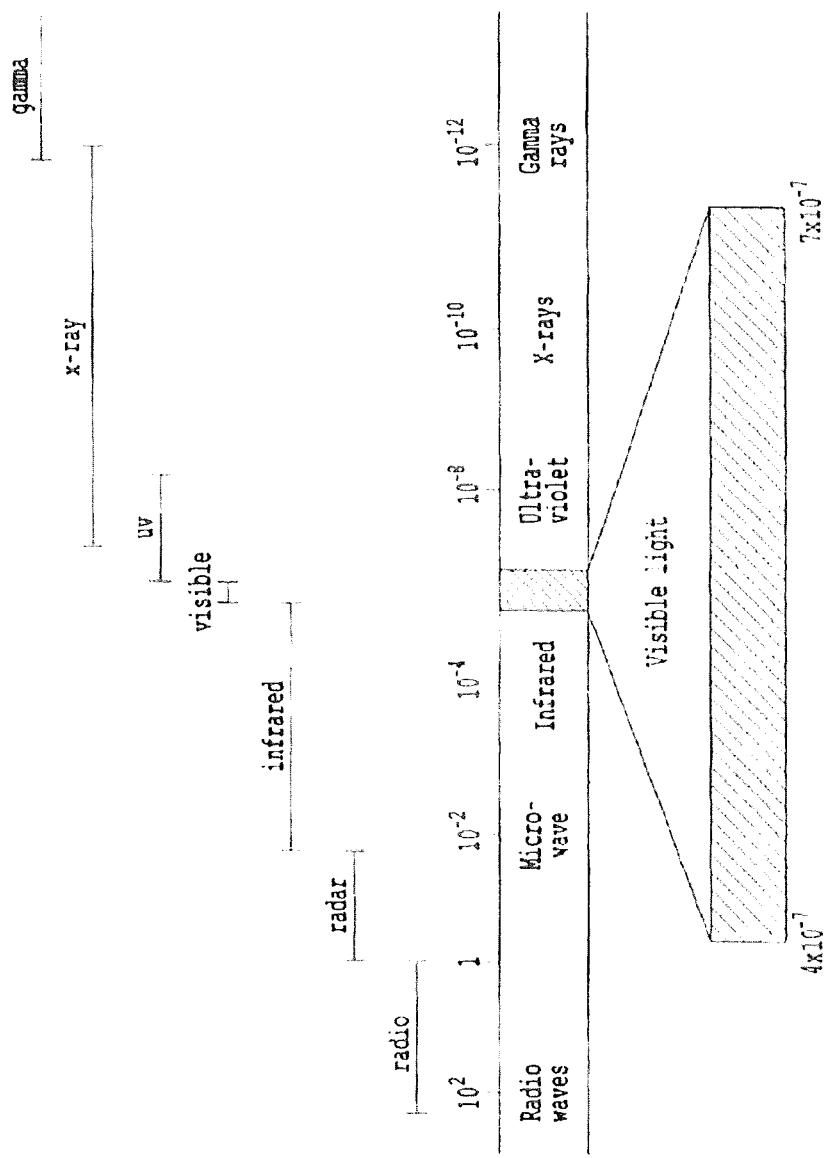
FIG. 33 provides an exemplary electromagnetic spectrum in meters (1 nm equals meters)

FIG. 33 provides an exemplary electromagnetic spectrum in meters (1 nm equals meters).

Figures 34A, 34B:
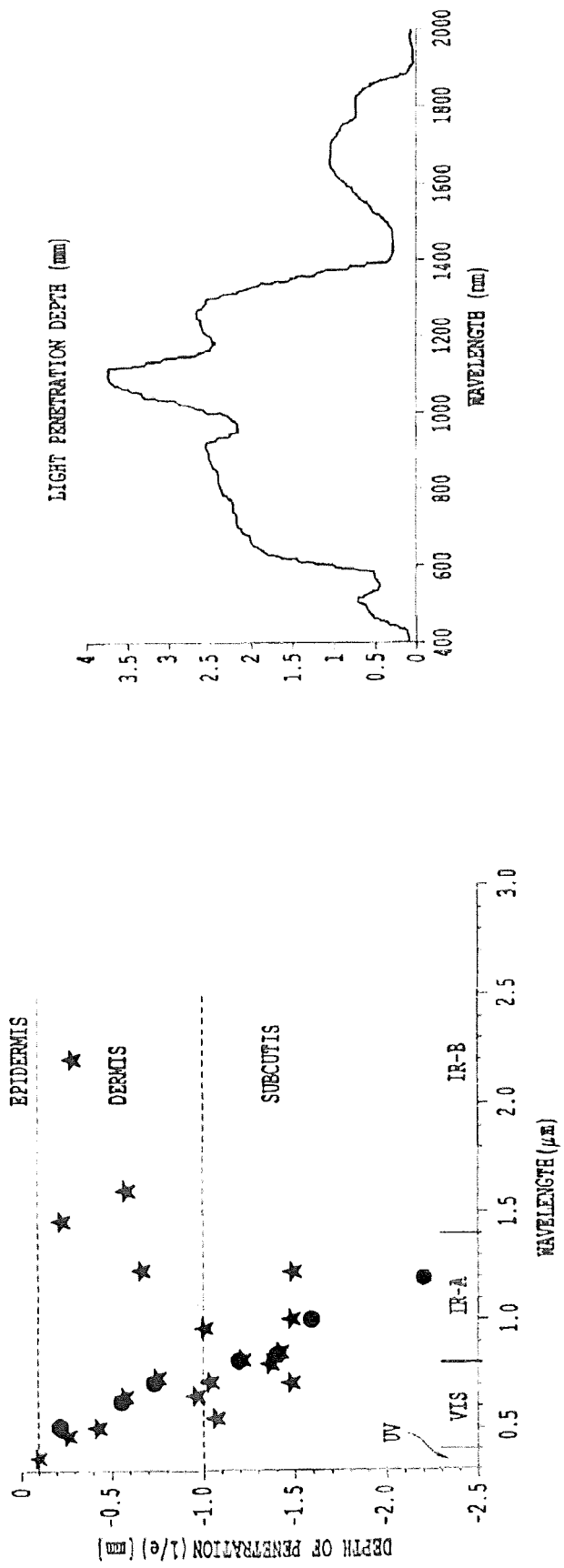
FIGS. 34A and 34B are graphical representations of the depth of penetration of various wavelengths of energy into living tissue.

FIG. 34A and FIG. 34B are graphical representations of the depth of penetration of various wavelengths of energy into living tissue.

The nature of the predetermined cellular change will depend on the desired pharmaceutical outcome. Exemplary cellular changes may include, but are not limited to, apoptosis, necrosis, up-regulation of certain genes, down-regulation of certain genes, secretion of cytokines, alteration of cytokine receptor responses, or a combination thereof.

As used herein, an "energy converter" refers to an agent that is capable of receiving an energy input from a source and then re-emitting a different energy to a receiving target. Energy transfer among molecules may occur in a number of ways. The form of energy may be electronic, thermal, electromagnetic, kinetic, or chemical in nature. Energy may be transferred from one molecule to another (intermolecular transfer) or from one part of a molecule to another part of the same molecule (intramolecular transfer). For example, a converter may receive electromagnetic energy and re-emit the energy e.g. in the form of light or thermal energy. In preferred embodiments, the energy converter receives higher energy (e.g. x-ray) and re-emits in lower energy (e.g. UV-A). Some converters may have a very short energy retention time (on the order of fs, e.g. fluorescent molecules) whereas others may have a very long half-life (on the order of minutes to hours, e.g. luminescent or phosphorescent molecules). Suitable energy converters include, but are not limited to, a biocompatible fluorescing metal nanoparticle, fluorescing dye molecule, gold nanoparticle, a water soluble quantum dot encapsulated by polyamidoamine dendrimers, a luciferase (bioluminescence), a biocompatible phosphorescent molecule, a combined electromagnetic energy harvester molecule, and a lanthanide chelate capable of intense luminescence, and/or any of the energy converters discussed above with or without energy augmentators. Various exemplary uses of these are described below in preferred embodiments.

The converters may further be coupled to a carrier for cellular targeting purposes. For example, a biocompatible molecule, such as a fluorescing metal nanoparticle or fluorescing dye molecule that emits in the UV-A band, may be selected as the energy converter.

The energy converter may be preferably directed to the desired site (e.g. a tumor) by systemic administration to a subject. For example, a UV-A emitting energy converter may be concentrated in the tumor site by physical insertion or by conjugating the UV-A emitting energy converter with a tumor specific carrier, such as a lipid, chitin or chitin-derivative, a chelate or other functionalized carrier that is capable of concentrating the UV-A emitting source in a specific target tumor.

Additionally, the energy converter can be used alone or as a series of two or more energy converters wherein the energy converters provide an energy cascade. Thus, the first energy converter in the cascade will absorb the activation energy, convert it to a different energy which is then absorbed by the second energy modulation in the cascade, and so forth until the end of the cascade is reached with the final energy converter in the cascade emitting the energy necessary to activate the activatable pharmaceutical agent.

Although the activatable pharmaceutical agent and the energy converter can be distinct and separate, it will be understood that the two agents need not be independent and separate entities. In fact, the two agents may be associated with each other via a number of different configurations. Where the two agents are independent and separately movable from each other, they generally interact with each other via diffusion and chance encounters within a common surrounding medium. Where the activatable pharmaceutical agent and the energy converter are not separate, they may be combined into one single entity.

The initiation energy source can be any energy source capable of providing energy at a level sufficient to activate the activatable agent directly, or to provide the energy converter with the input needed to emit the activation energy for the activatable agent (indirect activation). Preferable initiation energy sources include, but are not limited to, UV-A lamps or fiber optic lines, a light needle, an endoscope, and a linear accelerator that generates x-ray, gamma-ray, or electron beams. In a preferred embodiment the initiation energy is capable of penetrating completely through the subject. Within the context of the present invention, the phrase "capable of penetrating completely through the subject" is used to refer to energy that can penetrate to any depth within the subject to activate the activatable pharmaceutical agent.

It is not required that the any of the energy applied actually pass completely through the subject, merely that it be capable of doing so in order to permit penetration to a desired depth to activate the activatable pharmaceutical agent. Exemplary initiation energy sources that are capable of penetrating completely through the subject include, but are not limited to, x-rays, gamma rays, electron beams, microwaves, radio waves, and sound or acoustic waves.

In one embodiment, the source of the initiation energy can be a radiowave emitting nanotube, such as those described by K. Jensen, J. Weldon, H. Garcia, and A. Zettl in the Department of Physics at the University of California at Berkeley (see http://socrates.berkeley.edu/~argon/nanoradio/radio.html, the entire contents of which are hereby incorporated by reference). These nanotubes with or without energy augmentators can be administered to the subject, and preferably would be coupled to the activatable pharmaceutical agent or the energy converter, or both, such that upon application of the initiation energy, the nanotubes would accept the initiation energy (preferably radiowaves), then emit radiowaves in close proximity to the activatable pharmaceutical agent, or in close proximity to the energy converter, to then cause activation of the activatable pharmaceutical agent. In such an embodiment, the nanotubes would act essentially as a radiowave focusing or amplification device in close proximity to the activatable pharmaceutical agent or energy converter.

Alternatively, the energy emitting source may be an energy converter (or energy converter) that emits energy in a form suitable for absorption by the transfer agent. For example, the initiation energy source may be acoustic energy and one energy converter may be capable of receiving acoustic energy and emitting photonic energy (e.g. sonoluminescent molecules including for example the mechano-luminescent energy converters described above), which may or may not be received by another energy converter that is capable of receiving photonic energy or which may be received at a target site and may activate a photoactivatable drug. Other examples include transfer agents that receive energy at x-ray wavelength and emit energy at UV wavelength, preferably at UV-A wavelength. As noted above, a plurality of such energy converters may be used to form a cascade to transfer energy from initiation energy source via a series of energy converters to activate the activatable agent.

Signal transduction schemes as a drug delivery vehicle may be advantageously developed by careful modeling of the cascade events coupled with metabolic pathway knowledge to sequentially or simultaneously activate multiple activatable pharmaceutical agents to achieve multiple-point alterations in cellular function.

Photoactivatable agents may be stimulated by an energy source, such as irradiation, resonance energy transfer, exciton migration, electron injection, or chemical reaction, to an activated energy state that is capable of effecting the predetermined cellular change desired. In a preferred embodiment, the photoactivatable agent, upon activation, binds to DNA or RNA or other structures in a cell. The activated energy state of the agent is capable of causing damage to cells, inducing apoptosis. The mechanism of apoptosis is associated with an enhanced immune response that reduces the growth rate of cell proliferation disorders and may shrink solid tumors, depending on the state of the patient's immune system, concentration of the agent in the tumor, sensitivity of the agent to stimulation, and length of stimulation.

A preferred method of treating a cell proliferation disorder of the present invention administers a photoactivatable agent to a patient, stimulates the photoactivatable agent to induce cell damage, and generates an auto vaccine effect. In one further preferred embodiment, the photoactivatable agent is stimulated via a resonance energy transfer.

One advantage is that multiple wavelengths of emitted radiation may be used to selectively stimulate one or more photoactivatable agents or energy converters capable of stimulating the one or more photoactivatable agents. The energy converter (or one or more of the energy converters described above) is preferably stimulated at a wavelength and energy that causes little or no damage to healthy cells. Energy from one or more energy converters may be transferred, such as by Foerster Resonance Energy Transfer, to the photoactivatable agents that damage the cell and cause the onset of the desired cellular change, such as apoptosis of the cells. In one embodiment of the present invention, the transfer of energy by Foerster Resonance Energy Transfer is assisted/enhanced by use of one or more of the energy augmentators, particularly those at a treatment site generating an intense electric field in the vicinity of the treatment area. For example, the folded resonators depicted on the sheet in FIG. 7 or a distribution of the other resonating structures shown in FIGS. 2 through 25 at a target site, under resonating conditions (e.g., driven by a low power infrared laser or a microwave source), can generate local regions of intense electric fields that can enhance or accelerate the transfer of energy by Foerster Resonance Energy Transfer.

Another advantage is that side effects can be greatly reduced by limiting the production of free radicals, singlet oxygen, hydroxides and other highly reactive groups that are known to damage healthy cells. Furthermore, additional additives, such as antioxidants, may be used to further reduce undesired effects of irradiation.

Resonance Energy Transfer (RET) is an energy transfer mechanism between two molecules having overlapping emission and absorption bands. In the present invention, the energy augmentators produce regions of intensified electric fields which can enhance or accelerate the transfer. In general, electromagnetic emitters are capable of converting an arriving wavelength to a longer wavelength. For example, UV-B energy absorbed by a first molecule may be transferred by a dipole-dipole interaction to a UV-A-emitting molecule in close proximity to the UV-B-absorbing molecule.

Alternatively, a material absorbing a shorter wavelength may be chosen to provide RET to a non-emitting molecule that has an overlapping absorption band with the transferring molecule's emission band. Alternatively, phosphorescence, chemiluminescence, or bioluminescence may be used to transfer energy to a photoactivatable molecule.

Alternatively, one can administer the initiation energy source to the subject. Within the context of the present invention, the administering of the initiation energy source means the administration of an agent, that itself produces the initiation energy, in a manner that permits the agent to arrive at the target cell within the subject without being surgically inserted into the subject. The administration can take any form, including, but not limited to, oral, intravenous, intraperitoneal, inhalation, etc. Further, the initiation energy source in this embodiment can be in any form, including, but not limited to, tablet, powder, liquid solution, liquid suspension, liquid dispersion, gas or vapor, etc. In this embodiment, the initiation energy source includes, but is not limited to, chemical energy sources, bioluminescent sources, nanoemitters, nanochips, and other nanomachines that produce and emit energy of a desired frequency. Recent advances in nanotechnology have provided examples of various devices that are nanoscale and produce or emit energy, such as the Molecular Switch (or Mol-Switch) work by Dr. Keith Firman of the EC Research and Development Project, or the work of Cornell et al. (1997) who describe the construction of nanomachines based around ion-channel switches only 1.5 nm in size, which use ion channels formed in an artificial membrane by two gramicidin molecules: one in the lower layer of the membrane attached to a gold electrode and one in the upper layer tethered to biological receptors such as antibodies or nucleotides. When the receptor captures a target molecule or cell, the ion channel is broken, its conductivity drops, and the biochemical signal is converted into an electrical signal. These nanodevices (and/or for example the mechano-luminescent devices described above) could also be coupled with the present invention to provide targeting of the target cell, to deliver the initiation energy source directly at the desired site. In another embodiment, the present invention includes the administration of the activatable pharmaceutical agent, along with administration of a source of chemical energy such as chemiluminescence, phosphorescence or bioluminescence.

The source of chemical energy can be a chemical reaction between two or more compounds, or can be induced by activating a chemiluminescent, phosphorescent or bioluminescent compound with an appropriate activation energy, either outside the subject or inside the subject, with the chemiluminescence, phosphorescence or bioluminescence being allowed to activate the activatable pharmaceutical agent in vivo after administration. The administration of the activatable pharmaceutical agent and the source of chemical energy can be performed sequentially in any order or can be performed simultaneously. In the case of certain sources of such chemical energy, the administration of the chemical energy source can be performed after activation outside the subject, with the lifetime of the emission of the energy being up to several hours for certain types of phosphorescent materials for example. There are no known previous efforts to use resonance energy transfer of any kind to activate an intercalator to bind DNA.

Yet another example is that nanoparticles or nanoclusters of certain atoms may be introduced such that are capable of resonance energy transfer over comparatively large distances, such as greater than one nanometer, more preferably greater than five nanometers, even more preferably at least 10 nanometers. Functionally, resonance energy transfer may have a large enough "Foerster" distance ($R_0$), such that nanoparticles in one part of a cell are capable of stimulating activation of photoactivatable agents disposed in a distant portion of the cell, so long as the distance does not greatly exceed $R_0$. For example, gold nanospheres having a size of 5 atoms of gold have been shown to have an emission band in the ultraviolet range, recently.

The present invention treatment may also be used for inducing an auto vaccine effect for malignant cells, including those in solid tumors. To the extent that any rapidly dividing cells or stem cells may be damaged by a systemic treatment, then it may be preferable to direct the stimulating energy directly toward the tumor, preventing damage to most normal, healthy cells or stem cells by avoiding photoactivation or resonant energy transfer of the photoactivatable agent.

Alternatively, a treatment may be applied that slows or pauses mitosis. Such a treatment is capable of slowing the division of rapidly dividing healthy cells or stem cells during the treatment, without pausing mitosis of cancerous cells. Alternatively, a blocking agent is administered preferentially to malignant cells prior to administering the treatment that slows mitosis.

In one embodiment, an aggressive cell proliferation disorder has a much higher rate of mitosis, which leads to selective destruction of a disproportionate share of the malignant cells during even a systemically administered treatment. Stem cells and healthy cells may be spared from wholesale programmed cell death, even if exposed to photoactivated agents, provided that such photoactivated agents degenerate from the excited state to a lower energy state prior to binding, mitosis or other mechanisms for creating damage to the cells of a substantial fraction of the healthy stem cells. Thus, an auto-immune response may not necessarily be induced or required.

Alternatively, a blocking agent may be used that prevents or reduces damage to stem cells or healthy cells, selectively, which would otherwise be impaired. The blocking agent is selected or is administered such that the blocking agent does not impart a similar benefit to malignant cells, for example.

In one embodiment, stem cells are targeted, specifically, for destruction with the intention of replacing the stem cells with a donor cell line or previously stored, healthy cells of the patient. In this case, no blocking agent is used. Instead, a carrier or photosensitizer is used that specifically targets the stem cells.

Any of the photoactivatable agents may be exposed to an excitation energy source implanted in a tumor. The photoactive agent may be directed to a receptor site by a carrier having a strong affinity for the receptor site. Within the context of the present invention, a "strong affinity" is preferably an affinity having an equilibrium dissociation constant, $K_i$, at least in the nanomolar, nM, range or higher. Preferably, the carrier may be a polypeptide and may form a covalent bond with a photoactive agent, for example. The polypeptide may be an insulin, interleukin, thymopoietin or transferrin, for example. Alternatively, a photoactive agent may have a strong affinity for the target cell without binding to a carrier.

A receptor site may be any of the following: nucleic acids of nucleated blood cells, molecule receptor sites of nucleated blood cells, the antigenic sites on nucleated blood cells, epitopes, or other sites where photoactive agents are capable of destroying a targeted cell.

In one embodiment, thin fiber optic lines are inserted in the tumor and laser light is used to photoactivate the agents. These lines could provide also radiation to the energy augmentators at the resonant frequency of the augmentator to generate the afore-mentioned intensified fields. In another embodiment, a plurality of sources for supplying electromagnetic radiation energy or energy transfer are provided by one or more molecules administered to a patient. The molecules may emit stimulating radiation in the correct band of wavelength to stimulate the photoactivatable agents, or the molecules may transfer energy by a resonance energy transfer or other mechanism directly to the photoactivatable agent or indirectly by a cascade effect via other molecular interactions.

In another embodiment, the patient's own cells are removed and genetically modified to provide photonic emissions. For example, tumor or healthy cells may be removed, genetically modified to induce bioluminescence and may be reinserted at the site of the tumor to be treated. The modified, bioluminescent cells may be further modified to prevent further division of the cells or division of the cells only so long as a regulating agent is present. Administration of an intercalator, systemically or targeting tumor cells, that is capable of photoactivation by bioluminescent cells may produce conditions suitable for creating an auto vaccine effect due to apoptosis of malignant cells. Preferably, apoptosis triggers and stimulates the body to develop an immune response targeting the malignant cells. In a further embodiment, UV emitting bioluminescent materials can be injected into the site of the tumor without first having removed any of the tumor or healthy cells.

In a further embodiment, a biocompatible emitting source, such as a fluorescing metal nanoparticle or fluorescing dye molecule or a bioluminescent agent, is selected that emits in the UV-A band. The UV-A emitting source is directed to the site of a tumor. The UV-A emitting source may be directed to the site of the tumor by systemically administering the UV-A emitting source. Preferably, the UV-A emitting source is concentrated in the tumor site, such as by physical insertion or by conjugating the UV-A emitting molecule with a tumor specific carrier, such as a lipid, chitin or chitin-derivative, a chelate or other functionalized carrier that is capable of concentrating the UV-A emitting source in a specific target tumor, as is known in the art.

In one preferred embodiment, the UV-A emitting source is a gold nanoparticle comprising a cluster of 5 gold atoms, such as a water soluble quantum dot encapsulated by polyamidoamine dendrimers. The gold atom clusters may be produced through a slow reduction of gold salts (e.g. $HAuCl_4$ or $AuBr_3$) or other encapsulating amines, for example. One advantage of such a gold nanoparticle is the increased Foerster distance (i.e. $R_0$), which may be greater than 100 angstroms. The equation for determining the Foerster distance is substantially different from that for molecular fluorescence, which is limited to use at distances less than 100 angstroms. It is believed that the gold nanoparticles are governed by nanoparticle surface to dipole equations with a $1/R^4$ distance dependence rather than a $1/R^6$ distance dependence. For example, this permits cytoplasmic to nuclear energy transfer between metal nanoparticles and a photoactivatable molecule, such as a psoralen and more preferably an 8-methoxypsoralen (8-MOP) administered orally to a patient, which is known to be safe and effective at inducing an apoptosis of leukocytes.

In another embodiment, a UV- or light-emitting luciferase is selected as the emitting source for exciting a photoactivatable agent. A luciferase may be combined with ATP or another molecule, which may then be oxygenated with additional molecules to stimulate light emission at a desired wavelength. The luciferase may be used with or without the energy augmentators. Alternatively, a phosphorescent emitting source may be used with or without the energy augmentators. One advantage of a phosphorescent emitting source is that the phosphorescent emitting molecules or other source may be electroactivated or photoactivated prior to insertion into the tumor either by systemic administration or direct insertion into the region of the tumor. Phosphorescent materials may have longer relaxation times than fluorescent materials, because relaxation of a triplet state is subject to forbidden energy state transitions, storing the energy in the excited triplet state with only a limited number of quantum mechanical energy transfer processes available for returning to the lower energy state. Energy emission is delayed or prolonged from a fraction of a second to several hours. Otherwise, the energy emitted during phosphorescent relaxation is not otherwise different than fluorescence, and the range of wavelengths may be selected by choosing a particular phosphor. With the energy augmentators present, this invention can generate local regions of intense electric fields to enhance light or photon or electron emission from the phosphors in proximity to those local regions, and thereby assist in the treatment of cell proliferation.

Alternatively, a phosphorescent emitting source may be used as the energy converter. One advantage of a phosphorescent emitting source is that the phosphorescent emitting molecules or other source may be electroactivated or photoactivated prior to insertion into the tumor either by systemic administration or direct insertion into the region of the tumor. Phosphorescent materials may have longer relaxation times than fluorescent materials, because relaxation of a triplet state is subject to forbidden energy state transitions, storing the energy in the excited triplet state with only a limited number of quantum mechanical energy transfer processes available for returning to the lower energy state. Energy emission is delayed or prolonged from a fraction of a second to several hours. Otherwise, the energy emitted during phosphorescent relaxation is not otherwise different than fluorescence, and the range of wavelengths may be selected by choosing a particular phosphor.

In one embodiment, the energy converters of the invention can include persistent after-glow phosphor materials emitting light in the visible to near ultraviolet and ultraviolet range. In one embodiment, Eu-doped strontium aluminate is used as an energy converter in which deep UV light or x-ray or electron beans "charge" the photoluminescence such that these phosphors can be charged outside for example a patient and then injected into target or diseased site where UV photons would be emitted. In another embodiment, gadolinium strontium magnesium aluminate is used as an energy converter in which deep UV light or x-ray or electron beans "charge" the photoluminescence such that these phosphors can be charged outside for example a patient and then injected into target or diseased site where UV photons would be emitted. U.S. Pat. Appl. Publ. No. 20070221883 (the entire contents of which are incorporated herein by reference) describes specifically gadolinium-activated strontium magnesium aluminate having an excitation maximum at about 172 nm, and which emits in a narrow-band UV emission at about 310 nm. The '883 publication also describes other useful energy converters for this invention, making note of emission spectra between 300 nm and 320 nm for a $Sr(Al,Mg)_{12}O_{19}$:Gd phosphor and two 312 nm line emitting phosphors, $YMgB_5O_{10}$:Gd, Ce and $YMgB_5O_{10}$: Gd, Ce, Pr. WO2016200349 (the entire contents of which are incorporated herein by reference) describes long lasting yellowish-green emitting phosphorescent pigments in the strontium aluminate ($SrAl2O_4$) system, which could serve as energy converters in the present invention. WO 2016200348 (the entire contents of which are incorporated herein by reference) describes long lasting bluish-green emitting phosphorescent pigments in the strontium aluminate ($Sr4Al14O_{25}$) system, which could serve as energy converters in the present invention. Xiong et al in "Recent advances in ultraviolet persistent phosphors," Optical Materials X 2 (2019) (the entire contents of which are incorporated herein by reference) describes a number of ultraviolet persistent phosphors that could as energy converters in the present invention. The table below provides a listing of such persistent phosphors:

| | | |
|---|---|---|
| $SrO:Pb^{2+}$ | 390 | >1 h |
| $CaAl_2O_4:Ce^{3+}\ Tb^{3+}$ | 400 | >10 h |
| $CaAl_2O_4:Ce^{3+}\ Tb^{3+}$ | 413 | >10 h |
| $Sr_2Al_2SiO_7:Ce^{3+}$ | 400 | several minutes |
| $SrZrO_3$ | 395 | <1000 s |
| $BaZrO_3:Mg^{2+}$ | 400 | >2400 s |
| $SrZrO_3:Pr^{3+}$ | 356 | |
| $CdSiO_3:Bi^{3+}$ | 360 | |
| $CdSiO_3:Bi^{3+}\ Dy^{3+}$ | 360 | |
| $CdSiO_3:Bi^{3+}\ Gd^{3+}$ | 344 | >6 h |
| $Sr_2MgGe_2O_7:Pb^{2+}$ | 370 | >12 h |
| $NaLuGeO_4:Bi^{3+}\ Eu^{3+}$ | 400 | >63 h |
| $CaZnGe_2O_6:Bi^{3+}$ | 300-700 | >12 h |
| $Cs_2NaYF_6:Pr^{3+}$ | 250 | >2 h |

In one embodiment, the phosphor described by Xiong et al as $CaAl_2O_4:Ce^{3+}$ having an emission peak of 400 nm and a persistent time of more than 10 h could be used, where it would be charged by x-ray irradiation outside a patient and then injected at a diseased site to provide internally generated UV light.

In one embodiment, the persistent phosphors noted could be activated ex vivo and introduced along with psoralen (or other photoactivatable drug) into the patient by exchange of a bodily fluid or for example by supplying the persistent phosphors and the photoactivatable drug into a patient's blood stream.

In one embodiment, the persistent phosphors noted could be activated in vivo by injection of the phosphors into a diseased site and then exposure to x-rays.

In another embodiment, a combined electromagnetic energy harvester molecule is designed, such as the combined light harvester disclosed in J. Am. Chem. Soc. 2005, 127, 9760-9768, the entire contents of which are hereby incorporated by reference. By combining a group of fluorescent molecules in a molecular structure that may be used with or without the energy augmentators, a resonance energy transfer cascade may be used to harvest a wide band of electromagnetic radiation resulting in emission of a narrow band of fluorescent energy. By pairing a combined energy harvester with a photoactivatable molecule, a further energy resonance transfer excites the photoactivatable molecule, when the photoactivatable molecule is nearby stimulated combined energy harvester molecules. Another example of a harvester molecule is disclosed in FIG. 4 of "Singlet-Singlet and Triplet-Triplet Energy Transfer in Bichromophoric Cyclic Peptides," M. S. Thesis by M. O. Guler, Worcester Polytechnic Institute, May 18, 2002, which is incorporated herein by reference. With the energy augmentators present, this invention can generate local regions of intense electric fields to enhance light or photon or electron emission from the harvester molecules in proximity to those local regions, and thereby assist in the treatment of cell proliferation.

In another embodiment, a Stokes shift of an emitting source or a series of emitting sources arranged in a cascade is used with or without the energy augmentators, and selected to convert a shorter wavelength energy, such as X-rays, to a longer wavelength fluorescence emission such as optical or UV-A, which is used to stimulate a photoactivatable molecule at the location of the tumor cells. Preferably, the photoactivatable molecule is selected to cause an apoptosis sequence in tumor cells without causing substantial harm to normal, healthy cells. More preferably, the apoptosis sequence then leads to an auto vaccine effect that targets the malignant tumor cells throughout the patient's body.

In an additional embodiment, the photoactivatable agent can be a photocaged complex having an active agent (which can be a cytotoxic agent or can be an activatable pharmaceutical agent) contained within a photocage. The active agent is bulked up with other molecules that prevent it from binding to specific targets, thus masking its activity. When the photocage complex is photoactivated with or without the energy augmentators, the bulk falls off, exposing the active agent. In such a photocage complex, the photocage molecules can be photoactive (i.e. when photoactivated, they are caused to dissociate from the photocage complex, thus exposing the active agent within), or the active agent can be the photoactivatable agent (which when photoactivated causes the photocage to fall off), or both the photocage and the active agent are photoactivated, with the same or different wavelengths. For example, a toxic chemotherapeutic agent can be photocaged, which will reduce the systemic toxicity when delivered. Once the agent is concentrated in the tumor, the agent is irradiated with an activation energy. This causes the "cage" to fall off, leaving a cytotoxic agent in the tumor cell. Suitable photocages include those disclosed by Young and Deiters in "Photochemical Control of Biological Processes", *Org. Biomol. Chem.*, 5, pp. 999-1005 (2007) and "Photochemical Hammerhead Ribozyme Activation", *Bioorganic & Medicinal Chemistry Letters*, 16(10), pp. 2658-2661 (2006), the contents of which are hereby incorporated by reference.

In a further embodiment, some of the tumor cells are treated in vitro using a UV-A source to stimulate 8-MOP. Apoptosis of the tumor cells is monitored, and some or all of the fragments and remnants of the apoptosis process are reintroduced into the site of a tumor. Preferably, the portion of fragments, cellular structures and remnants are selected such that an auto vaccine effect is generated that leads to further apoptosis of tumor cells without substantially harming healthy tissues, causing solid tumors to shrink. In this embodiment, the energy augmentators of this invention may play a prominent role in distribution of UV light into the in vitro medium. For example, by use of the energy collectors/distributer shown in FIG. 25A, the UV-A light can be distributed more uniformly throughout the in vitro medium being treated.

In one embodiment, a lanthanide chelate capable of intense luminescence is used with or without the energy augmentators. For example, a lanthanide chelator may be covalently joined to a coumarin or coumarin derivative or a quinolone or quinolone-derivative sensitizer. Sensitizers may be a 2- or 4-quinolone, a 2- or 4-coumarin, or derivatives or combinations of these examples. A carbostyril 124 (7-amino-4-methyl-2-quinolone), a coumarin 120 (7-amino-4-methyl-2-coumarin), a coumarin 124 (7-amino-4-(trifluoromethyl)-2-coumarin), aminoinethyltrimethylpsoralen or other similar sensitizer may be used. Chelates may be selected to form high affinity complexes with lanthanides, such as terbium or europium, through chelator groups, such as DTPA. Such chelates may be coupled to any of a wide variety of well-known probes or carriers, and may be used for resonance energy transfer to a psoralen or psoralen-derivative, such as 8-MOP, or other photoactive molecules capable of binding DNA and causing the initiation of an apoptosis process of rapidly dividing cancer cells. In this way, the treatment may be targeted to especially aggressive forms of cell proliferation disorders that are not successfully treated by conventional chemotherapy, radiation or surgical techniques. In one alternative example, the lanthanide chelate is localized at the site of the tumor using an appropriate carrier molecule, particle or polymer, and a source of electromagnetic energy is introduced by minimally invasive procedures to irradiate the tumor cells, after exposure to the lanthanide chelate and a photoactive molecule. With the energy augmentators present, this invention can generate local regions of intense electric fields to enhance light or photon or electron emission from the lanthanide chelates in proximity to those local regions, and thereby assist in the treatment of cell proliferation.

In another embodiment, with or without the energy augmentators, a biocompatible, endogenous fluorophore emitter is selected to stimulate resonance energy transfer to a photoactivatable molecule. A biocompatible emitter with emission maxima within the absorption range of the biocompatible, endogenous fluorophore emitter may be selected to stimulate an excited state in fluorophore emitter. One or more halogen atoms may be added to any cyclic ring structure capable of intercalation between the stacked nucleotide bases in a nucleic acid (either DNA or RNA) to confer new photoactive properties to the intercalator. Any intercalating molecule (psoralens, coumarins, or other polycyclic ring structures) may be selectively modified by halogenation or addition of non-hydrogen bonding ionic substituents to impart advantages in its reaction photochemistry and its competitive binding affinity for nucleic acids over cell membranes or charged proteins, as is known in the art. With the energy augmentators present, this invention can generate local regions of intense electric fields to enhance light or photon or electron emission from the fluorophore emitters in proximity to those local regions, and thereby assist in the treatment of cell proliferation.

Recently, photosensitizers have been developed for treating cell proliferation disorders using photodynamic therapy. Table 3 provides an assortment of known photosensitizers that are useful in treating cell proliferation disorders.

TABLE 3

Exemplary Photosensitizers for cell proliferation disorders

| Photosensitizer | Dose | Drug-light interval | Wavelength of activation | Length of photosensitization |
|---|---|---|---|---|
| Photofrin (II) | 2 mg/kg | 48 hrs | 630 nm | 4-6 weeks |
| Foscan | 0.1 mg/kg | 4-6 days | 652 nm | 2 weeks |
| Lutetium texahyrin | 2-6 mg/kg | 3 to 24 hrs | 732 nm | 24-48 hrs |

Skin photosensitivity is a major toxicity of the photosensitizers. Severe sunburn occurs if skin is exposed to direct sunlight for even a few minutes. Early murine research hinted at a vigorous and long term stimulation of immune response; however, actual clinical testing has failed to achieve the early promises of photodynamic therapies. The early photosensitizers for photodynamic therapies targeted type II responses, which created singlet oxygen when photoactivated in the presence of oxygen. The singlet oxygen caused cellular necrosis and was associated with inflammation and an immune response. However, tumors are now known to down regulate the immune response over time, and it is thought that this is one of the reasons that clinical results are not as dramatic as promised by the early murine research. Some additional photosensitizers have been developed to induce type I responses, directly damaging cellular structures, which result in apoptosis of tumor cells.

Porfimer sodium (Photofrin; QLT Therapeutics, Vancouver, BC, Canada), is a partially purified preparation of hematoporphyrin derivative (HpD). Photofrin has been approved by the US Food and Drug Administration for the treatment of obstructing esophageal cancer, microinvasive endobronchial non-small cell lung cancer, and obstructing endobronchial non-small cell lung cancer. Photofrin is activated with 630 nm, which has a tissue penetration of approximately 2 to 5 mm. Photofrin has a relatively long duration of skin photosensitivity (approximately 4 to 6 weeks).

Tetra (m-hydroxyphenyl) chlorin (Foscan; Scotia Pharmaceuticals, Stirling, UK), is a synthetic chlorin compound that is activated by 652 nm light. Clinical studies have demonstrated a tissue effect of up to 10 mm with Foscan and 652 nm light. Foscan is more selectively a photosensitizer in tumors than normal tissues, and requires a comparatively short light activation time. A recommended dose of 0.1 mg/kg is comparatively low and comparatively low doses of light may be used. Nevertheless, duration of skin photosensitivity is reasonable (approximately 2 weeks). However, Foscan induces a comparatively high yield of singlet oxygen, which may be the primary mechanism of DNA damage for this molecule.

Motexafin lutetium (Lutetium texaphryin) is activated by light in the near infrared region (732 nm). Absorption at this wavelength has the advantage of potentially deeper penetration into tissues, compared with the amount of light used to activate other photosensitizers (FIGS. 2A and 2B). Lutetium texaphryin also has one of the greatest reported selectivities for tumors compared to selectivities of normal tissues. Young S W, et al.: Lutetium texaphyrin (PCI-0123) a near-infrared, water-soluble photosensitizer. Photochem Photobiol 1996, 63:892-897. In addition, its clinical use is associated with a shorter duration of skin photosensitivity (24 to 48 hours). Lutetium texaphryin has been evaluated for metastatic skin cancers. It is currently under investigation for treatment of recurrent breast cancer and for locally recurrent prostate cancer. The high selectivity for tumors promises improved results in clinical trials.

In general, the approach may be used with any source for the excitation of higher electronic energy states, such as electrical, chemical and/or radiation, individually or combined into a system for activating an activatable molecule. The process may be a photophoresis process or may be similar to photophoresis. While photophoresis is generally thought to be limited to photonic excitation, such as by UV-light, other forms of radiation may be used as a part of a system to activate an activatable molecule. Radiation includes ionizing radiation which is high energy radiation, such as an X-ray or a gamma ray, which interacts to produce ion pairs in matter. Radiation also includes high linear energy transfer irradiation, low linear energy transfer irradiation, alpha rays, beta rays, neutron beams, accelerated electron beams, and ultraviolet rays. Radiation also includes proton, photon and fission-spectrum neutrons. Higher energy ionizing radiation may be combined with chemical processes to produce energy states favorable for resonance energy transfer, for example. Other combinations and variations of these sources of excitation energy may be combined as is known in the art, in order to stimulate the activation of an activatable molecule, such as 8-MOP. In one example, ionizing radiation is directed at a solid tumor and stimulates, directly or indirectly, activation of 8-MOP, as well as directly damaging the DNA of malignant tumor cells. In this example, either the effect of ionizing radiation or the photophoresis-like activation of 8-MOP may be thought of as an adjuvant therapy to the other.

In one embodiment, the present invention provides a method for treating a cell proliferation disorder in a subject, comprising:

(1) administering to the subject an activatable pharmaceutical agent that is capable of effecting a predetermined cellular change when activated; and (2) applying an initiation energy from an initiation energy source to the subject, wherein the initiation energy source is a source of energy capable of penetrating completely through the subject, and wherein the applying activates the activatable agent in situ with or without the energy augmentators, thus causing the predetermined cellular change to occur, wherein occurrence of the predetermined cellular change causes an increase in rate or decrease in rate of cell proliferation to treat the cell proliferation disorder.

In a further embodiment, the present invention provides a method for treating a cell proliferation disorder in a subject, comprising:

(1) administering to the subject one or more energy converters and an activatable pharmaceutical agent that is capable of effecting a predetermined cellular change when activated; and (2) applying an initiation energy from an initiation energy source to the subject, wherein the one or more energy converters convert the initiation energy applied to UV-A or visible energy with or without the energy augmentators, which then activates the activatable agent in situ, thus causing the predetermined cellular change to occur, wherein occurrence of the predetermined cellular change causes an increase in rate or decrease in rate of cell proliferation to treat the cell proliferation disorder.

In a further embodiment, the present invention provides a method for treating a cell proliferation disorder in a subject, comprising:

(1) administering to the subject an activatable pharmaceutical agent that is capable of effecting a predetermined cellular change when activated; and (2) applying an initiation energy from an initiation energy source to the subject, wherein the initiation energy applied and activatable pharmaceutical agent upon activation with or without the energy augmentators produce insufficient singlet oxygen in the subject to produce cell lysis, and wherein the initiation energy activates the activatable pharmaceutical agent in situ, thus causing the predetermined cellular change to occur, wherein occurrence of the predetermined cellular change causes an increase in rate or decrease in rate of cell proliferation to treat the cell proliferation disorder.

Work in the area of photodynamic therapy has shown that the amount of singlet oxygen required to cause cell lysis, and thus cell death, is $0.32 \times 10^3$ mol/liter or more, or 109 singlet oxygen molecules/cell or more. However, in the present invention, it is most preferable to avoid production of an amount of singlet oxygen that would cause cell lysis, due to its indiscriminate nature of attack, lysing both target cells and healthy cells. Accordingly, it is most preferred in the present invention that the level of singlet oxygen production caused by the initiation energy used or activatable pharmaceutical agent upon activation be less than level needed to cause cell lysis.

In yet another embodiment, the activatable pharmaceutical agent, preferably a photoactive agent, is directed to a receptor site by a carrier having a strong affinity for the receptor site. The carrier may be a polypeptide and may form a covalent bond with a photo active agent, for example. The polypeptide may be an insulin, interleukin, thymopoietin or transferrin, for example. Alternatively, a photoactive pharmaceutical agent may have a strong affinity for the target cell without a binding to a carrier.

For example, a treatment may be applied that acts to slow or pause mitosis. Such a treatment is capable of slowing the division of rapidly dividing healthy cells or stem cells without pausing mitosis of cancerous cells. Thus, the difference in growth rate between the non-target cells and target cells are further differentiated to enhance the effectiveness of the methods of the present invention.

In another example, an aggressive cell proliferation disorder has a much higher rate of mitosis, which leads to selective destruction of a disproportionate share of the malignant cells during even a systemically administered treatment. Stem cells and healthy cells may be spared from wholesale programmed cell death even if exposed to photoactivated agents that cause apoptosis, provided that such photoactivated agents degenerate from the excited state to a lower energy state prior to binding, mitosis or other mechanisms for creating damage to the cells of a substantial fraction of the healthy stem cells. To further protect healthy cells from the effect of photoactivatable agents, blocking agents that block uptake of the photoactivatable agents, prior to their activation, may be administered.

U.S. Pat. No. 6,235,508, discloses that a variety of blocking agents have been found to be suitable for this purpose, some of which are traditional antioxidants, and some of which are not. Suitable blocking agents include, but are not limited to, histidine, cysteine, tyrosine, tryptophan, ascorbate, N-acetyl cysteine, propyl gallate, mercaptopropionyl glycine, butylated hydroxytoluene (BHT) and butylated hydroxyanisole (BHA).

In a further embodiment, methods in accordance with the present invention may further include adding an additive to alleviate treatment side-effects. Exemplary additives may include, but are not limited to, antioxidants, adjuvant, or combinations thereof. In one exemplary embodiment, psoralen is used as the activatable pharmaceutical agent, UV-A is used as the activating energy, and antioxidants are added to reduce the unwanted side-effects of irradiation.

The activatable pharmaceutical agent and derivatives thereof as well as the energy converter, can be incorporated into pharmaceutical compositions suitable for administration. Such compositions typically comprise the activatable pharmaceutical agent and a pharmaceutically acceptable carrier. The pharmaceutical composition also comprises at least one additive having a complementary therapeutic or diagnostic effect, wherein the additive is one selected from an antioxidant, an adjuvant, or a combination thereof.

As used herein, "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions. Modifications can be made to the compound of the present invention to affect solubility or clearance of the compound. These molecules may also be synthesized with D-amino acids to increase resistance to enzymatic degradation. If necessary, the activatable pharmaceutical agent can be co-administered with a solubilizing agent, such as cyclodextran.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, rectal administration, and direct injection into the affected area, such as direct injection into a tumor. Solutions or suspensions used for parenteral, intradermal, or subcutaneous application can include the following components: a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds with or without the energy augmentators are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The pharmaceutical compositions with or without the energy augmentators can be included in a container, pack, or dispenser together with instructions for administration.

Methods of administering agents according to the present invention are not limited to the conventional means such as injection or oral infusion, but include more advanced and complex forms of energy transfer. For example, genetically engineered cells that carry and express energy converters (for example the energy converters described above in the section entitled B. Energy Converters) may be used with or without the energy augmentators. Cells from the host may be transfected with genetically engineered vectors that express bioluminescent agents. Transfection may be accomplished via in situ gene therapy techniques such as injection of viral vectors or gene guns, or may be performed ex vivo by removing a sample of the host's cells and then returning to the host upon successful transfection.

Such transfected cells may be inserted or otherwise targeted at the site where diseased cells are located. In this embodiment, the initiation energy source may be a biochemical source as such ATP, in which case the initiation energy source is considered to be directly implanted in the transfected cell. Alternatively, a conventional micro-emitter device capable of acting as an initiation energy source may be transplanted at the site of the diseased cells.

It will also be understood that the order of administering the different agents is not particularly limited. Thus in some embodiments the activatable pharmaceutical agent may be administered before the energy converter, while in other embodiments the energy converter may be administered prior to the activatable pharmaceutical agent. It will be appreciated that different combinations of ordering may be advantageously employed depending on factors such as the absorption rate of the agents, the localization and molecular trafficking properties of the agents, and other pharmacokinetics or pharmacodynamics considerations.

An advantage of the methods of the present invention is that by specifically targeting cells affected by a cell proliferation disorder, such as rapidly dividing cells, and triggering a cellular change, such as apoptosis, in these cells in situ, the immune system of the host may be stimulated to have an immune response against the diseased cells. Once the host's own immune system is stimulated to have such a response, other diseased cells that are not treated by the activatable pharmaceutical agent may be recognized and be destroyed by the host's own immune system. Such autovaccine effects may be obtained, for example, in treatments using psoralen and UV-A with or without the energy augmentators. Here, in one embodiment of the invention, x-ray induced emission of UV light from phosphors or other light emitting materials can be enhanced by the intensified fields of the resonators described above. Thus, a lower x-ray dose will be required to deliver the same UV dose to the target site. If the energy augmentators resonate at infrared frequencies, in this example, the lower x-ray dose is achieved via a benign absorption of infrared light, which itself may have other therapeutic value.

In another aspect, the present invention also provides methods for producing an autovaccine, including: (1) providing a population of targeted cells; (2) treating the cells ex vivo with a psoralen or a derivative thereof; (3) activating the psoralen with a UV-A source to induce apoptosis in the targeted cells; and (4) returning the apoptic cells back to the host to induce an autovaccine effect against the targeted cell, wherein the apoptic cells cause an autovaccine effect. Here, the energy augmentators may assist in UV light generation (if generated by luminescence) or the distribution of UV light (if generated external).

A further embodiment is the use of the present invention for the treatment of skin cancer. In this example, a photo-activatable agent, preferably psoralen, is given to the patient, and is delivered to the skin lesion via the blood supply. An activation source having limited penetration ability (such as UV or IR) is shined directly on the skin—in the case of psoralen, it would be a UV light, or an IR source. With the use of an IR source, the irradiation would penetrate deeper and generate UV via two single photon events with psoralen. In a further embodiment, methods according to this aspect of the present invention further include a step of separating the components of apoptic cells into fractions and testing each fraction for autovaccine effect in a host. The components thus isolated and identified may then serve as an effective autovaccine to stimulate the host's immune system to suppress growth of the targeted cells.

The present invention methods can be used alone or in combination with other therapies for treatment of cell proliferation disorders. Additionally, the present invention methods can be used, if desired, in conjunction with recent advances in chronomedicine, such as that detailed in Giacchetti et al, *Journal of Clinical Oncology*, Vol 24, No 22 (August 1), 2006: pp. 3562-3569. In chronomedicine it has been found that cells suffering from certain types of disorders, such as cancer, respond better at certain times of the day than at others. Thus, chronomedicine could be used in conjunction with the present methods in order to augment the effect of the treatments of the present invention.

In another aspect, the present invention further provides systems and kits for practicing the above described methods.

In another embodiment, a system in accordance with the present invention may include an initiation energy source and one or more activatable pharmaceutical agents.

Figure 35A:
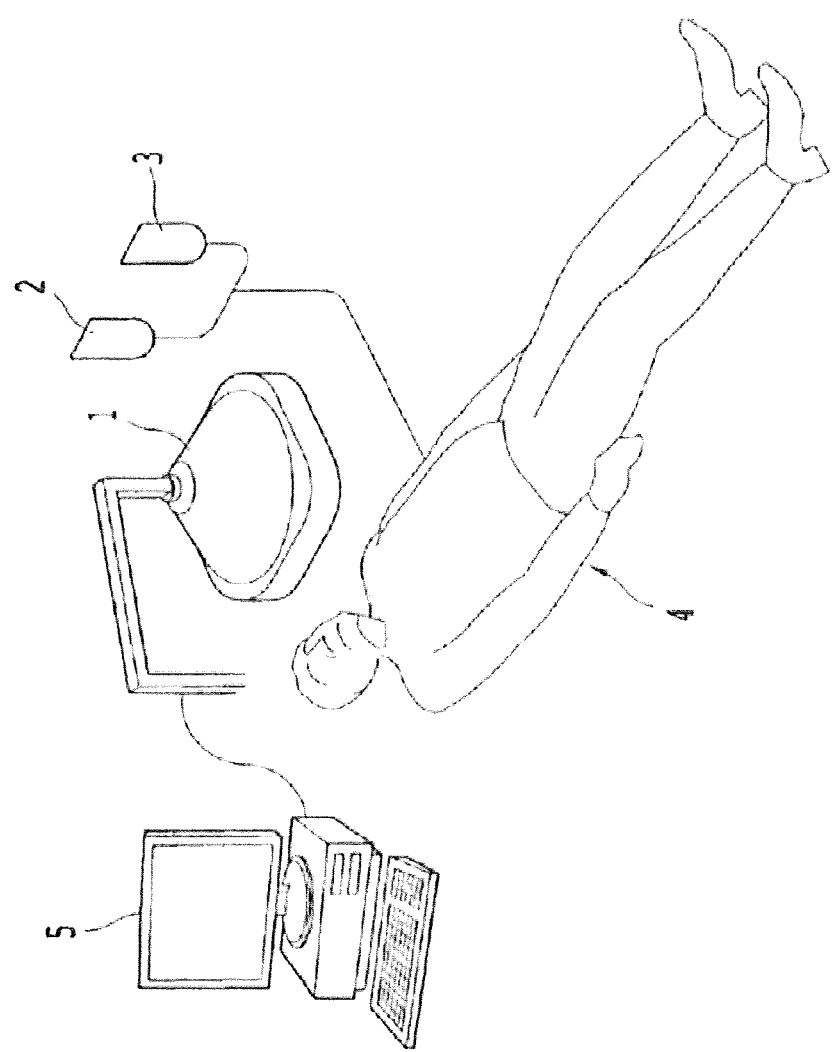
FIG. 35A illustrates a system according to one exemplary embodiment of the present invention.

FIG. 35A illustrates a system according to one exemplary embodiment of the present invention. Referring to FIG. 35A, an exemplary system according to one embodiment of the present invention may have an initiation energy source 1 directed at the subject 4. An activatable pharmaceutical agent 2 and an energy converter 3 are administered to the subject 4. The initiation energy source may additionally be controlled by a computer system 5 that is capable of directing the delivery of the initiation energy.

Figure 35B:
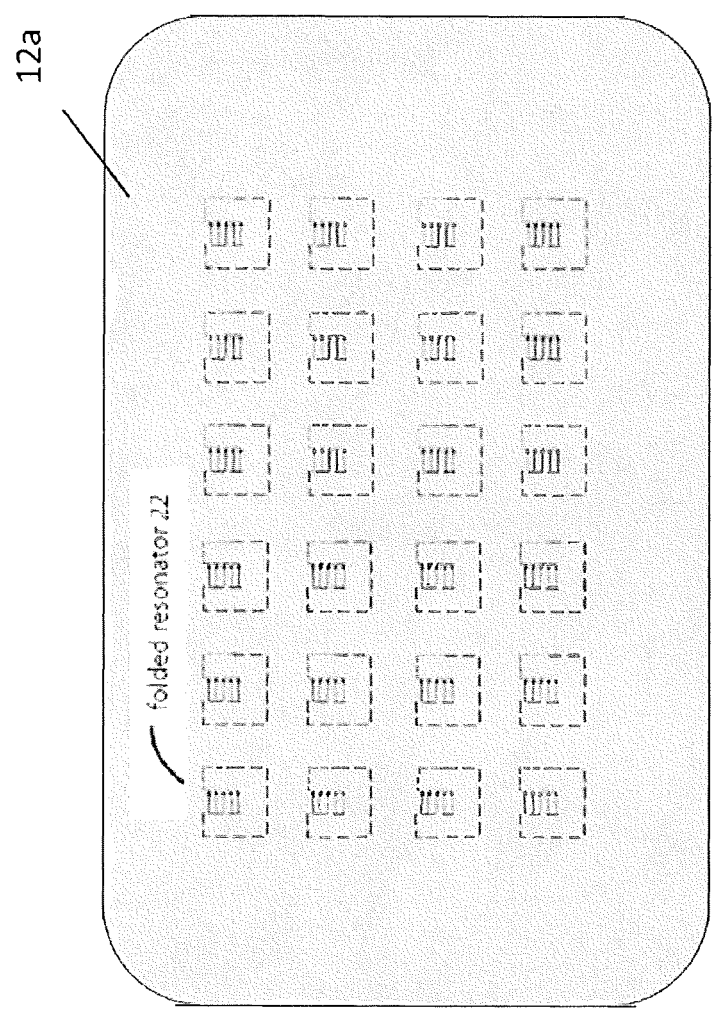
FIG. 35B illustrates an example of folded resonators 12 disposed in a target region 12a of a diseased site.

In one embodiment, a system in accordance with the present invention may include: an initiation energy source 1 one or more energy converters 3 with or without the energy augmentators such as the folded resonators 12 (not shown in the solution of modulations agents 3 shown in FIG. 57A; and one or more activatable pharmaceutical agents. The energy augmentators may be supplied in sheet form as seem in FIG. 6 or 7 or when in solution can be supplied in granulated form as in FIG. 7C or FIG. 43. FIG. 35B depicts an example of folded resonators 12 disposed in a target region 12a of a diseased site.

In preferred embodiments, the initiation energy source may be a linear accelerator equipped with image guided computer-control capability to deliver a precisely calibrated beam of radiation to a pre-selected coordinate. One example of such linear accelerators is the SmartBeam™ IMRT (intensity modulated radiation therapy) system from Varian medical systems (Varian Medical Systems, Inc., Palo Alto, California).

In other embodiments, endoscopic or laparoscopic devices equipped with appropriate initiation energy emitter may be used as the initiation energy source. In such systems, the initiation energy may be navigated and positioned at the pre-selected coordinate to deliver the desired amount of initiation energy to the site.

In further embodiments, dose calculation and robotic manipulation devices may also be included in the system.

In yet another embodiment, there is also provided a computer implemented system for designing and selecting suitable combinations of initiation energy source, energy transfer agent, and activatable pharmaceutical agent, comprising:

a central processing unit (CPU) having a storage medium on which is provided:
  a database of excitable compounds;
  a first computation module for identifying and designing an excitable compound that is capable of binding with a target cellular structure or component; and
  a second computation module predicting the resonance absorption energy of the excitable compound,
  wherein the system, upon selection of a target cellular structure or component, computes an excitable compound that is capable of binding with the target structure followed by a computation to predict the resonance absorption energy of the excitable compound.

Figure 36:
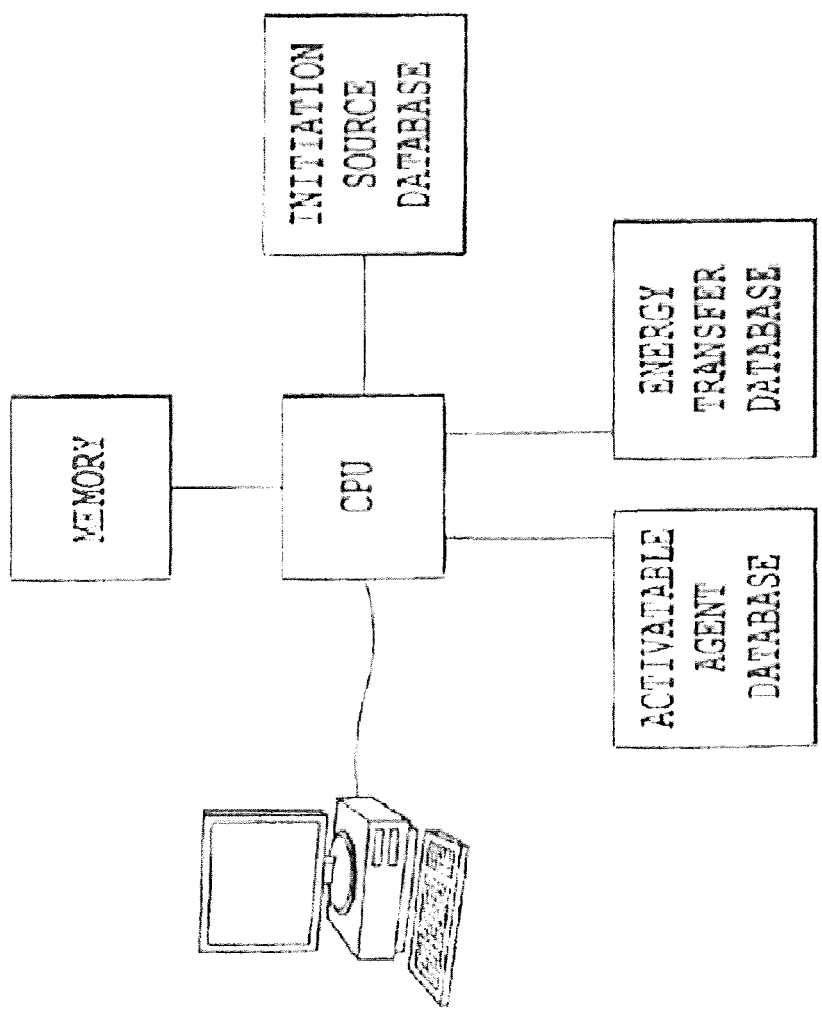
FIG. 36 illustrates an exemplary computer implemented system according to an embodiment of the present invention.

FIG. 36 illustrates an exemplary computer implemented system according to this embodiment of the present invention. Referring to FIG. 4, an exemplary computer-implemented system according to one embodiment of the present invention may have a central processing unit (CPU) connected to a memory unit, configured such that the CPU is capable of processing user inputs and selecting a combination of initiation source, activatable pharmaceutical agent, and energy transfer agent based on an energy spectrum comparison for use in a method of the present invention.

Figure 37:
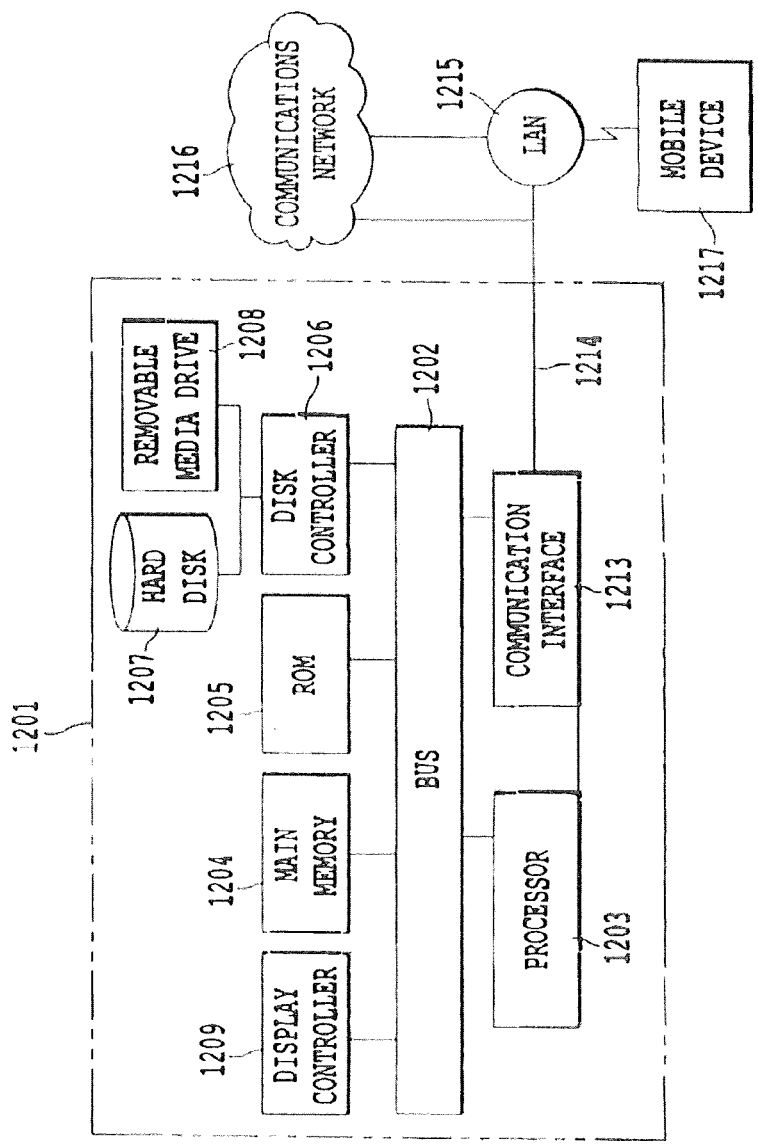
FIG. 37 illustrates an exemplary computer system (1201) for implementing various embodiments of the present invention.

FIG. 37 illustrates a computer system 1201 for implementing various embodiments of the present invention. The computer system 1201 may be used as the controller 55 to perform any or all of the functions of the CPU described above. The computer system 1201 includes a bus 1202 or other communication mechanism for communicating information, and a processor 1203 coupled with the bus 1202 for processing the information. The computer system 1201 also includes a main memory 1204, such as a random access memory (RAM) or other dynamic storage device (e.g., dynamic RAM (DRAM), static RAM (SRAM), and synchronous DRAM (SDRAM)), coupled to the bus 1202 for storing information and instructions to be executed by processor 1203. In addition, the main memory 1204 may be used for storing temporary variables or other intermediate information during the execution of instructions by the processor 1203. The computer system 1201 further includes a read only memory (ROM) 1205 or other static storage device (e.g., programmable ROM (PROM), erasable PROM (EPROM), and electrically erasable PROM (EEPROM)) coupled to the bus 1202 for storing static information and instructions for the processor 1203.

The computer system 1201 also includes a disk controller 1206 coupled to the bus 1202 to control one or more storage devices for storing information and instructions, such as a magnetic hard disk 1207, and a removable media drive 1208

(e.g., floppy disk drive, read-only compact disc drive, read/write compact disc drive, compact disc jukebox, tape drive, and removable magneto-optical drive). The storage devices may be added to the computer system 1201 using an appropriate device interface (e.g., small computer system interface (SCSI), integrated device electronics (IDE), enhanced-IDE (E-IDE), direct memory access (DMA), or ultra-DMA).

The computer system 1201 may also include special purpose logic devices (e.g., application specific integrated circuits (ASICs)) or configurable logic devices (e.g., simple programmable logic devices (SPLDs), complex programmable logic devices (CPLDs), and field programmable gate arrays (FPGAs)).

The computer system 1201 may also include a display controller 1209 coupled to the bus 1202 to control a display 1210, such as a cathode ray tube (CRT), for displaying information to a computer user. The computer system includes input devices, such as a keyboard 1211 and a pointing device 1212, for interacting with a computer user and providing information to the processor 1203. The pointing device 1212, for example, may be a mouse, a trackball, or a pointing stick for communicating direction information and command selections to the processor 1203 and for controlling cursor movement on the display 1210. In addition, a printer may provide printed listings of data stored and/or generated by the computer system 1201.

The computer system 1201 performs a portion or all of the processing steps of the invention (such as for example those described in relation to FIG. 5) in response to the processor 1203 executing one or more sequences of one or more instructions contained in a memory, such as the main memory 1204. Such instructions may be read into the main memory 1204 from another computer readable medium, such as a hard disk 1207 or a removable media drive 1208. One or more processors in a multi-processing arrangement may also be employed to execute the sequences of instructions contained in main memory 1204. In alternative embodiments, hard-wired circuitry may be used in place of or in combination with software instructions. Thus, embodiments are not limited to any specific combination of hardware circuitry and software.

As stated above, the computer system 1201 includes at least one computer readable medium or memory for holding instructions programmed according to the teachings of the invention and for containing data structures, tables, records, or other data described herein. Examples of computer readable media are compact discs, hard disks, floppy disks, tape, magneto-optical disks, PROMs (EPROM, EEPROM, flash EPROM), DRAM, SRAM, SDRAM, or any other magnetic medium, compact discs (e.g., CD-ROM), or any other optical medium, punch cards, paper tape, or other physical medium with patterns of holes, a carrier wave (described below), or any other medium from which a computer can read.

Stored on any one or on a combination of computer readable media, the present invention includes software for controlling the computer system 1201, for driving a device or devices for implementing the invention, and for enabling the computer system 1201 to interact with a human user (e.g., print production personnel). Such software may include, but is not limited to, device drivers, operating systems, development tools, and applications software. Such computer readable media further includes the computer program product of the present invention for performing all or a portion (if processing is distributed) of the processing performed in implementing the invention.

The computer code devices of the present invention may be any interpretable or executable code mechanism, including but not limited to scripts, interpretable programs, dynamic link libraries (DLLs), Java classes, and complete executable programs. Moreover, parts of the processing of the present invention may be distributed for better performance, reliability, and/or cost.

The term "computer readable medium" as used herein refers to any medium that participates in providing instructions to the processor 1203 for execution. A computer readable medium may take many forms, including but not limited to, non-volatile media, volatile media, and transmission media. Non-volatile media includes, for example, optical, magnetic disks, and magneto-optical disks, such as the hard disk 1207 or the removable media drive 1208. Volatile media includes dynamic memory, such as the main memory 1204. Transmission media includes coaxial cables, copper wire and fiber optics, including the wires that make up the bus 1202. Transmission media also may also take the form of acoustic or light waves, such as those generated during radio wave and infrared data communications.

Various forms of computer readable media may be involved in carrying out one or more sequences of one or more instructions to processor 1203 for execution. For example, the instructions may initially be carried on a magnetic disk of a remote computer. The remote computer can load the instructions for implementing all or a portion of the present invention remotely into a dynamic memory and send the instructions over a telephone line using a modem. A modem local to the computer system 1201 may receive the data on the telephone line and use an infrared transmitter to convert the data to an infrared signal. An infrared detector coupled to the bus 1202 can receive the data carried in the infrared signal and place the data on the bus 1202. The bus 1202 carries the data to the main memory 1204, from which the processor 1203 retrieves and executes the instructions. The instructions received by the main memory 1204 may optionally be stored on storage device 1207 or 1208 either before or after execution by processor 1203.

The computer system 1201 also includes a communication interface 1213 coupled to the bus 1202. The communication interface 1213 provides a two-way data communication coupling to a network link 1214 that is connected to, for example, a local area network (LAN) 1215, or to another communications network 1216 such as the Internet. For example, the communication interface 1213 may be a network interface card to attach to any packet switched LAN. As another example, the communication interface 1213 may be an asymmetrical digital subscriber line (ADSL) card, an integrated services digital network (ISDN) card or a modem to provide a data communication connection to a corresponding type of communications line. Wireless links may also be implemented. In any such implementation, the communication interface 1213 sends and receives electrical, electromagnetic or optical signals that carry digital data streams representing various types of information.

The network link 1214 typically provides data communication through one or more networks to other data devices. For example, the network link 1214 may provide a connection to another computer through a local network 1215 (e.g., a LAN) or through equipment operated by a service provider, which provides communication services through a communications network 1216. The local network 1214 and the communications network 1216 use, for example, electrical, electromagnetic, or optical signals that carry digital data streams, and the associated physical layer (e.g., CAT 5 cable, coaxial cable, optical fiber, etc.). The signals through the various networks and the signals on the network link 1214 and through the communication interface 1213, which carry the digital data to and from the computer system 1201 maybe implemented in baseband signals, or carrier wave based signals. The baseband signals convey the digital data as unmodulated electrical pulses that are descriptive of a stream of digital data bits, where the term "bits" is to be construed broadly to mean symbol, where each symbol conveys at least one or more information bits. The digital data may also be used to modulate a carrier wave, such as with amplitude, phase and/or frequency shift keyed signals that are propagated over a conductive media, or transmitted as electromagnetic waves through a propagation medium. Thus, the digital data may be sent as unmodulated baseband data through a "wired" communication channel and/or sent within a predetermined frequency band, different than baseband, by modulating a carrier wave. The computer system 1201 can transmit and receive data, including program code, through the network(s) 1215 and 1216, the network link 1214, and the communication interface 1213. Moreover, the network link 1214 may provide a connection through a LAN 1215 to a mobile device 1217 such as a personal digital assistant (PDA) laptop computer, or cellular telephone.

The exemplary energy spectrum previously noted in FIGS. 34A and 34B may also be used (encoded) in this computer-implemented system.

The reagents and chemicals useful for methods and systems of the present invention may be packaged in kits to facilitate application of the present invention. In one exemplary embodiment, a kit including a psoralen, and fractionating containers for easy fractionation and isolation of autovaccines is contemplated. A further embodiment of kit would comprise at least one activatable pharmaceutical agent capable of causing a predetermined cellular change, at least one energy converter capable of activating the at least one activatable agent when energized, and containers suitable for storing the agents in stable form, and preferably further comprising instructions for administering the at least one activatable pharmaceutical agent and at least one energy converter to a subject, and for applying an initiation energy from an initiation energy source to activate the activatable pharmaceutical agent. The instructions could be in any desired form, including but not limited to, printed on a kit insert, printed on one or more containers, as well as electronically stored instructions provided on an electronic storage medium, such as a computer readable storage medium. Also optionally included is a software package on a computer readable storage medium that permits the user to integrate the information and calculate a control dose, to calculate and control intensity of the irradiation source.

EXAMPLES

Example 1

In a first example, Vitamin B12 is used as a stimulating energy source for a photoactive agent overlapping its emission wavelength using dipole-dipole resonance energy transfer.

| Endogenous Fluorophore | Excitation Max. (nm) | Emission Max. (nm) |
|---|---|---|
| Vitamin $B_{12}$ | 275 | 305 |

Vitamin B12 has an excitation maximum at about 275 nm and an emission maximum at 305 nm, as shown above and in Table 2. Table 4 shows UV and light emission from gamma ray sources. In this example, $^{113}$Sn and/or $^{137}$Cs are chelated with the Vitamin B12. The Vitamin B12 preferentially is absorbed by tumor cells. Thus, it is in close proximity and capable of activating 8-MOP, which is administered in advance as the photoactivation molecules. The emission band of Vitamin B12 overlaps the excitation band of 8-MOP; therefore, photo and resonance energy transfer occurs, when Vitamin B12 is in close proximity to 8-MOP. 8-MOP is activated and binds to DNA of the tumor cells inducing an auto vaccine effect in vivo.

Example 2

In this example, gold nanoparticles are chelated with the Vitamin B12 complex. A suitable light source is used to stimulate the gold nanoparticles or Vitamin B12 may be chelated with one of the UV emitters listed in Table 4 in addition to the gold nanoparticles. The tumor cells preferentially absorb the Vitamin B12 complexes, such that the activated gold nanoparticles are within 50 nanometers of 8-MOP and/or other photoactivatable molecules previously administered. Therefore, resonance energy transfer activates the photoactivatable molecules, such as 8-MOP, and the activated 8-MOP binds to DNA in tumor cells inducing apoptosis and autovaccine effects.

In a further example, the nanoparticles of gold are clusters of 5 gold atoms encapsulated by poly-amidoamine dendrimers. Thus, the gold nanoparticles emit UV in the correct band for activating 8-MOP and other UV-activatable agents capable of exhibiting photophoresis and/or photodynamic effects.

Cells undergoing rapid proliferation have been shown to have increased uptake of thymidine and methionine. (See, for example, M. E. van Eijkeren et al., Acta Oncologica, 31, 539 (1992); K. Kobota et al., J. Nucl. Med., 32, 2118 (1991) and K. Higashi et al., J. Nucl. Med., 34,773 (1993)). Since methylcobalamin is directly involved with methionine synthesis and indirectly involved in the synthesis of thymidylate and DNA, it is not surprising that methylcobalamin as well as Cobalt-57-cyanocobalamin have also been shown to have increased uptake in rapidly dividing tissue (for example, see, B. A. Cooper et al., Nature, 191, 393 (1961); H. Flodh, Acta Radiol. Suppl., 284, 55 (1968); L. Bloomquist et al., Experientia, 25, 294 (1969)). Additionally, up regulation in the number of transcobalamin I1 receptors has been demonstrated in several malignant cell lines during their accelerated thymidine incorporation and DNA synthesis (see, J. Lindemans et al., Exp. Cell. Res., 184, 449 (1989); T. Amagasaki et al., Blood, 26, 138 (1990) and J. A. Begly et al., J. Cell Physiol. 156, 43 (1993). Vitamin B12 is water soluble, has no known toxicity, and in excess is excreted by glomerular filtration. In addition, the uptake of vitamin B12 could potentially be manipulated by the administration of nitrous oxide and other pharmacological agents (D. Swanson et al., Pharmaceuticals in Medical Imaging, MacMillan Pub. Co., NY (1990) at pages 621 628).

A preferred embodiment of the present invention uses a psoralen compound as the activatable pharmaceutical agent (most preferably 8-MOP or AMT), a fluorescent, phosphorescent, or luminescent energy converter (or energy modulation agent), x-rays as the initiation energy source, UV-A as the resultant energy emitted by the energy converter, which upon activation of the psoralen compound results in apoptosis in the target cells.

In another embodiment, the energy converter noted above is disposed with an energy augmentation structure such that x-ray induced photoluminescence or fluorescence is higher compared to if the energy converter (e.g., x-ray induced photoluminescence or fluorescence materials) were remote from the at least one energy augmentation structure.

In another embodiment, the above noted distributed energy collector can deliver light to different positions within a medium inside a patient.

In another embodiment, the above noted distributed energy collector can collect or deliver light from or to different positions within a patient, including for example collecting or delivering light to different positions within an organ.

In another embodiment, a UV-emitting luciferase may be used alone or in conjunction with the above-noted energy augmentation structures to generate light inside a patient.

Figure 38:
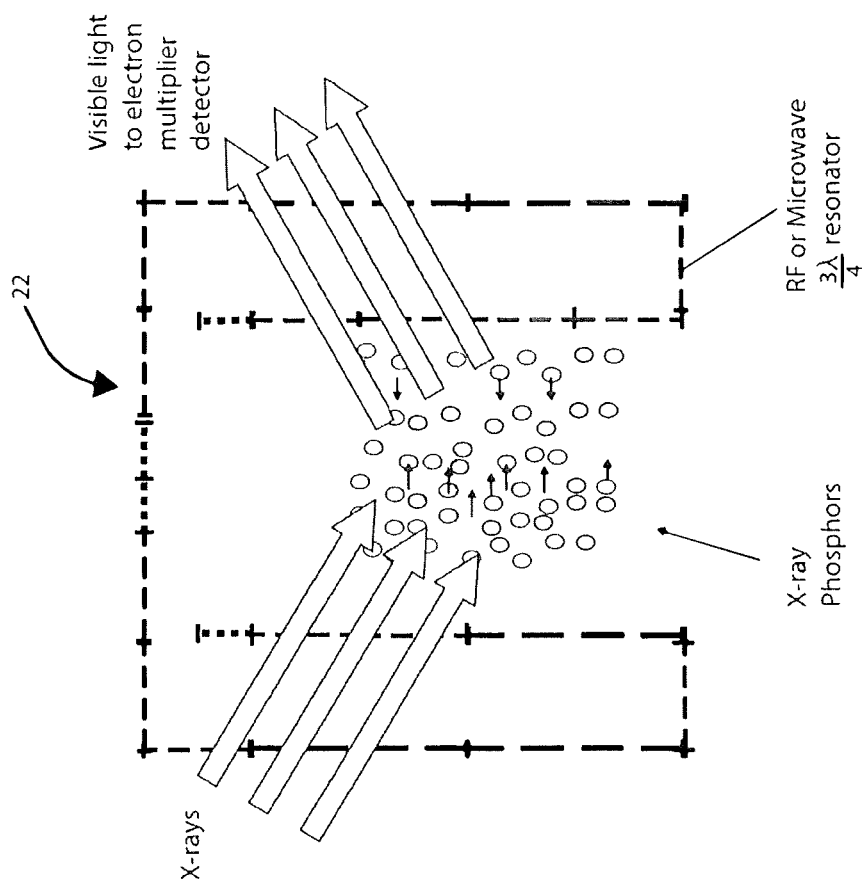
FIG. 38 is a schematic representation of x-ray detector utilizing a ¾λ folded resonator of the invention.

X-ray scintillator devices: The present invention in one embodiment (as noted above) light from scintillator materials (excited for example by high energy particles including x-rays, gamma rays, protons, and electrons) can have their emissions modulated by having those materials included in a vicinity of (including inside) the color enhancing structures described herein. For example, in medical or scientific instruments, simultaneous with irradiation by the high energy particles there could be applied electric fields to enhance emissions from these x-ray phosphors or scintillator materials. As shown in FIG. 38, a $3/4\lambda$ folded resonator (or $3/4\lambda$ the external electrode pair resonator) as described above (or any of the variations noted above) has included between the opposing electrodes x-ray phosphors or scintillator materials. The $3/4\lambda$ folded resonator or $3/4\lambda$ the external electrode pair resonator may be driven by microwave to RF frequency supplies, wherein the high Q of the resonator creates an intensified electric field enhancing light emission. Visible light then is collected or detected by an electron multiplier device.

Moreover, the composite mechano-luminescent emitters shown in FIG. 30 can be distributed inside a medium of interest for generation of light therein or therefrom could be placed inside a patient at a site of medical treatment. Light from these composite mechano-luminescent emitters (or from the non-composite mechano-luminescent emitters) activated by ultrasonic waves could be used at the medical site in a patient for a variety of uses, including, but not limited to photoactivating a drug, sterilizing a target structure, generating a reactive oxygen species, inducing an immune response, exciting a DNA strand of a cancer cell, redirecting a metabolic pathway, up-regulating genes, down-regulating genes, secreting cytokines, altering cytokine receptor responses, releasing metabolites, generating an autovaccine, wound healing, enhancement of tissue growth, nerve regeneration, neuronal stimulation and sensory regeneration/restoration. Other potential uses for the light so generated are detailed in the various published patent applications incorporated herein by reference below.

XPACT

Despite the positive clinical results noted above in extra-corporeal applications, use of psoralen traditionally has been restricted to superficial or extra-corporeal applications because of the inability of UVA light to penetrate into tissue (maximum penetration depth<1 mm). In one embodiment of this invention, X-PACT (X-ray Psoralen Activated Cancer Therapy) is utilized to extend psoralen therapy to a wide range of solid tumors, at various depths in tissue. In X-PACT, psoralen is combined with phosphors that absorb and down-convert x-ray energy to re-radiate as UV light or other light such as visible light which can activate a photo-activatable drug at a diseased site. In one embodiment of this invention, relatively low x-ray doses (~1 Gy) are sufficient to achieve photo-activation, greatly reducing the risks of normal tissue damage from radiation.

In one embodiment of this invention, the above-described energy converters including but not limited to phosphors, scintillators, fluorescent materials, and combinations and agglomerations thereof or the energy converters described above) with or without plasmonic inducing agents with and without energy augmentation can be used in X-PACT for the light source. With the energy augmentators present, this invention can generate local regions of intense electric fields to enhance light emission from these energy converters in proximity to those local regions.

Accordingly, the present invention sets forth a novel method of treating cell proliferation disorders with and without energy augmentation that is effective, specific, and has few side-effects. Those cells suffering from a cell proliferation disorder are referred to herein as the target cells. In one embodiment of the invention, treatment for cell proliferation disorders, including solid tumors, chemically binds cellular nucleic acids, including but not limited to, the DNA or mitochondrial DNA or RNA of the target cells. For example, a photoactivatable agent, such as a psoralen or a psoralen derivative, is exposed in situ to an energy source (e.g., x-rays) capable of activating energy converters which emit light to activate photoactivatable agents such as psoralen or coumarin.

In one embodiment of the invention, X-PACT activates with and without energy augmentation psoralen with UV light from non-tethered phosphors (co-incubated at the target cell with psoralen). The co-incubation process in one embodiment of the invention involves promoting the presence of psoralen (or other photoactivatable drugs) and the phosphor (energy converters) at a diseased site at the time of the x-ray exposure (or electron beam exposure). Of these two components (the psoralen component and the phosphor component), the psoralen component is more readily passed from the diseased site while the phosphor tends to be retained at the diseased site longer. Accordingly, in one embodiment of the invention, after a coinjection of a phosphor and psoralen mixture, the x-ray exposure would follow within 0.5 to 20 minutes, or 1 to 10 minutes, or 3 to 5 minutes or in general within 20 minutes. Longer times maybe used but at the potential loss in concentration of one of these components from the diseased site. In another embodiment of the invention, a separate injection of psoralen may be provided after the coinjection of the phosphor and psoralen mixture. In another embodiment of the invention, a separate injection of psoralen may be provided after an injection of phosphor alone into the diseased site. In these embodiments with separate psoralen injections, the x-ray exposure would follow within 0.5 to 20 minutes, or 1 to 10 minutes, or 3 to 5 minutes or in general within 20 minutes. Longer times maybe used but at the potential loss in concentration of one of these components from the diseased site. With the energy augmentators present, this invention can generate local regions of intense electric fields to enhance light emission from these energy converters in proximity to those local regions and the diseased site.

As noted above, the phosphors absorb x-rays and re-radiate (e.g., phosphoresce) at UV wavelengths with and without energy augmentation. With the energy augmentators present, this invention can generate local regions of intense electric fields to enhance light emission from the phosphors in proximity to those local regions and the tumor.

Described below is the efficacy of X-PACT in both in-vitro and in-vivo settings. In-vitro studies utilized breast (4T1), glioma (CT2A) and sarcoma (KP15B8) cell lines. Cells were exposed to X-PACT treatments where the concentrations of drug (e.g., an injection of psoralen and phosphor) were varied as well as the radiation parameters (energy, dose, and dose rate). Efficacy was evaluated primarily using flow cell cytometry. A multi-variable regression on 36 independent irradiation experiments revealed neither psoralen nor phosphor alone had a strong effect on cytotoxicity (Annexin V signal). However, when combined (e.g., an injection of psoralen and phosphor) in X-PACT, a significant increase was observed (p<0.0001), with 82% cytotoxicity compared to just 31% in treated but un-irradiated controls. In-vivo work, utilized X-PACT on BALBc mice with syngeneic 4T1 tumors was conducted, including control arms for X-PACT components. The results demonstrate a pronounced tumor growth delay compared to saline controls (42% reduction at 25 days, p=0.0002

Accordingly, in one embodiment of the invention, the dose of x-rays or electron beam to the target site of the tumor produces a cytotoxicity of greater than 20%, greater than 30%, greater than 50%, greater than 60%, greater than 70%, greater than 80%. In one embodiment of the invention, the dose of x-rays or electrons to the target site of the tumor produces a cytotoxicity between 20% and 100%, between 40% and 95%, between 60% and 90%, or between 70% and 80%. The cytotoxicity can be categorized into components involving 1) the toxicity of the phosphor itself without psoralen and 2) the apoptosis-induced cell death generated by UV activation of the psoralen. The apoptosis-induced cytotoxicity can range from greater than 20%, greater than 30%, greater than 50%, greater than 60%, greater than 70%, greater than 80%. In one embodiment of the invention, the apoptosis-induced cytotoxicity can range between 20% and 100%, between 40% and 95%, between 60% and 90%, or between 70% and 80%.

Medical applications of ionizing radiation have traditionally associated with diagnostic imaging and radiation therapy. Diagnostic imaging (planar x-rays and x-ray-CT) utilizes low energy x-rays, in order to obtain better soft-tissue-bone contrast, and lower dose exposure to the patient. In radiation therapy, higher energy MV radiation (6 MV and higher) is typically used to achieve skin sparing. The X-PACT therapeutic paradigm, in one embodiment of this invention, departs from these conventions by utilizing low energy radiation (and low doses) to initiate phosphorescence of UV light in-situ with and without energy augmentation, in potentially deep seated lesions, for the purpose of activating a potent anti-tumor photo-bio-therapeutic (psoralen). In one embodiment of the invention, X-PACT produces measurable anti-tumor response.

In general, the invention described here provides for a system (and an associated method) for treating a human or animal body with and without energy augmentation. The system has a photoactivatable drug (for treating a first diseased site. The photoactivatable drug can e.g., psoralen or coumarin or a derivative thereof or a photoactivatable drug selected from psoralens, pyrene cholesteryloleate, acridine, porphyrin, fluorescein, rhodamine, 16-diazorcortisone, ethidium, transition metal complexes of bleomycin, transition metal complexes of deglycobleomycin organoplatinum complexes, alloxazines, vitamin Ks, vitamin L, vitamin metabolites, vitamin precursors, naphthoquinones, naphthalenes, naphthols and derivatives thereof having planar molecular conformations, porphorinoporphyrins, dyes and phenothiazine derivatives, coumarins, quinolones, quinones, and anthroquinones. The system has a first pharmaceutically acceptable carrier, which optionally includes one or more phosphorescent or fluorescent agents, such as when using an applied energy of x-rays or other high energy ionizing type radiation (gamma rays, electron beams, proton beams, etc.) (e.g., sterile compositions including for example $Y_2O_3$; ZnS; ZnSe; MgS; CaS; Mn, Er ZnSe; Mn, Er MgS; Mn, Er CaS; Mn, Er ZnS; Mn,Yb ZnSe; Mn,Yb MgS; Mn, Yb CaS; Mn,Yb ZnS:$Tb^{3+}$, $Er^{3+}$; ZnS:$Tb^{3+}$; $Y_2O_3$:$Tb^{3+}$; $Y_2O_3$:$Tb^{3+}$, $Er^{3+}$; ZnS:$Mn^{2+}$; ZnS:Mn,$Er^{3+}$; $CaWO_4$, $YaTO_4$, $YaTO_4$:Nb, $BaSO_4$:Eu, $La_2O_2S$:Tb, $BaSi_2O_5$:Pb, NaI(Tl), CsI(Tl), CsI (Na), CsI(pure), CsF, KI(Tl), LiI(Eu), $BaF_2$, CaF, $CaF_2$(Eu), ZnS(Ag), $CaWO_4$, $CdWO_4$, YAG(Ce) ($Y_3Al_5O_{12}$(Ce)), $3Ca_3(PO4)_2 \cdot Ca(Fl,Cl)_2$: $Sb^{3+}$, $Mn^{2+}$, BGO bismuth germanate, GSO gadolinium oxyorthosilicate, LSO lutetium oxyorthosilicate, $LaCl_3$(Ce), $LaBr_3$(Ce), $LaPO_4$; Ce, Tb (doped), $Zn_2SiO_4$:Mn with Mn preferably doped between 0.05-10%, and YTaO4. The phosphorescent or fluorescent agents are capable of emitting an activation energy into the body which activates the photoactivatable drug. The system has a first device which infuses the first diseased site with a photoactivatable drug and the first pharmaceutically acceptable carrier, a source of energy generation in situ in the human or animal body sufficient to activate the photoactivatable drug, which can preferably be a first energy source which irradiates the diseased site with an initiation energy to thereby initiate emission of the activation energy into the body from the optional one or more phosphorescent or fluorescent agents to thereby activate the photoactivatable drug, and a supplemental treatment device which administers one or both of a therapeutic drug or radiation to the body at a second diseased site or the first diseased site, for example to provide an immune system stimulation in the body.

The source of energy generation in situ in the human or animal body can be any of a variety of sources or methods of generating the necessary energy in vivo in the human or animal body with and without energy augmentation, including, but not limited to, use of externally applied x-rays to generate Cherenkov UV/vis emissions within the body, use of micro or nano devices capable of generating UV light within the body, use of chemical energy sources such as chemiluminescence, phosphorescence, and bioluminescence agents, and application of external radiation (such as x-ray, gamma ray, electron beam, proton beam, infrared, microwave, etc.) which interacts with and without energy augmentation with one or more administered phosphorescent or fluorescent agents within the body. Ultimately, any desired method can be used to generate the activation energy within the body of the subject, including but not limited to those methods above and as detailed in the various related applications mentioned and incorporated by reference at the beginning of this application.

Described below are various embodiments of the present invention.

1.1 Phosphors and x-Ray Stimulation of UV Light with and without Energy Augmentation In one embodiment of the present X-PACT therapy, psoralen is activated by light generated in-situ from phosphor particles undergoing x-ray stimulated phosphorescence with and without energy augmentation. In one embodiment, the emission profiles from the phosphor preferably overlap the absorption/activation wavelengths of psoralen. While nano-scintillating particles have been developed which were tethered to psoralen, in one embodiment of this invention, a treatment system does not necessarily (but could) use tethered phosphors. In the embodiment without tethering, the functionally of the tethering is replaced by the above-noted co-incubation of psoralen and phosphor particles at the target or diseased site, as described above. The untethered psoralen benefits from a high degree of mobility and greater intercalation with DNA. In one embodiment, phosphors of different particle size and distribution are utilized or specific absorption and emission spectra.

onto a 96-well plate. The phosphors used in this evaluation were designated as NP 200 and GTP 4300. These phosphors have the following elemental compositions, as shown in Table 1 below:

GTP 4300=Ca, F, Cl, PO4, (96-99%)

Mn (1-3%) Sb (<1%)

$Zn_2SiO_4$: Mn with Mn doped between 0.05-10%.)

TABLE 1

|  |  | % Viability (1-Toxicity) | Psoralen & Phosphor | Fractional Kill |
| --- | --- | --- | --- | --- |
|  | $Zn_2SiO_4$:Mn | 75% | 0.51 | 32.0% |
| GTP 4300 | $3Ca_3(PO4)_2 \cdot Ca(Fl,Cl)_2$: $Sb^{3+}$ $Mn^{2+}$ | 70% | 0.54 | 22.9% |

Figure 39:
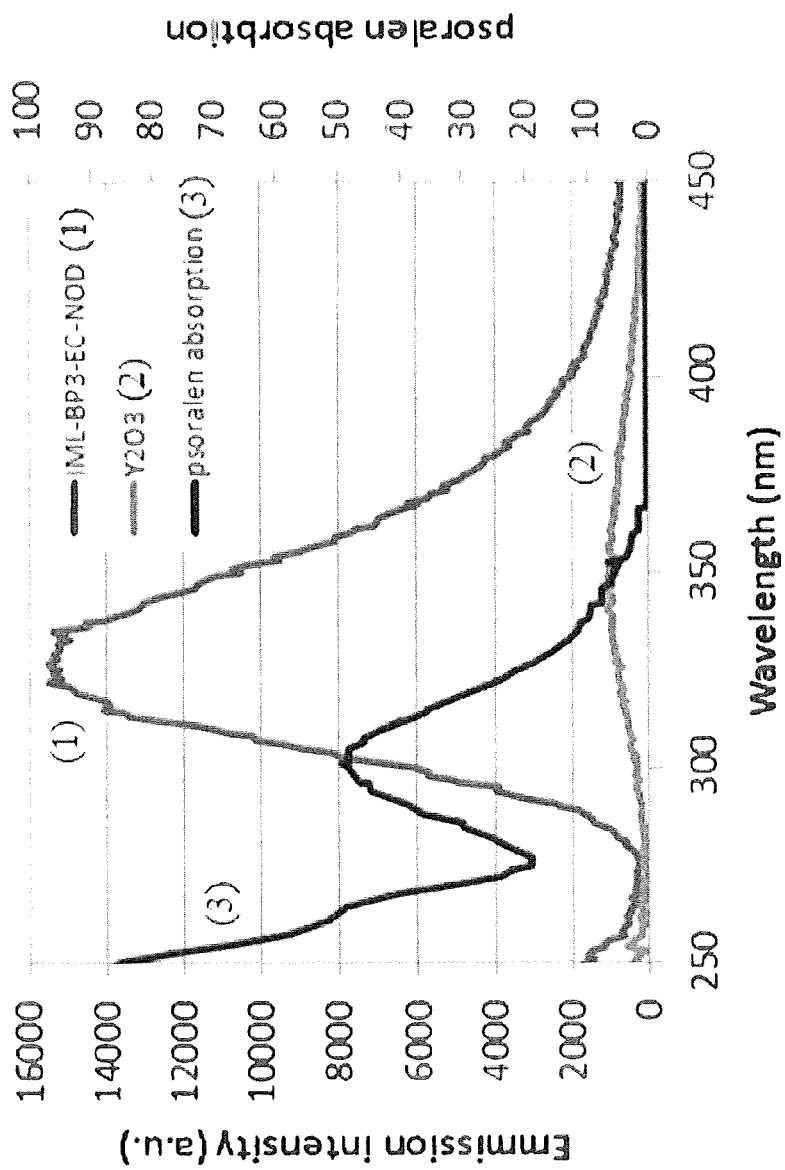
FIG. 39 is a schematic showing the emission of tethered and untethered phosphors under X-ray excitation.

In one embodiment of the invention, the phosphors shown in FIG. 161, (i.e., $YTaO_4$ coated with ethyl cellulose) may be used with and without energy augmentation. As shown in FIG. 39, the emission spectra of the $YTaO_4$ phosphor overlaps with the wavelength required to activate psoralen (~300-340 nm). FIG. 1 shows that the emission under X-Ray excitation of the $YTaO_4$ phosphor is ~16 times brighter than a tethered nano-particles $Y_2O_3$ phosphor. In one embodiment of the invention, both of the phosphors (as shown in FIG. 39) have output wavelengths that "match" the absorption spectrum of the bio-therapeutic agent to be activated (in this case the psoralen). In one embodiment of the invention, a variety of bio compatible coatings can added to the phosphors to provide biological inertness while maintaining sufficient transparency in the UV range, thus maintaining the ability of the in vivo generated UV light to activate psoralen. In one embodiment of the invention, the phosphors can be made from an inert lattice structure, which may not require a bio compatible coating.

Psoralen

Both commercially available UVADEX (formulated 8-MOP psoralen) and pure 8-MOP were used as alternative formulations of psoralen agents. Prior work has shown that the number of DNA photo-adducts is a linear function of the product of 8-MOP (psoralen) concentration and light-exposure. UVADEX and 8-MOP concentrations in the range 10-60 μM were evaluated. The stability of drug in the presence of phosphors was investigated using standard UV-Vis spectroscopy and HPLC-MS.

In-Vitro X-PACT Studies

Guava Annexin V flow cell cytometry was used in prior work to quantify cytotoxicity in 3 murine tumor cell lines (breast-4T1, glioma-CT2A, and sarcoma KP15B8). In-vitro X-PACT studies were conducted on cells prepared in the following manner. Cells were incubated in appropriate growing media and buffers before being trypsinized and plated evenly onto twelve (12) well plates for 24 hours. About 20 minutes prior to X-PACT irradiation, the wells of each plate were exposed to the following combinations of additives: (1) control—cells only with no additives, (2) UVADEX only, (3) phosphors only, (4) UVADEX+phosphors. Each plate had twelve (12) wells with three wells for each of the four treatment arms. The plates were then irradiated with x-rays by placing the plate at a known distance from the x-ray source (e.g., 50 cm). After irradiation the cells were incubated on the plate for 48 hours prior to performing flow cytometry. For compatibility with 96-well Guava Nexin® assay, the remaining cells were again trypsinized (after the 48 hour incubation) and plated Fractional kill: Added cell kill by the combination of Psoralen and phosphor and X-Ray In one embodiment of the invention, the phosphors with and without energy augmentation are mixed in combination at a ratio of 2 parts by weight of GTP 4300 for every one part by weight of ($Zn_2SiO_4$:Mn).

X-ray stimulated emission from this combination of phosphors without energy augmentation was taken from the following slurry using the following procedures Acetic acid diluted in di-ionized water at a rate of 1:10 by weight or by volume was prepared. A total of 2 mL of the diluted acetic acid solution was added to 0.3 grams of the combined phosphors. The slurry hence formed was stirred using a vortex mixer for at least 60 sec. The high viscosity slurry exhibits paste-like behavior from a viscosity stand point. The test tube containing the slurry was then set inside an X-Ray chamber to be exposed to X-Ray energy radiation produced by using a 6 mA beam at a voltage of 125 kV. The test tube was placed at a distance from the X-Ray source of ~20 cm. The fiber optic probe of a photo-spectrometer feeding to an ICCD camera was inserted inside the tube and was brought to a close proximity to the pasty slurry at a distance of 2 mm approximately. The fiber probe was then fixed in place using an adhesive tape. The X-Ray energy was turned on and the emission out of the slurry was collected.

Figure 40:
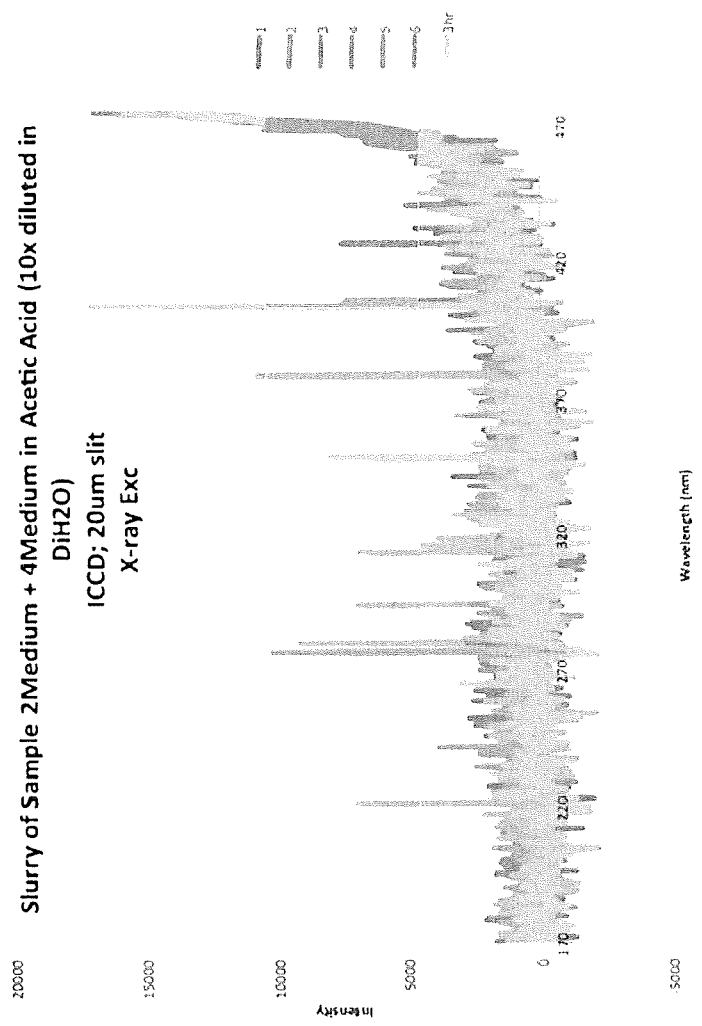
FIG. 40 is a schematic showing UV emission under X-Ray energy of a combined GTP 4300 and for $Zn_2SiO_4$: Mn phosphor.
Figure 41:
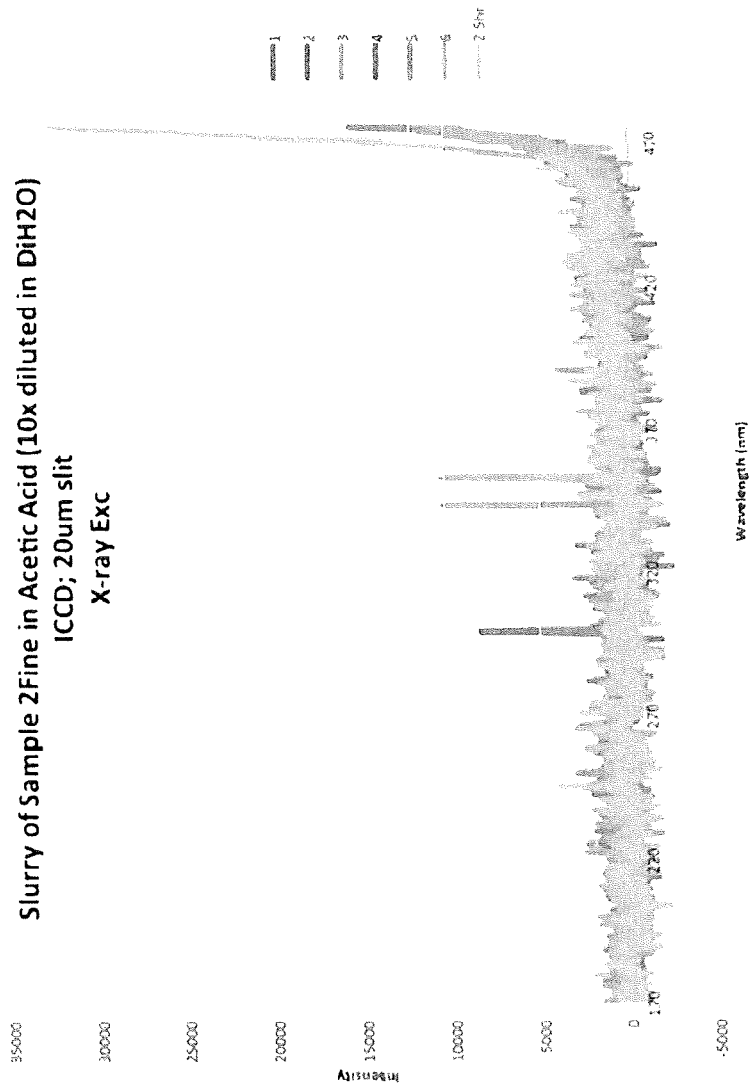
FIG. 41 is a schematic showing UV emission under X-Ray energy $Zn_2SiO_4$: Mn.
Figure 42:
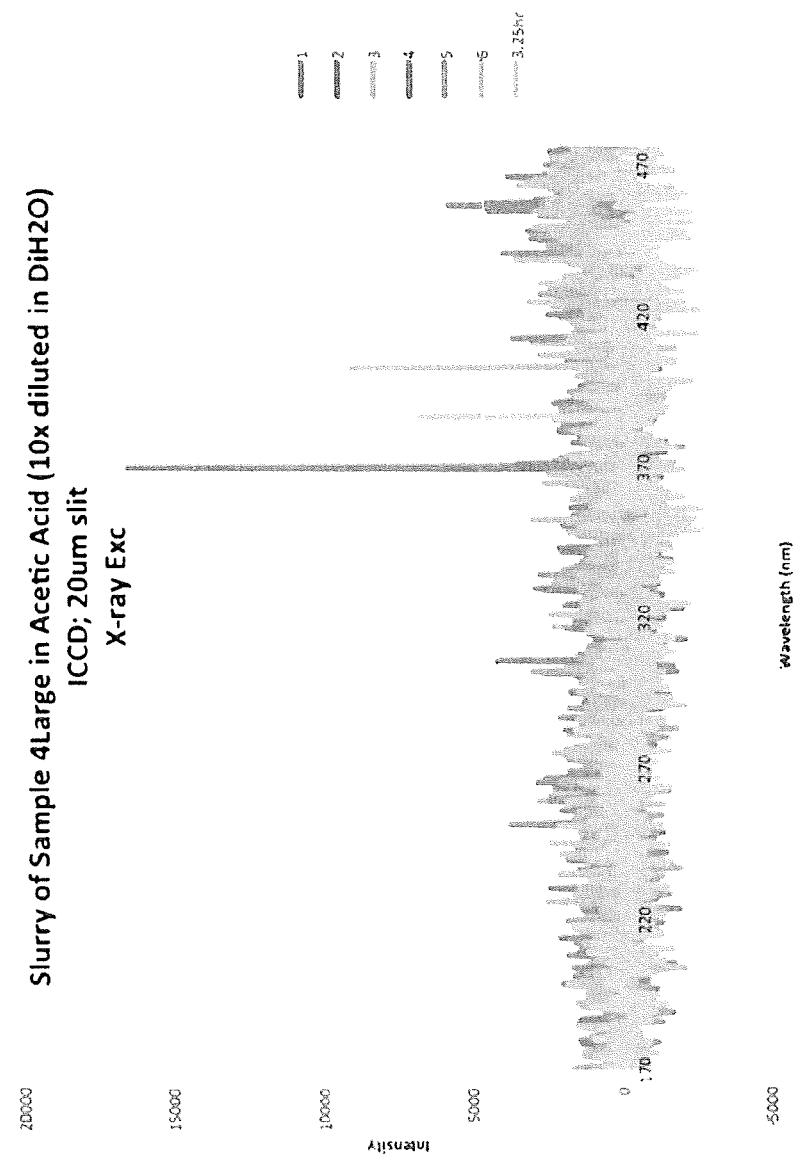
FIG. 42 is a schematic showing UV emission under X-Ray energy for GTP 4300 phosphor.
Figure 43:
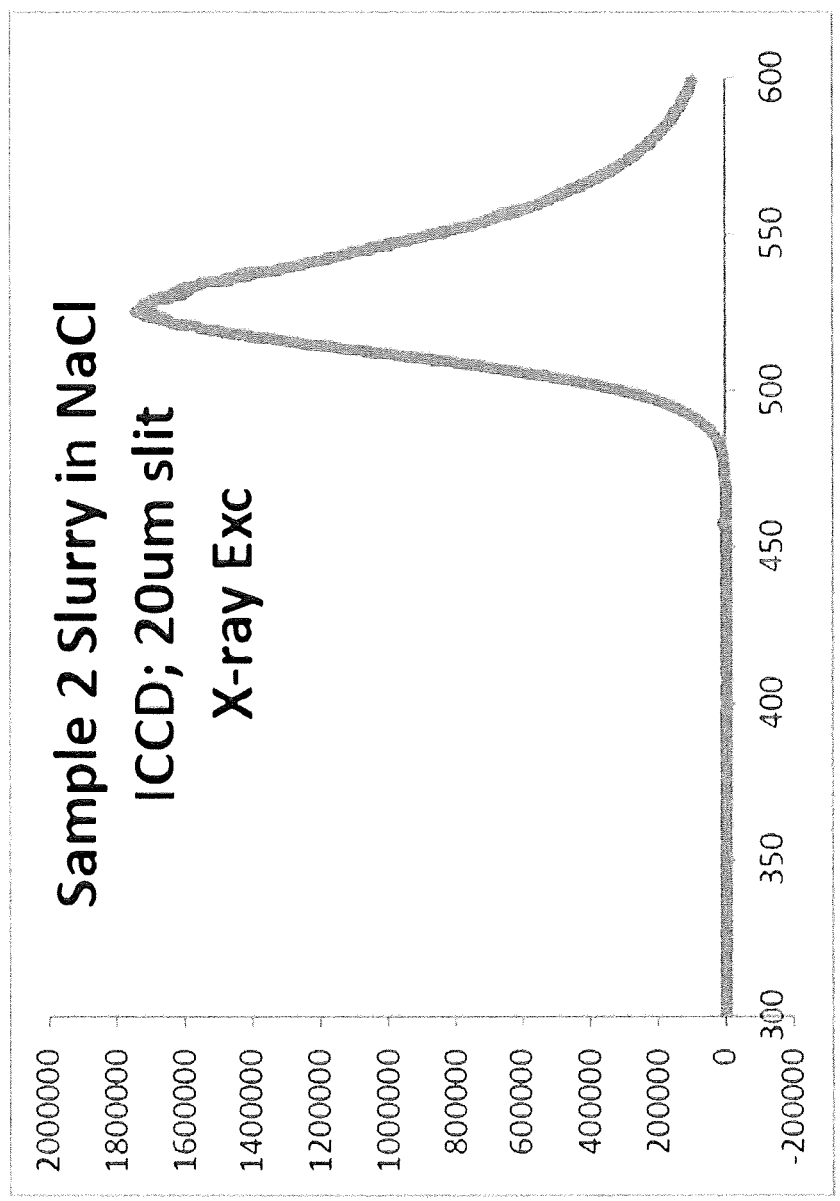
FIG. 43 is a schematic showing UV and visible emissions under X-Ray energy for $Zn_2SiO_4$:Mn in a NaCl slurry.
Figure 44:
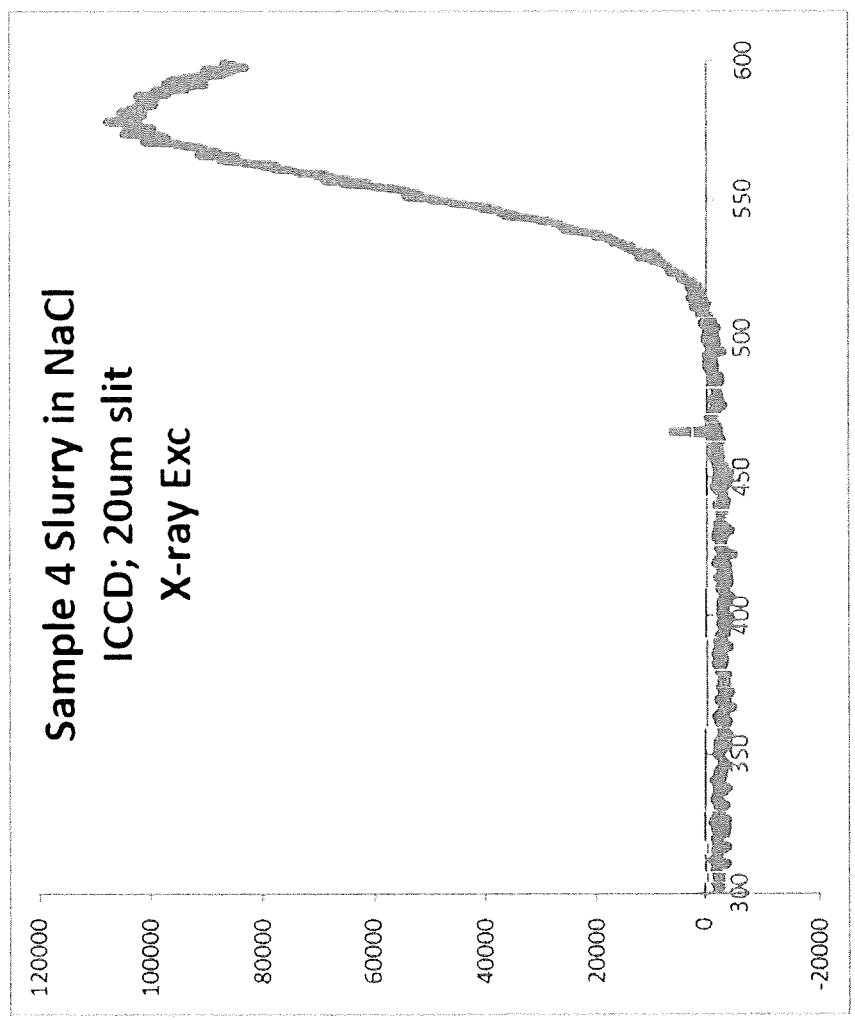
FIG. 44 is a schematic showing UV and visible emissions under X-Ray energy GTP 4300 in a NaCl slurry.
Figure 45:
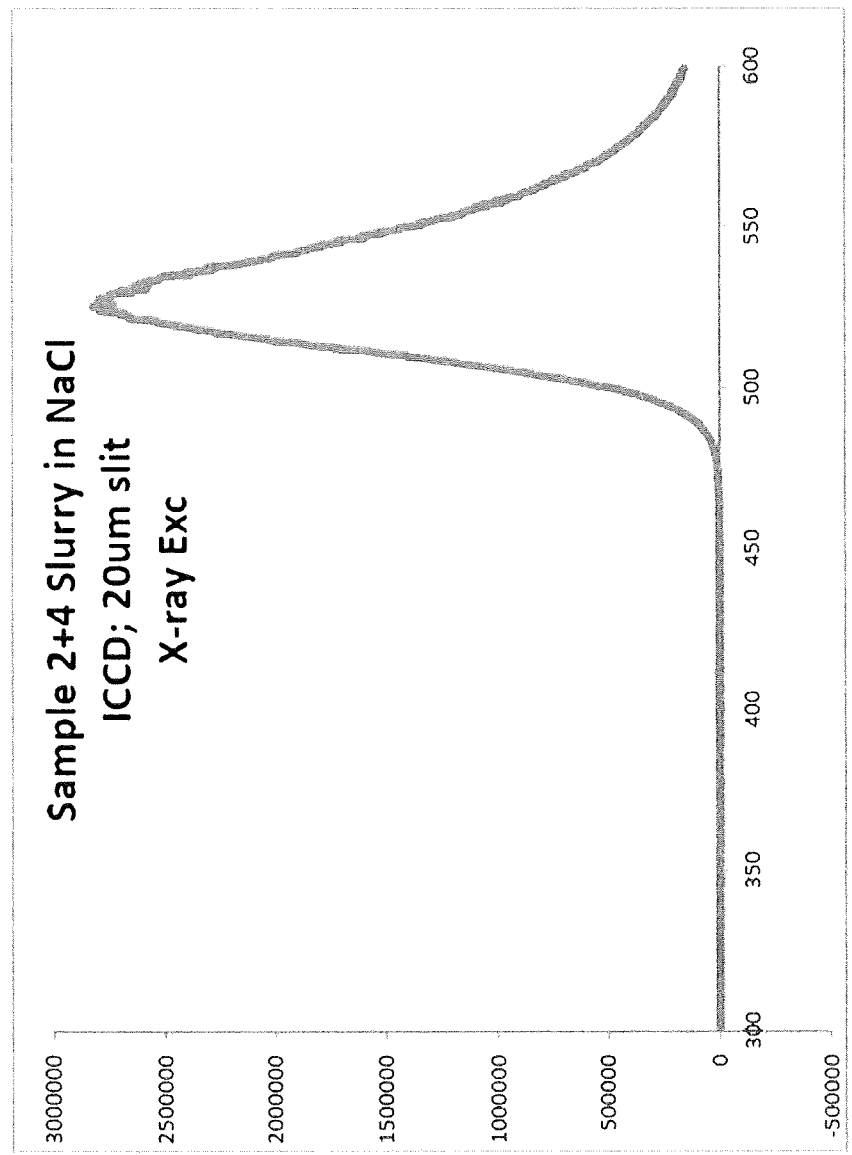
FIG. 45 is a schematic showing UV and visible emissions under X-Ray energy of the combined phosphors in a NaCl slurry.

Several emissions were collected. The slurry was found to emit both in the visible and the UV range as illustrated in FIG. 40, showing UV emission without energy augmentation under X-Ray energy of a combined GTP 4300 and for $Zn_2SiO_4$: Mn phosphor. The emissions measurements were collected 1, 2, 3, 4, 5, 6 hours after the slurry was made. Under similar conditions of preparation the slurry made of the individual phosphors ($Zn_2SiO_4$ and GTP 4300) is presented in FIGS. 41 and 42 (respectively). Visible emissions are stronger than the UV emission of both materials. FIG. 43 is a schematic showing UV and visible emissions under X-Ray energy $Zn_2SiO_4$: Mn without energy augmentation in a NaCl slurry. FIG. 44 is a schematic showing UV and visible emissions under X-Ray energy of GTP 4300 without energy augmentation in a NaCl slurry. FIG. 45 is a schematic showing UV and visible emissions under X-Ray energy of the combined phosphors in a NaCl slurry.

Figure 46:
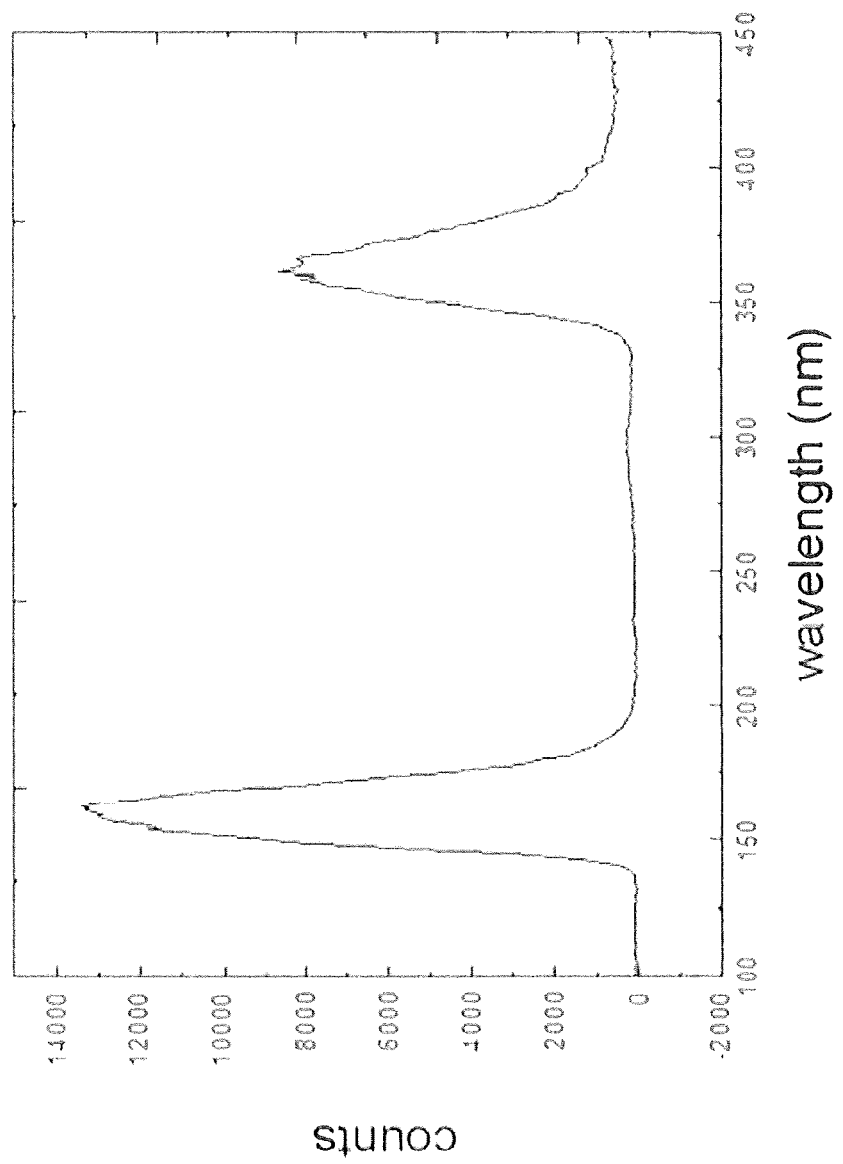
FIG. 46 is a schematic showing cathodoluminescence for the $Zn_2SiO_4$ phosphor discussed above.
Figure 47:
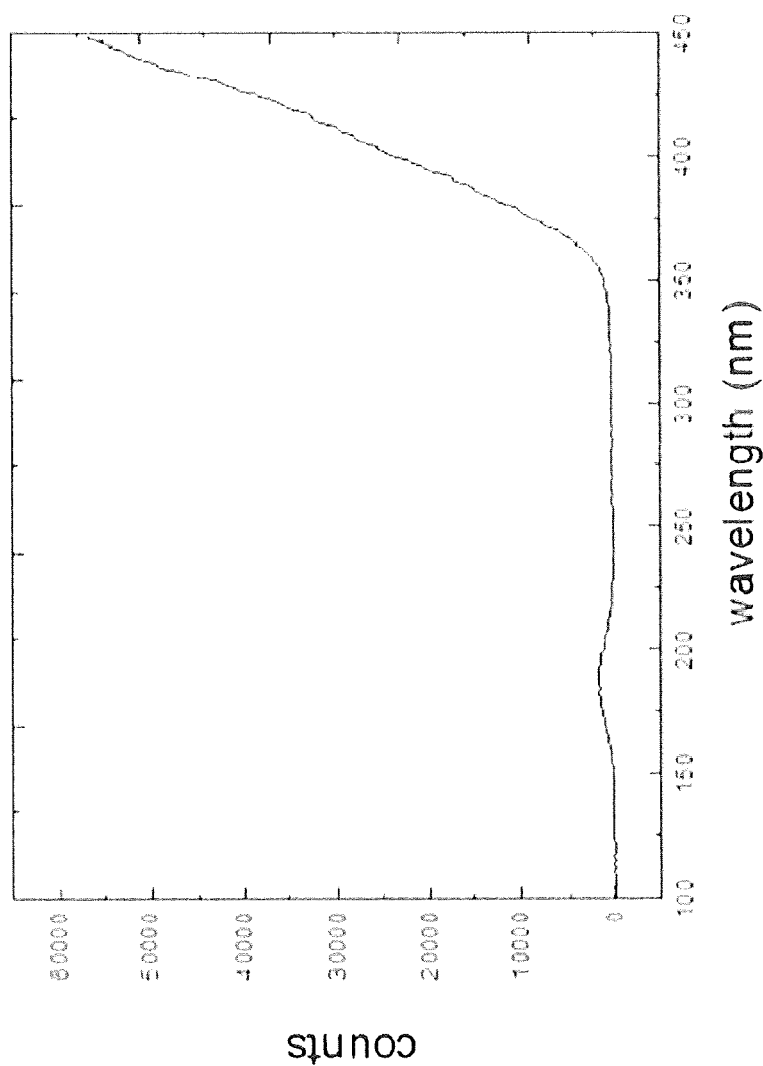
FIG. 47 is a schematic showing cathodoluminescence for the GTP 4300 phosphor discussed above.

FIG. 46 compares cathodoluminescence for the Zn2SiO4: Mn phosphor discussed above. FIG. 47 compares cathodoluminescence for the GTP 4300 phosphor discussed above.

Regardless of phosphor, the following injections shown in Table 2 were illustrative of the concentration used as a function of the measured or predicted tumor volume (or the calculated volume of the diseased site). In these evaluations, vials of sterilized phosphor were mixed with UVADEX™ (100 μg/mL 8-MOP) as the sole diluent.

TABLE 2

| Tumor volume | mL of slurry per | | milligrams of phosphor per cm³ of tumor | | Total volume injected |
|---|---|---|---|---|---|
| | Min | Max | Min | Max | |
| 8-15 cubic centimeters | 0.034 | 0.063 | 0.333 | 0.625 | 0.5 mL |
| 15-29.9 cubic centimeters | 0.033 | 0.067 | 0.334 | 0.667 | 1 mL |
| 30-49.9 cubic centimeters | 0.040 | 0.067 | 0.401 | 0.67 | 2 mL |
| 50-74.9 cubic centimeters | 0.040 | 0.060 | 0.401 | 0.600 | 3 mL |
| 75-99.9 cubic centimeters | 0.040 | 0.053 | 0.400 | 0.533 | 4 mL |
| >100 cubic centimeters | 0.044 | 0.050 | 0.435 | 0.500 | 5 mL |

In-Vitro Radiation Activation Technique

Previously, a range of x-ray activation protocols was investigated to determine X-PACT cytotoxic efficacy in relation to x-ray energy (kVp), total dose, and dose-rate. kVp beam energies ranging between 80 and 100 kV were investigated. kV beams were obtained from various x-ray generating equipment, including orthovoltage units, standard diagnostic radiographic, fluoroscopic, and cone-beam computed tomography (CBCT) systems. These results are reproduced here for completeness. The primary kV x-ray source was a Varian on-board-imaging x-ray source commonly found on Varian medical linear accelerators. In one embodiment of the invention, the x-ray dose may be relatively low (~1 Gy/fraction for 9 fractions). This low-dose requirement (as compared to conventional radiation therapy) provides in this embodiment safe delivery of the radiation component of X-PACT. In this embodiment, normal tissue tolerances (skin, bone) can be kept within tolerance doses. In one embodiment of the invention, the x-ray doses can specifically range from 0.2-2 Gy, with preferred doses of 0.5-1 Gy.

For x-ray irradiation, the well plates were positioned at a set distance (e.g., typically 50 cm) from the x-ray source on a solid water phantom and the position of the well plates within the x-ray beam was verified by low dose kV imaging. Irradiations were typically delivered in a "radiograph" mode; where multiple pulses of a set mA (e.g., typically 200 mA) and ms (e.g., typically 800 ms) and pulses were delivered e.g., every 5-15 seconds. In one embodiment, the radiation can be delivered in a "pulsed fluoroscopy mode" (e.g., at 10 Hz) at the maximum mA setting. In one embodiment, kVp settings of 80 and 100 kVp (and ranges in between) with no added filtration in the beam (Half Value Layer=3.3 and 3.9 mm Al, respectively) are suitable for the invention. Higher kVps and lower kVps can be used.

In-Vitro Analysis: Quantification of Cytotoxicity and Apoptosis

Two primary flow cytometry metrics were used to evaluate the X-PACT treatments, both determined at 48 h after X-PACT treatment. Cells plated in 12-well plates, where individual wells in each plate may receive different experimental conditions (e.g. psoralen concentration), but the same x-ray dose (i.e. all wells in a given plate receive the same x-ray dose). The first metric is metabolically viable cell count (or cell viability) determined from the number of whole cells per well as determined using forward scattering (FSC). For each well, the cell viability was normalized to that in a control well on the same plate, which had no additives but did receive the radiation of that plate. (All wells on a given plate receive the same dose.) The second metric is Annexin V (+) signal, which is the fraction of the metabolically viable cells which expressed a positive Annexin V signal as determined by flow cell cytometry, and include any cells advancing toward early or late apoptotic cell death. The Annexin V (+) signal was corrected by subtracting the control signal from the "no-additive" well on the same plate. For both metrics, correcting for the control on the same plate, minimizes any potential inter-plate systematic bias associated with plating constancy or Annexin V gating parameters. The majority of plots in the results either use metabolically viable cell count or Annexin V(+) signal as defined by Krysko, Vanden Berghe, D'Herde, & Vandenabeele, 2008.

Metabolic cell viability was also assessed visually using Methylene blue staining and ATP-induced Luminescence imaging (Cell-Titer-Glo® Luminescence Cell Viability Assay). The luminescence imaging permitted investigation of the cytotoxicity of psoralen activated directly with a UV lamp, and in the absence of phosphors and x-ray radiation.

Several statistical analyses were evaluated, including unequal variance two-sample t-tests, Analysis of Variance (ANOVA), and multi-variable regression. The unequal variance two-sample t-test tests the null hypothesis that the means of observations (e.g. viable cells, Annexin V signal) in two different populations are equal. The p-value gives the probability that the observed difference occurred by chance. The lower the p-value, the less likely the observed difference occurred by chance. Multi-variable regression was used to test the null hypothesis that psoralen and phosphor had no effect on Annexin V (+) signal and to test if there is a first-order interaction between the two therapeutic elements. Non-parametric statistical analysis were also evaluated for each test, and showed consistent results.

The results of statistical analyses were classified in four categories: weakly significant, moderately significant, significant, and very significant. A single asterisk indicates weakly significant statistics (*), where the p-value is in the range $0.01<p<0.05$. Double asterisks indicate moderately significant statistics (), where $0.001<p<0.01$. Triple asterisks indicate significant statistics (*), where $0.0001<p<0.001$. Quadruple asterisks indicate very significant statistics (****), where $p<0.0001$. This convention will be used throughout the remaining description.

In-Vivo X-PACT Experiments

An in-vivo trial was conducted for preliminary evaluation of X-PACT administered to syngeneic 4T1-HER2 tumors grown on BALB/c mice. There were 4 arms of the trial: (1) saline only (control), (2) phosphors alone with x-ray, (3) psoralen (AMT) alone with x-ray, and (4) full X-PACT treatment including both phosphor and psoralen and x-ray irradiation. X-PACT treatments were given in 3 fractions per week, to a total of 6 fractions. In arms 2-3 a consistent x-ray irradiation technique was used (about 1.2 Gy delivered at 75 kVp by 30 mA in 3 minutes) with 100 μg of phosphor, and 5 μM psoralen (AMT) (with M representing micromolar). 0.5 Million tumor cells were injected per mouse. There were 6-8 mice per arm, and the study was repeated a second time, yielding effective sample sizes of 12-16.

X-PACT: In-Vitro Studies without Energy Augmentation

Figure 48:
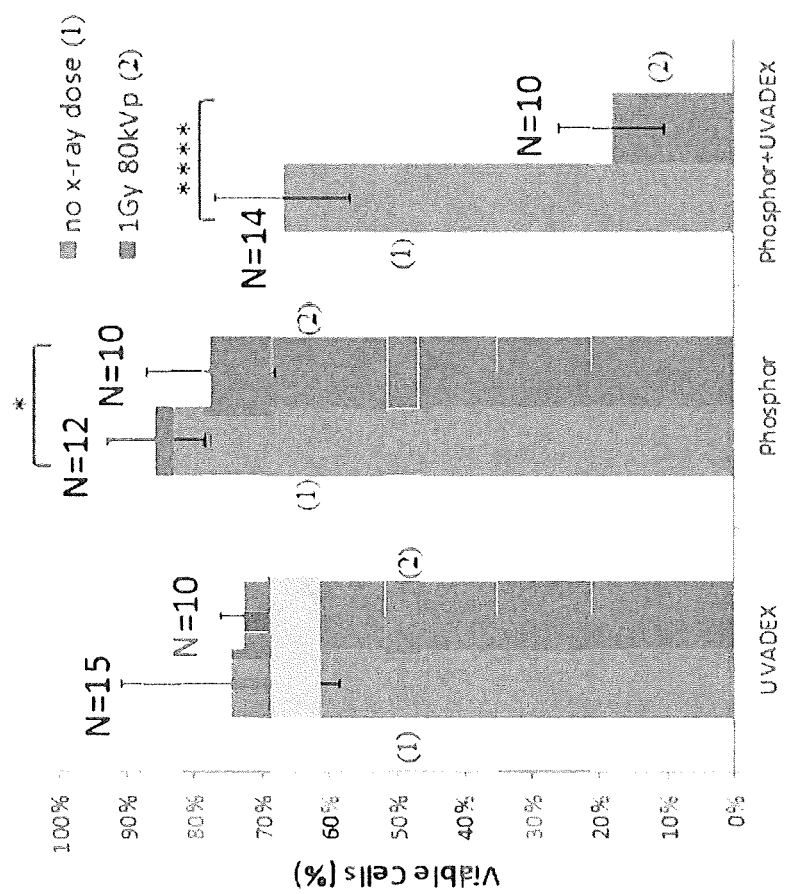
FIG. 48 is a schematic of cell viability after an X-PACT (X-ray Psoralen Activated Cancer Therapy) treatment as determined by Guava flow cytometry.
Figure 49:
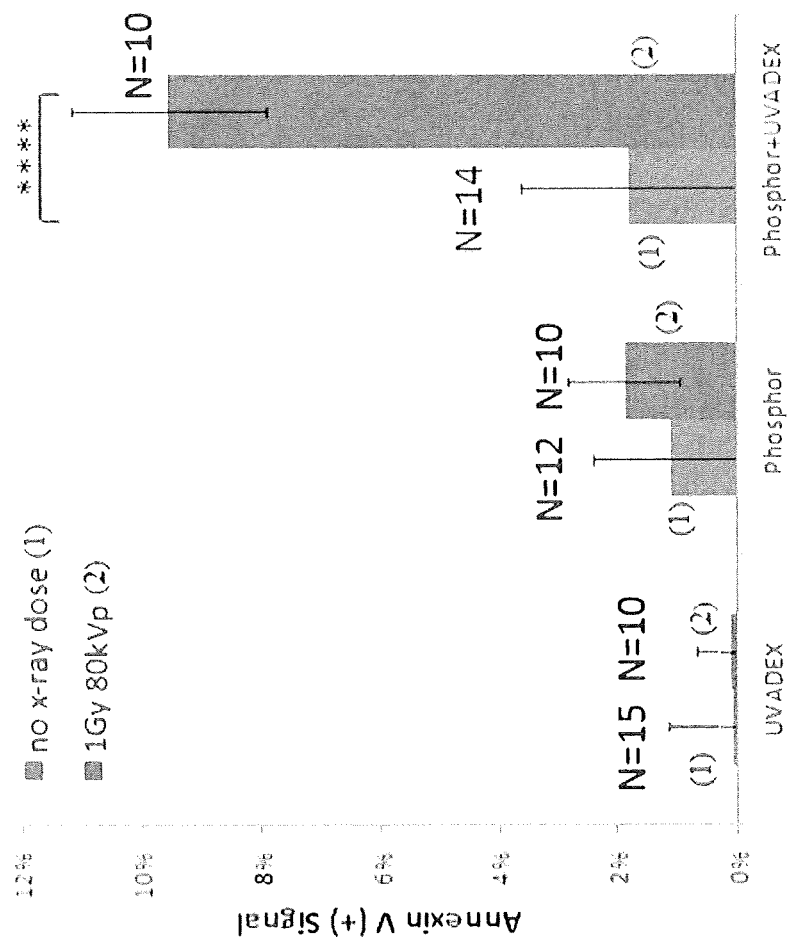
FIG. 49 is a schematic depicting the Annexin V (+) fraction of viable cells shown in FIG. 48.
Figure 50B:
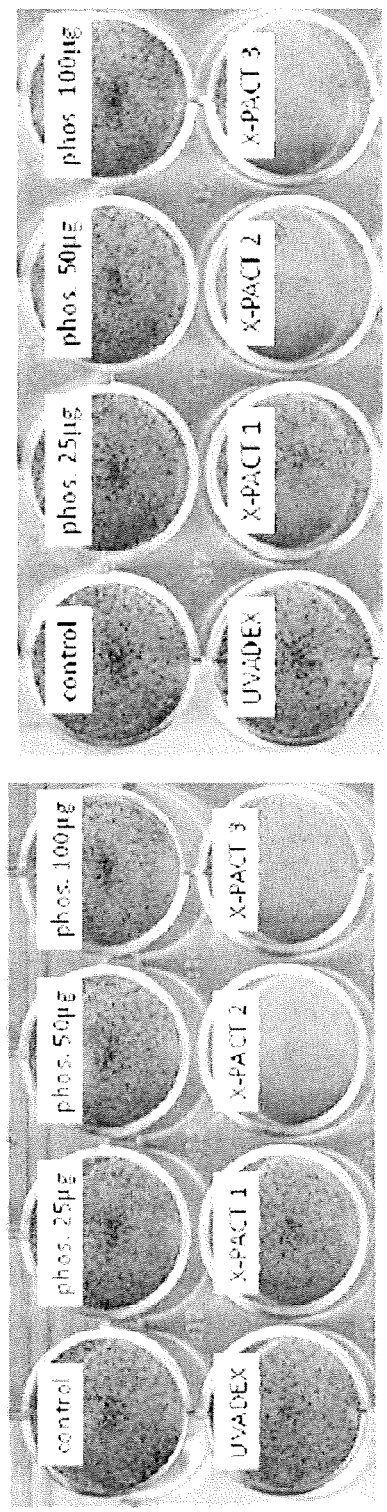
FIGS. 50A and 50B are depictions of cell viability illustrated by methyl blue staining for identical plates each receiving 1 Gy of 80kVp X-rays.
Figure 50A:
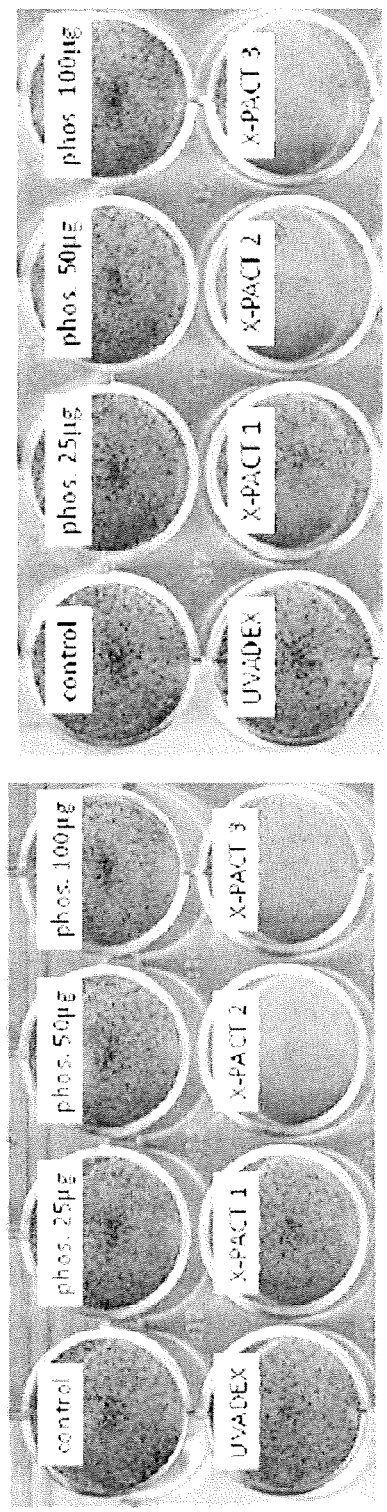

FIGS. 48-50B illustrate the efficacy of X-PACT treatment in-vitro in 4T1-HER2 cells, utilizing an X-PACT regimen of 1/10-diluted UVADEX (with equivalent of 10 μM 8-MOP), 50 μg/mL phosphor-0.6 Gy of 80 kVp x-rays. FIG. 48 presents the cell viability data for three treatment conditions: UVADEX alone, phosphors alone, and the X-PACT combination of UVADEX and phosphors (10 µM 8-MOP equivalent dilution of UVADEX, 50 µg/mL phosphor, and 0.6 Gy of 80 kVp radiation). The data were compiled from experiments performed on 5 different days (within 1 month), including 15 separate experimental and 10 control plate irradiations. FIG. 49 presents the Annexin V (+) signal for the same three conditions as in FIG. 48. FIGS. 50A and 50B show corresponding images of viable cell populations revealed by methylene blue staining. Two results from two separate plates are shown, each with identical preparations to investigate reproducibility. X-PACT variants were tested corresponding to three concentrations of phosphor (25, 50, and 100 µg/mL) with the UVADEX concentration fixed at 1/10 dilution (10 uM 8-MOP).

In-Vitro X-PACT and Other Cell Lines without Energy Augmentation

Figure 51A:
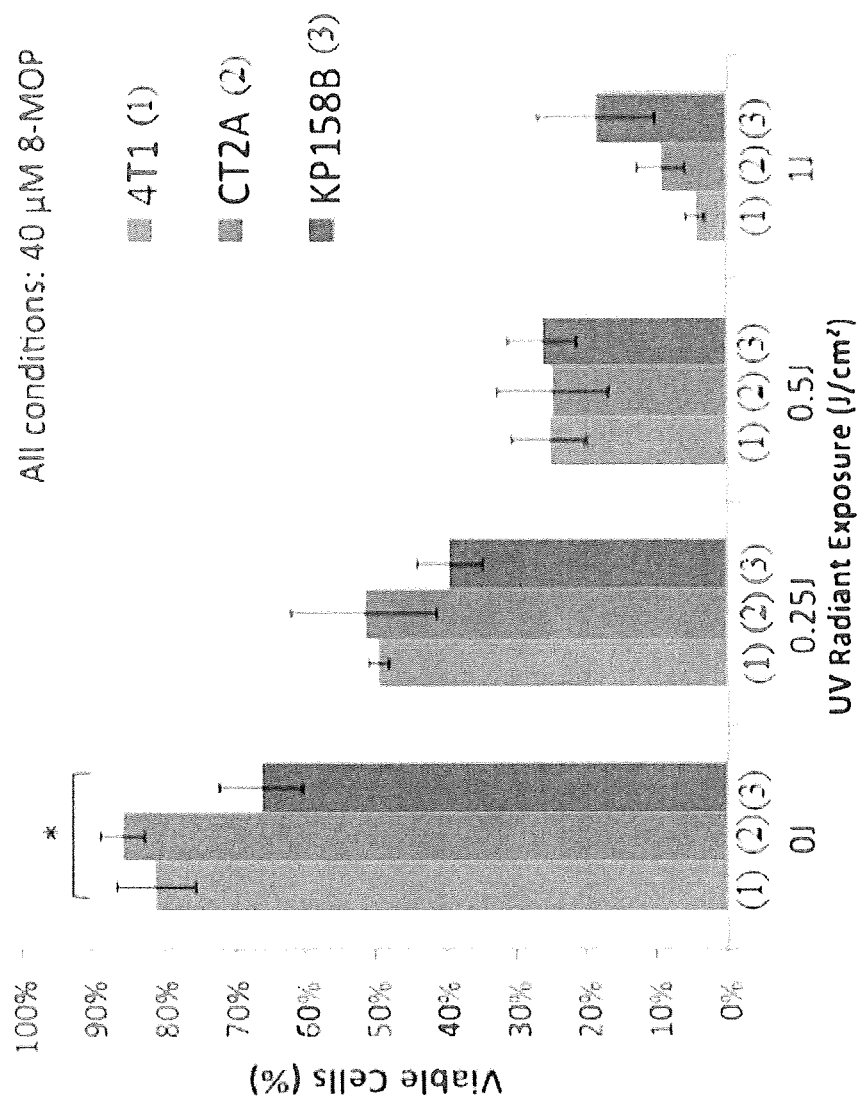
FIG. 51A is a schematic depicting the percentages of cell survival after UV light exposure.
Figure 51B:
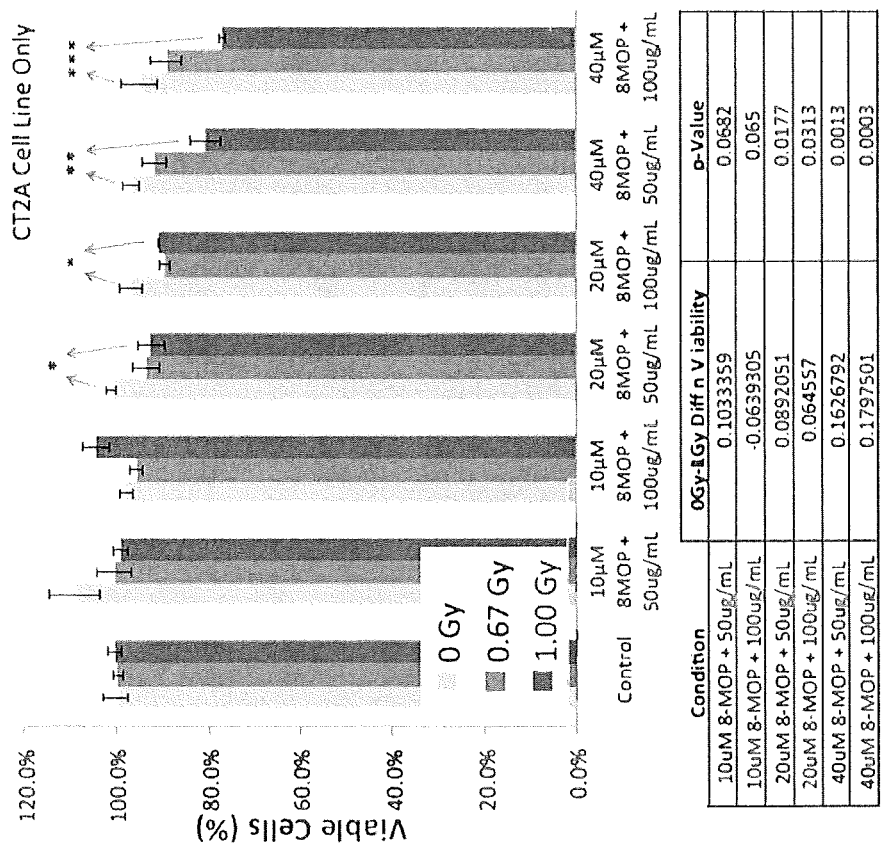
FIG. 51B is a schematic depicting, for CT2A cells, the X-PACT cytotoxicity under different X-ray doses, different concentrations of 8-MOP psoralen, and different concentration of phosphor.

The relative effectiveness of UV activated psoralen on three (3) independent cell lines is shown in FIGS. 51A and 51B. FIG. 51A shows comparable sensitivity of CT2A (murine malignant glioma), 4T1 and KP158B (sarcoma) cell lines to light-activated psoralen, which is one of the therapeutic mechanisms of X-PACT. More specifically, FIG. 51A shows the effect of UV light activated psoralen was to reduce viable cells in 3 cell lines (data from Cell-Titer-Glo© Luminescence Cell Viability Assay under UV light). N=4 for each cell line at each UV light condition (0, 0.25, 0.5, 1.0 J/cm$^2$). The psoralen concentration was 40 ρM.

FIG. 51B presents data on CT2A malignant glioma cells, for a range of X-PACT parameters including variable x-ray dose (0, 0.67 and 1 Gy), phosphor concentration (650 or 100 µg) and psoralen concentration (8-MOP) at 10, 20 and 40 µM respectively.

In-Vitro X-PACT: Psoralen and Phosphor Concentration

FIG. 52A presents a multi-variable linear regression analysis on 36 independent measurements (wells) of Annexin V (+) as a function of two variables: psoralen concentration, and phosphor concentration. All samples received an x-ray dose of 1 Gy at 80 kVp. Psoralen and phosphor concentrations ranged from 10 µM to 50 µM and from 25 µg to 200 µg respectively. The fitting equation is given at the top of the Table and in Equation 1. The overall fit was statistically significant as were each of the fit coefficients. All of the 36 X-PACT wells were irradiated with 1 Gy of x-ray radiation at 80 kVp. The fit had the following form given in Equation 1 (where P=phosphor, and Conc=concentration):

$$\text{Annexin } V(+) = A + B^*[\text{8-MOP Conc}] + C^*[P\text{ Conc}] + D^* [\text{8-MOP Conc.}]^*[P\text{ Conc.}] \quad \text{Eq 1}$$

Figure 52B:
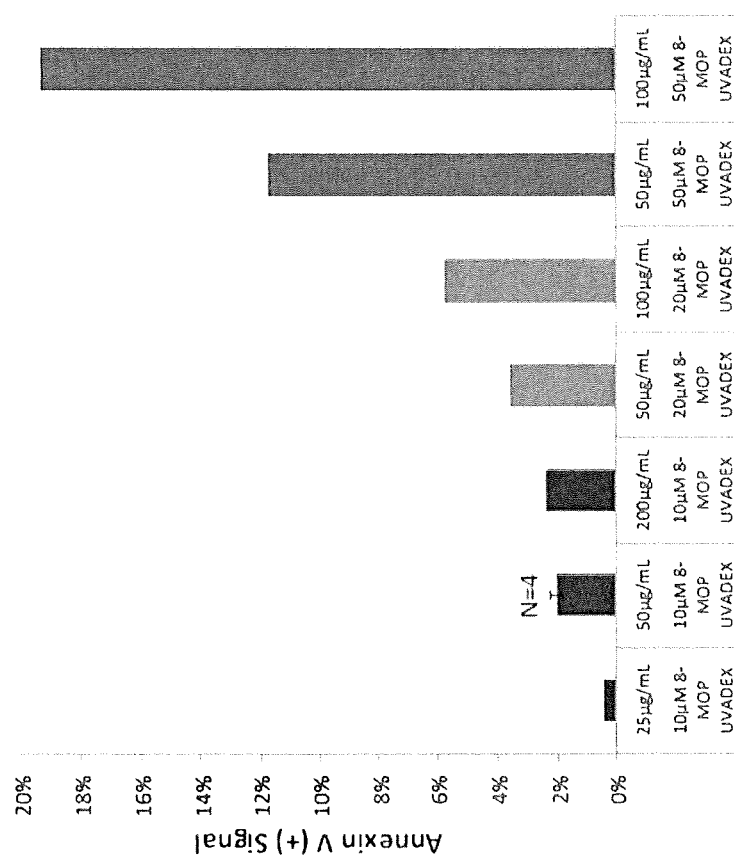
FIG. 52B is a schematic depicting a subset of data demonstrating the magnitudes and effects of increasing concentrations of psoralen and phosphor on the Annexin V (+) signal.

FIG. 52B shows a subset of data, collected on one day, demonstrating the magnitudes and effects of increasing concentrations of psoralen and phosphor on Annexin V (+) signal. More specifically, FIG. 52B is a subset of the data in FIG. 51A that was collected on a single day, indicating magnitude and trends. UVADEX (100 µM 8-MOP) was diluted to 10, 20, and 50 µM, or 1:10, 1:5, and 1:2 UVADEX. Four repeats (N=4) were performed for the condition with 50 µg/mL of phosphor and 10 µM of 8-MOP diluted from UVADEX.

In-Vitro X-PACT: X-Ray Energy and Total Dose without Energy Augmentation

Figure 53:
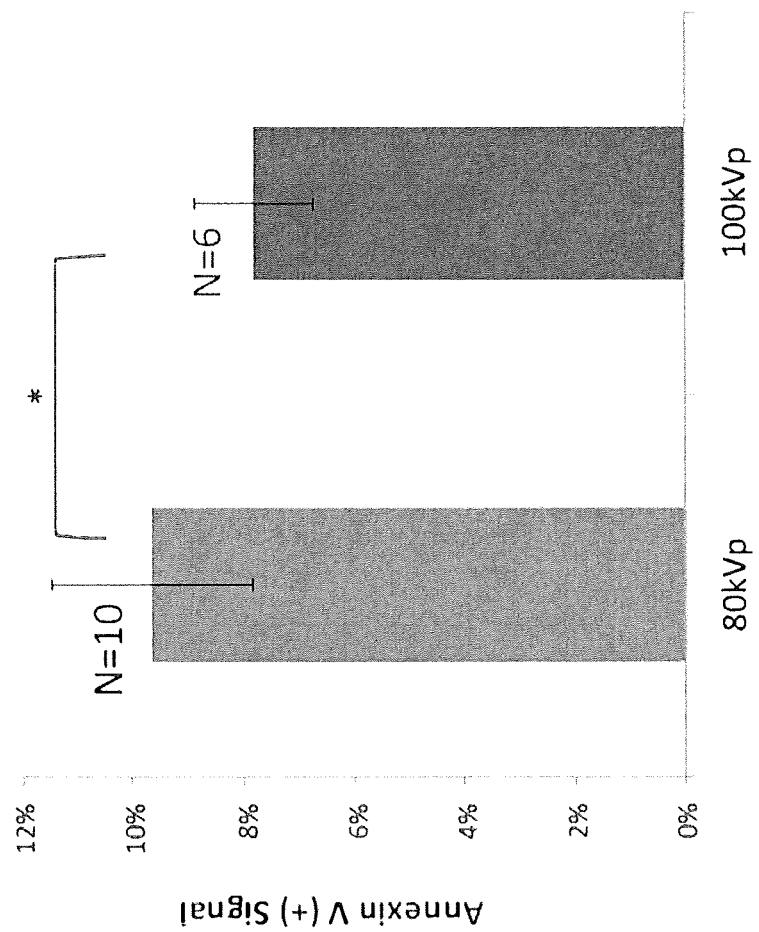
FIG. 53 is a schematic depicting the results of an X-PACT application to 4T1-her2 observed at both 80 and 100 kV.

FIG. 53 compares X-PACT at two different x-ray energies (80 and 100 kVp). An X-PACT effect in 4T1-her2 was observed at both 80 and 100 kV, with the 80 kVp does appearing to be slightly more effective than 100 kVp (p=0.011, *). This data acquired from X-PACT treatment of 4T1-HER2 cells with constant phosphor concentration of 50 µg/mL and UVADEX diluted to 8-MOP concentration of 10 µM (1:10 dilution). N is the number of independent measurements. These experiments involved 4T1-HER2 cells treated with 10 µM 8-MOP (or equivalent UVADEX), and 50 µg/mL phosphors.

In-Vivo X-Pact Experiments without Energy Augmentation

Figure 54:
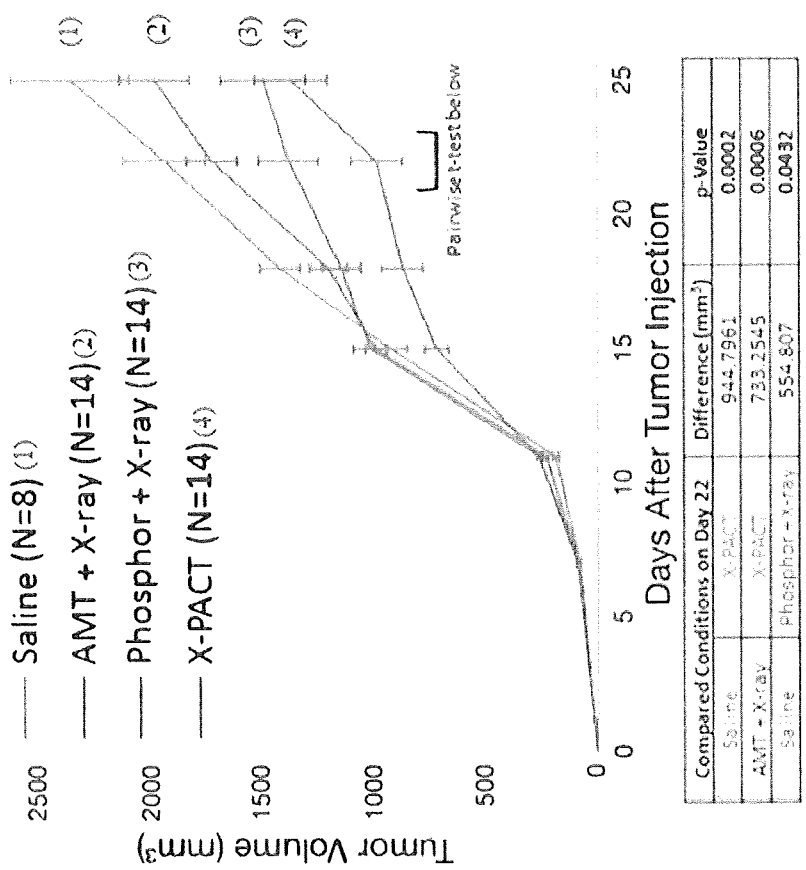
FIG. 54 is a schematic depicting the results of an X-PACT application to BALBC mice with syngeneic 4T1-HER2 tumors.

The results from the in-vivo irradiation of syngeneic 4T1-HER2 tumors are shown in FIG. 54. In this evaluation, X-PACT treatment was applied to BALBC mice with syngeneic 4T1-HER2 tumors. In the separate psoralen and phosphor control arms (blue and red respectively), 5 µM psoralen (AMT) and 100 µg of phosphor where applied. A consistent x-ray irradiation technique was used for all arms (except saline control) which was 2 Gy delivered at 75 kVp by 30 mA in 3 minutes.

In the 4T1 in-vitro cell viability analysis (FIG. 48), a very substantial reduction in viable cells (~48%, p<0.0001) was observed in the full X-PACT treatment condition, where all components (phosphor, psoralen, and x-ray) were present. Cell viability was much higher (70-85%) in the control conditions (left and middle bars in FIG. 48). Interestingly, the effect of adding radiation to the control conditions shows no or only a small decrease in viability. Cells exposed to UVADEX alone (left bars in FIG. 48) show no significant effect of adding radiation (p=0.97). Cells exposed to phosphors alone (middle bars in FIG. 48) show a slight reduction in cell viability (~8%, p=0.034) when radiation is added. The increased toxicity associated with the presence of both phosphors and x-rays could be attributed to DNA damage arising by UV light from x-ray induced phosphorescence from the phosphors. Substantial cytotoxicity (~80%) was only observed in the full X-PACT arm demonstrating the synergistic therapeutic effect of the combination of phosphor, UVADEX and radiation.

In the 4T1 in-vitro apoptotic analysis (FIG. 49), cells exposed to UVADEX alone (left bars) exhibit negligible apoptotic activity either with or without x-ray. For cells exposed to phosphor alone (middle bars), a small increase in Annexin V signal is observed (~1%, p=0.098) again suggesting a slight toxicity of the phosphors. However, it was only when both phosphor and UVADEX are combined (right bars) that a statistically significant increase in Annexin V signal was observed (~8%, p<0.0001), indicating an increase in apoptosis. The cytotoxicity typical of X-PACT is further illustrated in the methyl blue staining in FIGS. 50A and 50B. In both the X-PACT 2 and X-PACT 3 conditions, a relatively small effect was observed for the individual components of UVADEX and phosphor. The methyl blue staining results were consistent with the flow cytometry data, in that all X-PACT components are required for high cytotoxicity. Less cytotoxicity is manifest in the first X-PACT condition because of decreased phosphor concentration.

When X-PACT and components were evaluated on 3 different cell lines (FIG. 51A), an ANOVA analyses reveals no statistically significant differences in the sensitivity of these lines either to individual components or to full X-PACT treatment (p>0.05). In CT2A malignant glioma cells, X-PACT cell cytotoxicity was observed (FIG. 51B) to increase with the magnitude of X-ray dose (0, 0.66 and 1 Gy respectively), concentration of 8-MOP psoralen (10, 20 and 40 µM respectively), and phosphor (50 and 100 µg/ml respectively). ANOVA analyses revealed that the effect of radiation on each condition was significant for all conditions except for the control (p=0.88). The effect of radiation dose was significant overall (p<0.001) and progressive (cell cytotoxicity increases with dose) for all conditions where >20

µM of 8-MOP and 50 µg/mL of phosphors were used. In one condition (10 µM 8-MOP+100 µg/ml phosphor) only weakly significant influence of radiation dose (0.01<p<0.05) was observed.

The most comprehensive in-vitro 4T1 analysis (FIG. 52A) revealed a statistically significant multi-variable linear regression ($R^2$=0.72). The synergy interaction coefficient D was statistically significant (p<0.001) and positive indicating an enhanced effect when phosphor and psoralen were present. The interaction coefficients for psoralen and phosphor alone were only weakly suggestive (p~0.1 and 0.05 respectively). The p values indicate likely significance, but gave no indication of magnitude of effect, which is shown in FIG. 52B. A general observation from this data, acquired with constant x-ray dose, is that the apoptotic fraction induced by X-PACT increases with either increasing phosphor or psoralen concentration.

Another in-vitro study investigated whether changing x-ray energy affected X-PACT efficacy (FIG. 53). Phosphor design considerations indicated that ~80 kV would be optimal, but a higher energy would have an advantage from treatment delivery perspective (greater penetration in tissue). For this reason, a 100 kVp beam energy was investigated. An increase in apoptotic signal (over the control) was observed for X-PACT treatments at both energies. The data suggests the possibility of a slightly greater effect at 80 kVp.

X-PACT therapy seeks to engage the anti-tumor properties of psoralens activated in-situ, in solid tumors, with the potential for engaging a long term response. The data presented in FIG. 54, show the first in-vivo application. The first X-PACT treatment was delivered to the syngeneic 4T1-HER2 tumors, on day 10 after implantation. Over the next two weeks a growth delay was observed in the X-PACT treatment arm. By day 25, there was a 42% reduction in tumor volume (p=0.0002). A slightly higher component effect was observed for both the psoralen and phosphor arms, than was expected from the on-vitro data in FIG. 48.

Accordingly, in one embodiment of the invention, depending on the type of tumor being treated, the day-25 tumor volume change can range from stable (no growth), to a reduction of at least 10%, at least 20%, at least 30%, at least 40%, to complete dissolution of the tumor, or any values in between.

System Implementation

Figure 55:
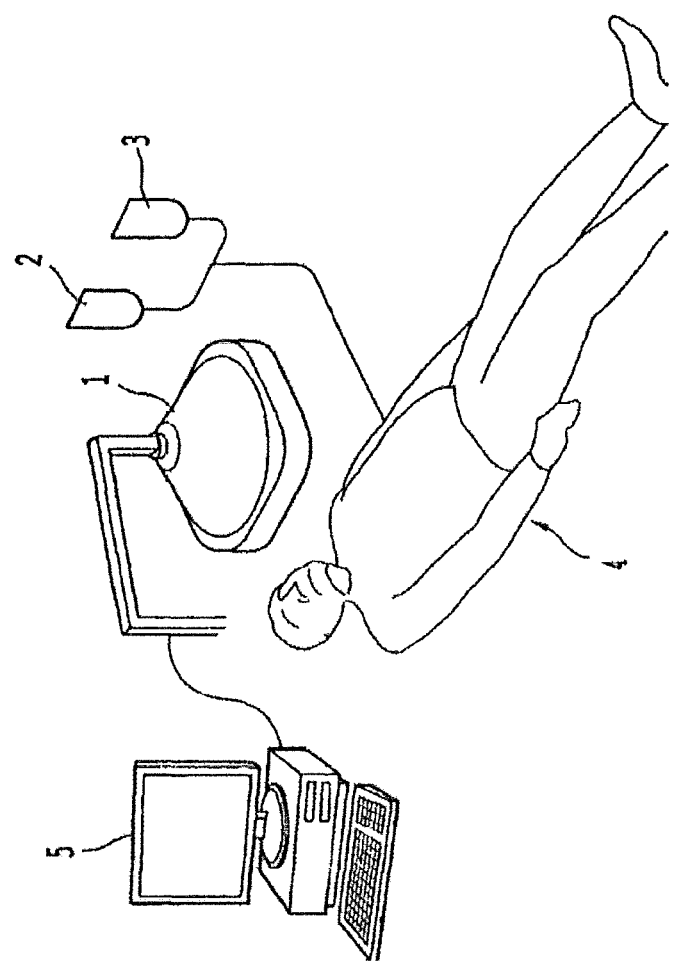
FIG. 55 is a schematic depicting an exemplary system according to one embodiment of the present invention.

The above-discussed medical treatments can be implemented by the system shown in FIG. 55.

Referring to FIG. 55, an exemplary system according to one embodiment of the present invention may have an initiation energy source 1 directed at the subject 4. An activatable pharmaceutical agent 2 and an energy converter 3 are administered to the subject 4. The initiation energy source may additionally be controlled by a computer system 5 that is capable of directing the delivery of the initiation energy.

In preferred embodiments, the initiation energy source may be a linear accelerator equipped with image guided computer-control capability to deliver a precisely calibrated beam of radiation to a pre-selected coordinate. One example of such linear accelerators is the SmartBeam™ IMRT (intensity modulated radiation therapy) system from Varian medical systems (Varian Medical Systems, Inc., Palo Alto, Calif.). In one embodiment of the invention, the initiation energy source comprises an x-ray source configured to generate x-rays from a peak applied cathode voltage at or below 300 kVp, at or below 200 kVp, at or below 120 kVp, at or below 105 kVp, at or below 80 kVp, at or below 70 kVp, at or below 60 kVp, at or below 50 kVp, at or below 40 kVp, at or below 30 kVp, at or below 20 kVp, at or below 10 kVp, or at or below 5 kVp.

In one embodiment of the invention, besides the YTaO4, noted above, other energy converter (with and without energy augmentation) can be used, including phosphor obtained from the following sources. "Ruby Red" obtained from Voltare, Masonlite & Kulka, Orange, CT, and referred to as "Neo Ruby"; "Flamingo Red" obtained from EGL Lighting, Berkeley Heights, NJ and referred to as "Flamingo"; "Green" obtained from EGL Lighting, Berkeley Heights, NJ and referred to as "Tropic Green"; "Orange" obtained from Voltare, Masonlite & Kulka, Orange, CT, and referred to as "Majestic Orange"; "Yellow" obtained from Voltare, Masonlite & Kulka, Orange, CT, and referred to as "Clear Bright Yellow." The "BP" phosphors are shown in detail below:

TABLE 3

| Code | Phosphor Material Color | Emission Spectrum Peak Emission (nm) | X-Ray Absorption Emiss Eff (%) | Eff (Z) | K-edge (keV) | Density g/cc Specific Gravity | Xtal Crystal Structure | Hygroscopic |
|---|---|---|---|---|---|---|---|---|
| BP1 | CaWO4: Pb | 425 | | | | | | N |
| BP2 | Y2SiO5: Ce | 410 | | | | | | N |
| BP3 | YTaO4 | 337 | 10 | 59.8 | 67.42 | 7.5 | Monolithic | N |
| BP3-C | YTaO4 | 337 | 10 | 59.8 | 67.42 | 7.5 | Monolithic | N |
| BP4 | BASF-1 | 460 | | | | | | |
| BP5 | BASF-2 | 490 | | | | | | |
| BP6 | YTaO4: Nb (*) | 410 | 11 | 59.8 | 67.42 | 7.5 | Monolithic | N |
| BP6-C | YTaO4: Nb (*) | | | | | | | |
| BP7-C | LaOBr: Tm3 + (coated) | 360, 460 | 14 | 49.3 | 38.92 | 6.3 | Tetragonal | N |
| BP8-C | LaF3: Ce | 280 | | | | | | |
| BP9 | Y2O3 | 365 | | | | | | |
| BP-10 | BaSO4-: Eu2 + (coated) | 390 | 6 | 45.5 | 37.38 | 4.5 | Rhombic | N |
| BP10-C | BaSO4-: Eu2 + (coated) | 390 | 6 | 45.5 | 37.38 | 4.5 | Rhombic | N |
| BP11 | LaOCl: Tm | | | | | | | |
| BP12 | Y2O2S: Tm | | | | | | | |

TABLE 3-continued

| Code | Phosphor Material Color | Emission Spectrum Peak Emission (nm) | Emiss Eff (%) | Eff (Z) | X-Ray Absorption K-edge (keV) | Density g/cc Specific Gravity | Xtal Crystal Structure | Hygroscopic |
|---|---|---|---|---|---|---|---|---|
| BP13 | BaSi2O5: Pb2 + | 350 | | | | | | N |
| | SrB6O10: Pb | 360 | | | | | | N |
| | CsI: Na (Coated) | 338 | | | | | | Y |
| | $Gd_2O_2S$: Tm | Blue to Green | | | | | | Y |

The "BP" phosphors are available from PhosphorTech Corporation of Kennesaw, Ga., from BASF Corporation, or from Phosphor Technology Ltd, Norton Park, Norton Road Stevenage, Herts, SGI 2BB, England. These phosphors can be used with and without energy augmentation.

Other useful energy converters that can be used with and without energy augmentation include semiconductor materials including for example $TiO_2$, ZnO, and $Fe_2O_3$ which are biocompatible, and CdTe and CdSe which would preferably be encapsulated because of their expected toxicity. Other useful energy converters include ZnS, CaS, BaS, SrS and $Y_2O_3$ which are less toxic. Other suitable energy converters which would seem the most biocompatible are zinc sulfide, $ZnS:Mn^{2+}$, ferric oxide, titanium oxide, zinc oxide, zinc oxide containing small amounts of $Al_2O_3$ and AgI nanoclusters encapsulated in zeolite. For non-medical applications, where toxicity may not be as critical a concern, the following materials (as well as those listed elsewhere) are considered suitable: lanthanum and gadolinium oxyhalides activated with thulium; $Er^{3+}$ doped $BaTiO_3$ nanoparticles, $Yb^{3+}$ doped $CsMnCl_3$ and $RbMnCl_3$, $BaFBr:Eu^{2+}$ nanoparticles, cesium iodide, bismuth germanate, cadmium tungstate, and CsBr doped with divalent Eu. Table 4 below provides a list of various useful energy converters In various embodiments of the invention, the following luminescent polymers that can be used with and without energy augmentation as energy converters include: poly (phenylene ethynylene), poly(phenylene vinylene), poly(p-phenylene), poly(thiophene), poly(pyridyl vinylene), poly (pyrrole), poly(acetylene), poly(vinyl carbazole), poly (fluorenes), and the like, as well as copolymers and/or derivatives thereof.

As a non-limiting list, the following that can be used with and without energy augmentation are suitable energy converters: $Y_2O_3$; ZnS; ZnSe; MgS; CaS; Mn, Er ZnSe; Mn, Er MgS; Mn, Er CaS; Mn, Er ZnS; Mn,Yb ZnSe; Mn,Yb MgS; Mn, Yb CaS; Mn,Yb $ZnS:Tb^{3+}$, $Er^{3+}$; $ZnS:Tb^{3+}$; $Y_2O_3:Tb^{3+}$; $Y_2O_3:Tb^{3+}$, $Er^{3+}$; $ZnS:Mn^{2+}$; $ZnS:Mn,Er^{3+}$; $CaWO_4$, $YaTO_4$, $YaTO_4:Nb$, $BaSO_4:Eu$, $La_2O_2S:Tb$, $BaSi_2O_5:Pb$, NaI(Tl), CsI(Tl), CsI(Na), CsI(pure), CsF, KI(Tl), LiI(Eu), $BaF_2$, CaF, $CaF_2(Eu)$, ZnS(Ag), $CaWO_4$, $CdWO_4$, YAG(Ce) ($Y_3Al_5O_{12}(Ce)$), BGO bismuth germanate, GSO gadolinium oxyorthosilicate, LSO lutetium oxyorthosilicate, $LaCl_3(Ce)$, $LaBr_3(Ce)$, $LaPO_4$; Ce, Tb (doped), $Zn_2SiO_4:Mn$ with Mn doped between 0.05-10%, and $YTaO_4$.

TABLE 4

| Phosphor Color | Emission Spectrum Peak Emission (nm) | Emiss Eff (%) | Eff (Z) | X-Ray Absorption K-edge (keV) | Specific Gravity | Crystal Structure | Hygroscopic |
|---|---|---|---|---|---|---|---|
| Zn3(PO4)2: Tl+ | 310 | | | | | | N |
| BaF2 | 310 | | | | | | Slightly |
| CsI | 315 | | | | | | N |
| Ca3(PO4)2: Tl+ | 330 | | | | | | N |
| YTaO4 | 337 | | 59.8 | 67.42 | 7.5 | Monolithic | N |
| CsI: Na | 338 | | | | | | Y |
| BaSi2O5: Pb2+ | 350 | | | | | | N |
| Borosilicate | 350 | | | | | | N |
| LaCl3(Ce) | 350 | | | | | | Y |
| SrB4O7E: Eu2+ | 360 | | | | | | N |
| RbBr: Tl+ | 360 | | | | | | ? |
| (Ba, Sr, Mg) 3Si2O7: Pb2+ | 370 | | | | | | N |
| YAlO3: Ce3+ | 370 | | | | | | N |
| BC-422 | 370 | | | | | Organic | ? |
| BaFCl: Eu2+ | 380 | 13 | 49.3 | 37.38 | 4.7 | Tetragonal | N |
| BaSO4—: Eu2+ | 390 | 6 | 45.5 | 37.38 | 4.5 | Rhombic | N |
| BaFBr: Eu2+ | 390 | | | | | | ? |
| BC-420 | 391 | | | | | Organic | 3 |
| BC-414 | 392 | | | | | Organic | 3 |
| SrMgP2O7: Eu2+ | 394 | | | | | | N |
| BaBr2: Eu2+ | 400 | | | | | | N |
| (Sr, Ba) Al2Si2O8: Eu2+ | 400 | | | | | | N |
| YTaO4: Nb (5) | 410 | 11 | 59.8 | 67.42 | 7.5 | Monolithic | N |
| Y2SiO5: Ce3+ | 410 | | | | | | N |

TABLE 4-continued

| Phosphor | Emission Spectrum Peak Emission (nm) | Emiss Eff (%) | X-Ray Absorption Eff (Z) | K-edge (keV) | Specific Gravity | Crystal Structure | Hygroscopic |
|---|---|---|---|---|---|---|---|
| CaWO4 | 410 | 5 | 61.8 | 69.48 | 6.1 | Tetragonal | N |
| LaOBr: Tb3+ | 420 | 20 | 49.3 | 38.92 | 6.3 | Tetragonal | N |
| Y2O2S: Tb3+ | 420 | 18 | 34.9 | 17.04 | 4.9 | Hexgonal | N |
| Lu2SiO5: Ce3+ | 420 | | | | | | N |
| Lu1.8 Y0.2SiO5: Ce | 420 | | | | | | N |
| ZnS: Ag | 450 | 17 | 26.7 | 9.66 | 3.9 | Hexgonal | N |
| CdWO4 | 475 | | | | | | Slightly |
| Bi4Ge3O12(BGO) | 480 | | | | | | N |
| (Zn,Cd)S: Ag | 530 | 19 | 38.4 | 9.66/26.7 | 4.8 | Hexgonal | N |
| Gd2O2S: Tb3+ | 545 | 13 | 59.5 | 50.22 | 7.3 | Hexgonal | N |
| La2O2S: Tb3+ | 545 | 12.5 | 51.6 | 38.92 | 6.5 | Hexgonal | N |
| Y3Al5O12(Ce) | 550 | | | | | | N |
| LaOBr: Tm3+ | 360, 460 | 14 | 49.3 | 38.92 | 6.3 | Tetragonal | N |
| CaF2(Eu) | 435/300 | | | | | | N |

In one embodiment, phosphors used in the invention as energy converters can include phosphor particles, ionic doped phosphor particles, single crystal or poly-crystalline powders, single crystal or poly-crystalline monoliths, scintillator particles, a metallic shell encapsulating at least a fraction of a surface of the phosphors, a semiconductor shell encapsulating at least a fraction of a surface of the phosphors, and an insulator shell encapsulating at least a fraction of a surface of the phosphors; and phosphors of a distributed particle size.

Alternatively, a phosphorescent emitting source may be used as the energy converter. One advantage of a phosphorescent emitting source is that the phosphorescent emitting molecules or other source may be electroactivated or photoactivated prior to insertion into the tumor either by systemic administration or direct insertion into the region of the tumor. Phosphorescent materials may have longer relaxation times than fluorescent materials, because relaxation of a triplet state is subject to forbidden energy state transitions, storing the energy in the excited triplet state with only a limited number of quantum mechanical energy transfer processes available for returning to the lower energy state. Energy emission is delayed or prolonged from a fraction of a second to several hours. Otherwise, the energy emitted during phosphorescent relaxation is not otherwise different than fluorescence, and the range of wavelengths may be selected by choosing a particular phosphor.

In one embodiment, the phosphorescent emitting sources or energy converters of the invention can include persistent after-glow phosphor materials emitting light in the visible to near ultraviolet and ultraviolet range. In one embodiment, Eu-doped strontium aluminate is used as an energy converter in which deep UV light or x-ray or electron beans "charge" the photoluminescence such that these phosphors can be charged outside for example a patient and then injected into target or diseased site where UV photons would be emitted. In another embodiment, gadolinium strontium magnesium aluminate is used as an energy converter in which deep UV light or x-ray or electron beans "charge" the photoluminescence such that these phosphors can be charged outside for example a patient and then injected into target or diseased site where UV photons would be emitted. U.S. Pat. Appl. Publ. No. 20070221883 (the entire contents of which are incorporated herein by reference) describes specifically gadolinium-activated strontium magnesium aluminate having an excitation maximum at about 172 nm, and which emits in a narrow-band UV emission at about 310 nm. The '883 publication also describes other useful energy converters for this invention, making note of emission spectra between 300 nm and 320 nm for a $Sr(Al.Mg)_{12}O_{19}$:Gd phosphor and two 312 nm line emitting phosphors, $YMgB_5O_{10}$:Gd, Ce and $YMgB_5O_{10}$:Gd, Ce, Pr. WO2016200349 (the entire contents of which are incorporated herein by reference) describes long lasting yellowish-green emitting phosphorescent pigments in the strontium aluminate ($SrAl_2O_4$) system, which could serve as energy converters in the present invention. WO 2016200348 (the entire contents of which are incorporated herein by reference) describes long lasting bluish-green emitting phosphorescent pigments in the strontium aluminate ($Sr_4Al_{14}O_{25}$) system, which could serve as energy converters in the present invention. Xiong et al in "Recent advances in ultraviolet persistent phosphors," Optical Materials X 2 (2019) (the entire contents of which are incorporated herein by reference) describes a number of ultraviolet persistent phosphors that could as energy converters in the present invention. The table below provides a listing of such persistent phosphors:

| | | |
|---|---|---|
| SrO:$Pb^{2+}$ | 390 | >1 h |
| $CaAl_2O_4$:$Ce^{3+}$ $Tb^{3+}$ | 400 | >10 h |
| $CaAl_2O_4$:$Ce^{3+}$ $Tb^{3+}$ | 413 | >10 h |
| $Sr_2Al_2SiO_7$:$Ce^{3+}$ | 400 | several minutes |
| $SrZrO_3$ | 395 | <1000 s |
| $BaZrO_3$:$Mg^{2+}$ | 400 | >2400 s |
| $SrZrO_3$:$Pr^{3+}$ | 356 | |
| $CdSiO_3$:$Bi^{3+}$ | 360 | |
| $CdSiO_3$:$Bi^{3+}$ $Dy^{3+}$ | 360 | |
| $CdSiO_3$:$Bi^{3+}$ $Gd^{3+}$ | 344 | >6 h |
| $Sr_2MgGe_2O_7$:$Pb^{2+}$ | 370 | >12 h |
| $NaLuGeO_4$:$Bi^{3+}$ $Eu^{3+}$ | 400 | >63 h |
| $CaZnGe_2O_6$:$Bi^{3+}$ | 300-700 | >12 h |
| $Cs_2NaYF_6$:$Pr^{3+}$ | 250 | >2 h |

In one embodiment, the phosphor described by Xiong et al as $CaAl_2O_4$:$Ce^{3+}$ having an emission peak of 400 nm and a persistent time of more than 10 h could be used, where it would be charged by x-ray irradiation outside a patient and then injected at a diseased site to provide internally generated UV light.

In one embodiment, the persistent phosphors noted could be activated ex vivo and introduced along with psoralen (or other photoactivatable drug) into the patient by exchange of a bodily fluid or for example by supplying the persistent phosphors and the photoactivatable drug into a patient's blood stream.

In one embodiment, the persistent phosphors noted could be activated in vivo by injection of the phosphors into a diseased site and then exposure to x-rays.

In further embodiments, dose calculation and robotic manipulation devices may also be included in the system.

Figure 56:
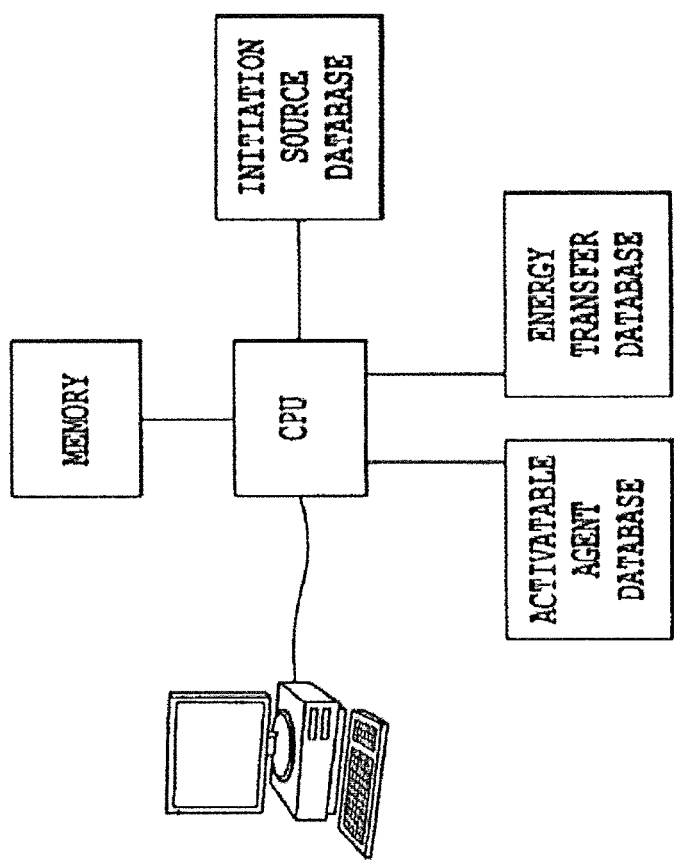
FIG. 56 is an exemplary computer-implemented system according to one embodiment of the present invention.

In yet another embodiment, there is also provided a computer implemented system for designing and selecting suitable combinations of initiation energy source (listed in the initiation energy source database), energy converter (listed in the energy transfer database), and activatable pharmaceutical agent (listed in the activatable agent database). FIG. 56 illustrates an exemplary computer implemented system according to this embodiment of the present invention.

Referring to FIG. 56, an exemplary computer-implemented system according to one embodiment of the present invention may have a central processing unit (CPU) connected to a memory unit, configured such that the CPU is capable of processing user inputs and selecting a combination of initiation source, activatable pharmaceutical agent, and energy transfer agent based on an energy spectrum comparison for use in a method of the present invention.

In one embodiment, a photoactivatable drug is selected from psoralens, pyrene cholesteryloleate, acridine, porphyrin, fluorescein, rhodamine, 16-diazorcortisone, ethidium, transition metal complexes of bleomycin, transition metal complexes of deglycobleomycin organoplatinum complexes, alloxazines, vitamin Ks, vitamin L, vitamin metabolites, vitamin precursors, naphthoquinones, naphthalenes, naphthols and derivatives thereof having planar molecular conformations, porphorinoporphyrins, dyes and phenothiazine derivatives, coumarins, quinolones, quinones, and anthroquinones.

Immune System Boosters

A patient's immune system is a complex network of cells, tissues, organs, and the substances that help the body fight infections and other diseases. White blood cells, or leukocytes, play the main role in immune responses. These cells carry out the many tasks required to protect the body against disease-causing microbes and abnormal cells. Some types of leukocytes patrol the circulatory system, seeking foreign invaders and diseased, damaged, or dead cells. These white blood cells provide a general—or nonspecific—level of immune protection. Other types of leukocytes, known as lymphocytes, provide targeted protection against specific threats, whether from a specific microbe or a diseased or abnormal cell. The most important groups of lymphocytes responsible for carrying out immune responses against such threats are B cells and T cells. B cells make antibodies, which are large secreted proteins that bind to, inactivate, and help destroy foreign invaders or abnormal cells. Cytotoxic T cells, which are also known as killer T cells, kill infected or abnormal cells by releasing toxic chemicals or by prompting the cells to self-destruct (in a process known as apoptosis).

Other types of lymphocytes and leukocytes play supporting roles to ensure that B cells and killer T cells do their jobs effectively. These supporting cells include helper T cells and dendritic cells, which help activate both B cells and killer T cells and enable them to respond to specific threats.

Antigens are substances that have the potential to cause the body to mount an immune response against them. Antigens help the immune system determine whether something is foreign, or "non-self." Normal cells in the body have antigens that identify them as "self." Self-antigens tell the immune system that normal cells are not a threat and should be ignored. In contrast, microbes are recognized by the immune system as a potential threat that should be destroyed because they carry foreign, or non-self, antigens.

Cancer cells can carry both self-antigens as well as what are referred to as cancer-associated antigens. Cancer-associated antigens mark cancer cells as abnormal or foreign and can cause killer T cells to mount an attack against them. Cancer-associated antigens may be: self-antigens that are made in much larger amounts by cancer cells than normal cells and, thus, are viewed as foreign by the immune system, self-antigens that are not normally made by the tissue in which the cancer developed (for example, antigens that are normally made only by embryonic tissue but are expressed in an adult cancer) and, thus, are viewed as foreign by the immune system, and/or newly formed antigens, or neoantigens, that result from gene mutations in cancer cells and have not been seen previously by the immune system.

In general, vaccines are medicines that boost the immune system's natural ability to protect the body against "foreign invaders," mainly infectious agents that may cause disease. When an infectious microbe invades the body, the immune system recognizes it as foreign, destroys it, and "remembers" it to prevent another infection should the microbe invade the body again in the future. Vaccines take advantage of this defensive memory response.

In one embodiment of the invention, there is provided a system for treating a human or animal body. This system includes a first pharmaceutically acceptable carrier, optionally and preferably including one or more phosphorescent or fluorescent agents with and without energy augmentation which are capable of emitting light (preferably ultraviolet or visible light) into the body, a photoactivatable drug for treating a first diseased site, a first device which infuses the first diseased site with the photoactivatable drug and the first pharmaceutically acceptable carrier, and a source for generating energy in situ in the human or animal body sufficient to activate the photoactivatable drug, which is optionally and preferably a first energy source, preferably an x-ray or high energy source, which irradiates the diseased site with an initiation energy (preferably at least one of x-rays, gamma rays, or electrons) to thereby initiate emission of the light (preferably ultraviolet or visible light) into the body from the preferred one or more phosphorescent or fluorescent agents, thus activating the photoactivatable drug. This part of this system provides the treatment to the first diseased site.

This system can include a supplemental treatment device which administers a therapeutic drug or radiation or both for treating a second diseased site or the first diseased site with and without energy augmentation. The supplemental treatment device can be at least one of 1) a second device which infuses a second diseased site with an immune system stimulant or chemotherapeutic drug or a targeted cancer growth suppressant, and 3) a second energy source (preferably an x-ray or high energy source) which irradiates a second diseased site, preferably with at least one of x-rays, gamma rays, or electrons. Alternatively, this system can use the initial energy source in a further irradiation of the first diseased site, preferably with x-rays, gamma rays, or electrons.

Accordingly, when a supplemental treatment of the human or animal body is prescribed, the second device infuses a second diseased site with an immune system stimulant. Alternatively or additionally, when a supplemental treatment of the human or animal body is prescribed, the second x-ray or high energy source irradiates a second diseased site with at least one of x-rays, gamma rays, or electrons.

The first and second energy (initiation energy) sources can be the same or different energy sources or the same or different x-ray or high energy electron sources. The first and second devices can be the same or different drug-infusion devices which infuse a diseased site with the photoactivatable drug or the immune system stimulant.

In one embodiment of the invention, one or more "booster" treatments with and without energy augmentation are used as an immune system stimulant. These one or more "booster" treatments can be performed after the initial treatment (considered a "priming treatment"), or when the initial treatment is performed as a series of treatments, the "booster" treatment(s) can be performed between sequential priming treatments, alternating with priming treatments, or even simultaneously with the priming treatments. A "booster treatment" in one embodiment could involve re-injecting the tumor with psoralen (or other photoactivatable drug) and radiating the tumor site again. A "booster treatment" in another embodiment could involve re-injecting the tumor with psoralen (or other photoactivatable drug) and an energy converter and radiating the tumor site again. A "booster treatment" in another embodiment could involve radiating the tumor site again, but at a radiation level considered to be at either a palliative or therapeutic level. The purpose of any of these "booster" treatments is to activate/stimulate/boost the immune response initially or originally generated within the patient during the initial treatments.

In one embodiment of the booster treatment as an immune system stimulant, the phosphor concentration is increased to 20 mg/mL, the amount of UVADEX is increased 2-4 times, and the treatment frequency is increased to five (5) treatments in five (5) consecutive days. Furthermore, the timing between the prime (initial treatment sessions such as the nine treatments described above) and the booster treatment is set to allow for an initial humoral or cellular immune response, followed by a period of homeostasis, most typically weeks or months after the initial priming treatment.

In another embodiment, particularly for more aggressive cancers, an intervening treatment between the prime and boost stages can be provided to stunt the growth of the tumor while the immune system develops a response. The intervening treatment can take the form of palliative radiation, or other treatments known to those skilled in the art. A "booster treatment" in a further embodiment can involve irradiating a different tumor site within the patient (such as a metastasis site), at a radiation level considered to be at either a palliative or therapeutic level or at a radiation induced cell kill level. Since the goal of the "booster treatments" is to activate/stimulate/boost the patient's immune system, any of the "booster treatments" can be performed after completion of all of the primer treatments, between primer treatments during a series of the primer treatments, or prior to the primer treatments (although this may seem odd to perform the primer treatment after the booster treatment, the booster treatment can activate/stimulate/boost the immune system, thus providing a boost or supplement to the primer treatment once performed).

While not limited to the following theory, the basic prime-boost strategy involves priming the immune system to a target antigen, or a plurality of antigens created by the drug and/or radiation induced cell kill and then selectively stimulating/boosting this immunity by re-exposing the antigen or plurality of antigens in the boost treatment. One aspect of this strategy is that greater levels of immunity are established by heterologous prime-boost than can be attained by a single vaccine administration or homologous boost strategies. For example, the initial priming events elicited by a first exposure to an antigen or a plurality of antigens appear to be imprinted on the immune system. This phenomenon is particularly strong in T cells and is exploited in prime-boost strategies to selectively increase the numbers of memory T cells specific for a shared antigen in the prime and boost vaccines. As described in the literature, these increased numbers of T cells 'push' the cellular immune response over certain thresholds that are required to fight specific pathogens or cells containing tumor specific antigens. Furthermore, the general avidity of the boosted T-cell response is enhanced, which presumably increases the efficacy of the treatment.

Here, in this invention and without limitation as to the details but rather for the purpose of explanation, the initial treatment protocol develops antibodies or cellular immune responses to the psoralen-modified or X-ray modified cancer cells. These "initial" responses can then be stimulated/boosted by the occurrence of a large number of newly created psoralen-modified or X-ray modified cancer cells. As such, the patient's immune system would mount a more robust response against the cancer than would be realized in a single treatment series.

In one embodiment of the invention, cancer cells can be removed from a diseased site in the patient, and then treated ex-vivo with psoralen and ultraviolet light to induce cell kill. The "killed" cancer cells are then as part of an initial treatment or a booster treatment injected into the disease region of the patient. In one embodiment of the invention, the removed cancer cells are cultured to provide a larger number of cells to be exposed to psoralen and ultraviolet light, and therefore to produce a larger number of "killed" cells to inject. The body in response to these "killed" cells (in a manner similar to how the psoralen-modified or X-ray modified cancer cells would be received) would trigger the patient's immune system to thereby activate/stimulate/boost the patient's immune system as an immune system stimulant.

In one embodiment of the invention, prior to the initial treatment or prior to booster treatments, the immune system of the subject could be further activated/stimulated/boosted by injection of a more conventional vaccine such as for example a tetanus vaccine. Prior work has shown the efficacy of a tetanus booster to bolster the immune system's attack on the tumor by helping cancer vaccines present in the subject migrate to the lymph nodes, activating an immune response. Here, in this invention, the autovaccines generated internally from the treatments described above could also benefit from this effect.

As noted above, a booster treatment is one way to activate/stimulate/boost the immune system.

Cancer vaccines belong to a class of substances known as biological response modifiers. Biological response modifiers work by stimulating or restoring the immune system's ability to fight infections and disease. Treatment (or therapeutic) vaccines treat an existing cancer by strengthening the body's natural immune response against the cancer as an immune system stimulant. More specifically, cancer treatment vaccines are used to treat cancers that have already developed. Cancer treatment vaccines are intended to delay or stop cancer cell growth; to cause tumor shrinkage; to prevent cancer from coming back; or to eliminate cancer cells that have not been killed by other forms of treatment.

Cancer treatment vaccines are designed to work by activating cytotoxic T cells and directing the cytotoxic T cells to recognize and act against specific types of cancer or by inducing the production of antibodies that bind to molecules on the surface of cancer cells. To do so, treatment vaccines introduce one or more antigens into the body, usually by injection, where they cause an immune response that results in T cell activation or antibody production. Antibodies recognize and bind to antigens on the surface of cancer cells, whereas T cells can also detect cancer antigens inside cancer cells. One cancer treatment vaccine which can be used with XPACT treatment with and without energy augmentation includes sipuleucel-T (Provenge®), approved for use in some men with metastatic prostate cancer. It is designed to stimulate an immune response to prostatic acid phosphatase (PAP), an antigen that is found on most prostate cancer cells.

One cancer treatment vaccine which can be used with XPACT treatment with and without energy augmentation includes talimogene laherparepvec (T-VEC, or Imlygic®) for the treatment of some patients with metastatic melanoma that cannot be surgically removed. In addition to infecting and lysing cancer cells when injected directly into melanoma tumors, T-VEC induces responses in non-injected lesions, suggesting that it triggers an antitumor immune response similar to those of other anticancer vaccines.

Other types of cancer treatment vaccines that can be used as the supplemental treatment include those made using molecules of DNA or RNA that contain the genetic instructions for cancer-associated antigens. The DNA or RNA can be injected alone into a patient as a "naked nucleic acid" vaccine, or packaged into a harmless virus. After the naked nucleic acid or virus is injected into the body, the DNA or RNA is taken up by cells, which begin to manufacture the tumor-associated antigens. In theory, the cells will make enough of the tumor-associated antigens to stimulate a strong immune response.

Accordingly, in one embodiment of the invention, cancer treatment vaccines are provided as the above-noted supplemental treatment providing an immune system stimulant. In this embodiment, a cancer vaccine would supplement the XPACT treatment with and without energy augmentation by delaying or stopping cancer cell growth or by causing tumor shrinkage while the XPACT autoimmune response develops. The cancer treatment vaccines could be injected at the same or a different site (different organ) from the XPACT treated area.

In one embodiment of the invention, hormone injections are used to promote white and red blood cell counts. In one embodiment of the invention, interleukin-2 (IL-2) injections are used to promote functions of the patient's immune system.

Other ways to activate/stimulate/boost the immune system include immunotherapy, also called biologic therapy, which is designed to boost the body's natural defenses to fight the cancer. Immunotherapy uses materials made either by the body or in a laboratory to improve, target, or restore immune system function. One particular focus in such immunotherapy approaches relates to immune checkpoints and their inhibition. Immune checkpoints are molecules in the immune system that either turn up a signal (co-stimulatory molecules) or turn down a signal (inhibitor molecules). Many cancers protect themselves from the immune system by inhibiting the T cell signal or other aspects of the immune system. Since around 2010, immune checkpoint inhibitors have been increasingly considered as new targets for cancer immunotherapies. For example, the PD-1 pathway may be critical in the immune system's ability to control cancer growth. PD-1, short for Programmed Death 1 (PD-1) receptor, has two ligands, PD-L1 and PD-L2. An advantage of targeting PD-1 is that it can restore immune function in the tumor microenvironment. Blocking this pathway with PD-L1 and/or PD-L2 antibodies has stopped or slowed the growth of lung cancer for some patients. In addition to PD-1, other immune checkpoint inhibitors include:

A2AR. The Adenosine A2A receptor

B7-H3, also called CD276

B7-H4, also called VTCN1

BTLA. This molecule, short for B and T Lymphocyte Attenuator and also called CD272, has HVEM (Herpesvirus Entry Mediator) as its ligand.

CTLA-4, short for Cytotoxic T-Lymphocyte-Associated protein 4 and also called CD152

IDO, short for Indoleamine 2,3-dioxygenase, is a tryptophan catabolic enzyme with immune-inhibitory properties.

TDO, short for tryptophan 2,3-dioxygenase.

KIR, short for Killer-cell Immunoglobulin-like Receptor, is a receptor for MHC Class I molecules on Natural Killer cells.

LAG3, short for Lymphocyte Activation Gene-3

TIM-3, short for T-cell Immunoglobulin domain and Mucin domain 3, expresses on activated human CD4+ T cells and regulates Th1 and Th17 cytokines.

VISTA (protein), Short for V-domain Ig suppressor of T cell activation

More recently, immunotherapy drugs are also being used to treat genetic cancers, including mismatch repair deficient cancers such as Lynch Syndrome, in which one or more of a set of mismatch repair genes are found to be defective, thus allowing the buildup of errors in DNA of those affected as cells divide. These mismatch repair deficiencies have been found to be the cause of cancer syndromes such as Lynch Syndrome, in which one or more of the MLH1, MSH2, MSH6, PMS2, or EPCAM genes are mutated to lose their ability to repair gene mismatches caused by cell division. Immunotherapy has shown to be effective in treating such genetic cancers, with Pembrolizumab (Keytruda) being recently approved for such use. Another immunotherapy drug is Nivolumab (Opdivo).

In general, cancer immunotherapy stimulates a patient's immune system to destroy tumors. A variety of strategies are possible. In one approach, G-CSF lymphocytes are extracted from the blood of a patient and expanded in vitro against a tumor antigen before reinjecting the cells with appropriate stimulatory cytokines. The cells then destroy the tumor cells that express the antigen.

In an embodiment of the present invention, the present treatment method with and without energy augmentation can be combined with administration of conventional immunotherapy drugs, such as Pembrolizumab (Keytruda) or Nivolumab (Opdivo), as a way to stimulate the immune system of the patient through two pathways, the autovaccine effect of the present treatment, and the immune stimulation provided by the immunotherapy drug.

In another related approach, substances known as adjuvants are often added to vaccines or separately injected to induce potent anticancer immune responses. Adjuvants used for cancer vaccines come from many different sources. Bacillus Calmette-Gudrin (BCG) immunotherapy which has been used for early stage (non-invasive) bladder cancer. BCG immunotherapy instills attenuated live bacteria into the bladder and is effective in preventing recurrence in up to two thirds of cases. More particularly, a live attenuated strain of *Mycobacterium bovis*, has been approved by the US Food and Drug Administration for this approach.

Additionally, substances produced by bacteria, such as Detox B (an oil droplet emulsion of monophosphoryl lipid A and mycobacterial cell wall skeleton), are also frequently used as adjuvants. Biological products derived from nonmicrobial organisms can also be used as adjuvants. One example is keyhole limpet hemocyanin (KLH), which is a large protein produced by a marine mollusk. Attaching antigens to KLH has been shown to increase their ability to stimulate immune responses. Even some nonbiological substances, such as an emulsified oil known as montanide ISA-51, can be used as adjuvants.

Natural or synthetic cytokines can also be used as adjuvants. Cytokines are substances that are naturally produced by white blood cells to regulate and fine-tune immune responses. Some cytokines increase the activity of B cells and killer T cells, whereas other cytokines suppress the activities of these cells. Cytokines frequently used in cancer treatment vaccines or given together with them include interleukin 2 (IL2, also known as aldesleukin), interferon alpha, and granulocyte-macrophage colony-stimulating factor (GM-CSF, also known as sargramostim).

Accordingly, in one embodiment of the invention, the above-noted adjuvants can be used as the supplemental treatment noted above used with the XPACT treatment as an immune system stimulant.

In another approach, topical immunotherapy utilizes an immune enhancement cream (imiquimod) which produces interferon, causing the recipient's killer T cells to destroy warts, actinic keratoses, basal cell cancer, vaginal intraepithelial neoplasia, squamous cell cancer, cutaneous lymphoma, and superficial malignant melanoma.

In another approach, injection immunotherapy ("intralesional" or "intratumoral") uses mumps, *candida*, the HPV vaccine or trichophytin antigen injections to treat warts (HPV induced tumors).

In another approach, adoptive cell transfer (ACT) can be used. In ACT, T cells are transferred into a patient. The transferred cells may have originated from the patient or from another individual. In cancer immunotherapy, T cells are extracted from the patient, genetically modified and cultured in vitro and returned to the same patient. As an example, T cells, referred to as tumor-infiltrating lymphocytes (TIL), are multiplied using high concentrations of Interleukin-2, anti-CD3 and allo-reactive feeder cells. These T cells are then transferred back into the patient along with administration of Interleukin-2 (IL-2) to further boost their anti-cancer activity. Before reinfusion, lymphodepletion of the recipient is used to eliminate regulatory T cells as well as unmodified, endogenous lymphocytes that compete with the transferred cells for homeostatic cytokines. Lymphodepletion can be achieved by total body irradiation. Transferred cells multiplied in vivo and persisted in peripheral blood in many people, sometimes representing levels of 75% of all CD8+ T cells at 6-12 months after infusion.

In another approach, dendritic cell-based pump-priming can be used. Dendritic cells can be stimulated to activate a cytotoxic response towards an antigen. Dendritic cells, a type of antigen presenting cell, are harvested from the patient. These cells are then either pulsed with an antigen or tumor lysate or transfected with a viral vector, causing them to display the antigen. Upon transfusion into the person, these activated cells present the antigen to the effector lymphocytes (CD4+ helper T cells, cytotoxic CD8+ T cells and B cells). This initiates a cytotoxic response against tumor cells expressing the antigen (against which the adaptive response has now been primed). The cancer vaccine Sipuleucel-T is one example of this approach.

In another approach, an autologous immune enhancement therapy uses a person's own peripheral blood-derived natural killer cells. In this approach, cytotoxic T lymphocytes and other relevant immune cells are expanded in vitro and then reinfused.

In another approach, genetically engineered T cells are created by harvesting T cells and then infecting the T cells with a retrovirus that contains a copy of a T cell receptor (TCR) gene that is specialized to recognize tumor antigens. The virus integrates the receptor into the T cells' genome. The cells are expanded non-specifically and/or stimulated. The cells are then reinfused and produce an immune response against the tumor cells. The technique has been tested on refractory stage IV metastatic melanomas and advanced skin cancer.

Any or all of these treatments above can be used with the XPACT treatment with and without energy augmentation as an immune system stimulant.

Supplemental Treatment for the Same or a Different Tumor or Diseased Site

In one embodiment of the invention, the supplemental treatment can include any number of conventional and developing cancer treatments such as for example radiation therapy, chemotherapy, targeted therapy to kill or block cancer cell growth, for example those noted above and others.

In one embodiment of the invention, the supplemental treatment provided includes radiation therapy, which is the use of high energy x-rays or other particles to destroy cancer cells. The most common type of radiation treatment is called external-beam radiation therapy, which is radiation given from a machine outside the body. Radiation destroys cancer cells directly in the path of the radiation beam. It also damages the healthy cells in its path; for this reason, it preferably not used to treat large areas of the body. However, in one embodiment of the invention, in conjunction with the XPACT treatment, a widespread radiation exposure could be used. With radiation therapy, a radiation therapy regimen (schedule) usually consists of a specific number of treatments given over a set period of time. The treatment can vary from just a few days of treatment to several weeks. In one embodiment of the invention, the status of the treatment site is monitored for an indication that the XPACT treatment of the patient has started to develop its autoimmune response to the cancer in the patient's body. Once tumor growth has stopped or is in regression, the radiation therapy can be stopped.

With radiation therapy, CT scans (imaging scans) can be used to plan out exactly where to direct the radiation to lower the risk of damaging healthy parts of the body. The CT scans can be part of the XPACT treatment when a supplemental treatment is directed to the same diseased site and the XPACT treatment. With radiation therapy, intensity modulated radiation therapy (IMRT) or stereotactic body radiation therapy (SBRT) can be used for the supplemental treatment of the same diseased site XPACT treated or a different diseased site.

In one embodiment of the invention, the supplemental treatment provided includes chemotherapy which is the use of drugs to destroy cancer cells, usually by stopping the cancer cells' ability to grow and divide. Chemotherapy has been shown to improve both the length and quality of life for people with cancer. Systemic chemotherapy gets into the bloodstream to reach cancer cells throughout the body. Common ways to give chemotherapy include an intravenous (IV) tube placed into a vein using a needle or in a pill or capsule that is swallowed (orally). Most chemotherapy used for lung cancer is given by IV injection. As known, chemotherapy may also damage healthy cells in the body, including blood cells, skin cells, and nerve cells. Accordingly, chemotherapy in the present invention as a supplemental treatment is used with restrictive amounts of the drug in an effort to slow the cancer progression until the XPACT autoimmune response develops.

Drugs of possible use in the present invention for chemotherapy include carboplatin (Paraplatin) or cisplatin (Platinol), docetaxel (Docefrez, Taxotere), Gemcitabine (Gemzar), Nab-paclitaxel (Abraxane), Paclitaxel (Taxol), Pemetrexed (Alimta), and Vinorelbine (Navelbine).

In one embodiment of the invention, the supplemental treatment provided the above noted chemotherapy drugs to supplement the XPACT treatment.

In one embodiment of the invention, the supplemental treatment provided includes targeted therapy which is a treatment that targets the cancer's specific genes, proteins, or the tissue environment that contributes to cancer growth and survival. This type of treatment blocks the growth and spread of cancer cells while limiting damage to healthy cells.

Not all tumors have the same targets. Of the targeted therapies, anti-angiogenesis therapy is focused on stopping angiogenesis, which is the process of making new blood vessels. Because a tumor needs the nutrients delivered by blood vessels to grow and spread, the goal of anti-angiogenesis therapies is to "starve" the tumor. The following and other anti-angiogenic drugs may be used at the XPACT treated site or a different site: Bevacizumab (Avastin), Ramucirumab (Cyramza), Epidermal growth factor receptor (EGFR) inhibitors, Erlotinib (Tarceva), Gefitinib (Iressa), Afatinib (Gilotrif), Osimertinib (Tagrisso), Necitumumab (Portrazza), anaplastic lymphoma kinase (ALK) inhibitors, Crizotinib (Xalkori), Ceritinib (Zykadia), and Alectinib (Alecensa).

In another embodiment, Avastin can be administered to reduce swelling in the treated tumors. Avastin is a monoclonal antibody, a synthetic version of antibodies that occur in our bodies and which fight foreign substances. Avastin typically binds to a molecule called vascular endothelial growth factor or VEGF. VEGF is a key player in the growth of new blood vessels. Avastin turns VEGF off. Blocking VEGF may prevent the growth of new blood vessels, including normal blood vessels and blood vessels that feed tumors. Avastin is FDA approved for 6 cancer types: metastatic colorectal cancer (MCRC), metastatic non-squamous non-small cell lung cancer (NSCLC), metastatic renal cell carcinoma (mRCC), recurrent glioblastoma (rGBM), persistent, recurrent, or metastatic cervical cancer (CC), and platinum-resistant recurrent epithelial ovarian, fallopian tube or primary peritoneal cancer (prOC).

Any or all of these treatments noted above can be used with the XPACT treatment as a treatment to kill or block cancer cell growth.

In a further embodiment, methods in accordance with the present invention may further include adding an additive to alleviate treatment side-effects. Exemplary additives may include, but are not limited to, antioxidants, adjuvant, or combinations thereof. In one exemplary embodiment, psoralen is used as the activatable pharmaceutical agent, UV-A is used as the activating energy, and antioxidants are added to reduce the unwanted side-effects of irradiation.

The activatable pharmaceutical agent and derivatives thereof as well as the energy converter, can be incorporated into pharmaceutical compositions suitable for administration. Such compositions typically comprise the activatable pharmaceutical agent and a pharmaceutically acceptable carrier. The pharmaceutical composition also comprises at least one additive having a complementary therapeutic or diagnostic effect, wherein the additive is one selected from an antioxidant, an adjuvant, or a combination thereof.

As used herein, "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions. Modifications can be made to the compound of the present invention to affect solubility or clearance of the compound. These molecules may also be synthesized with D-amino acids to increase resistance to enzymatic degradation. If necessary, the activatable pharmaceutical agent can be co-administered with a solubilizing agent, such as cyclodextran.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, rectal administration, and direct injection into the affected area, such as direct injection into a tumor. Solutions or suspensions used for parenteral, intradermal, or subcutaneous application can include the following components: a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. The oral compositions can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The pharmaceutical compositions can be included in a container, pack, or dispenser together with instructions for administration.

It will also be understood that the order of administering the different agents is not particularly limited. Thus in some embodiments the activatable pharmaceutical agent may be administered before the energy converter with and without energy augmentation, while in other embodiments the energy converter may be administered prior to the activatable pharmaceutical agent. It will be appreciated that different combinations of ordering may be advantageously employed depending on factors such as the absorption rate of the agents, the localization and molecular trafficking properties of the agents, and other pharmacokinetics or pharmacodynamics considerations.

In one embodiment of the invention, the reagents and chemicals useful for methods and systems of the present invention may be packaged in kits to facilitate application of the present invention. In one exemplary embodiment, a kit including a psoralen, and fractionating containers for easy fractionation and isolation of autovaccines is contemplated. A further embodiment of kit would comprise at least one activatable pharmaceutical agent capable of causing a predetermined cellular change, at least one energy converter with and without energy augmentation capable of activating the at least one activatable agent when energized, and containers suitable for storing the agents in stable form, and preferably further comprising instructions for administering the at least one activatable pharmaceutical agent and at least one energy converter to a subject, and for applying an initiation energy from an initiation energy source to activate the activatable pharmaceutical agent. The instructions could be in any desired form, including but not limited to, printed on a kit insert, printed on one or more containers, as well as electronically stored instructions provided on an electronic storage medium, such as a computer readable storage medium. Also optionally included is a software package on a computer readable storage medium that permits the user to integrate the information and calculate a control dose, to calculate and control intensity of the irradiation source.

Accordingly, the energy augmentation structures of the present invention can be used in conjunction with the energy converters described herein in a wide variety of applications, including but not limited to, medical treatments using energy generated in situ within a subject being treated (whether using an energy converter or not), solar cells, adhesives and other resins, sterilization treatment for various materials (such as wastewater, beverages, etc). The use of energy converters in such applications has been described in the following: US Published Application No. 2008/0248001; US Published Application No. 2009/0104212; US Published Application No. 2009/0294692; US Published Application No. 2010/0003316; US Published Application No. 2010/0016783; US Published Application No. 2010/0261263; US Published Application No. 2010/0266621; US Published Application No. 2011/0021970; US Published Application No. 2011/0117202; US Published Application No. 2011/0126889; US Published Application No. 2011/0129537; US Published Application No. 2011/0263920; US Published Application No. 2012/0064134; US Published Application No. 2012/0089180; US Published Application No. 2013/0102054; US Published Application No. 2013/0129757; US Published Application No. 2013/0131429; US Published Application No. 2013/0156905; US Published Application No. 2013/0171060; US Published Application No. 2013/0240758; US Published Application No. 2014/0134307; US Published Application No. 2014/0163303; US Published Application No. 2014/0166202; US Published Application No. 2014/0222117; US Published Application No. 2014/0242035; US Published Application No. 2014/0243934; US Published Application No. 2014/0272030; US Published Application No. 2014/0323946; US Published Application No. 2014/0341845; US Published Application No. 2014/0343479; US Published Application No. 2015/0182934; US Published Application No. 2015/0202294; US Published Application No. 2015/0246521; US Published Application No. 2015/0251016; US Published Application No. 2015/0265706; US Published Application No. 2015/0283392; US Published Application No. 2015/0290614; US Published Application No. 2016/0005503; US Published Application No. 2016/0067524; US Published Application No. 2016/0159065; US Published Application No. 2016/0243235; US Published Application No. 2016/0263393; US Published Application No. 2016/0325111; US Published Application No. 2016/0331731; US Published Application No. 2016/0354467; US Published Application No. 2016/0362534; US Published Application No. 2017/0027197; US Published Application No. 2017/0043178; US Published Application No. 2017/0050046; US Published Application No. 2017/0096585; US Published Application No. 2017/0113061; US Published Application No. 2017/0121472; US Published Application No. 2017/0154866; US Published Application No. 2017/0157418; US Published Application No. 2017/0162537; US Published Application No. 2017/0173350; US Published Application No. 2017/0186720; US Published Application No. 2017/0190166; US Published Application No. 2017/0196977; US Published Application No. 2017/0239489; US Published Application No. 2017/0239637; US Published Application No. 2017/0240717; US Published Application No. 2017/0258908; US Published Application No. 2017/0319868; US Published Application No. 2017/0319869; US Published Application No. 2018/0036408; US Published Application No. 2018/0154171; US Published Application No. 2018/0154178; US Published Application No. 2018/0169433; US Published Application No. 2018/0170028; US Published Application No. 2018/0269174; US Published Application No. 2018/0271121; US Published Application No. 2018/0304225; US Published Application No. 2018/0311355; US Published Application No. 2018/0317307; US Published Application No. 2018/0344850; US Published Application No. 2018/0358327; US Published Application No. 2019/0016869; US Published Application No. 2019/0022221; US Published Application No. 2019/0100680; US Published Application No. 2019/0134419; US Published Application No. 2019/0134595; US Published Application No. 2019/0134596; US Published Application No. 2019/0157234; US Published Application No. 2019/0168015; US Published Application No. 2019/0184190; US Published Application No. 2019/308030; US Published Application No. 2019/0336605; US Published Application No. 2019/0336785; US Published Application No. 2019/0336786; US Published Application No. 2019/0341364; U.S. application Ser. No. 16/074,707, filed Aug. 1, 2018; U.S. application Ser. No. 16/516,463, filed Jul. 19, 2019; U.S. application Ser. No. 16/554,831, filed Aug. 29, 2019 U.S. application Ser. No. 16/599,732, filed Oct. 11, 2019; U.S. application Ser. No. 16/674,435, filed Nov. 5, 2019; and U.S. application Ser. No. 16/728,803, filed Dec. 27, 2019; the contents of each of which are hereby incorporated by reference in their entireties. The energy augmentation structures and/or energy converters described herein have uses with the subject matter in the above noted published and unpublished US patent applications.

The following are exemplary embodiments of the present invention:

Embodiment 1. An energy emitter comprising:
at least one energy augmentation structure; and
an energy converter capable of receiving energy from an energy source, converting the energy and emitting therefrom an emitted light of a higher or lower energy than the received energy, and the energy converter being disposed in a vicinity of the at least one energy augmentation structure such that the emitted light is emitted with an intensity larger than if the energy converter were remote from the at least one energy augmentation structure, or if the energy augmentation structure were not present.

Embodiment 2. The emitter of Embodiment 1, wherein the at least one energy augmentation structure comprises a structure in which a locally intensified electric field exists in one part of the structure when the structure receives electromagnetic energy.

Embodiment 3. The emitter of Embodiment 2, wherein the at least one energy augmentation structure comprises at least one resonator dimensioned to be resonant with the applied electromagnetic energy.

Embodiment 4. The emitter of Embodiment 3, wherein the resonator comprises a folded resonator.

Embodiment 5. The emitter of Embodiment 4, wherein the folded resonator comprises electrical conductors configured as a fractal pattern.

Embodiment 6. The emitter of Embodiment 4, wherein the folded resonator comprises a % wavelength resonator having opposing ends folded inwards from a center of the folded resonator with a gap in between the opposing ends.

Embodiment 7. The emitter of Embodiment 6, wherein the locally intensified electric field exists in a vicinity of the opposing ends.

Embodiment 8. The emitter of Embodiment 4, wherein the folded resonator comprises a ¾ wavelength resonator having opposing ends folded outwards from a center of the folded resonator with a gap in between the opposing ends.

Embodiment 9. The emitter of Embodiment 8, wherein the locally intensified electric field exists in a vicinity of the opposing ends.

Embodiment 10. The emitter of Embodiment 3, wherein the resonator comprises a fractal pattern.

Embodiment 11. The emitter of Embodiment 10, wherein fractal pattern comprises a three-dimensional fractal pattern.

Embodiment 12. The emitter of Embodiment 3, wherein the at least one resonator comprises a plurality of resonators.

Embodiment 13. The emitter of Embodiment 12, wherein the resonators are disposed on a sheet.

Embodiment 14. The emitter of Embodiment 13, wherein the sheet comprises a sheet for disposal within a medium to be treated.

Embodiment 15. The emitter of Embodiment 13, wherein the sheet comprises a flexible sheet for disposal within a medium to be treated.

Embodiment 16. The emitter of Embodiment 13, wherein the sheet comprises a rigid sheet for disposal within a medium to be treated.

Embodiment 17. The emitter of Embodiment 13, wherein the plurality of resonators comprises an array of the resonators disposed on a sheet.

Embodiment 18. The emitter of Embodiment 12, wherein each of the resonators comprises a free-standing resonator.

Embodiment 19. The emitter of Embodiment 18, wherein the free-standing resonator is disposed within a medium to be treated.

Embodiment 20. The emitter of Embodiment 1, wherein the at least one energy augmentation structure comprises a first level of metallic patterns and a second level of metallic patterns offset in in at least one of a lateral or axial direction from the first level of metallic patterns.

Embodiment 21. The emitter of Embodiment 20, wherein at least one of the metallic patterns comprises a first resonator dimensioned to be resonant with an applied electromagnetic energy.

Embodiment 22. The emitter of Embodiment 21, wherein the at least one of the metallic patterns comprises a folded resonator having opposing electrodes with electric fields directed in between, and the energy converter is positioned between the opposing electrodes or within fringing electric field of the opposing electrodes.

Embodiment 23. The emitter of Embodiment 22, wherein the opposing electrodes are directed external to the folded resonator and parallel to one another.

Embodiment 24. The emitter of Embodiment 22, wherein the opposing electrodes are directed internal to the folded resonator and parallel to one another.

Embodiment 25. The emitter of any one of Embodiments 22-24, wherein the folded resonator comprises a ¾ λ folded resonator.

Embodiment 26. The emitter of Embodiment 20, wherein the at least one of the metallic patterns comprises a plurality of the folded resonators concentrically arranged and optionally co-planar to one another, such that the external opposing electrodes of each folded resonator do not overlap spatially with the external opposing electrodes of the other of the plurality of folded resonators.

Embodiment 27. The emitter of Embodiment 20, wherein the at least one of the metallic patterns comprises a plurality of the folded resonators concentrically arranged and optionally co-planar to one another, such that the external opposing electrodes of each folded resonator overlap spatially with the external opposing electrodes of one or more of the other of the plurality of folded resonators.

Embodiment 28. The emitter of claim 1, wherein the at least one energy augmentation structure comprises at least one of Au, Ag, Cu, Al, transparent metal oxides or refractory metals.

Embodiment 29. The emitter of Embodiment 1, further comprising an antireflection film disposed on the at least one energy augmentation structure or the energy converter.

Embodiment 30. The emitter of Embodiment 1, wherein the at least one energy augmentation structure is disposed in vicinity of a down conversion material comprising the energy converter.

Embodiment 31. The emitter of Embodiment 1, wherein the at least one energy augmentation structure is disposed in vicinity of an up-conversion material comprising the energy converter.

Embodiment 32. The emitter of Embodiment 1, wherein the at least one energy augmentation structure is disposed in vicinity of a phosphor comprising the energy converter.

Embodiment 33. The emitter of Embodiment 1, wherein the at least one energy augmentation structure is disposed in vicinity of a piezoelectric device comprising the energy converter.

Embodiment 34. The emitter of Embodiment 33, wherein the piezoelectric device is configured to receive sonic or acoustic energy and emit at least one of ultraviolet or visible light in response to absorbing the sonic or acoustic energy.

Embodiment 35. The emitter of Embodiment 1, wherein the at least one energy augmentation structure is disposed in vicinity of a mechanoluminescent device comprising the energy converter.

Embodiment 36. The emitter of Embodiment 35, wherein the mechanoluminescent device is configured to receive sonic or acoustic energy and emit at least one of ultraviolet or visible light in response to absorbing the sonic or acoustic energy.

Embodiment 37. The emitter of Embodiment 1, wherein the at least one energy augmentation structure is disposed inside a plasma capsule device comprising the energy converter.

Embodiment 38. The emitter of Embodiment 37, wherein the plasma capsule device is configured to receive radio frequency or microwave energy and emit at least one of ultraviolet or visible light in response to absorbing the radio frequency or microwave energy.

Embodiment 39. The emitter of Embodiment 1, wherein the at least one energy augmentation structure is disposed in vicinity of an x-ray stimulated phosphor comprising the energy converter.

Embodiment 40. The emitter of Embodiment 39, wherein the x-ray stimulated phosphor emits one of ultraviolet or visible light in response to absorbing x-rays.

Embodiment 41. The emitter of Embodiment 40, wherein the x-ray stimulated phosphor emits the one of ultraviolet or visible light for at least a time of 1 minute after x-ray stimulation.

Embodiment 42. The emitter of Embodiment 40, wherein the x-ray stimulated phosphor emits the one of ultraviolet or visible light for at least a time of 10 minutes after x-ray stimulation.

Embodiment 43. The emitter of Embodiment 40, wherein the x-ray stimulated phosphor emits the one of ultraviolet or visible light for at least a time of 60 minutes after x-ray stimulation.

Embodiment 44. The emitter of Embodiment 39, wherein the x-ray stimulated phosphor emits lower energy x-rays in response to absorbing higher energy x-rays.

Embodiment 45. The emitter of Embodiment 1, wherein the energy received from the energy source is one or more selected from acoustic waves, sound waves, radio waves, microwaves, far infrared, near infrared, visible light, UV, x-rays, gamma rays, electron beams, and proton beams.

Embodiment 46. The emitter of Embodiment 1, wherein the energy converter being disposed in a vicinity of the at least one energy augmentation structure comprises a conductive coupling of the energy converter to the at least one energy augmentation structure.

Embodiment 47. The emitter of Embodiment 46, wherein the conductive coupling comprises a physical conductive connection between the energy converter and the at least one energy augmentation structure.

Embodiment 48. The emitter of claim 1, wherein the energy converter comprises either one or both of (i) a down converter converting ultraviolet or blue light into red, yellow, or green light, or (ii) an up converter converting infrared or red light into yellow, green light, or blue light.

Embodiment 49. The emitter of Embodiment 1, wherein the at least one energy augmentation structure comprises a plurality of energy collectors.

Embodiment 50. The emitter of Embodiment 49, wherein the energy converters are positioned to convert energy being internally scattered within the energy collectors.

Embodiment 51. The emitter of Embodiment 49, wherein the energy collectors comprise a metal core cladded with a high-K dielectric and a subsequent cladding of a low-K dielectric.

Embodiment 52. The emitter of Embodiment 49, wherein the energy collectors comprise a radial pattern of collectors.

Embodiment 53. The emitter of Embodiment 7, wherein the energy collectors comprise a fractal pattern.

Embodiment 54. The emitter of Embodiment 53, wherein the fractal pattern is embedded within a dielectric material.

Embodiment 55. The emitter of any one or more of Embodiments 1-54, wherein the at least one energy augmentator comprises a component of at least one of a paint, an ink, a fabric, a thread, a road sign, a highway marking, an automobile, a boat, a plane, a reflector, a building product, a concrete product, an epoxy product, a jewelry product, colored contact lens, a candle product, a rubber product, a plastic product, a colored surface, a solar cell, a plasma capsule, an x-ray detector, or a sterilizer.

Embodiment 56. The emitter of any one or more of Embodiments 1-54, wherein the energy converter comprises a component of at least one of a paint, an ink, a fabric, a thread, a road sign, a highway marking, an automobile, a boat, a plane, a reflector, a building product, a concrete product, an epoxy product, a jewelry product, colored contact lens, a candle product, a rubber product, a plastic product, a colored surface, a solar cell, a plasma capsule, an x-ray detector, or a sterilizer.

Embodiment 57. The emitter of Embodiment 1, wherein the energy converter comprises a component of a colored reflective surface.

Embodiment 58. The emitter of Embodiment 1, wherein the energy converter comprises a component of a colored reflective surface in a pixel for a display.

Embodiment 59. The emitter of Embodiment 1, wherein the energy converter comprises a component of a white-light emitting pixel display element.

Embodiment 60. The emitter of Embodiment 1, wherein the energy converter comprises a component disposed in a retroreflective paint.

Embodiment 61. The emitter of Embodiment 1, wherein the energy converter comprises an ink component.

Embodiment 62. The emitter of Embodiment 1, wherein the energy converter comprises at least one of red, blue, and green emitters configured to produce red, blue, and green emissions from an up conversion process.

Embodiment 63. The emitter of Embodiment 1, wherein the energy converter comprises at least one of red, blue, and green emitters configured to produce red, blue, and green emissions from an up conversion process.

Embodiment 64. The emitter of Embodiment 1, wherein the energy converter comprises at least one of red, blue, and green emitters configured to produce red, blue, and green emissions from a down conversion process.

Embodiment 65. The emitter of Embodiment 1, wherein the energy converter comprises at least one of red, blue, and green emitters configured to produce red, blue, and green emissions from a down conversion process.

Embodiment 66. The emitter of Embodiment 1, wherein the energy converter comprises at least one of red, blue, and green emitters configured to produce red, blue, and green emissions from a mixture of up converters and down converters.

Embodiment 67. The emitter of Embodiment 1, wherein the energy converter comprises at least one of red, blue, and green emitters configured to produce red, blue, and green emissions from mixtures of up converters and down converters.

Embodiment 68. The emitter of Embodiment 1, wherein the energy converter comprises a mixture of fluorescent emitters including at least one of europium, terbium, cerium, and erbium or combinations thereof.

Embodiment 69. The emitter of Embodiment 1, wherein the energy converter comprises mixtures of fluorescent emitters including at least one of europium, terbium, cerium, and erbium or combinations thereof.

Embodiment 70. The emitter of Embodiment 1, wherein the energy converter comprises:
a first material configured to emit a first visible color in response to absorption of ultraviolet light; and
a second material configured to emit a second visible color in response to absorption of infrared light, wherein the second visible color is different from the first visible color.

Embodiment 71. The emitter of Embodiment 70, wherein the energy converter further comprises a third material configured to emit a third visible color in response to absorption of the ultraviolet light, wherein the third visible color is different from the first visible color and the second visible color.

Embodiment 72. The emitter of Embodiment 71, wherein the first visible color, the second visible color, and the third visible color are primary colors.

Embodiment 73. The emitter of Embodiment 70, wherein the energy converter further comprises a third material configured to emit a third visible color in response to absorption of the infrared light, wherein the third visible color is different from the first visible color and the second visible color.

Embodiment 74. The emitter of Embodiment 1, wherein the energy converter comprises:
a first material configured to emit a first visible color in response to absorption of ultraviolet light; and
a second material configured to emit a second visible color in response to absorption of infrared light, wherein the second visible color is substantially the same color as the first visible color.

Embodiment 75. The emitter of Embodiment 74, wherein the energy converter further comprises a third material configured to emit a third visible color in response to absorption of the ultraviolet light, wherein the third visible color is different from the first visible color and the second visible color.

Embodiment 76. The emitter of Embodiment 74, wherein the energy converter further comprises a third material configured to emit a third visible color in response to absorption of the infrared light, wherein the third visible color is different from the first visible color and the second visible color.

Embodiment 77. The emitter of Embodiment 76, wherein the first visible color, the second visible color, and the third visible color are at least two of the primary colors.

Embodiment 78. The emitter of Embodiment 1, wherein the energy converter comprises a component of a colored reflective surface.

Embodiment 79. The emitter of Embodiment 1, wherein the energy converter comprises a component of a colored reflective surface in a pixel for a display.

Embodiment 80. The emitter of Embodiment 1, wherein the energy converter comprises a component of a white-light emitting pixel display element.

Embodiment 81. The emitter of Embodiment 1, wherein the energy converter comprises a component disposed in a retroreflective paint.

Embodiment 82. The emitter of Embodiment 1, wherein the energy converter comprises an ink component.

Embodiment 83. The emitter of any of Embodiments 78-82, wherein the energy converter comprises at least one of red, blue, and green emitters configured to produce red, blue, and green emissions from an up conversion process.

Embodiment 84. The emitter of any of Embodiments 78-82, wherein the energy converter comprises at least one of red, blue, and green emitters configured to produce red, blue, and green emissions from an up conversion process.

Embodiment 85. The emitter of any of Embodiments 78-82, wherein the energy converter comprises at least one of red, blue, and green emitters configured to produce red, blue, and green emissions from a down conversion process.

Embodiment 86. The emitter of any of Embodiments 78-82, wherein the energy converter comprises at least one of red, blue, and green emitters configured to produce red, blue, and green emissions from a down conversion process.

Embodiment 87. The emitter of any of Embodiments 78-82, wherein the energy converter comprises at least one of red, blue, and green emitters configured to produce red, blue, and green emissions from a mixture of up converters and down converters.

Embodiment 88. The emitter of any of Embodiments 78-82, wherein the energy converter comprises at least one of red, blue, and green emitters configured to produce red, blue, and green emissions from mixtures of up converters and down converters.

Embodiment 89. The emitter of any of Embodiments 78-82, wherein the energy converter comprises a mixture of fluorescent emitters including at least one of europium, terbium, cerium, and erbium or combinations thereof.

Embodiment 90. The emitter of any of Embodiments 78-82, wherein the energy converter comprises mixtures of fluorescent emitters including at least one of europium, terbium, cerium, and erbium or combinations thereof.

Embodiment 91. The emitter of any of Embodiments 78-82, wherein the energy converter comprises:
a first material configured to emit a first visible color in response to absorption of ultraviolet light; and
a second material configured to emit a second visible color in response to absorption of infrared light, wherein the second visible color is different from the first visible color.

Embodiment 92. The emitter of Embodiment 91, wherein the energy converter further comprises a third material configured to emit a third visible color in response to absorption of the ultraviolet light, wherein the third visible color is different from the first visible color and the second visible color.

Embodiment 93. The emitter of Embodiment 92, wherein the first visible color, the second visible color, and the third visible color are primary colors.

Embodiment 94. The emitter of Embodiment 91, wherein the energy converter further comprises a third material configured to emit a third visible color in response to absorption of the infrared light, wherein the third visible color is different from the first visible color and the second visible color.

Embodiment 95. The emitter of any of Embodiments 78-82, wherein the energy converter comprises:
a first material configured to emit a first visible color in response to absorption of ultraviolet light; and
a second material configured to emit a second visible color in response to absorption of infrared light, wherein the second visible color is substantially the same color as the first visible color.

Embodiment 96. The emitter of Embodiment 95, wherein the energy converter further comprises a third material configured to emit a third visible color in response to absorption of the ultraviolet light, wherein the third visible color is different from the first visible color and the second visible color.

97. The emitter of Embodiment 95, wherein the energy converter further comprises a third material configured to emit a third visible color in response to absorption of the infrared light, wherein the third visible color is different from the first visible color and the second visible color.

Embodiment 98. The emitter of Embodiment 97, wherein the first visible color, the second visible color, and the third visible color are at least two of the primary colors.

Embodiment 99. The emitter of Embodiment 1, wherein the at least one energy augmentator comprises metallic conductors including at least one of Au, Ag, Cu, Ni, Pt, Pd, Co, Ru, Rh, Al, Ga, or a combination or alloys or layers thereof.

Embodiment 100. The emitter of Embodiment 1, wherein the energy converter comprises at least one of Y2O3, Y2O2S, NaYF4, NaYbF4, YAG, YAP, Nd2O3, LaF3, LaCl3, La2O3, TiO2, LuPO4, YVO4, YbF3, YF3, Na-doped YbF3, or SiO2 or alloys or layers thereof.

Embodiment 101. The emitter of Embodiment 100, wherein the energy converter further comprises a dopant including at least one of Er, Eu, Yb, Tm, Nd, Tb, Ce, Y, U, Pr, La, Gd and other rare-earth species or a combination thereof.

Embodiment 102. The emitter of Embodiment 101, wherein the dopant is included at a concentration of 0.01%-50% by mol concentration.

Embodiment 103. The emitter of Embodiment 1, wherein the energy converter comprises a down converter including at least one of Y2O3; ZnS; ZnSe; MgS; CaS; Mn, Er ZnSe; Mn, Er MgS; Mn, Er CaS; Mn, Er ZnS; Mn,Yb ZnSe; Mn,Yb MgS; Mn, Yb CaS; Mn,Yb ZnS:Tb3+, Er3+; ZnS: Tb3+; Y2O3:Tb3+; Y2O3:Tb3+, Er3+; ZnS:Mn2+; ZnS: Mn,Er3+.

Embodiment 104. The emitter of Embodiment 1, wherein the energy converter comprises an up converter including at least one of Y2O3, Y2O2S, NaYF4, NaYbF4, YAG, YAP, Nd2O3, LaF3, LaCl3, La2O3, TiO2, LuPO4, YVO4, YbF3, YF3, Na-doped YbF3, or SiO2 or alloys or layers thereof.

Embodiment 105. The emitter of Embodiment 1, wherein the energy converter comprises an up converter including at least one of Tm3+ doped flourozirconate glasses, LuPO4: Yb3+, Tm3+, and YbPO4:Er3+ nanocrystals, tellurium and germanium oxides, tellurium and germanium oxides doped with at least one Tm, Yb, Ho, Er, or Pr, Yb3+ doped BaZrO3, Nd3+:Cs2NaGdCl6, Nd3+, Yb3+:Cs2NaGdCl6, Nd3+ and Ho3+ co-doped-based ZrF4 fluoride glasses, Tm3+/Yb3+-codoped TeO2-Ga2O3-R2O (R=Li, Na, K) glasses, and metal-to-ligand charge transfer (MLCT) transition materials, and MLCT transition materials including [Ru(dmb)3]2+ (dmb=4,4-dimethyl-2,2-bipyridine).

Embodiment 106. An energy augmentation structure capable of capturing one or more wavelengths of electromagnetic energy, and augmenting the one or more wavelengths of electromagnetic energy in at least one property.

Embodiment 107. The energy augmentation emitter of Embodiment 106, wherein the energy augmentation structure is at least one non-plasmonic member selected from the group consisting of resonators, fractal antennas, electrical grid patterns, antennas, cavities, etalons, nanoparticles, microparticles, nanostructures, and microstructures.

Embodiment 108. The energy augmentation structure of Embodiment 106, comprising a folded resonator having opposing electrodes with electric fields directed in between.

Embodiment 109. The energy augmentation structure of Embodiment 108, wherein the opposing electrodes are directed external to the folded resonator and parallel to one another.

Embodiment 110. The energy augmentation structure of Embodiment 108, wherein the opposing electrodes are directed internal to the folded resonator and parallel to one another.

Embodiment 111. The energy augmentation structure of any one of Embodiments 108-110, wherein the folded resonator comprises a ¾λ folded resonator.

Embodiment 112. The energy augmentation structure of Embodiment 108, wherein the folded resonator is a plurality of the folded resonators concentrically arranged and optionally co-planar to one another, such that the external opposing electrodes of each folded resonator do not overlap spatially with the external opposing electrodes of the other of the plurality of folded resonators.

Embodiment 113. The energy augmentation structure of Embodiment 108, wherein the folded resonator is a plurality of the folded resonators concentrically arranged and optionally co-planar to one another, such that the external opposing electrodes of each folded resonator overlap spatially with the external opposing electrodes of one or more of the other of the plurality of folded resonators.

Embodiment 114. An energy collector comprising at least one energy augmentation structure; and at least one energy converter capable of receiving an applied electromagnetic energy, converting the applied electromagnetic energy and emitting therefrom an emitted electromagnetic energy shifted in wavelength or energy from the applied electromagnetic energy and the energy converter being disposed in a vicinity of the at least one energy augmentation structure such that the emitted electromagnetic energy is emitted with at least one augmented property compared to if the energy converter were remote from the at least one energy augmentation structure.

Embodiment 115. The energy collector of Embodiment 114, wherein the at least one energy converter is at least one member selected from the group consisting of phosphors, lumiphors, electroluminescent particles, up-converters, down-converters, and scintillators.

Embodiment 116. The energy collector of Embodiment 114, wherein the energy augmentation structure is at least one non-plasmonic member selected from the group consisting of resonators, fractal antennas, electrical grid patterns, antennas, cavities, etalons, nanoparticles, microparticles, nanostructures, and microstructures.

Embodiment 117. The energy collector of Embodiment 114, wherein having the energy converter disposed in a vicinity of the at least one energy augmentation structure comprises conductively coupling the at least one energy converter to the at least one energy augmentation structure.

Embodiment 118. The energy collector of Embodiment 117, wherein conductively coupling comprises having the at least one energy converter be proximate the at least one energy augmentation structure, physically located within the at least one energy augmentation structure, or located within a generated electric field of the at least one energy augmentation structure.

Embodiment 119. The energy collector of Embodiment 117, wherein conductively coupling comprises a physical conductive connection between the at least one energy converter and the at least one energy augmentation structure.

Embodiment 120. The energy collector of Embodiment 114, wherein the applied electromagnetic energy is selected from radio waves, microwaves, far infrared, near infrared, visible light, UV, x-rays, gamma rays, electron beams, and proton beams.

Embodiment 121. The energy collector of Embodiment 114, wherein the at least one energy augmentation structure comprises a first resonator dimensioned to be resonant with the applied electromagnetic energy, said first resonator optionally comprising a fractal pattern.

Embodiment 122. The energy collector of Embodiment 114, wherein the energy augmentation structure comprises a folded resonator having opposing electrodes with electric fields directed in between.

Embodiment 123. The energy collector of Embodiment 120, wherein the opposing electrodes are directed external to the folded resonator and parallel to one another.

Embodiment 124. The energy collector of Embodiment 120, wherein the opposing electrodes are directed internal to the folded resonator and parallel to one another.

Embodiment 125. The energy collector of any one of Embodiments 122-124, wherein the folded resonator comprises a ¾λ folded resonator.

Embodiment 126. The energy collector of Embodiment 122, wherein the folded resonator is a plurality of the folded resonators concentrically arranged and optionally co-planar to one another, such that the external opposing electrodes of each folded resonator do not overlap spatially with the external opposing electrodes of the other of the plurality of folded resonators.

Embodiment 127. The energy collector of Embodiment 122, wherein the folded resonator is a plurality of the folded resonators concentrically arranged and optionally co-planar to one another, such that the external opposing electrodes of each folded resonator overlap spatially with the external opposing electrodes of one or more of the other of the plurality of folded resonators.

Embodiment 128. A method of treating a disease, condition, or disorder using the energy emitter of any one of Embodiments 1-105, the energy augmentation structure of any one of Embodiments 106-113, or the energy collector of any one of Embodiments 114-127.

Embodiment 129. A method for treating a cell proliferation disorder in a subject, comprising:
(1) administering to the subject at least one activatable pharmaceutical agent that is capable of effecting a predetermined cellular change when activated and at least one energy emitter of any one of Embodiments 1-105, or at least one energy augmentation structure of any one of Embodiments 106-113, or at least one energy collector of any one of Embodiments 114-127; and
(2) applying an initiation energy from an initiation energy source to the subject,
wherein the initiation energy is capable of penetrating completely through the subject, and wherein the applied initiation energy interacts with the at least one energy emitter, at least one energy augmentation structure, or at least one energy collector and activates the activatable agent in situ, thus causing the predetermined cellular change to occur, wherein said predetermined cellular change treats the cell proliferation related disorder.

Embodiment 130. The method of Embodiment 129, wherein the initiation energy source is x-rays, gamma rays, an electron beam, microwaves or radio waves.

Embodiment 131. The method of Embodiment 129, wherein the cell proliferation disorder is at least one member selected from the group consisting of cancer, bacterial infection, viral infection, immune rejection response, autoimmune disorders, aplastic conditions, and combinations thereof.

Embodiment 132. The method of Embodiment 129, wherein the at least one activatable pharmaceutical agent is a photoactivatable agent.

Embodiment 133. The method of Embodiment 129, wherein the at least one activatable pharmaceutical agent is selected from psoralens, pyrene cholesteryloleate, acridine, porphyrin, fluorescein, rhodamine, 16-diazorcortisone, ethidium, transition metal complexes of bleomycin, transition metal complexes of deglycobleomycin organoplatinum complexes, alloxazines, vitamin Ks, vitamin L, vitamin metabolites, vitamin precursors, naphthoquinones, naphthalenes, naphthols and derivatives thereof having planar molecular conformations, porphyrins, dyes and phenothiazine derivatives, coumarins, quinolones, quinones, and anthroquinones.

Embodiment 134. The method of Embodiment 133, wherein the at least one activatable pharmaceutical agent is a psoralen, a coumarin, or a derivative thereof.

Embodiment 135. The method of Embodiment 133, wherein the at least one activatable pharmaceutical agent is 8-MOP or AMT.

Embodiment 136. The method of Embodiment 129, wherein the at least one activatable pharmaceutical agent is one selected from 7,8-dimethyl-O-ribityl, isoalloxazine, 7,8,10-trimethylisoalloxazine, 7,8-dimethylalloxazine, isoalloxazine-adenine dinucleotide, alloxazine mononucleotide, aluminum (III) phthalocyanine tetrasulonate, hematoporphyrin, and phthadocyanine.

Embodiment 137. The method of Embodiment 129, wherein the at least one activatable pharmaceutical agent is coupled to a carrier that is capable of binding to a receptor site.

Embodiment 138. The method of Embodiment 137, wherein the carrier is one selected from insulin, interleukin, thymopoietin or transferrin.

Embodiment 139. The method of Embodiment 137, wherein the at least one activatable pharmaceutical agent is coupled to the carrier by a covalent bond.

Embodiment 140. The method of Embodiment 137, wherein the at least one activatable pharmaceutical agent is coupled to the carrier by non-covalent bond.

Embodiment 141. The method of Embodiment 137, wherein the receptor site is one selected from nucleic acids of nucleated cells, antigenic sites on nucleated cells, or epitopes.

Embodiment 142. The method of Embodiment 129, wherein the at least one activatable pharmaceutical agent has affinity for a target cell.

Embodiment 143. The method of Embodiment 129, wherein the at least one activatable pharmaceutical agent is capable of being preferentially absorbed by a target cell.

Embodiment 144. The method of Embodiment 129, wherein the predetermined cellular change is apoptosis in a target cell.

Embodiment 145. The method of Embodiment 129, wherein the at least one activated pharmaceutical agent causes an auto-vaccine effect in the subject that reacts with a target cell.

Embodiment 146. The method of Embodiment 129, wherein the at least one activatable pharmaceutical agent is a DNA intercalator or a halogenated derivative thereof.

Embodiment 147. The method of Embodiment 129, wherein the at least one energy emitter or at least one energy collector is present.

Embodiment 148. The method of Embodiment 147, wherein said at least one energy converter is a single energy converter, and is coupled to said at least one activatable pharmaceutical agent.

Embodiment 149. The method of Embodiment 129, wherein the at least one activatable pharmaceutical agent is activated by one or more sequential single photon absorption events.

Embodiment 150. The method of Embodiment 129, wherein the at least one activatable pharmaceutical agent comprises an active agent contained within a photocage, wherein upon exposure to said initiation energy source, the photocage disassociates from the active agent, rendering the active agent available.

Embodiment 151. The method of Embodiment 129, wherein said predetermined cellular change treats the cell proliferation disorder by causing an increase or decrease in cell proliferation rate of a target cell.

Embodiment 152. A method for treating a cell proliferation disorder in a subject, comprising:
(1) administering to the subject at least one energy emitter of any one of Embodiments 1-105 or at least one energy collector of any one of Embodiments 114-127, and at least one activatable pharmaceutical agent that is capable of effecting a predetermined cellular change when activated; and
(2) applying an initiation energy from an initiation energy source to the subject,
wherein the energy converter in the at least one energy emitter or at least one energy collector converts the applied initiation energy to UV-A or visible energy, which then activates the activatable agent in situ, wherein the energy converter is disposed in a vicinity of the at least one energy augmentation structure such that the emitted UV-A or visible energy is emitted with an intensity larger than if the energy converter were remote from the at least one energy augmentation structure, or if the energy augmentation structure were not present
thus causing the predetermined cellular change to occur, wherein said predetermined cellular change treats the cell proliferation related disorder.

Embodiment 153. The method of Embodiment 152, wherein said predetermined cellular change treats the cell proliferation disorder by causing an increase or decrease in cell proliferation rate of a target cell.

Embodiment 154. The method of Embodiment 152, wherein the at least one energy converter is one or more selected from a biocompatible fluorescing metal nanoparticle, fluorescing dye molecule, gold nanoparticle, a water soluble quantum dot encapsulated by polyamidoamine dendrimers, a luciferase, a biocompatible phosphorescent molecule, a combined electromagnetic energy harvester molecule, and a lanthanide chelate capable of intense luminescence.

Embodiment 155. The method of Embodiment 152, wherein the initiation energy source is a source of higher energy than the resulting UV-A or visible energy.

Embodiment 156. The method of Embodiment 152, wherein the initiation energy source is a source of lower energy than the resulting UV-A or visible energy.

Embodiment 157. The method of Embodiment 152, wherein the initiation energy is applied via a thin fiber optic.

Embodiment 158. The method of Embodiment 152, wherein the cell proliferation disorder is at least one member selected from the group consisting of cancer, bacterial infection, viral infection, immune rejection response, autoimmune disorders, aplastic conditions, and combinations thereof.

Embodiment 159. The method of Embodiment 152, wherein the at least one activatable pharmaceutical agent is a photoactivatable agent.

Embodiment 160. The method of Embodiment 152, wherein the at least one activatable pharmaceutical agent is selected from psoralens, pyrene cholesteryloleate, acridine, porphyrin, fluorescein, rhodamine, 16-diazorcortisone, ethidium, transition metal complexes of bleomycin, transition metal complexes of deglycobleomycin organoplatinum complexes, alloxazines, vitamin Ks, vitamin L, vitamin metabolites, vitamin precursors, naphthoquinones, naphthalenes, naphthols and derivatives thereof having planar molecular conformations, porphyrins, dyes and phenothiazine derivatives, coumarins, quinolones, quinones, and anthroquinones.

Embodiment 161. The method of Embodiment 160, wherein the at least one activatable pharmaceutical agent is a psoralen, a coumarin, or a derivative thereof.

Embodiment 162. The method of Embodiment 160, wherein the at least one activatable pharmaceutical agent is 8-MOP or AMT.

Embodiment 163. The method of Embodiment 162, wherein the at least one activatable pharmaceutical agent is one selected from 7,8-dimethyl-10-ribityl, isoalloxazine, 7,8,10-trimethylisoalloxazine, 7,8-dimethylalloxazine, isoalloxazine-adenine dinucleotide, alloxazine mononucleotide, aluminum (III) phthalocyanine tetrasulonate, hematoporphyrin, and phthadocyanine.

Embodiment 164. The method of Embodiment 152, wherein the at least one activatable pharmaceutical agent is coupled to a carrier that is capable of binding to a receptor site.

Embodiment 165. The method of Embodiment 164, wherein the carrier is one selected from insulin, interleukin, thymopoietin or transferrin.

Embodiment 166. The method of Embodiment 164, wherein the at least one activatable pharmaceutical agent is coupled to the carrier by a covalent bond.

Embodiment 167. The method of Embodiment 164, wherein the at least one activatable pharmaceutical agent is coupled to the carrier by non-covalent bond.

Embodiment 168. The method of Embodiment 164, wherein the receptor site is one selected from nucleic acids of nucleated cells, antigenic sites on nucleated cells, or epitopes.

Embodiment 169. The method of Embodiment 152, wherein the at least one activatable pharmaceutical agent has affinity for a target cell.

Embodiment 170. The method of Embodiment 152, wherein the at least one activatable pharmaceutical agent is capable of being preferentially absorbed by a target cell.

Embodiment 171. The method of Embodiment 152, wherein the predetermined cellular change is apoptosis in a target cell.

Embodiment 172. The method of Embodiment 152, wherein the at least one activated pharmaceutical agent causes an auto-vaccine effect in the subject that reacts with a targets cell.

Embodiment 173. The method of Embodiment 152, wherein the at least one activatable pharmaceutical agent is a DNA intercalator or a halogenated derivative thereof.

Embodiment 174. The method of Embodiment 152, wherein the initiation energy is one of electromagnetic energy, acoustic energy, or thermal energy.

Embodiment 175. The method of Embodiment 152, further comprising a blocking agent, wherein the blocking agent is capable of blocking uptake of the at least one activatable pharmaceutical agent prior to its activation.

Embodiment 176. The method of Embodiment 175, wherein the blocking agent is capable of slowing down mitosis in non-target cells while allowing target cells to maintain an abnormal rate of mitosis.

Embodiment 177. The method of Embodiment 152, wherein said at least one energy converter is a single energy converter, and is coupled to said at least one activatable pharmaceutical agent.

Embodiment 178. The method of Embodiment 152, wherein the at least one activatable pharmaceutical agent comprises an active agent contained within a photocage, wherein upon exposure to said UV-A or visible energy, the photocage disassociates from the active agent, rendering the active agent available.

Embodiment 179. The method of Embodiment 152, wherein the at least one activatable pharmaceutical agent is activated by one or more sequential single photon absorption events.

Embodiment 180. A method for treating a cell proliferation disorder in a subject, comprising:
  (1) administering to the subject at least one activatable pharmaceutical agent that is capable of effecting a predetermined cellular change when activated, and at least one energy emitter of any one of Embodiments 1-105, or at least one energy augmentation structure of any one of Embodiments 106-113, or at least one energy collector of any one of Embodiments 114-127; and
  (2) applying an initiation energy from an initiation energy source to the subject,
  wherein the initiation energy applied and activatable pharmaceutical agent upon activation produce insufficient singlet oxygen in the subject to produce cell lysis, and wherein the initiation energy interacts with the at least one energy emitter, at least one energy augmentation structure, or at least one energy collector and activates the activatable pharmaceutical agent in situ, thus causing the predetermined cellular change to occur, wherein said predetermined cellular change treats the cell proliferation related disorder.

Embodiment 181. The method according to Embodiment 180, wherein said predetermined cellular change treats the cell proliferation disorder by causing an increase or decrease in cell proliferation rate of a target cell.

Embodiment 182. The method according to Embodiment 180, wherein the amount of singlet oxygen production is less than 109 singlet oxygen molecules/cell.

Embodiment 183. The method according to Embodiment 180, wherein the amount of singlet oxygen production is less than 0.32×10-3 mol/liter.

Embodiment 184. The method according to Embodiment 180, wherein the at least one activated pharmaceutical agent causes an auto-vaccine effect in the subject that reacts with a target cell.

Embodiment 185. The method according to Embodiment 180, wherein the at least one energy emitter or at least one energy collector is present.

Embodiment 186. The method of Embodiment 185, wherein said at least one energy converter is a single energy converter, and is coupled to said at least one activatable pharmaceutical agent.

Embodiment 187. The method of Embodiment 180, wherein the at least one activatable pharmaceutical agent comprises an active agent contained within a photocage, wherein upon exposure to said initiation energy, the photocage disassociates from the active agent, rendering the active agent available.

Embodiment 188. The method of Embodiment 180, wherein the initiation energy source is selected from the group consisting of x-rays, gamma rays, electron beams, phosphorescent compounds, chemiluminescent compounds, bioluminescent compounds, and light emitting enzymes.

Embodiment 189. The method of Embodiment 180, wherein the predetermined cellular change is apoptosis in a target cell.

Embodiment 190. The method of Embodiment 180, wherein the cell proliferation disorder is at least one member selected from the group consisting of cancer, bacterial infection, viral infection, immune rejection response, auto-immune disorders, and aplastic conditions.

Embodiment 191. The method of Embodiment 180, wherein the at least one activatable pharmaceutical agent is a photoactivatable agent.

Embodiment 192. The method of Embodiment 180, wherein the at least one activatable pharmaceutical agent is selected from psoralens, pyrene cholesteryloleate, acridine, porphyrin, fluorescein, rhodamine, 16-diazorcortisone, ethidium, transition metal complexes of bleomycin, transition metal complexes of deglycobleomycin organoplatinum complexes, alloxazines, vitamin Ks, vitamin L, vitamin metabolites, vitamin precursors, naphthoquinones, naphthalenes, naphthols and derivatives thereof having planar molecular conformations, porphyrins, dyes and phenothiazine derivatives, coumarins, quinolones, quinones, and anthroquinones.

Embodiment 193. The method of Embodiment 192, wherein the at least one activatable pharmaceutical agent is a psoralen, a coumarin, or a derivative thereof.

Embodiment 194. The method of Embodiment 192, wherein the at least one activatable pharmaceutical agent is 8-MOP or AMT.

Embodiment 195. The method of Embodiment 180, wherein the at least one activatable pharmaceutical agent is one selected from 7,8-dimethyl-10-ribityl, isoalloxazine, 7,8,10-trimethylisoalloxazine, 7,8-dimethylalloxazine, isoalloxazine-adenine dinucleotide, alloxazine mononucleotide, aluminum (III) phthalocyanine tetrasulonate, hematoporphyrin, and phthadocyanine.

Embodiment 196. The method of Embodiment 180, wherein the at least one activatable pharmaceutical agent is coupled to a carrier that is capable of binding to a receptor site.

Embodiment 197. The method of Embodiment 196, wherein the carrier is one selected from insulin, interleukin, thymopoietin or transferrin.

Embodiment 198. The method of Embodiment 196, wherein the at least one activatable pharmaceutical agent is coupled to the carrier by a covalent bond.

Embodiment 199. The method of Embodiment 196, wherein the at least one activatable pharmaceutical agent is coupled to the carrier by a non-covalent bond.

Embodiment 200. The method of Embodiment 196, wherein the receptor site is one selected from nucleic acids of nucleated cells, antigenic sites on nucleated cells, or epitopes.

Embodiment 201. The method of Embodiment 180, wherein the at least one activatable pharmaceutical agent has affinity for a target cell.

Embodiment 202. The method of Embodiment 180, wherein the at least one activatable pharmaceutical agent is capable of being preferentially absorbed by a target cell.

Embodiment 203. The method of Embodiment 180, wherein the at least one activatable pharmaceutical agent is a DNA intercalator or a halogenated derivative thereof.

Embodiment 204. The method of Embodiment 180, wherein the at least one activatable pharmaceutical agent is activated by one or more sequential single photon absorption events.

Embodiment 205. A method for treating a cell proliferation disorder in a subject, comprising:
(1) modifying one or more cells to incorporate a photon emitting modification or substance;
(2) inserting the modified cells at a targeted site of the subject; and
(3) administering at least one energy emitter of any one of Embodiments 1-105, at least one energy augmentation structure of any one of Embodiments 106-113, or at least one energy collector of any one of Embodiments 114-127, and at least one activatable pharmaceutical agent capable of being activated by the photons emitted from the modified cells after interaction of the photons with the energy emitter, the energy augmentation structure, or the energy collector, to cause a predetermined cellular change.

Embodiment 206. The method of Embodiment 205, wherein said one or more cells are subject's own cells that have been removed prior to said modifying.

Embodiment 207. The method of Embodiment 205, wherein the photon emitting modification or substance is a member selected from the group consisting of light emitting genes; phosphorescent compounds, chemiluminescent compounds, bioluminescent compounds and light emitting enzymes.

Embodiment 208. The method of Embodiment 205, wherein the targeted site is a tumor.

Embodiment 209. The method according to Embodiment 205, wherein the at least one activatable pharmaceutical agent, upon activation, causes an auto-vaccine effect in the subject that reacts with a target cell.

Embodiment 210. The method of Embodiment 205, wherein the predetermined cellular change is apoptosis in a target cell.

Embodiment 211. A method for generating an autovaccine for a subject, comprising:
(1) providing a population of target cells;
(2) treating the target cells ex vivo in an environment separate and isolated from the subject with a psoralen or a derivative thereof;

(3) activating the psoralen or the derivative thereof with an UV-A source, in the presence of at least one energy emitter of any one of Embodiments 1-105, at least one energy augmentation structure of any one of Embodiments 106-113, or at least one energy collector of any one of Embodiments 114-127, to induce a predetermined cellular change in the target cells;

(4) returning the thus changed cells back to the subject to induce in the subject an autovaccine effect against the target cell, wherein the changed cells act as an autovaccine.

Embodiment 212. The method of Embodiment 211, wherein the psoralen is 8-MOP.

Embodiment 213. The method of Embodiment 211, further comprising: fractionating the apoptic cells and testing the fractions for auto-vaccine effect of each isolated component to determine the component(s) associated with auto-vaccine before returning components to the subject.

Embodiment 214. The method of Embodiment 211, wherein the predetermined cellular change is apoptosis in a target cell affected by the cell proliferation disorder.

Embodiment 215. A system for producing an auto-vaccine in a subject, comprising:

at least one activatable pharmaceutical agent capable of inducing a predetermined cellular change in a target cell in said subject;

at least one energy emitter of any one of Embodiments 1-105, at least one energy augmentation structure of any one of Embodiments 106-113, or at least one energy collector of any one of Embodiments 114-127;

means for placing said at least one activatable pharmaceutical agent and said at least one energy emitter, said at least one energy augmentation structure, or at least one energy collector in said subject; and an initiation energy source to provide initiation energy capable, after interacting with the at least one energy emitter, at least one energy augmentation structure, or at least one energy collector, of activating the at least one activatable pharmaceutical agent in said target cell, wherein activation is either direct or indirect.

Embodiment 216. The system of Embodiment 215, wherein the predetermined cellular change is apoptosis in a target cell.

Embodiment 217. The system of Embodiment 215, wherein the initiation energy is capable of directly activating the at least one activatable pharmaceutical agent.

Embodiment 218. The system of Embodiment 215, wherein the at least one energy emitter or at least one energy collector is present and whereby the initiation energy source interacts with the at least one energy emitter or at least one energy collector, and is absorbed by the at least one energy converter and reemitted as an activation energy for the at least one activatable pharmaceutical agent, where the activation energy has at least one augmented property compared to if the energy converter were remote from the at least one energy emitter or at least one energy collector, such that the initiation energy source indirectly activates the at least one activatable pharmaceutical agent via the at least one energy converter.

Embodiment 219. The system of Embodiment 218, wherein said at least one energy converter is a single energy converter, and is coupled to said at least one activatable pharmaceutical agent.

Embodiment 220. The system of Embodiment 215, wherein the initiation energy is x-rays, gamma rays or an electron beam.

Embodiment 221. The system of Embodiment 215, wherein the at least one activatable pharmaceutical agent is a photoactivatable agent.

Embodiment 222. The system of Embodiment 215, wherein the at least one activatable pharmaceutical agent is selected from psoralens, pyrene cholesteryloleate, acridine, porphyrin, fluorescein, rhodamine, 16-diazorcortisone, ethidium, transition metal complexes of bleomycin, transition metal complexes of deglycobleomycin organoplatinum complexes, alloxazines, vitamin Ks, vitamin L, vitamin metabolites, vitamin precursors, naphthoquinones, naphthalenes, naphthols and derivatives thereof having planar molecular conformations, porphyrins, dyes and phenothiazine derivatives, coumarins, quinolones, quinones, and anthroquinones.

Embodiment 223. The system of Embodiment 222, wherein the at least one activatable pharmaceutical agent is a psoralen, a coumarin, or a derivative thereof.

Embodiment 224. The system of Embodiment 222, wherein the at least one activatable pharmaceutical agent is 8-MOP or AMT.

Embodiment 225. The system of Embodiment 215, wherein the at least one activatable pharmaceutical agent is one selected from 7,8-dimethyl-10-ribityl, isoalloxazine, 7,8,10-trimethylisoalloxazine, 7,8-dimethylalloxazine, isoalloxazine-adenine dinucleotide, alloxazine mononucleotide, aluminum (III) phthalocyanine tetrasulonate, hematoporphyrin, and phthadocyanine.

Embodiment 226. The system of Embodiment 215, wherein the at least one activatable pharmaceutical agent is coupled to a carrier that is capable of binding to a receptor site.

Embodiment 227. The system of Embodiment 226, wherein the carrier is one selected from insulin, interleukin, thymopoietin or transferrin.

Embodiment 228. The system of Embodiment 226, wherein the at least one activatable pharmaceutical agent is coupled to the carrier by a covalent bond.

Embodiment 229. The system of Embodiment 226, wherein the at least one activatable pharmaceutical agent is coupled to the carrier by a non-covalent bond.

Embodiment 230. The system of Embodiment 226, wherein the receptor site is one selected from nucleic acids of nucleated cells, antigenic sites on nucleated cells, or epitopes.

Embodiment 231. The system of Embodiment 215, wherein the at least one activatable pharmaceutical agent has affinity for a target cell.

Embodiment 232. The system of Embodiment 215, wherein the at least one activatable pharmaceutical agent is capable of being preferentially absorbed by a target cell.

Embodiment 233. The system of Embodiment 215, wherein the at least one activated pharmaceutical agent causes an auto-vaccine effect in the subject that reacts with a target cell.

Embodiment 234. The system of Embodiment 215, wherein the at least one activatable pharmaceutical agent is a DNA intercalator or a halogenated derivative thereof.

Embodiment 235. The system of Embodiment 215, wherein the at least one activatable pharmaceutical agent is activated by one or more sequential single photon absorption events.

Embodiment 236. The system of Embodiment 215, wherein the at least one activatable pharmaceutical agent comprises an active agent contained within a photocage, wherein upon exposure to said initiation energy source, the photocage disassociates from the active agent, rendering the active agent available.

Embodiment 237. A kit for performing a cell proliferation disorder treatment, comprising:
  at least one activatable pharmaceutical agent capable of causing a predetermined cellular change
  at least one energy emitter of any one of Embodiments 1-105, or at least one energy augmentation structure of any one of Embodiments 106-113, or at least one energy collector of any one of Embodiments 114-127; and
  containers suitable for storing the agents in stable form.

Embodiment 238. The kit of Embodiment 237, further comprising instructions for administering the at least one activatable pharmaceutical agent; and the at least one energy emitter or the at least one energy augmentation structure, or the at least one energy collector to a subject and for activating the at least one activatable pharmaceutical agent by application of an initiation energy.

Embodiment 239. The kit of Embodiment 237, wherein the at least one activatable pharmaceutical agent is a member selected from the group consisting of a psoralen, a coumarin, or a derivative thereof.

Embodiment 240. The kit of Embodiment 239, wherein the at least one activatable pharmaceutical agent is a psoralen selected from psoralen or 8-MOP.

Embodiment 241. The kit of Embodiment 239, wherein the at least one energy converter is one or more members selected from a biocompatible fluorescing metal nanoparticle, fluorescing dye molecule, gold nanoparticle, a water soluble quantum dot encapsulated by polyamidoamine dendrimers, a luciferase, a biocompatible phosphorescent molecule, a combined electromagnetic energy harvester molecule, and a lanthanide chelate capable of intense luminescence.

Embodiment 242. The kit of Embodiment 239, wherein said at least one energy converter is a single energy converter, and is coupled to said at least one activatable pharmaceutical agent.

Embodiment 243. The kit of Embodiment 239, wherein the at least one activatable pharmaceutical agent is coupled to a carrier that is capable of binding to a receptor site.

Embodiment 244. The kit of Embodiment 243, wherein the carrier is one selected from polypeptide, insulin, interleukin, thymopoietin or transferrin.

Embodiment 245. The kit of Embodiment 243, wherein the at least one activatable pharmaceutical agent is coupled to the carrier by a covalent bond.

Embodiment 246. The kit of Embodiment 243, wherein the at least one activatable pharmaceutical agent is coupled to the carrier by a non-covalent bond.

Embodiment 247. The kit of Embodiment 243, wherein the receptor site is one selected from nucleic acids of nucleated cells, antigenic sites on nucleated cells, or epitopes.

Embodiment 248. The kit of Embodiment 237, wherein the at least one activatable pharmaceutical agent has affinity for a target cell.

Embodiment 249. The kit of Embodiment 237, wherein the at least one activatable pharmaceutical agent is capable of being preferentially absorbed by a target cell.

Embodiment 250. The kit of Embodiment 237, wherein the at least one activated pharmaceutical agent causes an auto-vaccine effect in the subject that reacts with a target cell.

Embodiment 251. The kit of Embodiment 237, wherein the at least one activatable pharmaceutical agent is a DNA intercalator or a halogenated derivative thereof.

Embodiment 252. The kit of Embodiment 237, wherein the at least one activatable pharmaceutical agent is activated by one or more sequential single photon absorption events.

Embodiment 253. The kit of Embodiment 237, wherein the at least one activatable pharmaceutical agent comprises an active agent contained within a photocage, wherein upon exposure to said initiation energy source, the photocage disassociates from the active agent, rendering the active agent available.

Embodiment 254. A pharmaceutical composition for treating a cell proliferation disorder, comprising:
  at least one activatable pharmaceutical agent capable of causing a predetermined cellular change;
  at least one energy emitter of any one of Embodiments 1-105 or at least one energy collector of any one of Embodiments 114-127;
  optionally, at least one additive having a complementary therapeutic or diagnostic effect, wherein said additive is at least one member selected from the group consisting of antioxidants, adjuvants, chemical energy sources, and combinations thereof; and
  a pharmaceutically acceptable carrier.

Embodiment 255. The pharmaceutical composition of Embodiment 254, wherein the at least one activatable pharmaceutical agent is a photoactivatable agent.

Embodiment 256. The pharmaceutical composition of Embodiment 254, wherein the at least one activatable pharmaceutical agent is selected from psoralens, pyrene cholesteryloleate, acridine, porphyrin, fluorescein, rhodamine, 16-diazorcortisone, ethidium, transition metal complexes of bleomycin, transition metal complexes of deglycobleomycin organoplatinum complexes, alloxazines, vitamin Ks, vitamin L, vitamin metabolites, vitamin precursors, naphthoquinones, naphthalenes, naphthols and derivatives thereof having planar molecular conformations, porphyrins, dyes and phenothiazine derivatives, coumarins, quinolones, quinones, and anthroquinones.

Embodiment 257. The pharmaceutical composition of Embodiment 256, wherein the at least one activatable pharmaceutical agent is a psoralen, a coumarin, or a derivative thereof.

Embodiment 258. The pharmaceutical composition of Embodiment 256, wherein the at least one activatable pharmaceutical agent is 8-MOP or AMT.

Embodiment 259. The pharmaceutical composition of Embodiment 254, wherein the at least one activatable pharmaceutical agent is one selected from 7,8-dimethyl-10-ribityl, isoalloxazine, 7,8,10-trimethylisoalloxazine, 7,8-dimethylalloxazine, isoalloxazine-adenine dinucleotide, alloxazine mononucleotide, aluminum (III) phthalocyanine tetrasulonate, hematoporphyrin, and phthadocyanine.

Embodiment 260. The pharmaceutical composition of Embodiment 254, wherein the at least one activatable pharmaceutical agent is coupled to a carrier that is capable of binding to a receptor site.

Embodiment 261. The pharmaceutical composition of Embodiment 260, wherein the carrier is one selected from insulin, interleukin, thymopoietin or transferring.

Embodiment 262. The pharmaceutical composition of Embodiment 260, wherein the at least one activatable pharmaceutical agent is coupled to the carrier by a covalent bond.

Embodiment 263. The pharmaceutical composition of Embodiment 260, wherein the at least one activatable pharmaceutical agent is coupled to the carrier by a non-covalent bond.

Embodiment 264. The pharmaceutical composition of Embodiment 260, wherein the receptor site is one selected from nucleic acids of nucleated cells, antigenic sites on nucleated cells, or epitopes.

Embodiment 265. The pharmaceutical composition of Embodiment 254, wherein the at least one activatable pharmaceutical agent has affinity for a target cell.

Embodiment 266. The pharmaceutical composition of Embodiment 254, wherein the at least one activatable pharmaceutical agent is capable of being preferentially absorbed by a target cell.

Embodiment 267. The pharmaceutical composition of Embodiment 254, wherein the at least one activated pharmaceutical agent causes an auto-vaccine effect in the subject that reacts with a target cell.

Embodiment 268. The pharmaceutical composition of Embodiment 254, wherein the at least one activatable pharmaceutical agent is a DNA intercalator or a halogenated derivative thereof.

Embodiment 269. The pharmaceutical composition of Embodiment 254, wherein the at least one activatable pharmaceutical agent is activated by one or more sequential single photon absorption events.

Embodiment 270. The pharmaceutical composition of Embodiment 254, wherein the predetermined cellular change is apoptosis in a target cell.

Embodiment 271. The pharmaceutical composition of Embodiment 254, wherein the at least one energy collector is present and the at least one energy converter is capable of activating the at least one activatable pharmaceutical agent when energized.

Embodiment 272. The pharmaceutical composition of Embodiment 271, wherein said at least one energy converter is a single energy converter, and is coupled to said at least one activatable pharmaceutical agent.

Embodiment 273. The pharmaceutical composition of Embodiment 254, wherein the at least one activatable pharmaceutical agent comprises an active agent contained within a photocage, wherein upon exposure to said initiation energy source, the photocage disassociates from the active agent, rendering the active agent available.

Embodiment 274. The pharmaceutical composition of Embodiment 254, wherein the at least one additive is present and is a chemical energy source.

Embodiment 275. The pharmaceutical composition of Embodiment 274, wherein the chemical energy source is a member selected from the group consisting of phosphorescent compounds, chemiluminescent compounds, bioluminescent compounds and light emitting enzymes.

Embodiment 276. A method for treating a cell proliferation disorder in a subject, comprising:
(1) administering to the subject at least one activatable pharmaceutical agent that is capable of effecting a predetermined cellular change when activated and at least one energy emitter of any one of Embodiments 1-105, or at least one energy augmentation structure of any one of Embodiments 106-113, or at least one energy collector of any one of Embodiments 114-127; and
(2) administering an initiation energy source to the subject,
wherein the initiation energy source interacts with the at least one energy emitter, at least one energy augmentation structure, or at least one energy collector and produces an initiation energy that activates the activatable pharmaceutical agent in situ,
thus causing the predetermined cellular change to occur, wherein said predetermined cellular change treats the cell proliferation related disorder.

Embodiment 277. The method according to Embodiment 276, wherein said initiation energy source is a chemical energy source.

Embodiment 278. The method according to Embodiment 276, wherein said predetermined cellular change treats the cell proliferation disorder by causing an increase or decrease in cell proliferation rate of a target cell.

Embodiment 279. The method according to Embodiment 276, wherein the at least one activated pharmaceutical agent causes an auto-vaccine effect in the subject that reacts with a target cell.

Embodiment 280. The method according to Embodiment 276, wherein the at least one energy emitter or at least one energy collector are present.

Embodiment 281. The method of Embodiment 280, wherein said at least one energy converter is a single energy converter, and is coupled to said at least one activatable pharmaceutical agent.

Embodiment 282. The method of Embodiment 276, wherein the at least one activatable pharmaceutical agent comprises an active agent contained within a photocage, wherein upon exposure to said initiation energy, the photocage disassociates from the active agent, rendering the active agent available.

Embodiment 283. The method of Embodiment 277, wherein the chemical energy source is a member selected from the group consisting of phosphorescent compounds, chemiluminescent compounds, bioluminescent compounds, and light emitting enzymes.

Embodiment 284. The method of Embodiment 276, wherein the predetermined cellular change is apoptosis in a target cell.

Embodiment 285. The method of Embodiment 276, wherein the cell proliferation disorder is at least one member selected from the group consisting of cancer, bacterial infection, viral infection, immune rejection response, autoimmune disorders, and aplastic conditions.

Embodiment 286. The method of Embodiment 276, wherein the at least one activatable pharmaceutical agent is a photoactivatable agent.

Embodiment 287. The method of Embodiment 276, wherein the at least one activatable pharmaceutical agent is selected from psoralens, pyrene cholesteryloleate, acridine, porphyrin, fluorescein, rhodamine, 16-diazorcortisone, ethidium, transition metal complexes of bleomycin, transition metal complexes of deglycobleomycin organoplatinum complexes, alloxazines, vitamin Ks, vitamin L, vitamin metabolites, vitamin precursors, naphthoquinones, naphthalenes, naphthols and derivatives thereof having planar molecular conformations, porphyrins, dyes and phenothiazine derivatives, coumarins, quinolones, quinones, and anthroquinones.

Embodiment 288. The method of Embodiment 287, wherein the at least one activatable pharmaceutical agent is a psoralen, a coumarin, or a derivative thereof.

Embodiment 289. The method of Embodiment 287, wherein the at least one activatable pharmaceutical agent is 8-MOP or AMT.

Embodiment 290. The method of Embodiment 276, wherein the at least one activatable pharmaceutical agent is one selected from 7,8-dimethyl-10-ribityl, isoalloxazine, 7,8,10-trimethylisoalloxazine, 7,8-dimethylalloxazine, isoalloxazine-adenine dinucleotide, alloxazine mononucleotide, aluminum (III) phthalocyanine tetrasulonate, hematoporphyrin, and phthadocyanine.

Embodiment 291. The method of Embodiment 276, wherein the at least one activatable pharmaceutical agent is coupled to a carrier that is capable of binding to a receptor site.

Embodiment 292. The method of Embodiment 291, wherein the carrier is one selected from insulin, interleukin, thymopoietin or transferrin.

Embodiment 293. The method of Embodiment 291, wherein the at least one activatable pharmaceutical agent is coupled to the carrier by a covalent bond.

Embodiment 294. The method of Embodiment 291, wherein the at least one activatable pharmaceutical agent is coupled to the carrier by a non-covalent bond.

Embodiment 295. The method of Embodiment 291, wherein the receptor site is one selected from nucleic acids of nucleated cells, antigenic sites on nucleated cells, or epitopes.

Embodiment 296. The method of Embodiment 276, wherein the at least one activatable pharmaceutical agent has affinity for a target cell.

Embodiment 297. The method of Embodiment 276, wherein the at least one activatable pharmaceutical agent is capable of being preferentially absorbed by a target cell.

Embodiment 298. The method of Embodiment 276, wherein the at least one activatable pharmaceutical agent is a DNA intercalator or a halogenated derivative thereof.

Embodiment 299. The method of Embodiment 276, wherein the at least one activatable pharmaceutical agent is activated by one or more sequential single photon absorption events.

Embodiment 300. A method for treating a cell proliferation disorder in a subject, comprising:
(1) administering to the subject at least one activatable pharmaceutical agent that is capable of effecting a predetermined cellular change when activated and at least one energy emitter of any one of Embodiments 1-105, or at least one energy augmentation structure of any one of Embodiments 106-113, or at least one energy collector of any one of Embodiments 114-127; and
(2) indirectly applying an initiation energy from an initiation energy source to the at least one activatable pharmaceutical agent within the subject,
and wherein the initiation energy interacts with the at least one energy emitter, at least one energy augmentation structure or at least one energy collector and activates the activatable pharmaceutical agent in situ,
thus causing the predetermined cellular change to occur, wherein said predetermined cellular change treats the cell proliferation related disorder.

Embodiment 301. The method of Embodiment 300, wherein said at least one energy emitter is present and wherein said initiation energy is indirectly applied by co-administration of the at least one energy converter.

Embodiment 302. The method of Embodiment 300, wherein said initiation energy is indirectly applied by a chemical energy source.

Embodiment 303. The method of Embodiment 302, wherein said chemical energy source is a member selected from the group consisting of phosphorescent compounds, chemiluminescent compounds, bioluminescent compounds and light emitting enzymes.

Embodiment 304. The method according to Embodiment 300, wherein said predetermined cellular change treats the cell proliferation disorder by causing an increase or decrease in cell proliferation rate of a target cell.

Embodiment 305. The method according to Embodiment 300, wherein the at least one activated pharmaceutical agent causes an auto-vaccine effect in the subject that reacts with a target cell.

Embodiment 306. The method according to Embodiment 300, wherein said at least one energy collector is present and wherein said initiation energy is indirectly applied by co-administration of the at least one energy converter.

Embodiment 307. The method of one of Embodiments 301 or 306, wherein said at least one energy converter is a single energy converter, and is coupled to said at least one activatable pharmaceutical agent.

Embodiment 308. The method of Embodiment 300, wherein the at least one activatable pharmaceutical agent comprises an active agent contained within a photocage, wherein upon exposure to said initiation energy, the photocage disassociates from the active agent, rendering the active agent available.

Embodiment 309. The method of Embodiment 300, wherein the initiation energy source is selected from the group consisting of x-rays, gamma rays, electron beams, phosphorescent compounds, chemiluminescent compounds, bioluminescent compounds, and light emitting enzymes.

Embodiment 310. The method of Embodiment 300, wherein the predetermined cellular change is apoptosis in a target cell.

Embodiment 311. The method of Embodiment 300, wherein the cell proliferation disorder is at least one member selected from the group consisting of cancer, bacterial infection, viral infection, immune rejection response, auto-immune disorders, and aplastic conditions.

Embodiment 312. The method of Embodiment 300, wherein the at least one activatable pharmaceutical agent is a photoactivatable agent.

Embodiment 313. The method of Embodiment 300, wherein the at least one activatable pharmaceutical agent is selected from psoralens, pyrene cholesteryloleate, acridine, porphyrin, fluorescein, rhodamine, 16-diazorcortisone, ethidium, transition metal complexes of bleomycin, transition metal complexes of deglycobleomycin organoplatinum complexes, alloxazines, vitamin Ks, vitamin L, vitamin metabolites, vitamin precursors, naphthoquinones, naphthalenes, naphthols and derivatives thereof having planar molecular conformations, porphyrins, dyes and phenothiazine derivatives, coumarins, quinolones, quinones, and anthroquinones.

Embodiment 314. The method of Embodiment 313, wherein the at least one activatable pharmaceutical agent is a psoralen, a coumarin, or a derivative thereof.

Embodiment 315. The method of Embodiment 313, wherein the at least one activatable pharmaceutical agent is 8-MOP or AMT.

Embodiment 316. The method of Embodiment 300, wherein the at least one activatable pharmaceutical agent is one selected from 7,8-dimethyl-10-ribityl, isoalloxazine, 7,8,10-trimethylisoalloxazine, 7,8-dimethylalloxazine, isoalloxazine-adenine dinucleotide, alloxazine mononucleotide, aluminum (III) phthalocyanine tetrasulonate, hematoporphyrin, and phthadocyanine.

Embodiment 317. The method of Embodiment 300, wherein the at least one activatable pharmaceutical agent is coupled to a carrier that is capable of binding to a receptor site.

Embodiment 318. The method of Embodiment 317, wherein the carrier is one selected from insulin, interleukin, thymopoietin or transferrin.

Embodiment 319. The method of Embodiment 317, wherein the at least one activatable pharmaceutical agent is coupled to the carrier by a covalent bond.

Embodiment 320. The method of Embodiment 317, wherein the at least one activatable pharmaceutical agent is coupled to the carrier by a non-covalent bond.

Embodiment 321. The method of Embodiment 317, wherein the receptor site is one selected from nucleic acids of nucleated cells, antigenic sites on nucleated cells, or epitopes.

Embodiment 322. The method of Embodiment 300, wherein the at least one activatable pharmaceutical agent has affinity for a target cell.

Embodiment 323. The method of Embodiment 300, wherein the at least one activatable pharmaceutical agent is capable of being preferentially absorbed by a target cell.

Embodiment 324. The method of Embodiment 300, wherein the at least one activatable pharmaceutical agent is a DNA intercalator or a halogenated derivative thereof.

Embodiment 325. The method of Embodiment 300, wherein the at least one activatable pharmaceutical agent is activated by one or more sequential single photon absorption events.

Embodiment 326. The method of Embodiment 300, further comprising administering to the subject nanotubes configured to receive and transmit radiowaves, wherein said radiowaves activate the at least one activatable pharmaceutical agent.

Embodiment 327. The method of one of Embodiments 301 or 306, further comprising administering to the subject nanotubes configured to receive and transmit radiowaves, wherein said radiowaves are accepted by said at least one energy converter and transformed into an energy that activates said at least one activatable pharmaceutical agent.

Embodiment 328. A method for causing apoptosis in a subject in vivo, comprising:
(1) administering to the subject at least one pharmaceutical agent that is capable of inducing apoptosis and at least one energy emitter of any one of Embodiments 1-105, or at least one energy augmentation structure of any one of Embodiments 106-113, or at least one energy collector of any one of Embodiments 114-127; and
(2) causing the at least one pharmaceutical agent to induce apoptosis in vivo.

Embodiment 329. The method of Embodiment 328, wherein the at least one pharmaceutical agent is at least one activatable pharmaceutical agent, and said causing step (2) comprises activating the at least one activatable pharmaceutical agent.

Embodiment 330. The method of Embodiment 329, wherein the at least one activatable pharmaceutical agent is a photoactivatable agent.

Embodiment 331. The method of Embodiment 328, wherein the at least one activatable pharmaceutical agent is selected from psoralens, pyrene cholesteryloleate, acridine, porphyrin, fluorescein, rhodamine, 16-diazorcortisone, ethidium, transition metal complexes of bleomycin, transition metal complexes of deglycobleomycin organoplatinum complexes, alloxazines, vitamin Ks, vitamin L, vitamin metabolites, vitamin precursors, naphthoquinones, naphthalenes, naphthols and derivatives thereof having planar molecular conformations, porphyrins, dyes and phenothiazine derivatives, coumarins, quinolones, quinones, and anthroquinones.

Embodiment 332. The method of Embodiment 331, wherein the at least one activatable pharmaceutical agent is a psoralen, a coumarin, or a derivative thereof.

Embodiment 333. The method of Embodiment 329, wherein the at least one activatable pharmaceutical agent is 8-MOP or AMT.

Embodiment 334. The method of Embodiment 329, wherein the at least one activatable pharmaceutical agent is one selected from 7,8-dimethyl-10-ribityl, isoalloxazine, 7,8,10-trimethylisoalloxazine, 7,8-dimethylalloxazine, isoalloxazine-adenine dinucleotide, alloxazine mononucleotide, aluminum (III) phthalocyanine tetrasulonate, hematoporphyrin, and phthadocyanine.

Embodiment 335. The method of Embodiment 329, wherein the at least one activatable pharmaceutical agent is coupled to a carrier that is capable of binding to a receptor site.

Embodiment 336. The method of Embodiment 335, wherein the carrier is one selected from insulin, interleukin, thymopoietin or transferrin.

Embodiment 337. The method of Embodiment 335, wherein the at least one activatable pharmaceutical agent is coupled to the carrier by a covalent bond.

Embodiment 338. The method of Embodiment 335, wherein the at least one activatable pharmaceutical agent is coupled to the carrier by non-covalent bond.

Embodiment 339. The method of Embodiment 335, wherein the receptor site is one selected from nucleic acids of nucleated cells, antigenic sites on nucleated cells, or epitopes.

Embodiment 340. The method of Embodiment 328, wherein the at least one pharmaceutical agent has affinity for a target cell.

Embodiment 341. The method of Embodiment 328, wherein the at least one pharmaceutical agent is capable of being preferentially absorbed by a target cell.

Embodiment 342. The method of Embodiment 328, wherein the at least one pharmaceutical agent further causes an auto-vaccine effect in the subject that reacts with a target cell.

Embodiment 343. The method of Embodiment 328, wherein the at least one pharmaceutical agent is a DNA intercalator or a halogenated derivative thereof.

Embodiment 344. The method of Embodiment 329, wherein said activating comprises applying an initiation energy to the subject, which interacts with the at least one energy emitter, at least one energy augmentation structure or at least one energy collector, then activates the at least one activatable pharmaceutical agent in vivo.

Embodiment 345. The method of Embodiment 344, wherein the at least one energy emitter or at least one energy collector are present.

Embodiment 346. The method of Embodiment 345, wherein said at least one energy converter is a single energy converter, and is coupled to said at least one activatable pharmaceutical agent.

Embodiment 347. The method of Embodiment 346, wherein the at least one activatable pharmaceutical agent is activated by one or more sequential single photon absorption events.

Embodiment 348. The method of Embodiment 301, wherein the at least one activatable pharmaceutical agent comprises an active agent contained within a photocage, wherein upon exposure to said initiation energy source, the photocage disassociates from the active agent, rendering the active agent available.

Embodiment 349. A method for treating a condition, disorder or disease comprising:

administering to a subject in need thereof at least one energy emitter of any one of Embodiments 1-105, or at least one energy augmentation structure of any one of Embodiments 106-113, or at least one energy collector of any one of Embodiments 114-127;

causing a predetermined change to occur in the subject by providing an activation energy sufficient to cause said predetermined change either directly or upon interaction with the at least one energy emitter, at least one energy augmentation structure, or at least one energy collector, wherein the activation energy is generated in-situ in said subject, wherein said predetermined change treats the condition, disorder or disease.

Embodiment 350. The method of Embodiment 349, wherein the activation energy is capable of penetrating human tissue up to about 4 mm.

Embodiment 351. The method of Embodiment 350, wherein the activation energy is generated in-situ in said subject by application of an initiation energy which interacts with the at least one energy emitter, at least one energy augmentation device, or at least one energy collector, and is converted in-situ to said activation energy.

Embodiment 352. The method of Embodiment 349, further comprising, prior to or simultaneously with providing the activation energy, administering to the subject at least one activatable pharmaceutical agent that is activatable by the activation energy after it interacts with the at least one energy emitter, at least one energy augmentation device, or at least one energy collector, and is converted in-situ to said activation energy, wherein upon activation, the at least one activated pharmaceutical agent effects the predetermined change in the subject.

Embodiment 353. The method of Embodiment 349, wherein the predetermined change is a predetermined cellular change.

Embodiment 354. The method of Embodiment 353, wherein said condition, disorder or disease is a cell proliferation disorder and said predetermined cellular change treats the cell proliferation disorder by causing an increase or decrease in cell proliferation rate of a target cell.

Embodiment 355. The method of Embodiment 351, wherein the at least one activated pharmaceutical agent causes an auto-vaccine effect in the subject that reacts with a target cell.

Embodiment 356. The method of Embodiment 351, wherein the at least one energy emitter or at least one energy collector is present.

Embodiment 357. The method of Embodiment 352, wherein the at least one energy emitter or at least one energy collector is present.

Embodiment 358. The method of Embodiment 357, wherein said at least one energy converter is a single energy converter, and is coupled to said at least one activatable pharmaceutical agent.

Embodiment 359. The method of Embodiment 352, wherein the at least one activatable pharmaceutical agent comprises an active agent contained within a photocage, wherein upon exposure to said initiation energy, the photocage disassociates from the active agent, rendering the active agent available.

Embodiment 360. The method of Embodiment 349, wherein the initiation energy source is selected from the group consisting of x-rays, gamma rays, electron beams, phosphorescent compounds, chemiluminescent compounds, bioluminescent compounds, and light emitting enzymes.

Embodiment 361. The method of Embodiment 353, wherein the predetermined cellular change is apoptosis in a target cell.

Embodiment 362. The method of Embodiment 354, wherein the cell proliferation disorder is at least one member selected from the group consisting of cancer, bacterial infection, viral infection, immune rejection response, autoimmune disorders, and aplastic conditions.

Embodiment 363. The method of Embodiment 352, wherein the at least one activatable pharmaceutical agent is a photoactivatable agent.

Embodiment 364. The method of Embodiment 352, wherein the at least one activatable pharmaceutical agent is selected from psoralens, pyrene cholesteryloleate, acridine, porphyrin, fluorescein, rhodamine, 16-diazorcortisone, ethidium, transition metal complexes of bleomycin, transition metal complexes of deglycobleomycin organoplatinum complexes, alloxazines, vitamin Ks, vitamin L, vitamin metabolites, vitamin precursors, naphthoquinones, naphthalenes, naphthols and derivatives thereof having planar molecular conformations, porphyrins, dyes and phenothiazine derivatives, coumarins, quinolones, quinones, and anthroquinones.

Embodiment 365. The method of Embodiment 364, wherein the at least one activatable pharmaceutical agent is a psoralen, a coumarin, or a derivative thereof.

Embodiment 366. The method of Embodiment 364, wherein the at least one activatable pharmaceutical agent is 8-MOP or AMT.

Embodiment 367. The method of Embodiment 352, wherein the at least one activatable pharmaceutical agent is one selected from 7,8-dimethyl-10-ribityl, isoalloxazine, 7,8,10-trimethylisoalloxazine, 7,8-dimethylalloxazine, isoalloxazine-adenine dinucleotide, alloxazine mononucleotide, aluminum (III) phthalocyanine tetrasulonate, hematoporphyrin, and phthadocyanine.

Embodiment 368. The method of Embodiment 352, wherein the at least one activatable pharmaceutical agent is coupled to a carrier that is capable of binding to a receptor site.

Embodiment 369. The method of Embodiment 368, wherein the carrier is one selected from insulin, interleukin, thymopoietin or transferrin.

Embodiment 370. The method of Embodiment 368, wherein the at least one activatable pharmaceutical agent is coupled to the carrier by a covalent bond.

Embodiment 371. The method of Embodiment 368, wherein the at least one activatable pharmaceutical agent is coupled to the carrier by a non-covalent bond.

Embodiment 372. The method of Embodiment 368, wherein the receptor site is one selected from nucleic acids of nucleated cells, antigenic sites on nucleated cells, or epitopes.

Embodiment 373. The method of Embodiment 352, wherein the at least one activatable pharmaceutical agent has affinity for a target cell.

Embodiment 374. The method of Embodiment 352, wherein the at least one activatable pharmaceutical agent is capable of being preferentially absorbed by a target cell.

Embodiment 375. The method of Embodiment 352, wherein the at least one activatable pharmaceutical agent is a DNA intercalator or a halogenated derivative thereof.

Embodiment 376. The method of Embodiment 352, wherein the at least one activatable pharmaceutical agent is activated by one or more sequential single photon absorption events.

Embodiment 377. The method of Embodiment 352, wherein the at least one activatable pharmaceutical agent comprises an active agent contained within a photocage, and said activation energy is UV-A or visible energy, wherein upon exposure to said UV-A or visible energy, the photocage disassociates from the active agent, rendering the active agent available.

Embodiment 378. The method of Embodiment 351, wherein the initiation energy is one of electromagnetic energy, acoustic energy, or thermal energy.

Embodiment 379. The method of Embodiment 358, wherein, when there is no activatable pharmaceutical agent present and said initiation energy is x-ray, said activation energy is an energy other than UV.

Embodiment 380. The method of Embodiment 356, wherein the at least one energy converter is one or more selected from a biocompatible fluorescing metal nanoparticle, fluorescing dye molecule, gold nanoparticle, a water soluble quantum dot encapsulated by polyamidoamine dendrimers, a luciferase, a biocompatible phosphorescent molecule, a combined electromagnetic energy harvester molecule, and a lanthanide chelate capable of intense luminescence.

Embodiment 381. The method of Embodiment 357, wherein the at least one energy converter is one or more selected from a biocompatible fluorescing metal nanoparticle, fluorescing dye molecule, gold nanoparticle, a water soluble quantum dot encapsulated by polyamidoamine dendrimers, a luciferase, a biocompatible phosphorescent molecule, a combined electromagnetic energy harvester molecule, and a lanthanide chelate capable of intense luminescence.

Numerous modifications and variations of the invention are possible in light of the above teachings. It is therefore to be understood that within the scope of the appended claims, the invention may be practiced otherwise than as specifically described herein.

The invention claimed is:

1. A method for treating a cell proliferation disorder in a subject, comprising:
  (1) administering to the subject at least one activatable pharmaceutical agent that is capable of effecting a predetermined cellular change when activated and at least one energy augmentation structure capable of capturing one or more wavelengths of electromagnetic energy, and augmenting the one or more wavelengths of electromagnetic energy in at least one property; and
  (2) applying an initiation energy from an initiation energy source to the subject, wherein the initiation energy is capable of penetrating completely through the subject, and wherein the applied initiation energy interacts with the at least one energy augmentation structure and activates the activatable agent in situ,
  thus causing the predetermined cellular change to occur, wherein said predetermined cellular change treats the cell proliferation related disorder.

2. A method for treating a cell proliferation disorder in a subject, comprising:
  (1) administering to the subject at least one (i) energy emitter or (ii) energy collector, and at least one activatable pharmaceutical agent that is capable of effecting a predetermined cellular change when activated;
  wherein the (i) energy emitter, when present, comprises at least one energy augmentation structure capable of capturing one or more wavelengths of electromagnetic energy, and augmenting the one or more wavelengths of electromagnetic energy in at least one property; and an energy converter capable of receiving energy from an energy source, converting the energy and emitting therefrom an emitted light of a higher or lower energy than the received energy, and the energy converter being disposed in a vicinity of the at least one energy augmentation structure such that the emitted light is emitted with an intensity larger than if the energy converter were remote from the at least one energy augmentation structure, or if the energy augmentation structure were not present;
  wherein the (ii) energy collector, when present, comprises at least one energy augmentation structure; and at least one energy converter capable of receiving an applied electromagnetic energy, converting the applied electromagnetic energy and emitting therefrom an emitted electromagnetic energy shifted in wavelength or energy from the applied electromagnetic energy and the energy converter being disposed in a vicinity of the at least one energy augmentation structure such that the emitted electromagnetic energy is emitted with at least one augmented property compared to if the energy converter were remote from the at least one energy augmentation structure; and
  (2) applying an initiation energy from an initiation energy source to the subject, wherein the energy converter in the at least one energy emitter or at least one energy collector converts the applied initiation energy to UV-A or visible energy, which then activates the activatable agent in situ, wherein the energy converter is disposed in a vicinity of the at least one energy augmentation structure such that the emitted UV-A or visible energy is emitted with an intensity larger than if the energy converter were remote from the at least one energy augmentation structure, or if the energy augmentation structure were not present
  thus causing the predetermined cellular change to occur, wherein said predetermined cellular change treats the cell proliferation related disorder.

3. A method for treating a cell proliferation disorder in a subject, comprising:
  (1) administering to the subject at least one activatable pharmaceutical agent that is capable of effecting a predetermined cellular change when activated, and at least one (i) energy emitter, (ii) energy augmentation structure, or (iii) energy collector, wherein:
  the at least one (i) energy emitter, when present, comprises at least one energy augmentation structure capable of capturing one or more wavelengths of electromagnetic energy, and augmenting the one or more wavelengths of electromagnetic energy in at least one property; and an energy converter capable of receiving energy from an energy source, converting the energy and emitting therefrom an emitted light of a higher or lower energy than the received energy, and the energy converter being disposed in a vicinity of the at least one energy augmentation structure such that the emitted light is emitted with an intensity larger than if the energy converter were remote from the at least one energy augmentation structure, or if the energy augmentation structure were not present;
  the at least one (ii) energy augmentation structure, when present, is capable of capturing one or more wavelengths of electromagnetic energy, and augmenting the one or more wavelengths of electromagnetic energy in at least one property;

the at least one (iii) energy collector, when present, comprises at least one energy augmentation structure capable of capturing one or more wavelengths of electromagnetic energy, and augmenting the one or more wavelengths of electromagnetic energy in at least one property; and at least one energy converter capable of receiving an applied electromagnetic energy, converting the applied electromagnetic energy and emitting therefrom an emitted electromagnetic energy shifted in wavelength or energy from the applied electromagnetic energy and the energy converter being disposed in a vicinity of the at least one energy augmentation structure such that the emitted electromagnetic energy is emitted with at least one augmented property compared to if the energy converter were remote from the at least one energy augmentation structure; and (2) applying an initiation energy from an initiation energy source to the subject, wherein the initiation energy applied and activatable pharmaceutical agent upon activation produce insufficient singlet oxygen in the subject to produce cell lysis, and wherein the initiation energy interacts with the at least one (i) energy emitter, (ii) energy augmentation structure, or (iii) energy collector, and activates the activatable pharmaceutical agent in situ, thus causing the predetermined cellular change to occur, wherein said predetermined cellular change treats the cell proliferation related disorder.

4. A method for treating a cell proliferation disorder in a subject, comprising:
(1) modifying one or more cells to incorporate a photon emitting modification or substance;
(2) inserting the modified cells at a targeted site of the subject; and administering at least one (i) energy emitter, (ii) energy augmentation structure, or (iii) energy collector, and at least one activatable pharmaceutical agent capable of being activated by the photons emitted from the modified cells after interaction of the photons with the energy emitter, the energy augmentation structure, or the energy collector, to cause a predetermined cellular change, wherein:
the at least one (i) energy emitter, when present, comprises at least one energy augmentation structure capable of capturing one or more wavelengths of electromagnetic energy, and augmenting the one or more wavelengths of electromagnetic energy in at least one property; and an energy converter capable of receiving energy from an energy source, converting the energy and emitting therefrom an emitted light of a higher or lower energy than the received energy, and the energy converter being disposed in a vicinity of the at least one energy augmentation structure such that the emitted light is emitted with an intensity larger than if the energy converter were remote from the at least one energy augmentation structure, or if the energy augmentation structure were not present;
the at least one (ii) energy augmentation structure, when present, is capable of capturing one or more wavelengths of electromagnetic energy, and augmenting the one or more wavelengths of electromagnetic energy in at least one property;
the at least one (iii) energy collector, when present, comprises at least one energy augmentation structure capable of capturing one or more wavelengths of electromagnetic energy, and augmenting the one or more wavelengths of electromagnetic energy in at least one property; and at least one energy converter capable of receiving an applied electromagnetic energy, converting the applied electromagnetic energy and emitting therefrom an emitted electromagnetic energy shifted in wavelength or energy from the applied electromagnetic energy and the energy converter being disposed in a vicinity of the at least one energy augmentation structure such that the emitted electromagnetic energy is emitted with at least one augmented property compared to if the energy converter were remote from the at least one energy augmentation structure.

5. A method for generating an autovaccine for a subject, comprising:
(1) providing a population of target cells;
(2) treating the target cells ex vivo in an environment separate and isolated from the subject with a psoralen or a derivative thereof;
(3) activating the psoralen or the derivative thereof with an UV-A source, in the presence of at least one (i) energy emitter, (ii) energy augmentation structure, or (iii) energy collector, to induce a predetermined cellular change in the target cells, wherein:
the at least one (i) energy emitter, when present, comprises at least one energy augmentation structure capable of capturing one or more wavelengths of electromagnetic energy, and augmenting the one or more wavelengths of electromagnetic energy in at least one property; and an energy converter capable of receiving energy from an energy source, converting the energy and emitting therefrom an emitted light of a higher or lower energy than the received energy, and the energy converter being disposed in a vicinity of the at least one energy augmentation structure such that the emitted light is emitted with an intensity larger than if the energy converter were remote from the at least one energy augmentation structure, or if the energy augmentation structure were not present;
the at least one (ii) energy augmentation structure, when present, is capable of capturing one or more wavelengths of electromagnetic energy, and augmenting the one or more wavelengths of electromagnetic energy in at least one property;
the at least one (iii) energy collector, when present, comprises at least one energy augmentation structure capable of capturing one or more wavelengths of electromagnetic energy, and augmenting the one or more wavelengths of electromagnetic energy in at least one property; and at least one energy converter capable of receiving an applied electromagnetic energy, converting the applied electromagnetic energy and emitting therefrom an emitted electromagnetic energy shifted in wavelength or energy from the applied electromagnetic energy and the energy converter being disposed in a vicinity of the at least one energy augmentation structure such that the emitted electromagnetic energy is emitted with at least one augmented property compared to if the energy converter were remote from the at least one energy augmentation structure;
(4) returning the thus changed cells back to the subject to induce in the subject an autovaccine effect against the target cell, wherein the changed cells act as an autovaccine.

6. A system for producing an auto-vaccine in a subject, comprising:
- at least one activatable pharmaceutical agent capable of inducing a predetermined cellular change in a target cell in said subject;
- at least one (i) energy emitter, (ii) energy augmentation structure, or (iii) energy collector, wherein:
- the at least one (i) energy emitter, when present, comprises at least one energy augmentation structure capable of capturing one or more wavelengths of electromagnetic energy, and augmenting the one or more wavelengths of electromagnetic energy in at least one property; and an energy converter capable of receiving energy from an energy source, converting the energy and emitting therefrom an emitted light of a higher or lower energy than the received energy, and the energy converter being disposed in a vicinity of the at least one energy augmentation structure such that the emitted light is emitted with an intensity larger than if the energy converter were remote from the at least one energy augmentation structure, or if the energy augmentation structure were not present;
- the at least one (ii) energy augmentation structure, when present, is capable of capturing one or more wavelengths of electromagnetic energy, and augmenting the one or more wavelengths of electromagnetic energy in at least one property;
- the at least one (iii) energy collector, when present, comprises at least one energy augmentation structure capable of capturing one or more wavelengths of electromagnetic energy, and augmenting the one or more wavelengths of electromagnetic energy in at least one property; and at least one energy converter capable of receiving an applied electromagnetic energy, converting the applied electromagnetic energy and emitting therefrom an emitted electromagnetic energy shifted in wavelength or energy from the applied electromagnetic energy and the energy converter being disposed in a vicinity of the at least one energy augmentation structure such that the emitted electromagnetic energy is emitted with at least one augmented property compared to if the energy converter were remote from the at least one energy augmentation structure;
- means for placing said at least one activatable pharmaceutical agent and said at least one (i) energy emitter, (ii) energy augmentation structure, or (iii) energy collector in said subject; and
- an initiation energy source to provide initiation energy capable, after interacting with the at least one (i) energy emitter, (ii) energy augmentation structure, or (iii) energy collector, of activating the at least one activatable pharmaceutical agent in said target cell, wherein activation is either direct or indirect.

7. A kit for performing a cell proliferation disorder treatment, comprising:
- at least one activatable pharmaceutical agent capable of causing a predetermined cellular change
- at least one (i) energy emitter, (ii) energy augmentation structure, or (iii) energy collector, wherein:
- the at least one (i) energy emitter, when present, comprises at least one energy augmentation structure capable of capturing one or more wavelengths of electromagnetic energy, and augmenting the one or more wavelengths of electromagnetic energy in at least one property; and an energy converter capable of receiving energy from an energy source, converting the energy and emitting therefrom an emitted light of a higher or lower energy than the received energy, and the energy converter being disposed in a vicinity of the at least one energy augmentation structure such that the emitted light is emitted with an intensity larger than if the energy converter were remote from the at least one energy augmentation structure, or if the energy augmentation structure were not present;
- the at least one (ii) energy augmentation structure, when present, is capable of capturing one or more wavelengths of electromagnetic energy, and augmenting the one or more wavelengths of electromagnetic energy in at least one property;
- the at least one (iii) energy collector, when present, comprises at least one energy augmentation structure capable of capturing one or more wavelengths of electromagnetic energy, and augmenting the one or more wavelengths of electromagnetic energy in at least one property; and at least one energy converter capable of receiving an applied electromagnetic energy, converting the applied electromagnetic energy and emitting therefrom an emitted electromagnetic energy shifted in wavelength or energy from the applied electromagnetic energy and the energy converter being disposed in a vicinity of the at least one energy augmentation structure such that the emitted electromagnetic energy is emitted with at least one augmented property compared to if the energy converter were remote from the at least one energy augmentation structure; and
- containers suitable for storing the agents in stable form.

8. A pharmaceutical composition for treating a cell proliferation disorder, comprising:
- at least one activatable pharmaceutical agent capable of causing a predetermined cellular change;
- at least one (i) energy emitter or (ii) energy collector, wherein:
- the at least one (i) energy emitter, when present, comprises at least one energy augmentation structure capable of capturing one or more wavelengths of electromagnetic energy, and augmenting the one or more wavelengths of electromagnetic energy in at least one property; and an energy converter capable of receiving energy from an energy source, converting the energy and emitting therefrom an emitted light of a higher or lower energy than the received energy, and the energy converter being disposed in a vicinity of the at least one energy augmentation structure such that the emitted light is emitted with an intensity larger than if the energy converter were remote from the at least one energy augmentation structure, or if the energy augmentation structure were not present;
- the at least one (ii) energy collector, when present, comprises at least one energy augmentation structure capable of capturing one or more wavelengths of electromagnetic energy, and augmenting the one or more wavelengths of electromagnetic energy in at least one property; and at least one energy converter capable of receiving an applied electromagnetic energy, converting the applied electromagnetic energy and emitting therefrom an emitted electromagnetic energy shifted in wavelength or energy from the applied electromagnetic energy and the energy converter being disposed in a vicinity of the at least one energy augmentation structure such that the emitted electromagnetic energy is emitted with at least one augmented property compared to if the energy converter were remote from the at least one energy augmentation structure;

optionally, at least one additive having a complementary therapeutic or diagnostic effect, wherein said additive is at least one member selected from the group consisting of antioxidants, adjuvants, chemical energy sources, and combinations thereof; and a pharmaceutically acceptable carrier.

9. A method for treating a cell proliferation disorder in a subject, comprising:
(1) administering to the subject at least one activatable pharmaceutical agent that is capable of effecting a predetermined cellular change when activated and at least one (i) energy emitter, or (ii) energy augmentation structure, or (iii) energy collector, wherein:
the at least one (i) energy emitter, when present, comprises at least one energy augmentation structure capable of capturing one or more wavelengths of electromagnetic energy, and augmenting the one or more wavelengths of electromagnetic energy in at least one property; and an energy converter capable of receiving energy from an energy source, converting the energy and emitting therefrom an emitted light of a higher or lower energy than the received energy, and the energy converter being disposed in a vicinity of the at least one energy augmentation structure such that the emitted light is emitted with an intensity larger than if the energy converter were remote from the at least one energy augmentation structure, or if the energy augmentation structure were not present;
the at least one (ii) energy augmentation structure, when present, is capable of capturing one or more wavelengths of electromagnetic energy, and augmenting the one or more wavelengths of electromagnetic energy in at least one property;
the at least one (iii) energy collector, when present, comprises at least one energy augmentation structure capable of capturing one or more wavelengths of electromagnetic energy, and augmenting the one or more wavelengths of electromagnetic energy in at least one property; and at least one energy converter capable of receiving an applied electromagnetic energy, converting the applied electromagnetic energy and emitting therefrom an emitted electromagnetic energy shifted in wavelength or energy from the applied electromagnetic energy and the energy converter being disposed in a vicinity of the at least one energy augmentation structure such that the emitted electromagnetic energy is emitted with at least one augmented property compared to if the energy converter were remote from the at least one energy augmentation structure; and
(2) administering an initiation energy source to the subject,
wherein the initiation energy source interacts with the at least one (i) energy emitter, (ii) energy augmentation structure, or (iii) energy collector and produces an initiation energy that activates the activatable pharmaceutical agent in situ,
thus causing the predetermined cellular change to occur, wherein said predetermined cellular change treats the cell proliferation related disorder.

10. A method for treating a cell proliferation disorder in a subject, comprising:
(1) administering to the subject at least one activatable pharmaceutical agent that is capable of effecting a predetermined cellular change when activated and at least one (i) energy emitter, (ii) energy augmentation structure, or (iii) energy collector, wherein: the at least one (i) energy emitter, when present, comprises at least one energy augmentation structure capable of capturing one or more wavelengths of electromagnetic energy, and augmenting the one or more wavelengths of electromagnetic energy in at least one property; and an energy converter capable of receiving energy from an energy source, converting the energy and emitting therefrom an emitted light of a higher or lower energy than the received energy, and the energy converter being disposed in a vicinity of the at least one energy augmentation structure such that the emitted light is emitted with an intensity larger than if the energy converter were remote from the at least one energy augmentation structure, or if the energy augmentation structure were not present;
the at least one (ii) energy augmentation structure, when present, is capable of capturing one or more wavelengths of electromagnetic energy, and augmenting the one or more wavelengths of electromagnetic energy in at least one property;
the at least one (iii) energy collector, when present, comprises at least one energy augmentation structure capable of capturing one or more wavelengths of electromagnetic energy, and augmenting the one or more wavelengths of electromagnetic energy in at least one property; and at least one energy converter capable of receiving an applied electromagnetic energy, converting the applied electromagnetic energy and emitting therefrom an emitted electromagnetic energy shifted in wavelength or energy from the applied electromagnetic energy and the energy converter being disposed in a vicinity of the at least one energy augmentation structure such that the emitted electromagnetic energy is emitted with at least one augmented property compared to if the energy converter were remote from the at least one energy augmentation structure; and
(2) indirectly applying an initiation energy from an initiation energy source to the at least one activatable pharmaceutical agent within the subject,
and wherein the initiation energy interacts with the at least one energy emitter, at least one energy augmentation structure or at least one energy collector and activates the activatable pharmaceutical agent in situ,
thus causing the predetermined cellular change to occur, wherein said predetermined cellular change treats the cell proliferation related disorder.

11. A method for causing apoptosis in a subject in vivo, comprising:
(1) administering to the subject at least one pharmaceutical agent that is capable of inducing apoptosis and at least one (i) energy emitter, (ii) energy augmentation structure, or (iii) energy collector, wherein:
the at least one (i) energy emitter, when present, comprises at least one energy augmentation structure capable of capturing one or more wavelengths of electromagnetic energy, and augmenting the one or more wavelengths of electromagnetic energy in at least one property; and an energy converter capable of receiving energy from an energy source, converting the energy and emitting therefrom an emitted light of a higher or lower energy than the received energy, and the energy converter being disposed in a vicinity of the at least one energy augmentation structure such that the emitted light is emitted with an intensity larger than if the energy converter were remote from the at least one energy augmentation structure, or if the energy augmentation structure were not present;

the at least one (ii) energy augmentation structure, when present, is capable of capturing one or more wavelengths of electromagnetic energy, and augmenting the one or more wavelengths of electromagnetic energy in at least one property;

the at least one (iii) energy collector, when present, comprises at least one energy augmentation structure capable of capturing one or more wavelengths of electromagnetic energy, and augmenting the one or more wavelengths of electromagnetic energy in at least one property; and at least one energy converter capable of receiving an applied electromagnetic energy, converting the applied electromagnetic energy and emitting therefrom an emitted electromagnetic energy shifted in wavelength or energy from the applied electromagnetic energy and the energy converter being disposed in a vicinity of the at least one energy augmentation structure such that the emitted electromagnetic energy is emitted with at least one augmented property compared to if the energy converter were remote from the at least one energy augmentation structure; and (2) causing the at least one pharmaceutical agent to induce apoptosis in vivo.

12. A method for treating a condition, disorder or disease comprising:

administering to a subject in need thereof at least one (i) energy emitter, (ii) energy augmentation structure, or (iii) energy collector, wherein:

the at least one (i) energy emitter, when present, comprises at least one energy augmentation structure capable of capturing one or more wavelengths of electromagnetic energy, and augmenting the one or more wavelengths of electromagnetic energy in at least one property; and an energy converter capable of receiving energy from an energy source, converting the energy and emitting therefrom an emitted light of a higher or lower energy than the received energy, and the energy converter being disposed in a vicinity of the at least one energy augmentation structure such that the emitted light is emitted with an intensity larger than if the energy converter were remote from the at least one energy augmentation structure, or if the energy augmentation structure were not present;

the at least one (ii) energy augmentation structure, when present, is capable of capturing one or more wavelengths of electromagnetic energy, and augmenting the one or more wavelengths of electromagnetic energy in at least one property;

the at least one (iii) energy collector, when present, comprises at least one energy augmentation structure capable of capturing one or more wavelengths of electromagnetic energy, and augmenting the one or more wavelengths of electromagnetic energy in at least one property; and at least one energy converter capable of receiving an applied electromagnetic energy, converting the applied electromagnetic energy and emitting therefrom an emitted electromagnetic energy shifted in wavelength or energy from the applied electromagnetic energy and the energy converter being disposed in a vicinity of the at least one energy augmentation structure such that the emitted electromagnetic energy is emitted with at least one augmented property compared to if the energy converter were remote from the at least one energy augmentation structure; and causing a predetermined change to occur in the subject by providing an activation energy sufficient to cause said predetermined change either directly or upon interaction with the at least one (i) energy emitter, (ii) energy augmentation structure, or (iii) energy collector, wherein the activation energy is generated in-situ in said subject, wherein said predetermined change treats the condition, disorder or disease.

13. The method of claim 1, wherein the initiation energy source is x-rays, gamma rays, an electron beam, microwaves or radio waves.

14. The method of claim 1, wherein the cell proliferation disorder is at least one member selected from the group consisting of cancer, bacterial infection, viral infection, immune rejection response, autoimmune disorders, aplastic conditions, and combinations thereof.

15. The method of claim 1, wherein:
(i) the at least one activatable pharmaceutical agent is a photoactivatable agent; or
(ii) the at least one activatable pharmaceutical agent is selected from psoralens, pyrene cholesteryloleate, acridine, porphyrin, fluorescein, rhodamine, 16-diazorcortisone, ethidium, transition metal complexes of bleomycin, transition metal complexes of deglycobleomycin organoplatinum complexes, alloxazines, vitamin Ks, vitamin L, vitamin metabolites, vitamin precursors, naphthoquinones, naphthalenes, naphthols and derivatives thereof having planar molecular conformations, porphyrins, dyes and phenothiazine derivatives, coumarins, quinolones, quinones, and anthroquinones; or
(iii) the at least one activatable pharmaceutical agent is one selected from 7,8-dimethyl-10-ribityl, isoalloxazine, 7,8,10-trimethylisoalloxazine, 7,8-dimethylalloxazine, isoalloxazine-adenine dinucleotide, alloxazine mononucleotide, aluminum (III) phthalocyanine tetrasulonate, hematoporphyrin, and phthadocyanine; or
(iv) the at least one activatable pharmaceutical agent is coupled to a carrier that is capable of binding to a receptor site; or
(v) the at least one activatable pharmaceutical agent has affinity for a target cell; or
(vi) the at least one activatable pharmaceutical agent is capable of being preferentially absorbed by a target cell; or
(vii) the at least one activatable pharmaceutical agent is a DNA intercalator or a halogenated derivative thereof; or
(viii) the at least one activatable pharmaceutical agent is activated by one or more sequential single photon absorption events; or
(ix) the at least one activatable pharmaceutical agent comprises an active agent contained within a photocage, wherein upon exposure to said initiation energy source, the photocage disassociates from the active agent, rendering the active agent available.

16. The method of claim 1, wherein the at least one activatable pharmaceutical agent is a psoralen, a coumarin, or a derivative thereof.

17. The method of claim 1, wherein the at least one activatable pharmaceutical agent is 8-MOP or AMT.

18. The method of claim 1, wherein the at least one activated pharmaceutical agent causes an auto-vaccine effect in the subject that reacts with a target cell.

19. The method of claim 1, wherein the at least one energy emitter or at least one energy collector is present.

20. The method of claim 19, wherein said at least one energy converter is a single energy converter, and is coupled to said at least one activatable pharmaceutical agent.

21. The method of claim 1, wherein the predetermined cellular change is:
(i) apoptosis in a target cell; or
(ii) treats the cell proliferation disorder by causing an increase or decrease in cell proliferation rate of a target cell.

22. The method of claim 1, wherein the at least one energy augmentation structure comprises a structure in which a locally intensified electric field exists in one part of the structure when the structure receives electromagnetic energy.

23. The method of claim 22, wherein the at least one energy augmentation structure comprises at least one resonator dimensioned to be resonant with the applied electromagnetic energy.

24. The method of claim 23, wherein the resonator comprises a folded resonator, wherein the folded resonator comprises:
(i) electrical conductors configured as a fractal pattern; or
(ii) a ¾ wavelength resonator having opposing ends folded inwards from a center of the folded resonator with a gap in between the opposing ends; or
(iii) a ¾ wavelength resonator having opposing ends folded outwards from a center of the folded resonator with a gap in between the opposing ends.

25. The method of claim 2, wherein the at least one (i) energy emitter is present.

26. The method of claim 2, wherein the at least one (i) energy collector is present.

27. The method of claim 2, wherein said predetermined cellular change:
(i) treats the cell proliferation disorder by causing an increase or decrease in cell proliferation rate of a target cell; or
(ii) the predetermined cellular change is apoptosis in a target cell.

28. The method of claim 2, wherein the at least one energy converter is one or more selected from a biocompatible fluorescing metal nanoparticle, fluorescing dye molecule, gold nanoparticle, a water soluble quantum dot encapsulated by polyamidoamine dendrimers, a luciferase, a biocompatible phosphorescent molecule, a combined electromagnetic energy harvester molecule, and a lanthanide chelate capable of intense luminescence.

29. The method of claim 2, wherein the initiation energy source is a source of higher energy than the resulting UV-A or visible energy.

30. The method of claim 2, wherein the initiation energy source is a source of lower energy than the resulting UV-A or visible energy.

31. The method of claim 2, wherein the initiation energy is applied via a thin fiber optic.

32. The method of claim 2, wherein the cell proliferation disorder is at least one member selected from the group consisting of cancer, bacterial infection, viral infection, immune rejection response, autoimmune disorders, aplastic conditions, and combinations thereof.

33. The method of claim 2, wherein:
(i) the at least one activatable pharmaceutical agent is a photoactivatable agent; or
(ii) the at least one activatable pharmaceutical agent is selected from psoralens, pyrene cholesteryloleate, acridine, porphyrin, fluorescein, rhodamine, 16-diazorcortisone, ethidium, transition metal complexes of bleomycin, transition metal complexes of deglycobleomycin organoplatinum complexes, alloxazines, vitamin Ks, vitamin L, vitamin metabolites, vitamin precursors, naphthoquinones, naphthalenes, naphthols and derivatives thereof having planar molecular conformations, porphyrins, dyes and phenothiazine derivatives, coumarins, quinolones, quinones, and anthroquinones; or
(iii) the at least one activatable pharmaceutical agent is one selected from 7,8-dimethyl-10-ribityl, isoalloxazine, 7,8,10-trimethylisoalloxazine, 7,8-dimethylalloxazine, isoalloxazine-adenine dinucleotide, alloxazine mononucleotide, aluminum (phthalocyanine tetrasulonate, hematoporphyrin, and phthadocyanine; or
(iv) the at least one activatable pharmaceutical agent is coupled to a carrier that is capable of binding to a receptor site; or
(v) the at least one activatable pharmaceutical agent has affinity for a target cell; or
(vi) the at least one activatable pharmaceutical agent is capable of being preferentially absorbed by a target cell; or
(vii) the at least one activatable pharmaceutical agent is a DNA intercalator or a halogenated derivative thereof; or
(viii) the at least one activatable pharmaceutical agent comprises an active agent contained within a photocage, wherein upon exposure to said UV-A or visible energy, the photocage disassociates from the active agent, rendering the active agent available; or
(ix) the at least one activatable pharmaceutical agent is activated by one or more sequential single photon absorption events.

34. The method of claim 2, wherein the at least one activatable pharmaceutical agent is a psoralen, a coumarin, or a derivative thereof.

35. The method of claim 2, wherein the at least one activatable pharmaceutical agent is 8-MOP or AMT.

36. The method of claim 2, wherein the at least one activated pharmaceutical agent causes an auto-vaccine effect in the subject that reacts with a targets cell.

37. The method of claim 2, wherein the initiation energy is one of electromagnetic energy, acoustic energy, or thermal energy.

38. The method of claim 2, further comprising a blocking agent, wherein the blocking agent is capable of blocking uptake of the at least one activatable pharmaceutical agent prior to its activation.

39. The method of claim 38, wherein the blocking agent is capable of slowing down mitosis in non-target cells while allowing target cells to maintain an abnormal rate of mitosis.

40. The method of claim 2, wherein said at least one energy converter is a single energy converter, and is coupled to said at least one activatable pharmaceutical agent.

41. The method of claim 2, wherein the at least one energy augmentation structure comprises a structure in which a locally intensified electric field exists in one part of the structure when the structure receives electromagnetic energy.

42. The method of claim 41, wherein the at least one energy augmentation structure comprises at least one resonator dimensioned to be resonant with the applied electromagnetic energy.

43. The method of claim 42, wherein the resonator comprises a folded resonator, wherein the folded resonator comprises:
(i) electrical conductors configured as a fractal pattern; or
(ii) a ¾ wavelength resonator having opposing ends folded inwards from a center of the folded resonator with a gap in between the opposing ends; or
(iii) a ¾ wavelength resonator having opposing ends folded outwards from a center of the folded resonator with a gap in between the opposing ends.

44. The method according to claim 3, wherein said predetermined cellular change treats the cell proliferation disorder by causing an increase or decrease in cell proliferation rate of a target cell.

45. The method according to claim 3, wherein the amount of singlet oxygen production is:
(i) less than 109 singlet oxygen molecules/cell; or
(ii) less than 0.32×10-3 mol/liter.

46. The method according to claim 3, wherein the at least one activated pharmaceutical agent causes an auto-vaccine effect in the subject that reacts with a target cell.

47. The method according to claim 3, wherein the at least one energy emitter or at least one energy collector is present.

48. The method of claim 47, wherein said at least one energy converter is a single energy converter, and is coupled to said at least one activatable pharmaceutical agent.

49. The method of claim 3, wherein the initiation energy source is selected from the group consisting of x-rays, gamma rays, electron beams, phosphorescent compounds, chemiluminescent compounds, bioluminescent compounds, and light emitting enzymes.

50. The method of claim 3, wherein the predetermined cellular change is apoptosis in a target cell.

51. The method of claim 3, wherein the cell proliferation disorder is at least one member selected from the group consisting of cancer, bacterial infection, viral infection, immune rejection response, autoimmune disorders, and aplastic conditions.

52. The method of claim 3, wherein:
(i) the at least one activatable pharmaceutical agent is a photoactivatable agent; or
(ii) the at least one activatable pharmaceutical agent is selected from psoralens, pyrene cholesteryloleate, acridine, porphyrin, fluorescein, rhodamine, 16-diazorcortisone, ethidium, transition metal complexes of bleomycin, transition metal complexes of deglycobleomycin organoplatinum complexes, alloxazines, vitamin Ks, vitamin L, vitamin metabolites, vitamin precursors, naphthoquinones, naphthalenes, naphthols and derivatives thereof having planar molecular conformations, porphyrins, dyes and phenothiazine derivatives, coumarins, quinolones, quinones, and anthroquinones; or
(iii) the at least one activatable pharmaceutical agent is one selected from 7,8-dimethyl-10-ribityl, isoalloxazine, 7,8,10-trimethylisoalloxazine, 7,8-dimethylalloxazine, isoalloxazine-adenine dinucleotide, alloxazine mononucleotide, aluminum (III) phthalocyanine tetrasulonate, hematoporphyrin, and phthadocyanine; or
(iv) the at least one activatable pharmaceutical agent is coupled to a carrier that is capable of binding to a receptor site; or
(v) the at least one activatable pharmaceutical agent has affinity for a target cell; or
(vi) the at least one activatable pharmaceutical agent is capable of being preferentially absorbed by a target cell; or
(vii) the at least one activatable pharmaceutical agent is a DNA intercalator or a halogenated derivative thereof; or
(viii) the at least one activatable pharmaceutical agent is activated by one or more sequential single photon absorption events; or
(ix) the at least one activatable pharmaceutical agent comprises an active agent contained within a photocage, wherein upon exposure to said initiation energy, the photocage disassociates from the active agent, rendering the active agent available.

53. The method of claim 3, wherein the at least one activatable pharmaceutical agent is a psoralen, a coumarin, or a derivative thereof.

54. The method of claim 3, wherein the at least one activatable pharmaceutical agent is 8-MOP or AMT.

55. The method of claim 3, wherein the at least one energy augmentation structure comprises a structure in which a locally intensified electric field exists in one part of the structure when the structure receives electromagnetic energy.

56. The method of claim 55, wherein the at least one energy augmentation structure comprises at least one resonator dimensioned to be resonant with the applied electromagnetic energy.

57. The method of claim 56, wherein the resonator comprises a folded resonator, wherein the folded resonator comprises:
(i) electrical conductors configured as a fractal pattern; or
(ii) a ¾ wavelength resonator having opposing ends folded inwards from a center of the folded resonator with a gap in between the opposing ends; or
(iii) a ¾ wavelength resonator having opposing ends folded outwards from a center of the folded resonator with a gap in between the opposing ends.

58. The method of claim 4, wherein:
(i) said one or more cells are subject's own cells that have been removed prior to said modifying; or
(ii) the photon emitting modification or substance is a member selected from the group consisting of light emitting genes; phosphorescent compounds, chemiluminescent compounds, bioluminescent compounds and light emitting enzymes; or
(iii) the targeted site is a tumor; or
(iv) the at least one activatable pharmaceutical agent, upon activation, causes an auto-vaccine effect in the subject that reacts with a target cell; or
(v) the predetermined cellular change is apoptosis in a target cell; or
(vi) the at least one (i) energy emitter is present; or
(vii) the at least one (ii) energy augmentation structure is present; or
(viii) the at least one (iii) energy collector is present.

59. The method of claim 4, wherein the at least one energy augmentation structure comprises a structure in which a locally intensified electric field exists in one part of the structure when the structure receives electromagnetic energy.

60. The method of claim 59, wherein the at least one energy augmentation structure comprises at least one resonator dimensioned to be resonant with the applied electromagnetic energy.

61. The method of claim 60, wherein the resonator comprises a folded resonator, wherein the folded resonator comprises:
(i) electrical conductors configured as a fractal pattern; or
(ii) a ¾ wavelength resonator having opposing ends folded inwards from a center of the folded resonator with a gap in between the opposing ends; or
(ii) a ¾ wavelength resonator having opposing ends folded outwards from a center of the folded resonator with a gap in between the opposing ends.

62. The method of claim 5, wherein the psoralen is 8-MOP.

63. The method of claim 5, further comprising:
fractionating the apoptic cells and testing the fractions for auto-vaccine effect of each isolated component to determine the component(s) associated with auto-vaccine before returning components to the subject.

64. The method of claim 5, wherein the predetermined cellular change is apoptosis in a target cell affected by the cell proliferation disorder.

65. The method of claim 5, wherein the at least one (i) energy emitter is present.

66. The method of claim 5, wherein the at least one (ii) energy augmentation structure is present.

67. The method of claim 5, wherein the at least one (iii) energy collector is present.

68. The method of claim 5, wherein the at least one energy augmentation structure comprises a structure in which a locally intensified electric field exists in one part of the structure when the structure receives electromagnetic energy.

69. The method of claim 68, wherein the at least one energy augmentation structure comprises at least one resonator dimensioned to be resonant with the applied electromagnetic energy.

70. The method of claim 69, wherein the resonator comprises a folded resonator, wherein the folded resonator comprises:
(i) electrical conductors configured as a fractal pattern; or
(ii) a ¾ wavelength resonator having opposing ends folded inwards from a center of the folded resonator with a gap in between the opposing ends; or
(iii) a ¾ wavelength resonator having opposing ends folded outwards from a center of the folded resonator with a gap in between the opposing ends.

71. The system of claim 6, wherein the predetermined cellular change is apoptosis in a target cell.

72. The system of claim 6, wherein the initiation energy is capable of directly activating the at least one activatable pharmaceutical agent.

73. The system of claim 6, wherein the at least one (i) energy emitter or (iii) energy collector is present and whereby the initiation energy source interacts with the at least one (i) energy emitter or (ii) energy collector, and is absorbed by the at least one energy converter and reemitted as an activation energy for the at least one activatable pharmaceutical agent, where the activation energy has at least one augmented property compared to if the energy converter were remote from the at least one (i) energy emitter or at least one (ii) energy collector, such that the initiation energy source indirectly activates the at least one activatable pharmaceutical agent via the at least one energy converter.

74. The system of claim 73, wherein said at least one energy converter is a single energy converter, and is coupled to said at least one activatable pharmaceutical agent.

75. The system of claim 6, wherein the initiation energy is x-rays, gamma rays or an electron beam.

76. The system of claim 6, wherein:
(i) the at least one activatable pharmaceutical agent is a photoactivatable agent; or
(ii) the at least one activatable pharmaceutical agent is selected from psoralens, pyrene cholesteryloleate, acridine, porphyrin, fluorescein, rhodamine, 16-diazorcortisone, ethidium, transition metal complexes of bleomycin, transition metal complexes of deglycobleomycin organoplatinum complexes, alloxazines, vitamin Ks, vitamin L, vitamin metabolites, vitamin precursors, naphthoquinones, naphthalenes, naphthols and derivatives thereof having planar molecular conformations, porphyrins, dyes and phenothiazine derivatives, coumarins, quinolones, quinones, and anthroquinones; or
(iii) the at least one activatable pharmaceutical agent is one selected from 7,8-dimethyl-10-ribityl, isoalloxazine, 7,8,10-trimethylisoalloxazine, 7,8-dimethylalloxazine, isoalloxazine-adenine dinucleotide, alloxazine mononucleotide, aluminum (III) phthalocyanine tetrasulonate, hematoporphyrin, and phthadocyanine; or
(iv) the at least one activatable pharmaceutical agent is coupled to a carrier that is capable of binding to a receptor site; or
(v) the at least one activatable pharmaceutical agent has affinity for a target cell; or
(vi) the at least one activatable pharmaceutical agent is capable of being preferentially absorbed by a target cell; or
(vii) the at least one activatable pharmaceutical agent is a DNA intercalator or a halogenated derivative thereof; or
(viii) the at least one activatable pharmaceutical agent is activated by one or more sequential single photon absorption events; or
(ix) the at least one activatable pharmaceutical agent comprises an active agent contained within a photocage, wherein upon exposure to said initiation energy source, the photocage disassociates from the active agent, rendering the active agent available.

77. The system of claim 6, wherein the at least one activatable pharmaceutical agent is a psoralen, a coumarin, or a derivative thereof.

78. The system of claim 6, wherein the at least one activatable pharmaceutical agent is 8-MOP or AMT.

79. The system of claim 6, wherein the at least one activated pharmaceutical agent causes an auto-vaccine effect in the subject that reacts with a target cell.

80. The system of claim 6, wherein the at least one energy augmentation structure comprises a structure in which a locally intensified electric field exists in one part of the structure when the structure receives electromagnetic energy.

81. The system of claim 80, wherein the at least one energy augmentation structure comprises at least one resonator dimensioned to be resonant with the applied electromagnetic energy.

82. The system of claim 81, wherein the resonator comprises a folded resonator, wherein the folded resonator comprises:
(i) electrical conductors configured as a fractal pattern; or
(ii) a ¾ wavelength resonator having opposing ends folded inwards from a center of the folded resonator with a gap in between the opposing ends; or (iii) a ¾ wavelength resonator having opposing ends folded outwards from a center of the folded resonator with a gap in between the opposing ends.

83. The kit of claim 7, further comprising instructions for administering the at least one activatable pharmaceutical agent; and the at least one (i) energy emitter, (ii) energy augmentation structure, or (iii) energy collector to a subject and for activating the at least one activatable pharmaceutical agent by application of an initiation energy.

84. The kit of claim 7, wherein the at least one activatable pharmaceutical agent is a member selected from the group consisting of a psoralen, a coumarin, or a derivative thereof.

85. The kit of claim 7, wherein the at least one activatable pharmaceutical agent is a psoralen selected from psoralen or 8-MOP.

86. The kit of claim 7, wherein the at least one energy converter is:
(i) one or more members selected from a biocompatible fluorescing metal nanoparticle, fluorescing dye molecule, gold nanoparticle, a water soluble quantum dot encapsulated by polyamidoamine dendrimers, a luciferase, a biocompatible phosphorescent molecule, a combined electromagnetic energy harvester molecule, and a lanthanide chelate capable of intense luminescence; or
(ii) a single energy converter, and is coupled to said at least one activatable pharmaceutical agent.

87. The kit of claim 7, wherein:
(i) the at least one activatable pharmaceutical agent is coupled to a carrier that is capable of binding to a receptor site; or
(ii) the at least one activatable pharmaceutical agent has affinity for a target cell; or
(iii) the at least one activatable pharmaceutical agent is capable of being preferentially absorbed by a target cell; or
(iv) the at least one activatable pharmaceutical agent is a DNA intercalator or a halogenated derivative thereof; or
(v) the at least one activatable pharmaceutical agent is activated by one or more sequential single photon absorption events; or
(vi) the at least one activatable pharmaceutical agent comprises an active agent contained within a photocage, wherein upon exposure to said initiation energy source, the photocage disassociates from the active agent, rendering the active agent available.

88. The kit of claim 7, wherein the at least one activated pharmaceutical agent causes an auto-vaccine effect in the subject that reacts with a target cell.

89. The kit of claim 7, wherein the at least one (i) energy emitter is present.

90. The kit of claim 7, wherein the at least one (ii) energy augmentation structure is present.

91. The kit of claim 7, wherein the at least one (iii) energy collector is present.

92. The kit of claim 7, wherein the at least one energy augmentation structure comprises a structure in which a locally intensified electric field exists in one part of the structure when the structure receives electromagnetic energy.

93. The kit of claim 92, wherein the at least one energy augmentation structure comprises at least one resonator dimensioned to be resonant with the applied electromagnetic energy.

94. The kit of claim 93, wherein the resonator comprises a folded resonator, wherein the folded resonator comprises:
(i) electrical conductors configured as a fractal pattern; or
(ii) a ¾ wavelength resonator having opposing ends folded inwards from a center of the folded resonator with a gap in between the opposing ends; or
(iii) a ¾ wavelength resonator having opposing ends folded outwards from a center of the folded resonator with a gap in between the opposing ends.

95. The pharmaceutical composition of claim 8, wherein:
(i) the at least one activatable pharmaceutical agent is a photoactivatable agent; or
(ii) the at least one activatable pharmaceutical agent is selected from psoralens, pyrene cholesteryloleate, acridine, porphyrin, fluorescein, rhodamine, 16-diazorcortisone, ethidium, transition metal complexes of bleomycin, transition metal complexes of deglycobleomycin organoplatinum complexes, alloxazines, vitamin Ks, vitamin L, vitamin metabolites, vitamin precursors, naphthoquinones, naphthalenes, naphthols and derivatives thereof having planar molecular conformations, porphyrins, dyes and phenothiazine derivatives, coumarins, quinolones, quinones, and anthroquinones; or
(iii) the at least one activatable pharmaceutical agent is one selected from 7,8-dimethyl-10-ribityl, isoalloxazine, 7,8,10-trimethylisoalloxazine, 7,8-dimethylalloxazine, isoalloxazine-adenine dinucleotide, alloxazine mononucleotide, aluminum (II phthalocyanine tetrasulonate, hematoporphyrin, and phthadocyanine; or
(iv) the at least one activatable pharmaceutical agent is coupled to a carrier that is capable of binding to a receptor site; or
(v) the at least one activatable pharmaceutical agent has affinity for a target cell; or
(vi) the at least one activatable pharmaceutical agent is capable of being preferentially absorbed by a target cell; or
(vii) the at least one activatable pharmaceutical agent is a DNA intercalator or a halogenated derivative thereof; or
(viii) the at least one activatable pharmaceutical agent is activated by one or more sequential single photon absorption events; or
(ix) the at least one activatable pharmaceutical agent comprises an active agent contained within a photocage, wherein upon exposure to said initiation energy source, the photocage disassociates from the active agent, rendering the active agent available.

96. The pharmaceutical composition of claim 8, wherein the at least one activatable pharmaceutical agent is a psoralen, a coumarin, or a derivative thereof.

97. The pharmaceutical composition of claim 8, wherein the at least one activatable pharmaceutical agent is 8-MOP or AMT.

98. The pharmaceutical composition of claim 8, wherein the at least one activated pharmaceutical agent causes an auto-vaccine effect in the subject that reacts with a target cell.

99. The pharmaceutical composition of claim 8, wherein the predetermined cellular change is apoptosis in a target cell.

100. The pharmaceutical composition of claim 8, wherein the at least one energy collector is present and the at least one energy converter is capable of activating the at least one activatable pharmaceutical agent when energized.

101. The pharmaceutical composition of claim 100, wherein said at least one energy converter is a single energy converter, and is coupled to said at least one activatable pharmaceutical agent.

102. The pharmaceutical composition of claim 8, wherein the at least one additive is present and is a chemical energy source.

103. The pharmaceutical composition of claim 8, wherein the chemical energy source is a member selected from the group consisting of phosphorescent compounds, chemiluminescent compounds, bioluminescent compounds and light emitting enzymes.

104. The pharmaceutical composition of claim 8, wherein the at least one energy augmentation structure comprises a structure in which a locally intensified electric field exists in one part of the structure when the structure receives electromagnetic energy.

105. The pharmaceutical composition of claim 104, wherein the at least one energy augmentation structure comprises at least one resonator dimensioned to be resonant with the applied electromagnetic energy.

106. The pharmaceutical composition of claim 105, wherein the resonator comprises a folded resonator, wherein the folded resonator comprises:
  (i) electrical conductors configured as a fractal pattern; or
  (ii) a ¾ wavelength resonator having opposing ends folded inwards from a center of the folded resonator with a gap in between the opposing ends; or
  (iii) a ¾ wavelength resonator having opposing ends folded outwards from a center of the folded resonator with a gap in between the opposing ends.

107. The method according to claim 9, wherein said initiation energy source is a chemical energy source.

108. The method according to claim 9, wherein said predetermined cellular change treats the cell proliferation disorder by causing an increase or decrease in cell proliferation rate of a target cell.

109. The method according to claim 9, wherein the at least one activated pharmaceutical agent causes an auto-vaccine effect in the subject that reacts with a target cell.

110. The method according to claim 9, wherein the at least one energy emitter or at least one energy collector are present.

111. The method of claim 110, wherein said at least one energy converter is a single energy converter, and is coupled to said at least one activatable pharmaceutical agent.

112. The method of claim 107, wherein the chemical energy source is a member selected from the group consisting of phosphorescent compounds, chemiluminescent compounds, bioluminescent compounds, and light emitting enzymes.

113. The method of claim 9, wherein the predetermined cellular change is apoptosis in a target cell.

114. The method of claim 9, wherein the cell proliferation disorder is at least one member selected from the group consisting of cancer, bacterial infection, viral infection, immune rejection response, autoimmune disorders, and aplastic conditions.

115. The method of claim 9, wherein:
  (i) the at least one activatable pharmaceutical agent is a photoactivatable agent; or
  (ii) the at least one activatable pharmaceutical agent is selected from psoralens, pyrene cholesteryloleate, acridine, porphyrin, fluorescein, rhodamine, 16-diazorcortisone, ethidium, transition metal complexes of bleomycin, transition metal complexes of deglycobleomycin organoplatinum complexes, alloxazines, vitamin Ks, vitamin L, vitamin metabolites, vitamin precursors, naphthoquinones, naphthalenes, naphthols and derivatives thereof having planar molecular conformations, porphyrins, dyes and phenothiazine derivatives, coumarins, quinolones, quinones, and anthroquinones; or
  (iii) the at least one activatable pharmaceutical agent is one selected from 7,8-dimethyl-10-ribityl, isoalloxazine, 7,8,10-trimethylisoalloxazine, 7,8-dimethylalloxazine, isoalloxazine-adenine dinucleotide, alloxazine mononucleotide, aluminum phthalocyanine tetrasulonate, hematoporphyrin, and phthadocyanine; or
  (iv) the at least one activatable pharmaceutical agent is coupled to a carrier that is capable of binding to a receptor site; or
  (v) the at least one activatable pharmaceutical agent has affinity for a target cell; or
  (vi) the at least one activatable pharmaceutical agent is capable of being preferentially absorbed by a target cell; or
  (vii) the at least one activatable pharmaceutical agent is a DNA intercalator or a halogenated derivative thereof; or
  (viii) the at least one activatable pharmaceutical agent comprises an active agent contained within a photocage, wherein upon exposure to said initiation energy, the photocage disassociates from the active agent, rendering the active agent available; or
  (ix) the at least one activatable pharmaceutical agent is activated by one or more sequential single photon absorption events.

116. The method of claim 9, wherein the at least one activatable pharmaceutical agent is a psoralen, a coumarin, or a derivative thereof.

117. The method of claim 9, wherein the at least one activatable pharmaceutical agent is 8-MOP or AMT.

118. The method of claim 9, wherein the at least one (i) energy emitter is present.

119. The method of claim 9, wherein the at least one (ii) energy augmentation structure is present.

120. The method of claim 9, wherein the at least one (iii) energy collector is present.

121. The method of claim 9, wherein the at least one energy augmentation structure comprises a structure in which a locally intensified electric field exists in one part of the structure when the structure receives electromagnetic energy.

122. The method of claim 121, wherein the at least one energy augmentation structure comprises at least one resonator dimensioned to be resonant with the applied electromagnetic energy.

123. The method of claim 122, wherein the resonator comprises a folded resonator, wherein the folded resonator comprises:
  (i) electrical conductors configured as a fractal pattern; or
  (ii) a ¾ wavelength resonator having opposing ends folded inwards from a center of the folded resonator with a gap in between the opposing ends; or
  (iii) a ¾ wavelength resonator having opposing ends folded outwards from a center of the folded resonator with a gap in between the opposing ends.

124. The method of claim 10, wherein said at least one energy emitter is present and wherein said initiation energy is indirectly applied by co-administration of the at least one energy converter.

125. The method of claim 10, wherein said initiation energy is indirectly applied by a chemical energy source.

126. The method of claim 125, wherein said chemical energy source is a member selected from the group consisting of phosphorescent compounds, chemiluminescent compounds, bioluminescent compounds and light emitting enzymes.

127. The method according to claim 10, wherein said predetermined cellular change treats the cell proliferation disorder by causing an increase or decrease in cell proliferation rate of a target cell.

128. The method according to claim 10, wherein the at least one activated pharmaceutical agent causes an autovaccine effect in the subject that reacts with a target cell.

129. The method according to claim 10, wherein said at least one energy collector is present and wherein said initiation energy is indirectly applied by co-administration of the at least one energy converter.

130. The method of claim 10, wherein the initiation energy source is selected from the group consisting of x-rays, gamma rays, electron beams, phosphorescent compounds, chemiluminescent compounds, bioluminescent compounds, and light emitting enzymes.

131. The method of claim 10, wherein the predetermined cellular change is apoptosis in a target cell.

132. The method of claim 10, wherein the cell proliferation disorder is at least one member selected from the group consisting of cancer, bacterial infection, viral infection, immune rejection response, autoimmune disorders, and aplastic conditions.

133. The method of claim 10, wherein:
(i) the at least one activatable pharmaceutical agent is a photoactivatable agent; or
(ii) the at least one activatable pharmaceutical agent is selected from psoralens, pyrene cholesteryloleate, acridine, porphyrin, fluorescein, rhodamine, 16-diazorcortisone, ethidium, transition metal complexes of bleomycin, transition metal complexes of deglycobleomycin organoplatinum complexes, alloxazines, vitamin Ks, vitamin L, vitamin metabolites, vitamin precursors, naphthoquinones, naphthalenes, naphthols and derivatives thereof having planar molecular conformations, porphyrins, dyes and phenothiazine derivatives, coumarins, quinolones, quinones, and anthroquinones; or
(ii)) the at least one activatable pharmaceutical agent is one selected from 7,8-dimethyl-10-ribityl, isoalloxazine, 7,8,10-trimethylisoalloxazine, 7,8-dimethylalloxazine, isoalloxazine-adenine dinucleotide, alloxazine mononucleotide, aluminum (III) phthalocyanine tetrasulonate, hematoporphyrin, and phthadocyanine; or
(iv) the at least one activatable pharmaceutical agent is coupled to a carrier that is capable of binding to a receptor site; or
(v) the at least one activatable pharmaceutical agent has affinity for a target cell; or
(vi) the at least one activatable pharmaceutical agent is capable of being preferentially absorbed by a target cell; or
(vii) the at least one activatable pharmaceutical agent is a DNA intercalator or a halogenated derivative thereof; or
(viii) the at least one activatable pharmaceutical agent is activated by one or more sequential single photon absorption events; or
(ix) the at least one activatable pharmaceutical agent comprises an active agent contained within a photocage, wherein upon exposure to said initiation energy, the photocage disassociates from the active agent, rendering the active agent available.

134. The method of claim 10, wherein the at least one activatable pharmaceutical agent is a psoralen, a coumarin, or a derivative thereof.

135. The method of claim 10, wherein the at least one activatable pharmaceutical agent is 8-MOP or AMT.

136. The method of claim 10, further comprising administering to the subject nanotubes configured to receive and transmit radiowaves, wherein said radiowaves activate the at least one activatable pharmaceutical agent.

137. The method of claim 124, further comprising administering to the subject nanotubes configured to receive and transmit radiowaves, wherein said radiowaves are accepted by said at least one energy converter and transformed into an energy that activates said at least one activatable pharmaceutical agent.

138. The method of claim 10, wherein the at least one energy augmentation structure comprises a structure in which a locally intensified electric field exists in one part of the structure when the structure receives electromagnetic energy.

139. The method of claim 138, wherein the at least one energy augmentation structure comprises at least one resonator dimensioned to be resonant with the applied electromagnetic energy.

140. The method of claim 139, wherein the resonator comprises a folded resonator, wherein the folded resonator comprises:
(i) electrical conductors configured as a fractal pattern; or
(ii) a ¾ wavelength resonator having opposing ends folded inwards from a center of the folded resonator with a gap in between the opposing ends; or
(iii) a ¾ wavelength resonator having opposing ends folded outwards from a center of the folded resonator with a gap in between the opposing ends.

141. The method of claim 11, wherein the at least one pharmaceutical agent is at least one activatable pharmaceutical agent, and said causing step (2) comprises activating the at least one activatable pharmaceutical agent.

142. The method of claim 141, wherein:
(i) the at least one activatable pharmaceutical agent is a photoactivatable agent; or
(ii) the at least one activatable pharmaceutical agent is selected from psoralens, pyrene cholesteryloleate, acridine, porphyrin, fluorescein, rhodamine, 16-diazorcortisone, ethidium, transition metal complexes of bleomycin, transition metal complexes of deglycobleomycin organoplatinum complexes, alloxazines, vitamin Ks, vitamin L, vitamin metabolites, vitamin precursors, naphthoquinones, naphthalenes, naphthols and derivatives thereof having planar molecular conformations, porphyrins, dyes and phenothiazine derivatives, coumarins, quinolones, quinones, and anthroquinones; or
(iii) the at least one activatable pharmaceutical agent is one selected from 7,8-dimethyl-10-ribityl, isoalloxazine, 7,8,10-trimethylisoalloxazine, 7,8-dimethylalloxazine, isoalloxazine-adenine dinucleotide, alloxazine mononucleotide, aluminum (III) phthalocyanine tetrasulonate, hematoporphyrin, and phthadocyanine; or (iv) the at least one activatable pharmaceutical agent is coupled to a carrier that is capable of binding to a receptor site; or
(v) the at least one activatable pharmaceutical agent has affinity for a target cell; or
(vi) the at least one activatable pharmaceutical agent is capable of being preferentially absorbed by a target cell; or
(vii) the at least one activatable pharmaceutical agent is a DNA intercalator or a halogenated derivative thereof; or
(viii) the at least one activatable pharmaceutical agent is activated by one or more sequential single photon absorption events; or
(ix) the at least one activatable pharmaceutical agent comprises an active agent contained within a photocage, wherein upon exposure to said initiation energy, the photocage disassociates from the active agent, rendering the active agent available.

143. The method of claim 11, wherein the at least one activated pharmaceutical agent causes an auto-vaccine effect in the subject that reacts with a target cell.

144. The method of claim 11, wherein the at least one activatable pharmaceutical agent is a psoralen, a coumarin, or a derivative thereof.

145. The method of claim 11, wherein the at least one activatable pharmaceutical agent is 8-MOP or AMT.

146. The method of claim 141, wherein said activating comprises applying an initiation energy to the subject, which interacts with the at least one (i) energy emitter, (ii) energy augmentation structure, or (iii) energy collector, then activates the at least one activatable pharmaceutical agent in vivo.

147. The method of claim 146, wherein the at least one (i) energy emitter or (ii) energy collector are present.

148. The method of claim 147, wherein said at least one energy converter is a single energy converter, and is coupled to said at least one activatable pharmaceutical agent.

149. The method of claim 11, wherein the at least one energy augmentation structure comprises a structure in which a locally intensified electric field exists in one part of the structure when the structure receives electromagnetic energy.

150. The method of claim 149, wherein the at least one energy augmentation structure comprises at least one resonator dimensioned to be resonant with the applied electromagnetic energy.

151. The method of claim 150, wherein the resonator comprises a folded resonator, wherein the folded resonator comprises:
(i) electrical conductors configured as a fractal pattern; or
(ii) a ¾ wavelength resonator having opposing ends folded inwards from a center of the folded resonator with a gap in between the opposing ends; or
(iii) a ¾ wavelength resonator having opposing ends folded outwards from a center of the folded resonator with a gap in between the opposing ends.

152. The method of claim 12, wherein the activation energy is capable of penetrating human tissue up to about 4 mm.

153. The method of claim 152, wherein the activation energy is generated in-situ in said subject by application of an initiation energy which interacts with the at least one (i) energy emitter, (ii) energy augmentation device, or (iii) energy collector, and is converted in-situ to said activation energy.

154. The method of claim 12, further comprising, prior to or simultaneously with providing the activation energy, administering to the subject at least one activatable pharmaceutical agent that is activatable by the activation energy after it interacts with the at least one (i) energy emitter, (ii) energy augmentation device, or (iii) energy collector, and is converted in-situ to said activation energy, wherein upon activation, the at least one activated pharmaceutical agent effects the predetermined change in the subject.

155. The method of claim 12, wherein the predetermined change is a predetermined cellular change.

156. The method of claim 155, wherein said condition, disorder or disease is a cell proliferation disorder and said predetermined cellular change treats the cell proliferation disorder by causing an increase or decrease in cell proliferation rate of a target cell.

157. The method of claim 154, wherein the at least one activated pharmaceutical agent causes an auto-vaccine effect in the subject that reacts with a target cell.

158. The method of claim 12, wherein the initiation energy source is selected from the group consisting of x-rays, gamma rays, electron beams, phosphorescent compounds, chemiluminescent compounds, bioluminescent compounds, and light emitting enzymes.

159. The method of claim 155, wherein the predetermined cellular change is apoptosis in a target cell.

160. The method of claim 154, wherein:
(i) the at least one activatable pharmaceutical agent is a photoactivatable agent; or
(ii) the at least one activatable pharmaceutical agent is selected from psoralens, pyrene cholesteryloleate, acridine, porphyrin, fluorescein, rhodamine, 16-diazorcortisone, ethidium, transition metal complexes of bleomycin, transition metal complexes of deglycobleomycin organoplatinum complexes, alloxazines, vitamin Ks, vitamin L, vitamin metabolites, vitamin precursors, naphthoquinones, naphthalenes, naphthols and derivatives thereof having planar molecular conformations, porphyrins, dyes and phenothiazine derivatives, coumarins, quinolones, quinones, and anthroquinones; or
(iii) the at least one activatable pharmaceutical agent is one selected from 7,8-dimethyl-10-ribityl, isoalloxazine, 7,8,10-trimethylisoalloxazine, 7,8-dimethylalloxazine, isoalloxazine-adenine dinucleotide, alloxazine mononucleotide, aluminum (III) phthalocyanine tetrasulonate, hematoporphyrin, and phthadocyanine; or
(iv) the at least one activatable pharmaceutical agent is coupled to a carrier that is capable of binding to a receptor site; or
(v) the at least one activatable pharmaceutical agent has affinity for a target cell; or
(vi) the at least one activatable pharmaceutical agent is capable of being preferentially absorbed by a target cell; or
(vii) the at least one activatable pharmaceutical agent is a DNA intercalator or a halogenated derivative thereof; or
(viii) the at least one activatable pharmaceutical agent is activated by one or more sequential single photon absorption events; or
(ix) the at least one activatable pharmaceutical agent comprises an active agent contained within a photocage, wherein upon exposure to said initiation energy, the photocage disassociates from the active agent, rendering the active agent available; or (x) the at least one activatable pharmaceutical agent comprises an active agent contained within a photocage, and said activation energy is UV-A or visible energy, wherein upon exposure to said UV-A or visible energy, the photocage disassociates from the active agent, rendering the active agent available.

161. The method of claim 154, wherein the at least one activatable pharmaceutical agent is a psoralen, a coumarin, or a derivative thereof.

162. The method of claim 154, wherein the at least one activatable pharmaceutical agent is 8-MOP or AMT.

163. The method of claim 153, wherein the initiation energy is one of electromagnetic energy, acoustic energy, or thermal energy.

164. The method of claim 12, wherein the at least one energy augmentation structure comprises a structure in which a locally intensified electric field exists in one part of the structure when the structure receives electromagnetic energy.

165. The method of claim 164, wherein the at least one energy augmentation structure comprises at least one resonator dimensioned to be resonant with the applied electromagnetic energy.

166. The method of claim 165, wherein the resonator comprises a folded resonator, wherein the folded resonator comprises:
   (i) electrical conductors configured as a fractal pattern; or
   (ii) a ¾ wavelength resonator having opposing ends folded inwards from a center of the folded resonator with a gap in between the opposing ends; or
   (iii) a ¾ wavelength resonator having opposing ends folded outwards from a center of the folded resonator with a gap in between the opposing ends.

* * * * *